United States Patent [19]

Kamiya et al.

[11] 4,207,234
[45] Jun. 10, 1980

[54] 4-UNSUBSTITUTED AZETIDINONE DERIVATIVES AND PROCESS FOR PREPARATION THEREOF

[75] Inventors: Takashi Kamiya, Suita; Yoshihisa Saito, Takarazuka; Masashi Hashimoto, Toyonaka; Osamu Nakaguti; Teruo Oku, both of Osaka; Youichi Shiokawa, Takatsuki; Takao Takaya, Sakai; Tadaaki Komori, Takatsuki; Tsutomu Teraji, Toyonaka; Keiji Hemmi, Kyoto; Hisashi Takasugi, Osaka, all of Japan

[73] Assignee: Fujisawa Pharmaceutical Co., Ltd., Osaka, Japan

[21] Appl. No.: 858,375

[22] Filed: Dec. 7, 1977

Related U.S. Application Data

[63] Continuation-in-part of Ser. No. 694,891, Jun. 10, 1976, abandoned, which is a continuation-in-part of Ser. No. 593,668, Jul. 7, 1975, abandoned.

[51] Int. Cl.$^2$ .............. C07D 205/08; C07D 403/12; C07D 401/12; C07D 409/12
[52] U.S. Cl. .............. 260/239 A; 260/245.4; 260/330.3; 260/347.3; 260/345.7 R; 542/416; 542/455; 544/111; 544/276; 544/312; 546/275

[58] Field of Search .................. 260/239 AL

[56] References Cited

U.S. PATENT DOCUMENTS

2,923,977  12/1975  Aoki et al. .............. 195/80 R

FOREIGN PATENT DOCUMENTS

2529941  4/1976  Fed. Rep. of Germany ... 260/239 AL

OTHER PUBLICATIONS

Hosoda et al., Chem. Abs., 87, 100673m (1977).

*Primary Examiner*—Mark L. Berch
*Attorney, Agent, or Firm*—Dayton R. Stemple, Jr.

[57] ABSTRACT

New antimicrobial azetidinone derivatives and their salt of the formula:

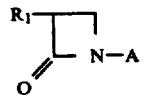

wherein $R_1$ is amino or acylamino, and A is selected from a variety of groups.

4 Claims, No Drawings

4-UNSUBSTITUTED AZETIDINONE DERIVATIVES AND PROCESS FOR PREPARATION THEREOF

CROSS-REFERENCE TO RELATED APPLICATION

This invention is a continuation-in-part application of copending application Ser. No. 694,891, filed on June 10, 1976, abandoned which is a continuation-in-part application of copending application Ser. No. 593,668, filed on July 7, 1975 now abandoned.

BACKGROUND OF THE INVENTION

This invention is based on the successful identification of the chemical structure of FR-1923 substance. That is, FR-1923 substance is a known antibiotic isolated from the fermentation broth of a strain of the genus Nocardia deposited with the American Type Culture Collection under ATCC No. 21806, the details of which are described for example, in German Patent application No. 2,242,699, which corresponds to U.S. Pat. No. 3,923,977 issued on Dec. 2, 1975.

In said prior literature, the FR-1923 substance is defined by the various physico-chemical properties without any disclosure of its chemical structure. As a result of extensive structural determination study, the inventors of this invention have established the structure of the FR-1923 substance as 1-(α-Carboxy-4-hydroxybenzyl)-3-(((2-((4-(3-amino-3-carboxypropoxy)phenyl))-2-hydroxyiminoacetamido)))-2-azetidinone of the following formula.

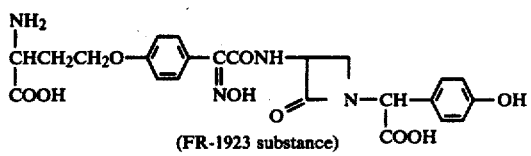

(FR-1923 substance)

The above attractive and unique single β-lactam structure of the antibiotic FR-1923 substance encouraged the inventors of this invention to study the chemical syntheses of FR-1923 substance per se and other related new single β-lactam compounds to learn the structure-activity relationship and other active derivarives, analogues or homologues and further any possibility of an industrial synthetic process for the preparation thereof.

From the above viewpoint, the inventors of this invention have synthesized a lot of novel and unique modified compounds of FR-1923 substance and have made intensive efforts to prepare some useful intermediary 3-amino-2-azetidinone compounds, so far as practical.

For the purpose of illustrating the state of prior arts, all of the known related compounds which were synthesized from penicillins by degradative reactions and the relevant literatures are mentioned as follows:

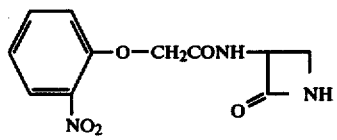

(U.S. Pat. No. 3487,072)

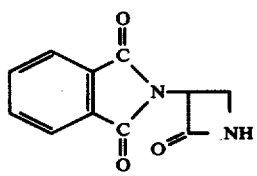

"

(Journal of Organic Chemistry, Vol. 38, p. 940–943, 1973)

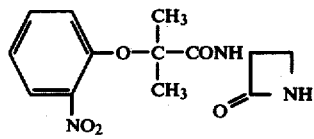

(ARCHIV DER PHARMAZIE und Berichte der Deutschen Pharmazeutishen Gesellshaft Vol. 303, p. 834, 1970)

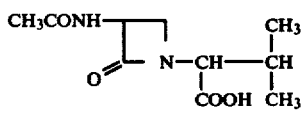

"

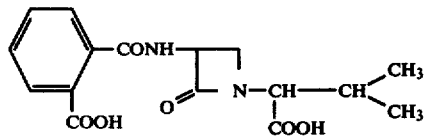

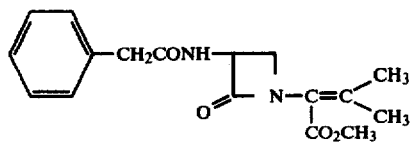

(MOLECULAR MODIFICATION IN DRUG DESIGN, Page 23, 1964, published by American Chemical Society)

-continued

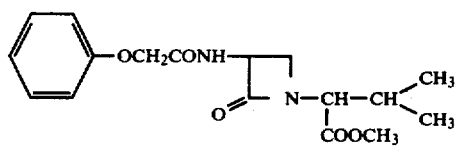
(Journal of Medical Chemistry, Vol. 11 (4), P. 933-936, 1968)

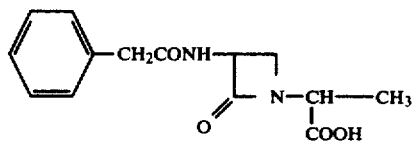
(The Chemistry of Penicillin,) P 977

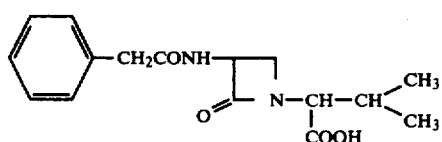
"

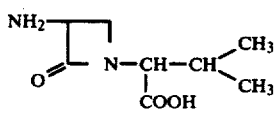
(ARCHIV DER PHARMAZIE und Berichte der Deutschen Pharmazeutischen Gesellschaft Vol. 303, P 832, 1970)

DETAILED DESCRIPTION OF THE PREFERRED EMBODIMENTS OF THE INVENTION

This invention relates to azetidinone derivatives. More particularly, it relates to novel azetidinone derivatives having antimicrobial activities and to process for preparation thereof.

Accordingly, it is an object of this invention to provide azetidinone derivatives having antimicrobial activities.

Another object of this invention is to provide a process for preparation of the azetidinone derivatives.

The azetidinone derivatives of this invention are new compounds in the art and represented by the following general formula (I)

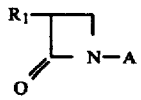

wherein $R_1$ is amino or acylamino, and A is hydrogen or a group represented by the formula:

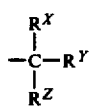

wherein $R^X$ is hydrogen;

$R^Y$ is hydrogen, alkyl containing up to 6 carbon atoms which may be substituted by one or more groups selected from hydroxy and amino, or phenyl which may be substituted by one or more groups selected from hydroxy, amino, nitro, alkyl containing up to 6 carbon atoms, alkoxy containing up to 6 carbon atoms, aralkoxy in which alkane moiety contains up to 6 carbon atoms, alkylthio containing up to 6 carbon atoms and halogen; or $R^X$ and $R^Y$ are linked together to form alkylidene containing up to 6 carbon atoms; and $R^Z$ is carboxy or pharmaceutically acceptable salt thereof, hydroxy, amino, cyano or alkyl containing up to 6 carbon atoms which is substituted by carboxy or pharmaceutically acceptable salt thereof;

provided that when $R_1$ is 2[4-(3-amino-3-carboxypropoxy)phenyl]-2-hydroxyiminoacelamido, A is hydrogen or a group represented by the formula:

wherein $R^X$ is hydrogen;

$R^{Ya}$ is hydrogen, alkyl containing up to 6 carbon atoms, or phenyl which may be substituted by one or more groups selected from amino, nitro, alkyl containing up to 6 carbon atoms, alkoxy containing up to 6 carbon atoms, aralkoxy in which alkane moiety contains up to 6 carbon atoms, alkylthio containing up to 6 carbon atoms and halogen; or $R^X$ and $R^{Ya}$ are linked together to form alkylidene containing up to 6 carbon atoms; and $R^Z$ is carboxy or pharmaceutically acceptable salt thereof, hydroxy, amino, cyano or alkyl containing up to 6 carbon atoms which is substituted by carboxy or pharmaceutically acceptable salt thereof:

when $R_1$ is acetamido, benzamido or phenylacetamido,

A is hydrogen or a group represented by the formula:

wherein $R^X$ is hydrogen;

$R^{Yb}$ is hydrogen or phenyl which may be substituted by one or more groups selected from hydroxy, amino, nitro, alkyl containing up to 6 carbon atoms, alkoxy containing up to 6 carbon atoms, aralkoxy in which alkane moiety contains up to 6 carbon atoms, or alkylthio containing up to 6 carbon atoms and halogen; and $R^Z$ is carboxy or pharmaceutically acceptable salt thereof, hydroxy, amino, cyano or alkyl containing up to 6 carbon atoms which is substituted by carboxy or pharmaceutically acceptable salt thereof:

when $R_1$ is 2-(2-nitrophenoxy)acetamido or 2-(2-nitrophenoxy)-2-methylpropionamido or phthalimido, A is a group represented by the formula:

wherein $R^X$ is hydrogen;

$R^Y$ is hydrogen; alkyl containing up to 6 carbon atoms which may be substituted by one or more groups selected from hydroxy and amino, or phenyl which may be substituted by one or more groups selected from hydroxy, amino, nitro, alkyl containing up to 6 carbon atoms, alkoxy containing up to 6 carbon atoms, aralkoxy in which alkane moiety contains up to 6 carbon atoms, alkylthio containing up to 6 carbon atoms and halogen; or $R^X$ and $R^Y$ are linked together to form alkylidene containing up to 6 carbon atoms; and $R^Z$ is carboxy or pharmaceutically acceptable salt thereof, hydroxy, amino, cyano or alkyl containing up to 6 carbon atoms which is substituted by carboxy or pharmaceutically acceptable salt thereof.

With regard to the definition of the compound of the formula (I), "acyl" in acylamino for $R_1$ is intended and restricted to mean "acyl consisting of an organic carbonyl (—CO—) and organic sulfonyl (—SO$_2$—)", more particularly, in other words, "acyl derived from organic carboxylic acid (i.e. organic carboxylic acyl), organic carbamic acid (i.e. organic carbamic acyl), organic carbonic acid (i.e. organic carbonic acyl) and organic sulfonic acid (i.e. organic sulfonic acyl)". Further, it is to be understood that the present object compound of the formula (I), within the scope thereof, includes its equivalences such as the conventionally blocked functional derivatives at the carboxy group (e.g. esterified carboxy), the amino group (e.g. conventionally protected amino), and the hydroxy group (e.g. conventionally protected hydroxy) of the molecule of compound (I), respectively. The detail of such equivalences of the compound (I) will be apparent in the descriptions as disclosed hereinafter.

Further, the compound of the present invention includes the compound of the following formula:

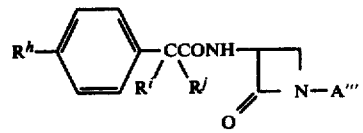

wherein $R^h$ is hydrogen or a radical of the formula:

wherein $R^j$ is hydrogen or lower alkoxycarbonyl;

$R^i$ and $R^j$ are each hydrogen or combined to form OXO; and $A'''$ is a radical of the formula:

According to this invention, the azetidinone derivatives (I) can be prepared by various synthetic methods, which are illustrated collectively by the following schemes for convenience's sake.

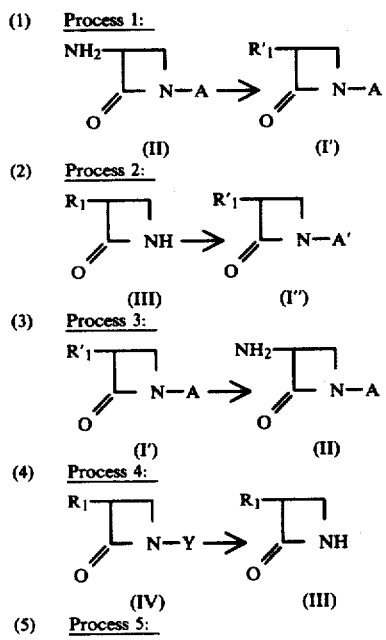

4,207,234
-continued
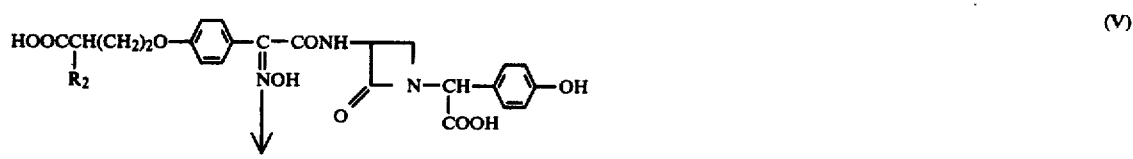
(V)
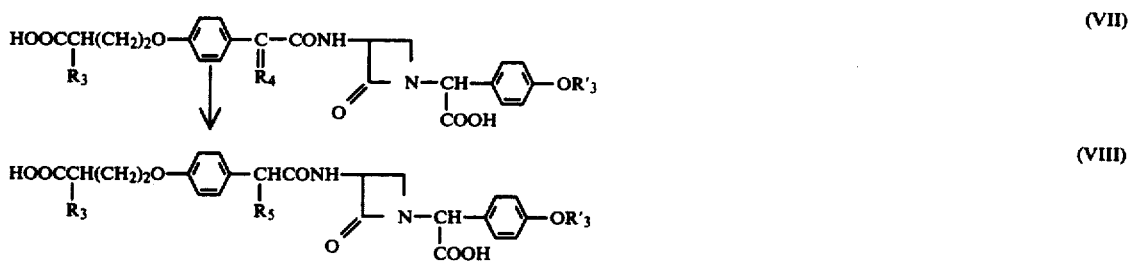
(VI)
(6) Process 6:
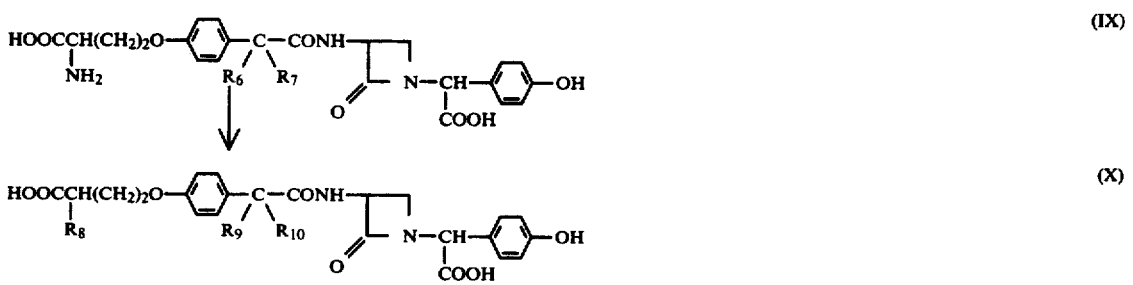
(VII)
(VIII)
(7) Process 7:
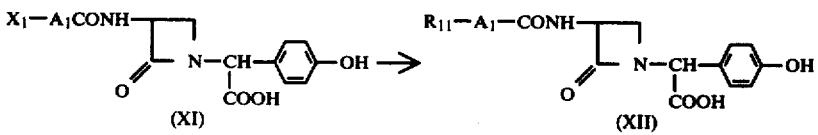
(IX)
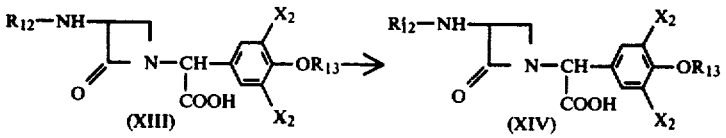
(X)
(8) Process 8:
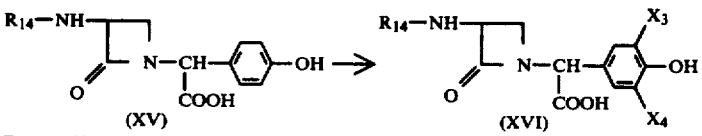
(9) Process 9:
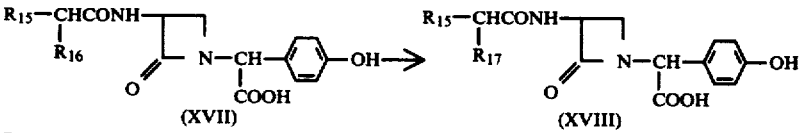
(10) Process 10:
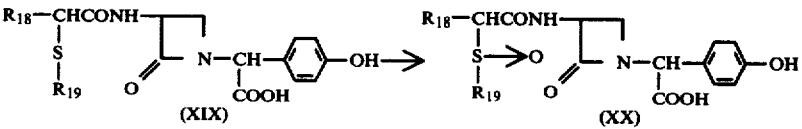
(11) Process 11:
(12) Process 12:
(13) Process 13:

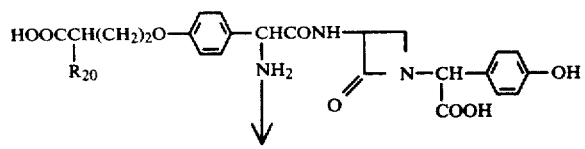
(XXI)
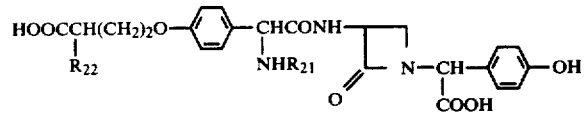
(XXII)
Process 14:
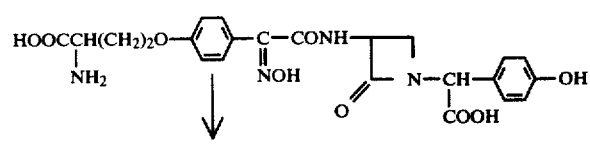
(XXIII)
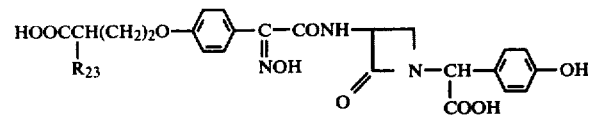
(XXIV)
Process 15:
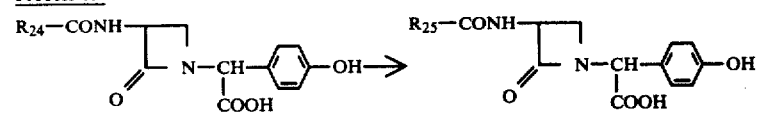
(XXV) (XXVI)
Process 16:
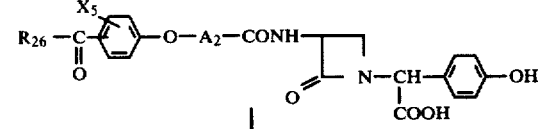
(XXVII)
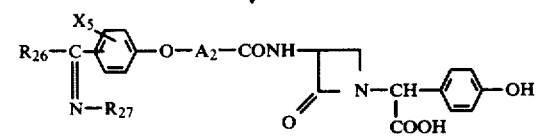
(XXVIII)
Process 17:
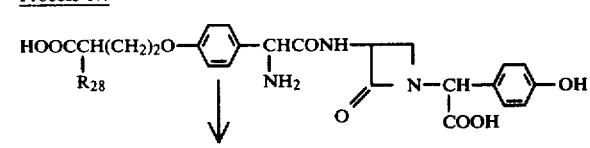
(XXIX)
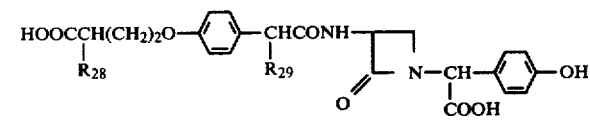
(XXX)
Process 18:
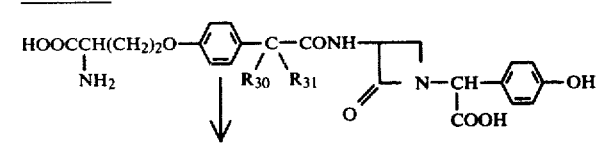
(XXXI)
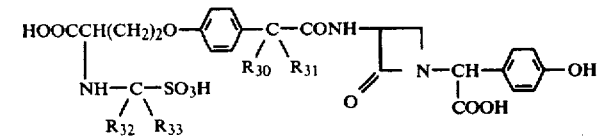
(XXXII)
Process 19:

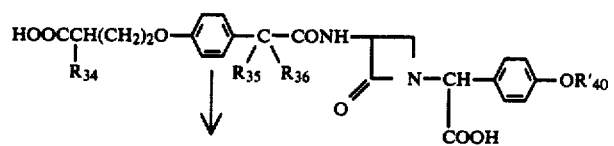
(XXXIII)
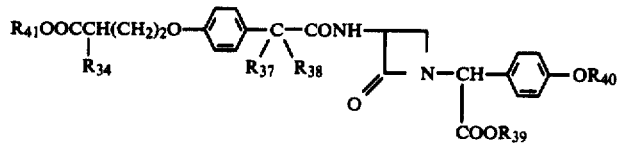
(XXXIV)
(20) Process 20:
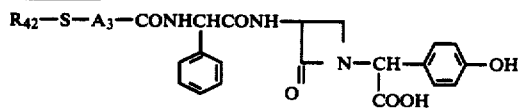
(XXXV)
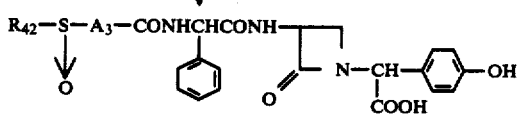
(XXXVI)
(21) Process 21:
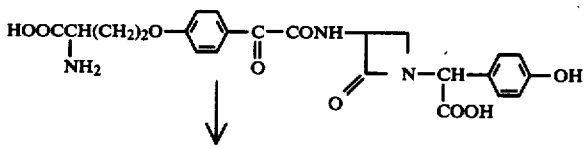
(XXXVII)
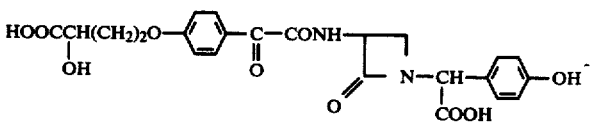
(XXXVIII)
(22) Process 22:
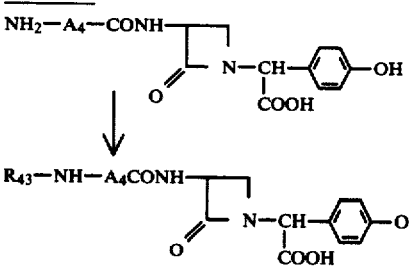
(XXXIX)
(XXXX)
(23) Process 23:
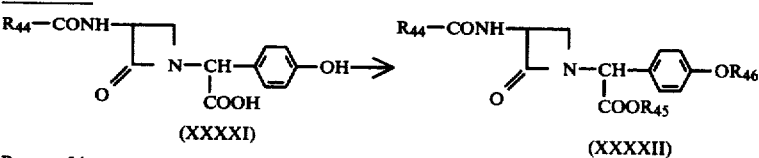
(XXXXI) (XXXXII)
(24) Process 24:
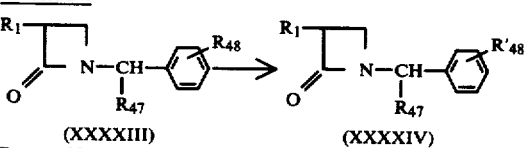
(XXXXIII) (XXXXIV)
(25) Process 25:
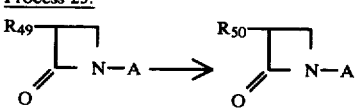
(XXXXV) (XXXXVI)
(26) Process 26:

-continued
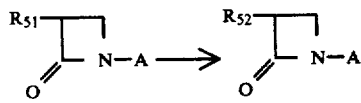
(XXXXVII) (XXXXVIII)
(27) Process 27:
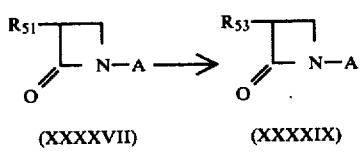
(XXXXVII) (XXXXIX)
(28) Process 28:
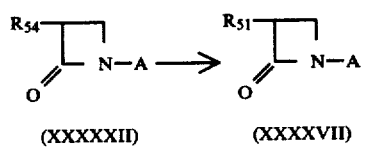
(XXXXXII) (XXXXVII)
(29) Process 29:
(a)
$R_{55}$ ... $N-A$ → $R_{56}$ ... $N-A$
(XXXXXIII) (XXXXXIV)
(b)
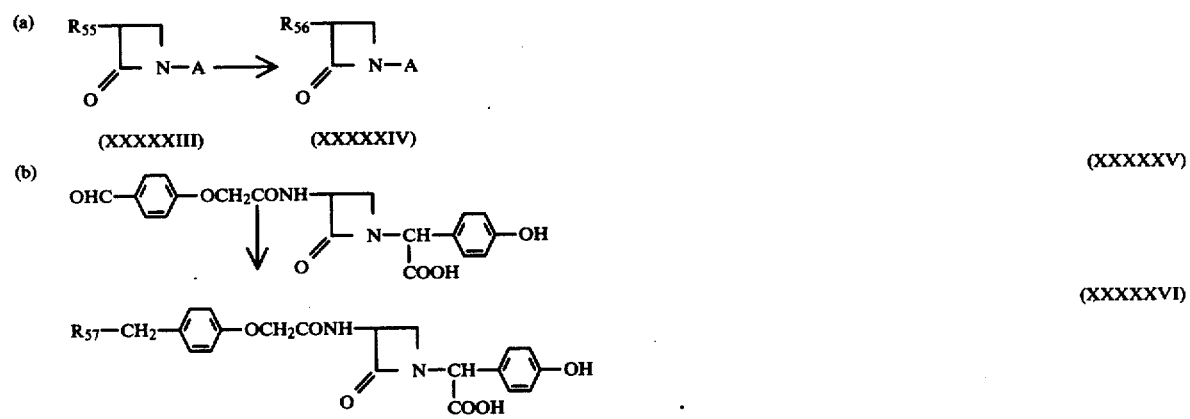
(XXXXXV)
(XXXXXVI)
(30) Process 30:
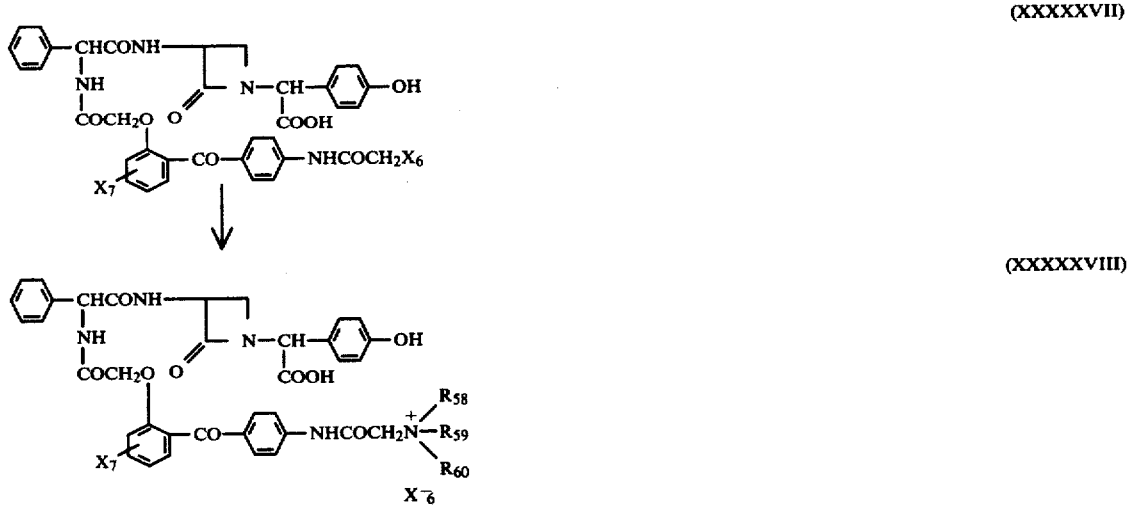
(XXXXXVII)
(XXXXXVIII)
(31) Process 31:
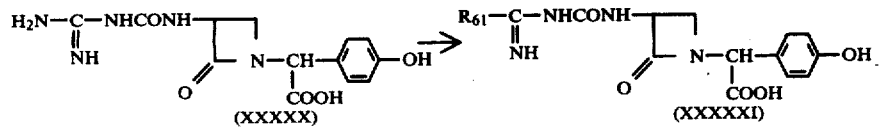
(XXXXX) (XXXXXI)
(32) Process 32:

(33) Process 33:
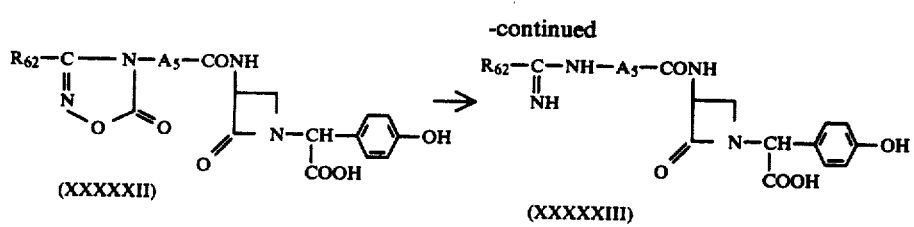
-continued
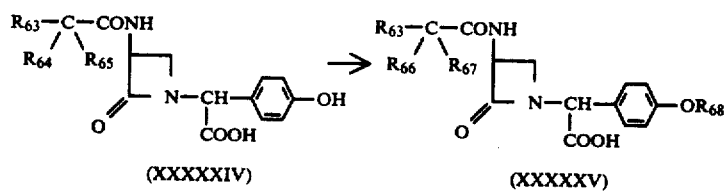
(34) Process 34:
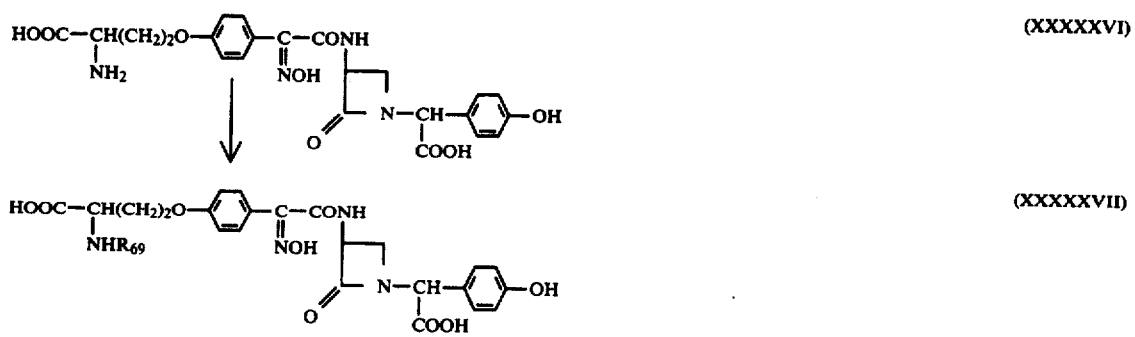
(35) Process 35:
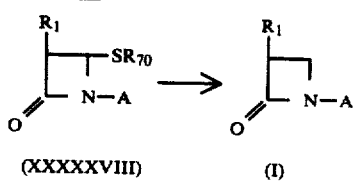
(36) Process 36:
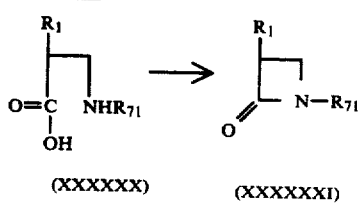
(37) Process 37:
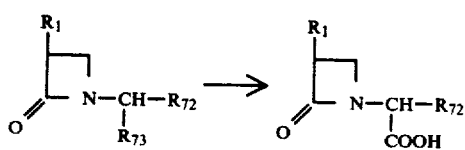
(38) Process 38:
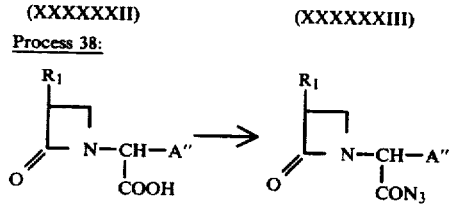
(39) Process 39:

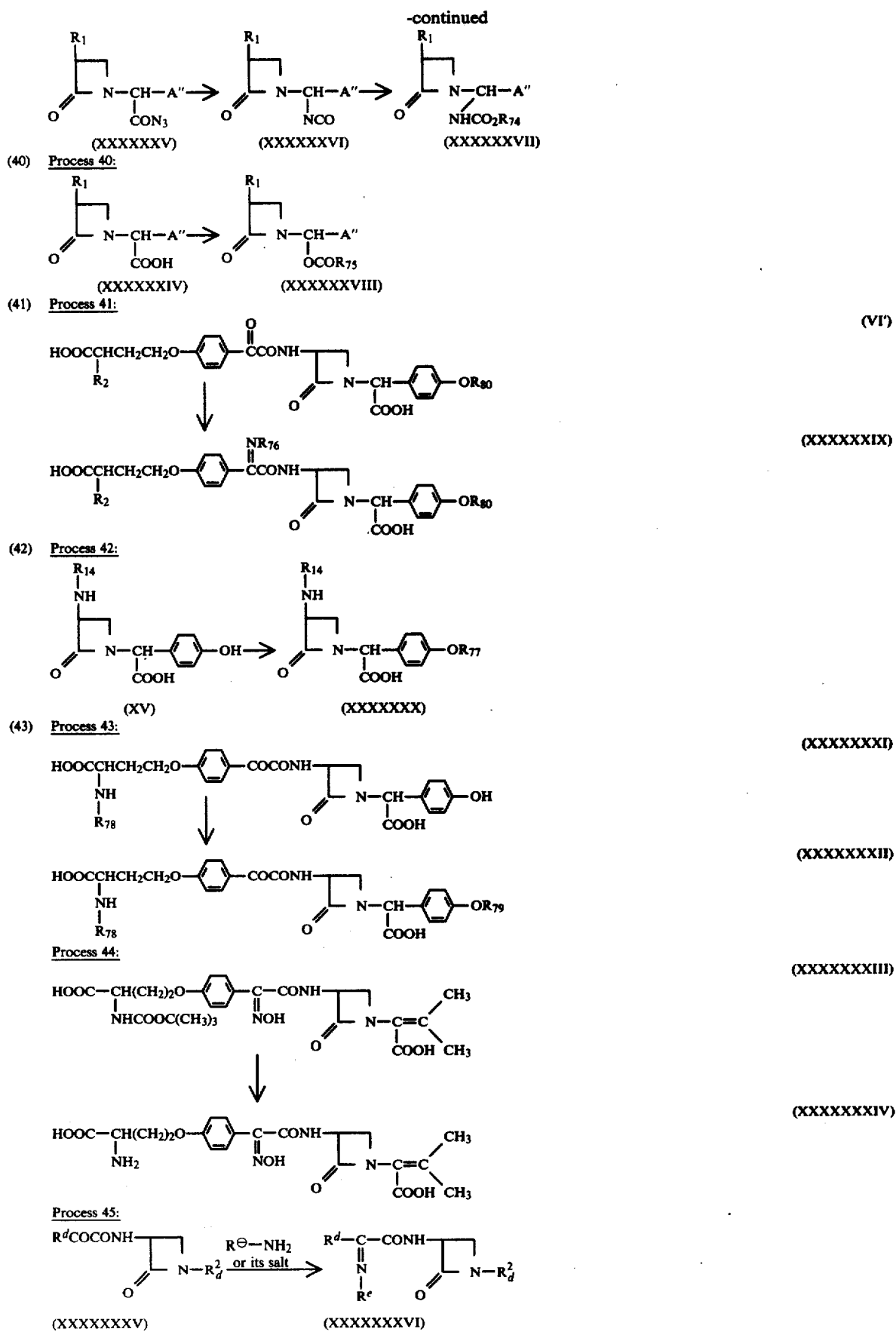

Process 46:

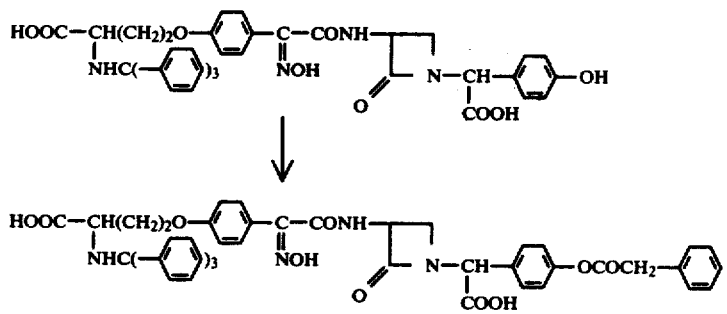

(XXXXXXXVII)

(XXXXXXXVIII)

Process 47:

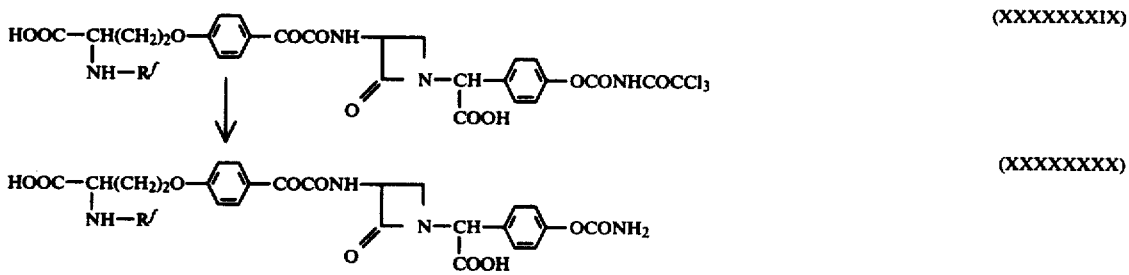

(XXXXXXXIX)

(XXXXXXXX)

Process 48:

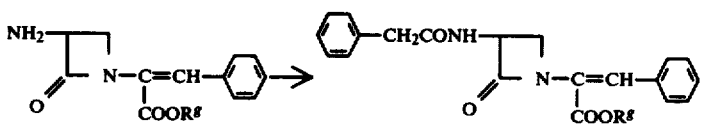

(XXXXXXXXI)   (XXXXXXXXII)

Process 49:

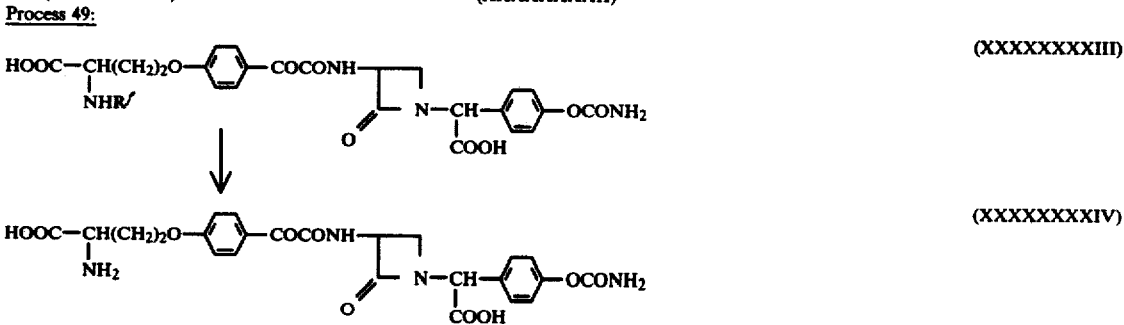

(XXXXXXXXIII)

(XXXXXXXXIV)

With regard to the above processes, it is to be understood that the Process 1 and Process 2 are fundamental processes and the remaining Processes are alternative ones.

The definitions of the symbols used in the above formulae are mentioned in the following:

$R_1$ is as defined above;

A is as defined above;

A' is as defined in the symbol "A" excepting hydrogen;

$R'_1$ is acylamino;

Y is oxalo, esterified oxalo, 1-(protected amino)alkyl or 1-(protected hydroxy)alkyl;

$R_2$ is amino or acylamino;

$R_3$ is amino or acylamino;

$R'_3$ is hydrogen or aralkyl;

$R_4$ is oxo or hydroxyimino;

$R_5$ is amino or hydroxy;

$R_6$ and $R_7$ are combined to form oxo or hydroxyimino, or $R_6$ is hydrogen, and $R_7$ is amino or hydroxy;

$R_8$ is acylamino;

$R_9$ and $R_{10}$ are combined to form oxo or hydroxyimino, or $R_9$ is hydrogen and $R_{10}$ is amino, hydroxy, acylamino or acyloxy;

$X_1$ is acid residue;

$A_1$ is bivalent aliphatic hydrocarbon radical;

$R_{11}$ is residue of nucleophile;

$R_{12}$ is acyl having protected amino, protected hydroxy or protected carboxy function(s);

$R'_{12}$ is acyl having amino, hydroxy or carboxy function(s);

$R_{13}$ is hydrogen, aralkyl, acyl or alkyl;

$X_2$ is hydrogen or halogen;

$R_{14}$ is acyl;

$X_3$ is hydrogen or halogen;

$X_4$ is halogen;

$R_{15}$ is hydrogen, alkyl, aryl, aralkyl, aryloxy, heterocyclic group or heterocyclic alkyl;

$R_{16}$ is amino or hydrocarbon radical having amino;

$R_{17}$ is acylamino or acylamino-substituted-hydrocarbon residue;

$R_{18}$ is hydrogen or aryl;

$R_{19}$ is alkyl, N-arylcarbamoylalkyl or aryl;

$R_{20}$ is amino or acylamino;

$R_{21}$ is aryl substituted by at least one of nitro and esterified carboxy;

$R_{22}$ is acylamino or arylamino whose aryl ring is substituted by at least one of nitro and esterified carboxy;

$R_{23}$ is mono- or di-alkylamino;

$R_{24}$ is nitroaryl;

$R_{25}$ is aminoaryl;

$R_{26}$ is hydrogen, alkyl or aryl;

$X_5$ is hydrogen or halogen;

$A_2$ is bivalent aliphatic hydrocarbon radical;

$R_{27}$ is hydroxy, alkoxy or alkanoyl amino;

$R_{28}$ is acylamino;

$R_{29}$ is acylamino;

$R_{30}$ and $R_{31}$ are combined to form oxo or hydroxyimino, or $R_{30}$ is hydrogen and $R_{31}$ is hydroxy;

$R_{32}$ and $R_{33}$ are hydrogen or alkyl;

$R_{34}$ is acylamino;

$R_{35}$ and $R_{36}$ are combined to form oxo or hydroxyimino, acyloxyimino, or $R_{35}$ is hydrogen and $R_{36}$ is acylamino or hydroxy;

$R_{37}$ and $R_{38}$ are combined to form oxo, hydroxyimino, acyloxyimino, alkoxyimino or substituted alkoxyimino, or $R_{37}$ is hydrogen and $R_{38}$ is acylamino, hydroxy, alkoxy or substituted alkoxy;

$R_{39}$ is alkyl or substituted alkyl;

$R'_{40}$ is hydrogen or acyl;

$R_{40}$ is hydrogen, acyl or substituted or unsubstituted alkyl;

$R_{41}$ is alkyl or substituted alkyl;

$R_{42}$ is alkyl, aryl or aralkyl;

$A_3$ is alkylene;

$A_4$ is bivalent aliphatic hydrocarbon radical;

$R_{43}$ is aromatic heterocyclic group or aryl substituted by at least one of nitro and esterified carboxy;

$R_{44}$ is aralkyl;

$R_{45}$ is alkyl;

$R_{46}$ is hydrogen or alkyl;

$R_{47}$ is carboxy or its derivative;

$R_{48}$ is a protected amino or a protected hydroxy;

$R'_{48}$ is amino or hydroxy;

$R_{49}$ is an acylamino having carboxy or its reactive derivative;

$R_{50}$ is an acylamino having a substituent selected from carbazoyl, N-(hydroxyalkyl)-carbamoyl and N-aralkylcarbamoyl;

$R_{51}$ is an acylamino having amino;

$R_{52}$ is an acylamino having esterified carboxy substituted alkylamino;

$R_{53}$ is an acylamino having esterified carboxy substituted alkenyl amino;

$R_{54}$ is an acylamino having at least one of nitro and azido;

$R_{55}$ is an acylamino having a substituent selected from formyl, alkanoyl and aroyl;

$R_{56}$ is an acylamino having at least one of hydroxyalkyl and α-hydroxyaralkyl;

$R_{57}$ is aralkylamino;

$X_6$ is halogen;

$X_7$ is hydrogen or halogen;

$R_{58}$, $R_{59}$ and $R_{60}$ are each alkyl; and $R_{61}$ is aralkanoylamino;

$R_{62}$ is aryl;

$A_5$ is alkylene;

$R_{63}$ is aryl or heterocyclic group;

$R_{64}$ and $R_{65}$ are each hydrogen, or both are combined to form hydroxyimino;

$R_{66}$ and $R_{67}$ are each hydrogen, or both are combined to form aroyloxyimino or aralkoxycarbonyloxyimino;

$R_{68}$ is aroyl or aralkoxycarbonyloxyimino;

$R_{69}$ is aralkyl;

$R_{70}$ is alkyl, heterocyclicthio or a radical of the formula:

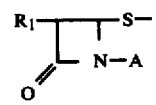

wherein A is as defined above;

$R_{71}$ is alkyl having at least one of carboxy and esterified carboxy;

$R_{72}$ is hydrogen, alkyl, or substituted or unsubstituted aryl;

$R_{73}$ is esterified carboxy;

A" is alkyl, alkenyl or aryl;

$R_{74}$ is alkyl;

$R_{75}$ is lower alkyl;

$R_{76}$ is alkoxy, (carboxy or esterified carboxy)alkoxy, aralkoxy, ureido, thioureido, or amino;

$R_{77}$ is aralkyl;

$R_{78}$ is amino-protecting group;

$R_{79}$ is acyl;

$R_{80}$ is hydrogen, hydroxy, acyloxy, alkyloxy or aralkyloxy;

$R^d$ is 4-(3-amino-3-carboxypropoxy)-3-chlorophenyl, 2-amino-4-thiazoly, 4-(3-t-butoxycarbonylamino-3-carboxy)-3-chlorophenyl, 3-(3-amino-3-carboxypropoxy)-phenyl, 4-(3-carboxypropoxy)phenyl, or 4-(3-t-butoxycarbonylamino-3-carboxypropoxy)phenyl;

$R^e$ is hydroxy, methoxy or 2-t-butoxycarbonylaminoethoxy;

$R_d^2$ is a radical of the following formula;

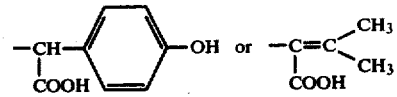

$R^f$ is hydrogen or lower alkoxycarbonyl;

$R^g$ is hydrogen or lower alkyl; and $R^f$ is lower alkoxycarbonyl:

Examples of the definitions for the above symbols are illustrated below, respectively.

(1) With respect to the compound (I):

An acyl moiety in the acylamino for $R_1$ is intended to mean an acyl consisting of carbonyl radical (—CO—) or sulfonyl radical (—$SO_2$—) as stated hereinabove, including an aliphatic acyl, an aromatic acyl, a heterocyclic acyl and an aliphatic acyl whose aliphatic moiety is substituted by aromatic group or heterocyclic group. Examples of such acyl are illustrated in the following:

An aliphatic moiety in said aliphatic acyl may include saturated or unsaturated acyclic or cyclic hydrocarbon residue, in which the acyclic hydrocarbon residue may be branched and partially cyclized.

Suitable examples of said acyclic or alicyclic hydrocarbon residue (hereinafter referred to aliphatic-hydrocarbon residue) are mentioned in more concrete as follows:

alkyl (e.g., methyl, ethyl, propyl, butyl, isobutyl, pentyl, neopentyl, octyl, undecyl, tridecyl, pentadecyl, cyclohexylmethyl, cyclohexylethyl, bornanyl, etc.);

alkenyl (e.g., vinyl, propenyl, isopropenyl, 3-methylbutenyl, butenyl, 2-methylpropenyl, pentenyl, octadecenyl, 3-cyclohexenylmethyl, etc.);

alkynyl (e.g., ethynyl, 2-propynyl, etc.);

cycloalkyl (e.g., cyclopropyl, cyclopentyl, cyclohexyl, indanyl, bornyl, adamantyl, etc.); and cycloalkenyl (e.g., 1-cyclopenten-1-yl, 2-cyclopenten-1-yl, 3-cyclohexene-1-yl, bornenyl etc.)

A suitable aromatic group in said aromatic acyl may include aryl such as phenyl, tolyl, naphthyl and the like.

A heterocyclic group in said heterocyclic acyl may include monocyclic or polycyclic heterocyclic group containing at least one hetero-atom selected from oxygen, sulfur nitrogen and the like. Suitable examples of said heterocyclic group are mentioned in more concrete as follows:

a 3- to 8-membered monocyclic heterocyclic group containing at least one sulfur atom (e.g., thienyl dihydrothiopyranyl, etc.);

a 3- to 8-membered monocyclic heterocyclic group containing at least one oxygen atom (e.g., oxiranyl, furyl, dihydrofuryl, pyranyl, dihydropyranyl, tetrahydropyranyl, dioxanyl, etc.);

a 3- to 8-membered monocyclic heterocyclic group containing at least one nitrogen atom (e.g., aziridinyl, azetidinyl, pyrrolyl, 2- or 3H-pyrrolyl, 2 or 3 pyrrolinyl, pyrrolidinyl, imidazolyl, imidazolidinyl, pyrazolyl, pyridyl, pyrimidyl, pyrazinyl, piperidinyl, pyridazinyl, tetrazolyl, etc.);

a 3- to 8-membered monocyclic heterocyclic group containing at least one oxygen atom and at least one nitrozen atom (e.g., oxazolyl, isoxazolyl, oxadiazolyl, sydnonyl, etc.);

a 3- to 8-membered monocyclic heterocyclic group containing at least one sulfur atom and at least one nitrogen atom (e.g., thiazolyl, isothiazolyl, thiadiazolyl, etc.);

a polycyclic heterocyclic group containing at least one sulfur atom (e.g., benzene-fused heterocyclic group such as benzothienyl, benzothiopyranyl, etc.);

a polycyclic heterocyclic group containing at least one nitrogen atom (e.g., indolyl, isoindolyl, indolizinyl, benzimidazolyl, quinolyl, isoquinoyl, dihydroisoqunolyl, quinazolyl, 1 or 2H-indazolyl, 1 or 2H-benzotriazolyl, purinyl, carbazolyl, etc.);

a polycyclic heterocyclic group containing at least one oxygen atom and at least one nitrogen atom (e.g. benzoxazolyl, benzoxadiazolyl, etc.); and a polycyclic heterocyclic group containing at least one sulfur atom and at least one nitrogen atom (e.g., benzothiazolyl, benzothiadiazolyl, etc.).

An aliphatic moiety in said aliphatic acyl whose aliphatic moiety is substituted by aromatic group or heterocyclic group is intended to mean the same meaning as defined in the above explanation of the aliphatic moiety in the aliphatic acyl, and include the same suitable examples thereof as stated in more concrete above. And in the same manner, each of the aromatic group and an heterocyclic group also are intended to mean the same meaning as defined in the above explanation of the aromatic group in the aromatic acyl and of the heterocyclic group in the heterocyclic acyl as well, and include the same suitable examples thereof as stated in more concrete above, respectively.

The optional carbon atom of the aliphatic acyl as defined above may be replaced and/or interrupted by one or more radicals selected from a bivalent aromatic radical, a bivalent heterocyclic radical, —O—, —N=, —S—, —SO—, —SO$_2$—, and —NH— whose hydrogen atom may be replaced by alkyl or aryl.

Each of the aliphatic moiety, aromatic group and heterocyclic group in the aliphatic acylamino, the aromatic acylamino, the heterocyclic acylamino and the aliphatic acylamino whose aliphatic moiety is substituted by aromatic group or heterocyclic group as defined above may optionally be substituted by one or more substituents selected from halogen, nitro, amino, carboxy, esterified carboxy, hydroxy, —N$_3$, —CN, —NHNH$_2$, =O, =NH, =S, sulfo and =NOH whose hydrogen atom may be replaced by alkyl or aralkyl, and the said heterocyclic group in the foregoing acylamino group may optionally be substituted by alkyl and/or an aromatic group.

Particularly, preferred examples of the aforementioned acylamino for $R_1$ may be illustrated as follows. As acylamino, the acyl moiety consisting of carbonyl radical (—CO—), i.e. organic carboxylic acylamino:

alkanoylamino;

alkenoylamino;

aroylamino;

heterocycle carboxamino;

alkanoylamino substituted by aryl or heterocyclic group;

alkenoylamino substituted by aryl or heterocyclic group;

alkanoyl or alkenoyl amino, whose optional carbon chain(s) is interrupted by bivalent-aromatic radical and/or bivalent-heterocyclic radical;

alkanoyl or alkenoyl amino substituted by aryl and/or heterocyclic group, in which an optional carbon chain(s) of the acyclic hydrocarbon moiety is interrupted by bivalent-aromatic radical and/or bivalent-heterocyclic radical;

alkanoyl or alkenoyl amino substituted by aryl and/or heterocyclic group, in which an optional carbon chain(s) of the -acyclic hydrocarbon moiety is interrupted by one or more radicals selected from —O—, —N=,

—SO$_2$—, and —NH— whose hydrogen atom may be replaced by alkyl or aryl;

alkanoyl or alkenoyl amino substituted by aryl and/or heterocyclic group, in which an optional carbon chain(s) of the acyclic hydrocarbon moiety is interrupted by aromatic radical and/or bivalent heterocyclic radical, and further is interrupted by one or more radicals selected from —O—, —N=, —S—,

—SO$_2$—, and —NH— whose hydrogen atom may be replaced by alkyl or aryl;

alkanoyl or alkenoyl amino whose optional carbon chain is interrupted by one or more radicals selected from —O—, —N=, —S—,

—SO$_2$—, and —NH— whose hydrogen atom may be replaced by alkyl or aryl;

alkanoyl or alkenoylamino whose optional carbon chain is interrupted by bivalent-aromatic radical and/or bivalent-heterocyclic radical and further interrupted by one or more radicals selected from —O—, —N=, —S—,

—SO$_2$—, and —NH— whose hydrogen atom may be replaced by alkyl or aryl;

aroylamino or heterocycle carboxamino, in which the bond between the ring and the carbonyl is interrupted by one or more radicals selected from —O—, —N=, —S—,

—SO$_2$—, and —NH—, whose hydrogen atom may be replaced by alkyl or aryl;

alkanoyl or alkenoyl amino substituted by cycloalkyl, aryl and/or heterocyclic group, in which the bond between the ring and the acyclic hydrocarbon moiety is interrupted by one or more radicals selected from —O—, —N=, —S—,

—SO$_2$—, and —NH—, whose hydrogen atom may be replaced by alkyl or aryl;

alkanoyl or alkenoyl amino substituted by cycloalkyl, aryl and/or heterocyclic group, in which each of the bond between the ring and the acyclic hydrocarbon moiety, and an optional carbon chain of the acyclic hydrocarbon moiety is interrupted by bivalent-aromatic radical and/or bivalent-heterocyclic radical, and/or one or more radicals selected from —O—, —N=, —S—,

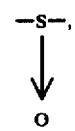

—SO$_2$— and —NH—, whose hydrogen atom may be replaced by alkyl or aryl;

aroylamino or heterocycle carboxamino in which the bond between the ring and the carbonyl is interrupted by one or more bivalent-aromatic radical and/or bivalent-heterocyclic radical;

alkanoyl or alkenoyl amino substituted by aryl and/or heterocyclic group, in which the bond between the ring and the acyclic hydrocarbon moiety are interrupted by bivalent-aromatic radical and/or bivalent-heterocyclic radical, and further one or more radicals selected from —O—, —N=, —S—,

—SO$_2$— and —NH—, whose hydrogen atom may be replaced by alkyl or aryl, and alkanoyl or alkenoyl amino substituted by aryl and/or heterocyclic group, in which the bond between the ring and the acyclic hydrocarbon moiety is interrupted by one or more bivalent-aromatic radicals and/or bivalent-heterocyclic radicals;

An optional carbon atom of above defined acylamino group may be substituted by one or more substituents selected from halogen, nitro, amino, carboxy, esterified carboxy, hydroxy, —N$_3$, —CN, —NHNH$_2$, =O, =NH, =S, sulfo, =NOH whose hydrogen atom may be replaced by alkyl or aralkyl, and the heterocyclic group in the foregoing acylamino group may optionally be substituted by alkyl.

As acylamino, the acyl moiety consisting of sulfonyl radical (—SO$_2$—), i.e. organic sulfonic acylamino: Preferred examples of the organic sulfonic acylamino can be exemplified by an acylamino, in which "carbonyl radical (—CO—)" in the preferred examples of the acylamino as exemplified above is replaced by "sulfonyl radical (—SO$_2$—)". Accordingly, preferred examples of the organic sulfonic acylamino are to be referred to the preferred examples of the organic carboxylic acylamino by changing "oylamino" in the terms of the preferred examples to read as—e(or ene)sulfonylamino—, for example, "alkanoylamino" to read as —alkanesulfonylamino—, "alkenoylamino" to —alkenesulfonylamino—, "aroylamino" to —arenesulfonylamino and so on.

alkanoylamino, in which an optional carbon chain is interrupted by one phenylene and further optional carbon atoms are substituted by one halogen and one oxo;

phenylalkanoylamino, in which an optional carbon atom may be substituted by one substituent selected from amino, carboxy, esterified carboxy, hydroxy, halogen, nitro, sulfo, oxo, hydroxyimino and benzyloxyimino;

naphthylalkanoylamino;

dihydropyranylalkanoylamino, in which an optional carbon atom is substituted by one hydroxy;

morpholinoalkanoylamino;

thienylalkanoylamino in which an optional carbon atom may be substituted by one substituent selected from amino, hydroxy, oxo and hydroxyimino;

furylalkanoylamino;

tetrazolylalkanoylamino;

indolylalkanoylamino, in which an optional carbon atom is substituted by one amino;

diphenylalkanoylamino;

alkanoylamino substituted by phenyl and thienyl;

3-alkyl-1,2,5-oxadiazol-4-yl-alkanoylamino;

phenylalkenoylamino;

phenylalkanoylamino, in which an optional carbon chain of the alkane moiety is interrupted by one phenylene;

phenylalkanoylamino, in which an optional carbon chain of alkane moiety is interrupted by one or two bivalent radicals selected from —O—, —N=, —S—, —NH—,

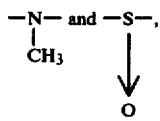

and further an optional carbon atom(s) of the group thus defined may be substituted by one to four substituents selected from amino, carboxy, esterified carboxy, halogen, oxo and =NH;

thienylalkanoylamino, in which an optional carbon chain(s) of the alkane moiety is interrupted by one to two bivalent radicals selected from —O—, —S— and —NH—, and further an optional carbon atom(s) of the group thus defined is substituted by one to four substituents selected from amino, carboxy, halogen and oxo;

dihydropyranylalkanoylamino, in which an optional carbon chain of the alkane moiety is interrupted by —NH— and an optional carbon atom of the group thus defined is substituted by halogen;

diphenylalkanoylamino, in which an optional carbon chain(s) of the alkane moiety is interrupted by one to three bivalent radicals selected from —O—, —N= and —NH—, and further an optional carbon atom(s) of the group thus defined may be substituted by one or two substituents selected from carboxy, hydroxy and oxo;

alkanoylamino substituted by phenyl and thienyl, in which an optional carbon chain(s) of the alkane moiety is interrupted by one to two bivalent radicals selected from —O—, —N= and —NH—, and further an optional carbon atom(s) of the group thus defined may be substituted by one to five substituents selected from amino, halogen, oxo and thioxo;

alkanoylamino substituted by phenyl and indolyl, in which an optional carbon chain(s) of the alkane moiety is interrupted by one —O— and one —NH—, and further an optional carbon atom of the group thus defined is substituted by one oxo;

alkanoylamino substituted by phenyl and benzo[d]isoxazolyl, in which an optional carbon chain(s) of the alkane moiety is interrupted by one —O— and one —NH—, and further an optional carbon atom of the group thus defined is substituted by one oxo;

phenylalkanoylamino, in which an optional carbon chain(s) of the alkane moiety is interrupted by one or two bivalent radicals selected from phenylene, 2-oxo-azetidin-1, 3-diyl, 1,3,4-thiadiazol-1,5-diyl and 1,3-oxazolidin-3,4-diyl and one to four bivalent radicals selected from —O—, —N=, —S—, —NH— and

and further an optional atom(s) of the group thus defined may be substituted by one to six substituents selected from amino, halogen, hydroxy, esterified carboxy, oxo, hydroxyimino, benzyloxyimino and hydrazino;

thienylalkanoylamino, in which an optional carbon chain(s) of the alkane moiety is interrupted by one phenylene, and two bivalent radicals of selected from —O— and —NH— and further an optional carbon atom(s) of the group thus defined is substituted by carboxy, oxo and hydroxyimino.

benzo[c]pyrrolidinylalkanoylamino, in which an optional carbon chain of the alkane moiety is interrupted by one phenylene and one —O—, and further optional carbon atoms of the group thus defined are substituted by four substituents selected from amino, carboxy, hydroxy, esterified carboxy, oxo, hydroxyimino and methoxyimino;

diphenylalkanoylamino, in which optional carbon chain(s) of the alkane moiety are interrupted by one phenylene and one —O— and one —NH—, and further an optional carbon atom(s) of the group thus defined is substituted by two to four substituents selected from amino, halogen, nitro, oxo and hydroxyimino;

alkanoylamino substituted by phenyl and furyl, in which optional carbon chains of the alkane moiety are interrupted by one phenylene and one —NH— and one —O— and further an optional carbon atom(s) of the group thus defined is substituted by three substituents selected from halogen and oxo;

alkanoylamino, in which an optional carbon chain(s) is interrupted by one or two bivalent radicals selected from —O—, —S—, —NH—, —SO₂— and

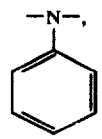

and further an optional carbon atom(s) of the group thus defined may be substituted by one to two substituents selected from amino, azido, carboxy, hydroxy, oxo, thioxo and =NH;

alkenoylamino, whose optional carbon chain is interrupted by one —S—;

alkanoylamino, in which an optional carbon chain(s) is interrupted by one or two phenylenes and one to five bivalent radicals selected from —O—, —N=, —S—, —NH— and

and further an optional carbon atom(s) of the group thus defined may be substituted by one to seven substituents selected from amino, carboxy, hydroxy, halogen, azido, sulfo, esterified carboxy, oxo, thioxo, hydroxyimino and methoxyimino;

alkanoylamino, in which an optional carbon chain is interrupted by one 1,3,4-thiadiazol-2,5-diyl and one or two bivalent radicals selected from —S and —NH—, and further an optional carbon atom(s) of the group thus defined is substituted by one or six substituents selected from amino, hydroxy and oxo;

alkenoylamino, in which an optional carbon chain is interrupted by one phenylene and one or two bivalent radicals selected from —O— and —NH—, and further an optional carbon atom(s) of the group thus defined is substituted by one or three substituents selected from carboxy, esterified carboxy, nitro, oxo and hydroxyimino;

1,2-oxazolidinylcarbonylamino, in which the bond between the 1,2-oxazolidinyl and the carbonyl is interrupted by —NH—, and further an optional carbon atom of the group thus defined is substituted by one oxo;

bicyclo[2,2,1]heptylalkanoylamino, in which the bond between the bicyclo[2,2,1]heptyl and the alkane moiety is interrupted by one —O—, and further an optional carbon atom(s) of the bicyclo[2,2,1]heptane ring is substituted by three alkyl;

phenylalkanoylamino, in which the bond between the phenyl and the alkane moiety is interrupted by one or two bivalent radicals selected from —O—, —S—, —NH— and —SO$_2$—, and further an optional carbon atom of the group thus defined may be substituted by one substituent selected from halogen and nitro;

naphthylalkanoylamino, in which the bond between the naphthyl and the alkane moiety is interrupted by bivalent radical selected from —O— and —NH—;

pyridylalkanoylamino, in which the bond between the pyridyl and the alkane moiety is interrupted by one —O—;

1,3,4-thiadiazolylalkanoylamino, in which the bond between the 1,3,4-thiadiazolyl and the alkane moiety is interrupted by one —S—;

1H-1,2,3-benzotriazolylalkanoylamino, in which the bond between the 1H-1,2,3-benzotriazolyl and the alkane moiety is interrupted by one —O—;

pyridyl-1-oxidealkanoylamino, in which the bond between the pyridyl-1-oxide and the alkane moiety is interrupted by one —S—;

diphenylalkanoylamino, in which the bond between the one or two phenyl and the alkane moiety is interrupted by one or two bivalent radicals selected from —O—, —S—, —NH— and —SO$_2$—, and further an optional carbon atom(s) of the group thus defined is substituted by one or two substituents selected from nitro, carboxy, halogen, hydroxy and oxo;

alkanoylamino substituted by phenyl and naphthyl, in which the bond between the naphthyl and the alkane moiety is interrupted by one —O—;

alkanoylamino substituted by phenyl and pyrimidinyl, in which the bond between the pyrimidinyl and the alkane moiety is interrupted by —S—, and further an optional carbon atom(s) of the group thus defined is substituted by one amino and one hydroxy;

alkanoylamino substituted by bicyclo[2,2,1]heptyl and phenyl, in which the bond between the bicyclo[2,2,1]heptyl and the alkane moiety is interrupted by one —O— and an optional carbon chain of the alkane moiety is interrupted by one —NH—, and further an optional carbon atom of the alkane moiety is substituted by oxo and optional carbon atoms of the bicyclo[2,2,1-]heptane ring are substituted by three alkyl;

diphenylalkanoylamino, in whcih the bond between one of the diphenyl and the alkane moiety is interrupted by one or two bivalent radicals selected from —O—, —NH—, —S—,

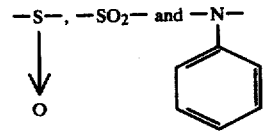

and an optional carbon chain of the alkane moiety is interrupted by one or two bivalent radicals selected from —NH— and —S—, and further an optional carbon atom(s) of the group thus defined is substituted by one to three substituents selected from carboxy, esterified carboxy, halogen, nitro and oxo;

alkanoylamino substituted by 9H-purinyl and phenyl, in which the bond between the 9H-purinyl and the alkane moiety is interrupted by one —S— and an optional carbon chain of the alkane moiety is interrupted by one —NH—, and further an optional carbon atom of the group thus defined is substituted by one oxo;

alkanoylamino substituted by phenyl and thienyl, in which the bond between the phenyl and the alkane moiety is interrupted by one bivalent radical selected from —O— and —NH— and an optional carbon chain of the alkane moiety is interrupted by one —NH—, and further optional carbon atoms of the group thus defined are substituted by three substituents selected from esterified carboxy, halogen, nitro and oxo;

alkanoylamino substituted by phenyl and pyridyl-1-oxide, in which the bond between the pyridyl-1-oxide and the alkane moiety is interrupted by one —S— and an optional carbon chain of the alkane moiety is interrupted by one —NH—, and further an optional carbon atom of the group thus defined is substituted by oxo;

alkanoylamino substituted by naphthyl and phenyl, in which the bond between the naphthyl and the alkane moiety is interrupted by one bivalent radical selected from —O— and —NH— and an optional carbon chain of the alkane moiety is interrupted by one or two bivalent radicals selected from —O—, —S—, —NH— and

and further an optional carbon atom of the group thus defined is substituted by oxo;

alkanoylamino substituted by phenyl and pyrimidinyl, in which the bond between the pyrimidinyl and the alkane moiety is interrupted by one —S— and an optional carbon chain of the alkane moiety is interrupted by one —NH—, and further optional carbon atoms of the group thus defined are substituted by one amino, one hydroxy and one oxo;

triphenylalkanoylamino, in which the bond between the one or two phenyls and the alkane moiety is interrupted by one or two bivalent radicals selected from —O— and —NH— and an optional carbon chain of the alkane moiety is interrupted by one —NH—, and further an optional carbon atom(s) of the group thus defined is substituted by one or two substituents selected from halogen and oxo;

alkanoylamino substituted by naphthyl and diphenyl, in which the bond between the naphthyl and the alkane moiety is interrupted by one —O— and an optional carbon chain of the alkane moiety is interrupted by one —NH—, and further an optional carbon atom of the group thus defined is substituted by oxo;

alkanoylamino substituted by dinaphthyl and phenyl, in which the bond between the two naphthyl and the alkane moiety is interrupted by one —O— and an optional carbon chain of the alkane moiety is interrupted by one —NH—, and further an optional carbon atom of the group thus defined is substituted by oxo;

phenylalkanoylamino, in which the bond between the phenyl and the alkane moiety is interrupted by one bivalent radical selected from —O—, —NH— and —S— and optional carbon chains of the alkane moiety are interrupted by one phenylene and one to three bivalent radicals selected from —O— and —NH—, and further an optional carbon atom(s) of the group thus defined is substituted by one to five substituents selected from carboxy, esterified carboxy, halogen, nitro, oxo, thioxo and hydroxyimino;

naphthylalkanoylamino, in which the bond between the naphthyl and the alkane moiety is interrupted by one —NH— and optional carbon chains of the alkane moiety are interrupted by one phenylene and three bivalent radicals selected from —O— and —NH—, and further optional carbon atoms of the group thus defined are substituted by one carboxy, one oxo and one thioxo;

alkanoylamino substituted by pyridyl and phenyl, in which the bond between the pyridyl and the alkane moiety is interrupted by one —S— and the optional carbon chains of the alkane moiety are interrupted by two phenylenes and three bivalent radicals selected from —O— and —NH—, and further optional carbon atoms of the group thus defined are substituted by four substituents selected from halogen and oxo;

alkanoylamino substituted by phenyl and benzo[c]pyrrolidinyl, in which the bond between the phenyl and the alkane moiety is interrupted by one —NH— and an optional carbon chain(s) of the alkane moiety is interrupted by one phenylene and one —O—, and furhter optional carbon atoms of the group thus defined are substituted by five substituents selected from carboxy, esterified carboxy, nitro and oxo;

diphenylalkanoylamino, in which the bond between the one or two phenyls and the alkane moiety is interrupted by one or two —NH— and an optional carbon chain(s) of the alkane moiety is interrupted by one phenylene and one to three bivalent radicals selected from —O— and —NH—, and further an optional carbon atom(s) of the group thus defined is substituted by one to five substituents selected from carboxy, nitro, esterified carboxy, oxo and thioxo;

dinaphthylalkanoylamino, in which bonds between the two naphthyl and the alkane moiety are interrupted by one —NH— and optional carbon chains of the alkane moiety are interrupted by one phenylene and three bivalent radicals selected from —O— and —NH—, and further optional carbon atoms of the group thus defined are substituted by three substituents selected from carboxy and thioxo;

alkanoylamino substituted by phenyl and thienyl, in which the bond between the thenyl and the alkane moiety is interrupted by one tetrazol-1,5-diyl and an optional carbon chain of the alkane moiety is interrupted by one —NH—, and further an optional carbon atom of the group thus defined is substituted by one oxo;

phenylalkanoylamino, in which the bond between the phenyl and the alkane moiety is interrupted by one —O— and an optional carbon chain of the alkane moiety is interrupted by one —NH—, and further the optional carbon atoms of the group thus defined are substituted by one halogen, one nitro and one oxo;

diphenylalkanoylamino, in which the bond between the phenyl and the alkane moiety is interrupted by one phenylene and one —O— and an optional carbon chain of the alkane moiety is interrupted by one —NH—, and further an optional carbon atom of the group thus defined is substituted by one oxo;

diphenylalkanoylamino, in which the bond between the phenyl and the alkane moiety is interrupted by one isoxazol-3,4-diyl which is interrupted by one alkyl and an optional carbon chain of the alkane moiety is interrupted by one —NH—, and further an optional carbon atom of the group thus defined is substituted by one oxo;

benzamido, in which the bond between the phenyl and the carbonyl is interrupted by isoxazol-3,4-diyl which is substituted by one alkyl, and further an optional carbon atom of the group thus defined is substituted by halogen;

phenylalkanoylamino, in which the bond between the phenyl and the alkane moiety is interrupted by one bivalent radical selected from phenylene and 1,3,5-oxadiazol-2,4-diyl and one or two bivalent radicals selected from —O—, —NH— and —SO$_2$—, and further the optional carbon atom of the group thus defined may be substituted by one carboxy and one hydroxy;

phenylalkanoylamino, in which the bond between the phenyl and the alkane moiety is interrupted by one 4,5-dihydro-1,2,4-oxadiazol-3,4-diyl, and an optional carbon atom of the group thus defined is substituted by one oxo;

thienylalkanoylamino, in which the bond between the thienyl and the alkane moiety is interrupted by 1H-tetrazol-1,5-diyl.

As acylamino, the acyl moiety consisting of sulfonyl radical (—SO$_2$—), i.e. organic sulfonic acylamino: Preferred examples of the organic sulfonic acylamino can be exemplified by an acylamino, in which "carbonyl radical (—CO—)" in the preferred examples of the acylamino as exemplified above is replaced by "sulfonyl radical (—SO$_2$—)". Accordingly, preferred examples of the organic sulfonic acylamino are to be referred to the preferred examples of the organic carboxylic acylamino by changing "oylamino" in the terms of the preferred examples to read as—e(or ene)sulfonylamino—, for example, "alkanoylamino" to read as—alkanesulfonylamino—, "alkenoylamino" to—alkenesulfonylamino—, "aroylamino" to—arenesulfonylamino and so on.

(2) With respect to the compounds [I], [I'] and [II]:

Suitable examples of alkyl containing up to 6 carbon atoms in the definition for $R^Y$ may include methyl, ethyl, propyl, butyl, pentyl and isopropyl.

Suitable examples of alkoxy containing up to 6 carbon atoms in the definition for $R^Y$ may include methoxy, ethoxy, propoxy, butoxy, pentyloxy and isopropoxy.

Suitable examples of aralkoxy containing up to 12 carbon atoms in the definition for $R^Y$ may include benzyloxy, phenethyloxy, phenylpropoxy, phenylbutoxy and the like.

Suitable examples of alkylthio containing up to 6 carbon atoms in the definition for $R^Y$ may include methylthio, ethylthio, propylthio, butylthio, pentylthio and the like.

Suitable examples of halogen in the definition for $R^Y$ may include chlorine, bromine, iodine and the like.

Suitable examples of alkylidene containing up to 6 carbon atoms in the definitions for $R^X$ and $R^Y$ may include methylene, ethylidene, propylidene, butylidene and the like.

Suitable examples of pharmaceutically acceptable salts may include salt with inorganic base (e.g., sodium salt, potassium salt, magnesium salt, ammonium salt, etc.), and organic base (e.g., dicyclohexylamine salt, pyridine salt, ethanolamine salt, etc.).

Suitable examples of the derivative of the carboxy for $R^Z$ which is to be understood to be included within the scope of this invention may include an ester and an acid amide, and are exemplified as follows.

(a) Ester:

Esters are conventional ones, including silyl esters, aliphatic esters and esters containing an aromatic or a heterocyclic ring.

The suitable silyl esters may be illustrated by examples of tri(lower)alkylsilyl (e.g., trimethylsilyl, triethylsilyl, etc.) esters, etc.

The suitable aliphatic esters may include saturated or unsaturated acyclic or cyclic aliphatic esters which may be branched or which may contain a cyclic ring, such as aliphatic esters, for example, lower alkyl (e.g., methyl, ethyl, propyl, isopropyl, 1-cyclopropylethyl, butyl, tertbutyl, octyl, nonyl, undecyl, etc.) esters; alkenyl (e.g., vinyl, 1-propenyl, allyl, 3-butenyl, etc.) esters; alkynyl (e.g., 3-butynyl, 4-pentynyl, etc.) esters; cycloalkyl (e.g., cyclopentyl, cyclohexyl, cycloheptyl, etc.) esters; etc., and aliphatic esters containing at least one heteroatom of nitrogen, sulfur or oxygen atom, for example, lower alkoxyalkyl (e.g., methoxymethyl, ethoxyethyl, methoxyethyl, etc.) esters; lower alkanoyloxyalkyl (e.g., acetoxymethyl, propionyloxymethyl, pivaloyloxymethyl) esters; alkylthioalkyl (e.g., methylthiomethyl, ethylthioethyl, methylthiopropyl, etc.) esters; lower alkylsulfinyl(lower)alkyl (e.g., methylsulfinylmethyl, ethylsulfinylmethyl, etc.) esters, etc.

The suitable esters containing an aromatic ring may include, for example, aryl (e.g., phenyl, xylyl, tolyl, naphthyl, indanyl, dihydroanthryl, etc.) esters; aralkyl (e.g., benzyl, phenethyl) esters; aryloxyalkyl (e.g., phenoxymethyl, phenoxyethyl, phenoxypropyl, etc.) esters; arylthioalkyl (e.g., phenylthiomethyl, phenylthioethyl, phenylthiopropyl, etc.) esters; arylsulfinylalkyl (e.g., phenylsulfinylmethyl, phenylsulfinylethyl, etc.) esters; aryloxyalkyl (e.g., benzoylmethyl, toluoylethyl, etc.) esters; aryloylamino (e.g., phthalimido, etc.) esters; etc.;

The suitable esters containing an heterocyclic ring may include, for example, heterocyclic esters, heterocyclicalkyl esters, etc.; in which the suitable heterocyclic ester may include, for example, saturated or unsaturated, condensed alkanesulfonylphenyl (e.g., 4-methanesulfonylphenyl, 2-ethanesulfonylphenyl, etc.) esters, 2-(or 3 or 4-)phenylazophenyl esters, mono(or di or tri)nitrophenyl (e.g., 4-nitrophenyl, 2,4-dinitrophenyl, 3,4,5-trinitrophenyl, etc.) esters, mono(or di or tetra or penta)halophenyl(lower)alkyl (e.g., 2-chlorobenzyl, 2,4-dibromobenzyl, 3,4,5-trichlorobenzyl, pentachlorobenzyl, etc.) esters, mono(or di or tri)-nitrophenyl(lower)alkyl (e.g., 2-nitrobenzyl, 2,4-dinitrobenzyl, 3,4,5-trinitrobenzyl, etc.) esters, mono(or di or tri)(lower)alkoxyphenyl(lower)alkyl (e.g., 2-methoxybenzyl, 3,4-dimethoxybenzyl, 3,4,5-trimethoxybenzyl, etc.) esters, hydroxy and di(lower)alkylphenyl(lower)alkyl (e.g., 3,5-dimethyl-4-hydroxybenzyl, 3,5-ditert-butyl-4-hydroxybenzyl, etc.) esters, etc.

(b) Acid amide:

The suitable acid amides may include, for example, N-unsubstituted acid amide, N-lower alkyl acid amide (e.g., N-methyl acid amide, N-ethyl acid amide, etc.), N,N-di(lower)alkyl acid amide (e.g., N,N-dimethyl acid amide, N,N-diethyl acid amide, N-methyl-N-ethyl acid amide, etc.), N-phenyl acid amide, or an acid amide with pyrazole, imidazole, 4-lower alkylimidazole (e.g., 4-methylimidazole, 4-ethylimidazole, etc.), etc.

(3) With respect to the compound (IV):

Suitable examples of alkyl moiety in the definition for "Y" may include methyl, ethyl, propyl, butyl, pentyl, isopropyl, isobutyl, t-butyl and the like.

Suitable examples of the protected group in protected amino or protected hydroxy in the definition for "Y" may include a conventional acyl such as alkanoyl (e.g., formyl, acetyl, etc.), haloalkanoyl (e.g., dichloroacetyl, trifluoroacetyl, etc.), aroyl (e.g., benzoyl, toluoyl, etc.), alkoxycarbonyl (e.g., ethoxycarbonyl, tertbutoxycarbonyl, adamantyloxycarbonyl, etc.), haloalkoxycarbonyl (e.g., trichloroethoxycarbonyl, etc.), substituted or unsubstituted aralkoxycarbonyl (e.g., benzyloxycarbonyl, p-nitrobenzyloxycarbonyl, etc.) and the like.

(4) With respect to the compounds (VII) and (VIII):

Suitable examples of aralkyl for $R'_3$ may include benzyl, diphenylmethyl, trityl, phenethyl, phenylpropyl and the like.

(5) With respect to the compound (I'), (XXXXXVIII), (XXXXXIX), (XXXXXX), (XXXXXXI), (XXXXXXII) and (XXXXXXIII):

Suitable examples of acyl in the acylamino for $R_1$ may include the same ones as illustrated before for the acyl in the definition for $R_1$.

(6) With respect to the compound (I''):

Suitable examples of groups for "A'" may include the same ones as illustrated for the groups in the definition for "A" excepting hydrogen.

(7) With respect to the compounds (V), (VI), (VII), (VIII), (X), (XXI), (XXIX), (XXX), (XXXIII) and (XXXIV):

A suitable acyl moiety in the acyl amino for $R_2$, $R_3$, $R_8$, $R_{10}$, $R_{20}$, $R_{22}$, $R_{28}$, $R_{29}$, $R_{34}$, $R_{36}$ and $R_{38}$, and in the acyloxy for $R_{10}$ and in the acyloxyimino for $R_{35}$, $R_{36}$, $R_{37}$ and $R_{38}$ may include the same aliphatic acyl, aromatic acyl, heterocyclic acyl and aliphatic acyl whose aliphatic moiety is substituted by aromatic group or heterocyclic group as illustrated for the acyl in the acylamino for $R_1$. Accordingly, the detail of explanation, preferred examples, etc. of said acyl moiety is to be referred to the descriptions for the acyl in the acylamino for $R_1$ as made hereinabove.

Preferred examples of the above acyl may be: alkanoyl or cycloalkanoyl (e.g., formyl, acetyl, propionyl, butyryl, isobutyryl, pivaloyl, cyclohexanecarbonyl, etc.); aralkanoyl (e.g., phenylacetyl), phenylpropionyl, naphthylacetyl, etc.); heterocyclic alkanoyl (e.g., thienylacetyl, tetrazolylacetyl, furylacetyl, thiadiazolylacetyl, thiazolylacetyl, morpholinoacetyl, piperazionoacetyl, benzothiazolylacetyl, thienylpropionyl, etc.); aroyl (e.g., benzoyl, toluoyl, xyloyl, naphthoyl, phthaloyl, etc.); heterocyclic carbonyl (e.g., thenoyl, furoyl, prolyl, nicotinoyl, isonicotinoyl, benzodioxanecarbonyl, etc.) or cycloalkylalkanoyl (e.g., cyclopentylacetyl, cyclohexylacetyl, etc.).

In the above examples; the optional bond of the alkylene moiety, the bond between the carbonyl and the aliphatic, aromatic or heterocyclic group, and/or the bond between the alkylene and the cycloalkyl, aryl or heterocyclic group may be interrupted by a bivalent radical —O—, —S— or —NH—. Suitable examples of such acyl may be alkoxycarbonyl (e.g., methoxycarbonyl, ethoxycarbonyl, propoxycarbonyl, tert-butoxycarbonyl, etc.); cycloalkoxycarbonyl (e.g., cyclopropoxycarbonyl, cyclohexyloxycarbonyl, bornyloxycarbonyl, adamantyloxycarbonyl, etc.); aralkoxycarbonyl (e.g., benzyloxycarbonyl, phenethyloxycarbonyl, etc.); heterocyclic alkoxycarbonyl (e.g., furfuryloxycarbonyl, pyrrolidinyloxycarbonyl, pyridylmethoxycarbonyl, etc.); aryloxycarbonyl (e.g., phenoxycarbonyl, naphthoxycarbonyl, etc.); alkoxythiocarbonyl (e.g., methoxythiocarbonyl, ethoxythiocarbonyl, propoxythiocarbonyl, etc.); alkoxyalkanolyl (e.g., methoxyacetyl, ethoxypropionyl, etc.); cycloalkoxyalkanoyl (e.g., cyclohexyloxyacetyl, bornyloxyacetyl, adamantyloxyacetyl, etc.); alkylthioalkanoyl (e.g., methylthioacetyl, ethylthioacetyl, isopropylthioacetyl, butylthioacetyl, etc.); arylthioalkanoyl (e.g., phenylthioacetyl, etc.); heterocyclicthioalkanoyl (e.g., thienylthioacetyl, thienylthiopropionyl, thiazolylthioacetyl, thiadiazolylthioacetyl, oxazolylthioacetyl, oxadiazolylthioacetyl, triazolylthioacetyl, tetrazolylthioacetyl, benzothiazolylthioacetyl, etc.); N-alkylcarbamoyl (e.g., N-methylcarbamoyl, N-ethylcarbamoyl etc.); N-arylcarbamoyl (e.g., N-phenylcarbamoyl, N-naphthylcarbamoyl, etc.); N-alkylthiocarbamoyl (e.g., N-methylthiocarbamoyl, N-ethylthiocarbamoyl, etc.), N-arylthiocarbamoyl (e.g., N-phenylthiocarbamoyl, etc.) and the like.

The optional carbon atom of said acyl group may be substituted by one or more suitable substituents such as a halogen atom (e.g., chlorine, bromine, etc.), nitro or formyl.

(8) With respect to the compound (XI):

Suitable examples of acid residue for $X_1$ may include an acid residue of:

an inorganic acid (e.g., hydrochloric, hydrobromic, hydroiodic, sulfuric acid, etc.), an organic acid such as organic sulfonic acid (e.g., methanesulfonic, benzenesulfonic or toluenesulfonic acid), an organic carbamic acid (e.g., dimethylcarbamic or diethylcarbamic acid, etc.).

Suitable examples of bivalent aliphatic hydrocarbon radial in the definition for "$A_1$" may include alkylene or alkenylene (e.g., methylene, ethylene, trimethylene, propylene, propenylene, butenylene, hexamethylene, etc.), in which the optional carbon atom may be replaced by at least one radicals selected from —NH—, —O—, and

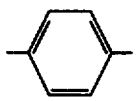

and further may be substituted by oxo, aryl such as phenyl, naphthyl, etc. or heterocyclic group such as thienyl.

(9) With respect to the compound (XII):

Suitable examples of residue of nucleophile in the definition for $R_{11}$ may include (a) the residue S-nucleophile such as substituted or unsubstituted alkylthio (e.g., methylthio, ethylthio, propylthio, isopropylthio, etc.); alkenylthio (e.g., vinylthio, propenylthio, isopropenylthio, butenylthio, etc.); alkynylthio (e.g., 2-propynylthio, etc.); arylthio (e.g., phenylthio, naphthylthio, etc.); substituted or unsubstituted aralkylthio (e.g., benzylthio, phenethylthio, phenylpropylthio, phenylbutylthio, etc.), in which the optional carbon atom of said alkyl moiety may be replaced by at least one radical selected from —O—, —NH— and further may be substituted by oxo; substituted or unsubstituted heterocyclicthio (e.g., morpholinylthio, thiadiazolylthio, oxadiazolylthio, triazolylthio, pyrimidinylthio, oxazolylthio, tetrazolylthio, purinylthio, pyridin-1-oxide-2-ylthio, 5-methyl-1,3,4-thiadiazolylthio, 5-ethyl-1,3,4-thiadiazolylthio, 1-methyltetrazolylthio, 2-aminothiazolylthio, 1-methyltriazolylthio, etc.); (b) the residue of O-nucleophile such as substituted or unsubstituted aryloxy (e.g., phenoxy, tolyloxy, chlorophenoxy, biphenylyloxy, naphthoxy, methoxyphenoxy, phenoxyphenoxy, vinylphenoxy, propenylphenoxy, acetylphenoxy, benzoylphenyloxy, benzoylnaphthoxy, etc.); and (c) the residue of N-nucleophile such as substituted or unsubstituted arylamino (e.g., anilino, N-methylanilino, naphthylamino, etc.) or substituted or unsubstituted aralkylamino (e.g., benzylamino, N-methylbenzylamino, phenethylamino, naphthymethylamino, etc.).

In the above, the residue of nucleophile may be substituted by at least one substituent selected from carboxy, esterified carboxy (e.g., methoxycarbonyl, ethoxycarbonyl, propoxycarbonyl, etc.), halogen (e.g., bromine, chlorine, etc.), nitro, formyl amino, hydroxy, protected amino or protected hydroxy and the like.

(10) With respect to compounds (XIII) and (XIV):

Suitable example of acyl moiety in an acyl having protected amino, protected hydroxy and/or protected carboxy for $R_{12}$ may include the same ones as defined and illustrated before for the acyl in the acylamino for $R_1$.

Suitable example of acyl moiety of an acyl having amino, hydroxy or carboxy function in $R'_{12}$ may include the same ones as defined and illustrated before for the acyl in the acylamino for $R_1$.

Suitable examples of alkyl in the definition for $R_{13}$ may include methyl, ethyl, propyl and the like.

Suitable examples of acyl for $R_{13}$ may include the same ones as defined and illustrated for the acyl in the acylamino for $R_1$, and suitable examples of aralkyl for $R_{13}$ may include benzyl and phenethyl.

Suitable halogen in the definition for $X_2$ may include bromine, chlorine and the like.

(11) With respect to compounds (XV) and (XVI):

Suitable example of acyl for $R_{14}$ may include the same ones as defined and illustrated for the acyl in the acylamino for $R_1$, and more particularly aroyl (e.g., benzoyl, naphthoyl, etc.), aralkanoyl (e.g., phenylacetyl, phenylpropionyl, etc.); heterocyclic-alkanoyl such as thienylalkanoyl (e.g., thienylacetyl, thienylpropionyl, thienylbutyryl, etc.);an alkoxyaralkanoyl, in which the optional carbon atom is substituted by at least one substituent selected from hydroxyimino, carboxy, amino, protected amino and the like, the examples of which are illustrated as follows.

2-[4-(3-carboxy-3-acetamidopropoxy)phenyl]-2-hydroxyiminoacetyl,

2-[4-{3-carboxy-3-(3-phenylureido)propoxy}phenyl]-2-hydroxyiminoacetyl,

2-[4-{3-(2,2,2,-trifluoroacetamido)-3-carboxypropoxy}-phenyl]-2-hydroxyiminoacetyl, etc.

Suitable examples of halogen for $X_3$ and $X_4$ may be the same ones as illustrated before for the halogen for $X_2$.

(12) With respect to the compounds (XVII) and (XVIII):

Suitable examples for the definition for $R_{15}$ are as follows: alkyl (e.g., methyl, ethyl, propyl, etc.); aryl (e.g., phenyl, naphthyl, etc.); aralkyl (e.g., benzyl, phenylpropyl, etc.); aryloxy (e.g., phenoxy, naphthoxy, etc.); heterocyclic group (e.g., thienyl, pyranyl, 5,6-dihydro-2H-pyranyl, isobenzofuranyl, indolyl, etc.); heterocyclicalkyl (e.g., thienylmethyl, thienylpropyl, furylmethyl, furylethyl, furylpropyl, indolylethyl, thiadiazolylmethyl, thiadiazolylethyl, oxazolylmethyl, etc.).

Suitable examples of hydrocarbon residue having amino in the definition for $R_{16}$ may include aminoalkyl (e.g., aminomethyl, aminoethyl, aminopropyl, etc.), and aminoaryl (e.g., aminophenyl, aminonaphthyl, etc.), and the like.

Suitable examples for the definition for $R_{17}$ are as follows.

The hydrocarbon moiety in acylamino-substituted-hydrocarbon residue for $R_{17}$ may include alkyl (e.g., methyl, ethyl, propyl, butyl, pentyl, hexyl, etc.); alkenyl (e.g., vinyl, propenyl, isopropenyl, etc.); aryl (e.g., phenyl, naphthyl, etc.); aralkyl (e.g., benzyl, phenethyl, phenylpropyl, phenylbutyl, etc.), and the optional carbon atom of said hydrocarbon moiety may be substituted by at least one substituent selected from halogen (e.g., bromine, chlorine, etc.), hydroxy, carboxy, and the like, and further optional carbon atom of said hydrocarbon moiety may be replaced by at least one radical selected from oxygen, nitrogen, sulfur, imino, carbonyl, thiocarbonyl and carbamoyl.

And suitable examples of the acyl moiety in acylamino and acylamino-substituted-hydrocarbon residue for $R_{17}$ are the same ones as defined and illustrated before for the acyl in the acylamino for $R_1$.

(13) With respect to compounds (XIX) and (XX):

Suitable examples of aryl for $R_{18}$ may be the same as mentioned above.

Suitable examples of alkyl and aryl for $R_{19}$ may be the same as mentioned above.

Suitable examples of N-arylcarbamoylalkyl for $R_{19}$ may include N-phenylcarbamoylmethyl, N-phenylcarbamoylethyl, N-naphthylcarbamoylmethyl, N-naphthylcarbamoylethyl, and the like.

(14) With respect to the compound (XXII):

Suitable examples of "aryl substituted by at least one substituent of nitro and esterified carboxy" for $R_{21}$ may include p-nitrophenyl, 2,4-dinitrophenyl, 2-nitro-4-methoxycarbonyl phenyl and the like, and suitable examples of substituted aryl moiety in aryl amino whose aryl ring is substituted by at least one substituent of nitro and esterified carboxy for $R_{22}$ may be the same as illustrated for the definition for $R_{21}$.

(15) With respect to the compound (XXIV):

Suitable examples of mono- or di-alkylamino for $R_{23}$ may include mono-alkylamino such as methylamino, ethylamino, propylamino, isopropylamino, butylamino, etc. and dialkylamino such as dimethylamino, diethylamino, methyl-propylamino, etc., and the optional carbon atom of said mono- or di-alkylamino may be substituted by esterified carboxy such as alkoxycarbonyl (e.g., methoxycarbonyl, ethoxycarbonyl, etc.), and the like.

(16) With respect to the compound (XXV):

Suitable examples of nitroaryl for $R_{24}$ may include mono- or di-nitrophenyl, mono or dinitronaphthyl, and the like.

(17) With respect to the compound (XXVI):

Suitable examples of aminoaryl for $R_{25}$ may include mono or diaminophenyl, mono or diaminonaphthyl and the like.

(18) With respect to the compounds (XXVII) and (XXVIII):

Suitable examples of aryl for $R_{26}$ may include phenyl tolyl and naphthyl and the like.

A suitable example of bivalent aliphatic hydrocarbon residue for "$A_2$" is the same as illustrated before in the definition for "$A_1$".

Suitable examples of halogen atom for $X_5$ may include bromine, chlorine and the like.

Suitable examples of alkoxy for $R_{27}$ may include methoxy, ethoxy, propoxy, tert-butoxy, etc., whose alkyl moiety may be substituted by suitable substituent such as carboxy, esterified carboxy and the like, for example, carboxymethoxy, methoxycarbonylmethoxy, tert-butoxycarbonylethoxy, etc.

Suitable examples of alkanoylamino for $R_{27}$ may include formamido, acetamido, propionamido, butyramido, etc.), whose alkyl moiety may be substituted by ammonio radical (e.g., N,N,N-trimethylammonio, N,N,N-triethylammonio or pyridinio, etc.) which bears an anion such as chloro, bromo, iodo, hydroxy, sulfoxy, methylsulfoxy, ethylsulfoxy, formyloxy or p-toluenesulfonyloxy, and the like.

(19) With respect to the compound (XXXII):

A suitable example of alkyl for $R_{32}$ and $R_{33}$ is the same as illustrated before for the alkyl for $R_{13}$.

(20) With respect to the compounds (XXXIII) and (XXXIV):

Suitable examples of acylamino in the definitions for $R_{38}$ is the same as illustrated before for the acylamino for $R_{36}$.

A suitable example of alkyl for $R_{39}$, $R_{40}$ and $R_{41}$ and alkyl moiety in alkoxy and substituted alkoxy for $R_{38}$ is the same as illustrated before for the alkyl for $R_{13}$.

Suitable examples of substituent in substituted alkoxy for $R_{38}$ is a conventional alkanoyl (e.g., acetyl, propionyl, butyryl, isobutyryl, pivaloyl, etc.), etc. as illustrated before for the protected group for Y.

Suitable examples of substituted-alkyl in the definitions for $R_{39}$ and $R_{41}$ may include acyloxyalkyl such as alkanoyloxyalkyl (e.g., acetoxymethyl, acetoxyethyl, acetoxypropyl, propionyloxymethyl, propionyloxyethyl, butyryloxymethyl, pivaloyloxymethyl, etc.) and haloalkyl such as monohaloalkyl (e.g., fluoromethyl, chloromethyl, bromomethyl, chloroethyl, bromoethyl, chloropropyl, bromopropyl, etc.), dihaloalkyl (e.g., dichloroethyl, 2,3-dichloropropyl, etc.) and trihaloalkyl (e.g., trichloromethyl, etc.), and the like.

(21) With respect to the compounds (XXXV) and (XXXVI):

Suitable aryl in the definition for $R_{42}$ may include aryl which may be substituted by suitable substituent such as carboxy, etc., the examples of which are phenyl, carboxyphenyl, tolyl, naphthyl and the like.

A suitable example of alkylene for "$A_3$" may include methylene, ethylene, propylene, etc.

(22) With respect to the compounds (XXXIX) and (XXXX):

Suitable examples of aryl substituted by at least one substituent of nitro and esterified carboxy for $R_{43}$ are the same as illustrated for the same group for $R_{21}$.

Suitable examples of aromatic heterocyclic group for $R_{43}$ may include the same as illustrated in the explanation of the heterocyclic group for $R_1$ of the compound (I), and the more particular examples thereof are pyridyl, pyridyl-1-oxide, pyrimidynyl, oxadiazolyl, etc., which may be substituted by an aryl such as phenyl, tolyl, naphthyl and the like.

(23) With respect to the compounds (XXXXI) and (XXXXII):

Suitable examples of aralkyl for $R_{44}$ are the same as illustrated for $R_{15}$.

Suitable examples of alkyl for $R_{45}$ and $R_{46}$ are the same as illustrated for $R_{13}$.

(24) With respect to the compounds (XXXXIII) and (XXXXIV):

Suitable examples of the derivative in "carboxy or its derivative" for $R_{47}$ are the same as illustrated before in the explanation for the derivative of the carboxy for $R^Z$.

Suitable examples of protected group in the protected amino for $R_{48}$ may include the same as illustrated in the explanation for Y.

(25) With respect to the compounds (XXXXV), (XXXXVI), (XXXXVII), (XXXXVIII), (XXXXIX), (XXXXIII), (XXXXXIII) and (XXXXXIV):

Suitable examples of acyl moiety in the acylamino group in the definition for $R_{49}$, $R_{50}$, $R_{51}$, $R_{52}$, $R_{53}$, $R_{54}$, $R_{55}$ and $R_{56}$ may include the same ones as illustrated in the acylamino for $R_1$.

Suitable examples of the reactive derivative in "carboxy or its reactive derivative" moiety in the definition for $R_{49}$ are the same as illustrated in explanation of the derivative of the carboxy for $R^Z$, and there may be also exemplified aryl (e.g., phenyl, naphthyl, etc.) esters.

Suitable examples of "N-(hydroxyalkyl)carbamoyl" moiety in the definition for $R_{50}$ may include N-(hydroxymethyl)carbamoyl, N-(hydroxyethyl)carbamoyl, N-(hydroxypropyl)carbamoyl, etc.

Suitable examples of "N-aralkylcarbamoyl" moiety in the definition for $R_{50}$ may include N-benzylcarbamoyl, N-phenethylcarbamoyl, etc., in which aryl moiety may be substituted by suitable substituent(s).

Suitable examples of the esterified carboxy in "esterified carboxyalkylamino and esterified carboxyalkenylamino" moieties in the definition for $R_{52}$ and $R_{53}$ may include the same ones as illustrated in the explanation of ester in the derivative of the carboxy for $R^Z$, and suitable examples of alkylamino moiety therein are methylamino, ethylamino, propylamino and the like; and further suitable examples of alkenylamino moiety therein are vinylamino, propenylamino, 1-methylvinylamino, 2-propenylamino and the like, respectively.

Suitable examples of alkanoyl in the definition for $R_{55}$ and aroyl moiety in the definition for $R_{55}$ may include the same ones as those illustrated in the explanation of an acyl moiety in the acylamino for $R_1$, respectively.

Suitable examples of alkyl moiety in the definition for $R_{56}$ is the same as illustrated for $R_{13}$.

Suitable examples of α-hydroxy aralkyl moiety in the definition for $R_{56}$ may include α-hydroxybenzyl, 1-hydroxy-1-(1-naphthyl)methyl, etc.

(26) With respect to the compound (XXXXVI):

Suitable examples of aralkyl moiety in aralkylamino for $R_{57}$ may include the same as illustrated for $R_{15}$.

(27) With respect to the compounds (XXXXVI) and (XXXXVII):

Suitable examples of halogen for $X_6$ may include the same as illustrated in the definition for $X_2$.

Suitable examples of alkyl for $R_{58}$, $R_{59}$ and $R_{60}$ are the same as illustrated for $R_{13}$.

(28) With respect to the compound (XXXXXI):

Suitable examples of aralkanoyl moiety in aralkanoylamino for $R_{61}$ may include the same as illustrated in the explanation of the acyl moiety in the acylamino for $R_1$.

(29) With respect to compounds (XXXXXII) and (XXXXXIII):

Suitable examples of aryl in the definition for $R_{62}$ may include the same ones as illustrated for $R_{15}$, and suitable examples of alkylene for $A_5$ may include the same ones as illustrated for $A_3$.

(30) With respect to compounds (XXXXXIV) and (XXXXXV):

Suitable examples of aryl and heterocyclic group for $R_{63}$ may include the same examples as those illustrated for $R_{15}$, respectively.

Suitable examples of aroyl moiety and aroyl for $R_{66}$, $R_{67}$ and $R_{68}$ may include benzoyl, toluoyl, xyloyl and the like, and suitable examples of aralkoxy for the same may include benzyloxy, phenethyloxy, phenylpropionyloxy, tolylmethoxy, diphenylmethoxy, trityloxy and the like.

(31) With respect to the compound (XXXXXVII):

Suitable examples of aralkyl for $R_{69}$ may include the same examples as illustrated for $R_{15}$.

(32) With respect to the compound (XXXXXVIII):

Suitable examples of alkyl for $R_{70}$ may include the same examples as illustrated for $R_{13}$, and suitable examples of heterocyclic moiety in the definition for $R_{70}$ may include the same examples as illustrated for $R_{15}$.

(33) With respect to the compounds (XXXXXX) and (XXXXXXI):

Suitable examples of esterified carboxy moiety in the definition for $R_{71}$ may include the same examples as illustrated in the explanation of ester in the derivative of the carboxy for $R^Z$, and suitable ones of alkyl moiety for $R_{71}$ may include the same as illustrated for $R_{13}$.

(34) With respect to the compounds (XXXXXXII) and (XXXXXXIII):

Suitable examples of aryl for $R_{72}$ may include the same examples as illustrated for $R_{15}$, and suitable ones of alkyl for $R_{72}$ may include the same examples as illustrated for $R_{13}$, and further suitable ones of esterified carboxy moiety in the definition for $R_{73}$ may include the same ones as illustrated in the explanation of ester in the derivative of the carboxy for $R^Z$.

(35) With respect to the compounds (XXXXXXIV), (XXXXXXV), (XXXXXXVI) and (XXXXXXVII):

Suitable examples of alkyl, alkenyl and aryl for A" and $R_{74}$ may include the same examples as those of illustrated in the alkyl for $R_{13}$, in the alkenyl for $R_1$, and in the aryl for $R_{15}$, respectively.

(36) With respect to the compound (XXXXXXVIII):

Suitable examples of lower alkyl for $R_{75}$ may include methyl, ethyl, propyl and the like.

(37) With respect to the compound (XXXXXXIX):

Suitable examples of alkoxy for $R_{76}$ may include methoxy, ethoxy, propoxy, butoxy and the like, and suitable ones of aralkyl moiety in aralkoxy for $R_{76}$ may include the same examples as illustrated for $R_{15}$.

Suitable examples of alkyl, acyl and aralkyl for $R_{80}$ may include the same examples as those illustrated for $R_{13}$, respectively.

(38) With respect to the compound (XXXXXXX):

Suitable examples of aralkyl for $R_{77}$ may include the same examples as illustrated for $R_{15}$.

(39) With respect to the compounds (XXXXXXXI) and (XXXXXXXII):

Suitable examples of the protecting group on amino group for $R_{78}$ may include the same examples as illustrated for Y, and suitable ones of acyl for $R_{79}$ may include the same examples as ones of acyl moiety in the acylamino for $R_2$.

(40) With respect to the compounds (XXXXXXXIX), (XXXXXXXX), (XXXXXXXXI), (XXXXXXXXII) and (XXXXXXXXIII):

Suitable examples lower alkyl for $R^g$, and alkyl moiety in lower alkoxycarbonyl for $R^f$ and $R^{f'}$ may include methyl, ethyl, propyl, tert-buthyl and the like.

As previously mentioned, the compounds produced by the processes according to this invention are new. Particularly, the compounds represented by the following formula are preferred compounds of the present invention.

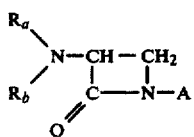

in which
(1) $R_a$ and $R_b$ are each hydrogen;
(2) $R_a$ is hydrogen and $R_b$ is arenesulfonyl,
(3) $R_a$ and $R_b$ together form a imido group derived from a dicarboxylic acid; or
(4) $R_a$ is hydrogen and $R_b$ is an acyl group selected from the following groups:

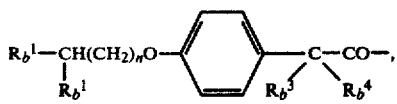

wherein
n is an integer 0–4
$R_b{}^1$ is hydrogen: or carboxy
$R_b{}^2$ is
hydroxy;
halogen;
azido;
amino;
mo- or di-alkylamino;
alkenylamino;
cycloalkylamino;
arylamino;
aralkylamino;
alkanoylamino;
alkoxy(thiocarbonyl)amino;
alkoxycarbonylamino;
aryloxyalkanoylamino;
aralkanoylamino;
heterocyclic alkanoylamino;
aroylamino;
N'-arylureido;
N'-arylthioureido; or
arylthio;
$R_b{}^3$ is
hydrogen;
hydroxy;
amino;
arylamino;
alkanoylamino;
alkoxy(thiocarbonyl)amino;
alkoxycarbonylamino;
aroylamino;
aralkanoylamino;
N'-arylureido; or
N'-arylthioureido;
$R_b{}^4$ is hydrogen, or
$R_b{}^3$ and $R_b{}^4$ together form
oxo;
hydroxyimino;
alkoxyimino; or
alkanoyloxyimino;

in which the alkane or alkene moiety may be substituted by at least one suitable substituent of carboxy, halogen, sulfo, and the aryl and heterocyclic ring may be substituted by at least one suitable substituent of nitro, halogen or carboxy;

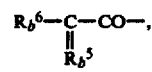 (ii)

wherein
$R_b{}^5$ is
oxo
hydroxyimino;
alkoxyimino;
aralkoxyimino; or
aroyloxyimino;
$R_b{}^6$ is
cyano;
alkyl;
aryl;
heterocyclic radical;
alkylamino;
aralkylamino;
aralkoxyaryl;
alkenyloxyaryl; or
alkoxyaryl;

in which the alkane moiety may be substituted by at least one suitable substituent such as hydroxy or carboxy;

 (iii), wherein
$R_b{}^7$ is
hydrogen; aryl;
alkoxyaryl;
aryloxy;
alkenyl;
(arylaminoalkylaryloxy)alkyl;
alkylthioalkenyl;
aralkyloxy;
aralkenyl;
arylamino;
alkyl-and(or)aryl-substituted heterocyclic radical;
aryloxyalkanamido;
heterocyclic-amino;
guanidino; or
3-aralkanoylguanidino;

in which each of aryl and heterocyclic rings may have at least one suitable substituent such as nitro, halogen, oxo or amino;

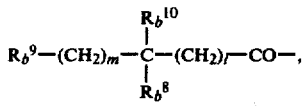

wherein
m and l are each an integer of 0–4,
$R_b{}^8$ is
  hydrogen;
  alkyl;
  aryl;
  aryloxy;
  heterocyclic radical;
  N-arylcarbamoyl; or
  N-(aralkanamidoalkyl)carbamoyl;
in which each of aryl and heterocyclic rings may be substituted by hydroxy;
$R_b{}^9$ is
hydrogen;
  amino;
  azido;
  halogen;
  hydroxy;
  carboxy;
  sulfo; or
  arenesulfonyloxy;
  alkyl; or alkenyl
in which alkyl and alkenyl may have at least one substituent selected from amino, azido, halogen, hydroxy, carboxy, sulfo, aroyl, substituted or unsubstituted aryl and substituted or unsubstituted heterocyclic radical;
aryl which may have at least one substituent selected from hydroxy, nitro, carboxy, halogen, alkanoyl, arenesulfonamido and carboxy- or hydroxy-substituted arenesulfonamido
  heterocyclic radical;
  alkylheterocyclic radical;
  aryl- and oxo-substituted heterocyclic radical;
  aralkoxy- and oxo-substituted heterocyclic radical;
  bi-heterocyclic radical;
  (heterocyclicalkanamido)heterocyclic radical;
  oxo-aralkanamidoheterocyclic radical;
  aroyl;
  heterocyclicalkanoyl which may be substituted by alkyl, halogen, heterocyclic group, amino, aryl or haloaryl;
  alkoxy;
  cycloalkoxy;
  aryloxy whose aryl ring may have at least one substituent selected from nitro, halogen, alkanoyl, alkanoylamino, aryl, halo- and nitroaryloxy, aralkylamino, alkyl and alkenyl, alkyl and alkenyl may be further substituted by at least one substituent selected from carboxy, amino, hydroxy, nitro, hydroxyimino, alkoxyimino, carboxyalkoxyimino, (N-halo-N,N,N-trialkylammonioalkanoyl)hydrazono, alkylthioalkanamido of which alkyl moiety may be substituted by at last one substituent of amino and carboxy;
  aralkylaminoalkyl which may be substituted by esterified carboxy or carboxyalkoxy;
  heterocyclicoxy;
  alkylthio, alkenylthio, aryloxyalkanamidoalkylthio, aroylalkylthio and N-arylcarbamoylalkylthio, of which arene moieties may have at least one substituent of halogen, nitro, amino and carboxy;
  alkanesulfinyl;
  N-arylcarbamoylalkanesulfinyl;
  carboxyarylthio;
  heterocyclicthio which may have hydroxy;
  aminoalkylheterocyclicthio;
  (alkanamidoalkyl)heterocyclic thio, of which heterocyclic moiety may have hydroxy;
  substituted or unsubstituted arylamino;
  heterocyclicamino which may have at least one substituent selected from oxo and aryl;
  aralkylamino;
  imino substituted or unsubstituted-N-aralkylamino;
  N-alkyl-N-aralkylamino;
  alkylamino;
  N-aryl-alkanamido;
  N-alkyl-N-arylamino in which alkyl moiety may have at least one substituent of azido and carboxy;
  N-alkanesulfonyl-N-arylamino; alkanamido of which alkane moiety may be substituted by at least one substituent of halogen, amino and azido;
  substituted or unsubstituted cycloalkoxyalkanoylamino; alkylthioalkanamido, in which alkyl moiety may be substituted by at least one substituent of amino, halogen and carboxy;
  aralkanamido;
  alkoxyaralkanamido or aryloxyaralkanamido, in which alkane moiety and aryl ring may have at least one substituent of halogen, aralkoxyimino, arylamino, amino, and hydroxy;
  arylaminoalkanamido, in which aryl ring and alkane moiety may be substituted by at least one substituent of halogen, carboxy, nitro and amino;
  (N-arenesulfonylarylamino)alkanamido;
  aryloxyalkanamido, which may be substituted by at least one substituent of halogen, nitro, carboxy, formyl and carbazoyl;
  alkylaryloxyalkanamido, which may be substituted by hydroxy;
  arylaryloxyalkanamido, which may be substituted by at least one substituent of halogen and nitro;
  aralkylaryloxyalkanamido, which may be substituted by at least one substituent of hydroxyimino and halogen;
  aralkylaminoalkylaryloxyalkanamido, which may be substituted by at least one substituent of carboxymethoxy and carboxy derivative;
  alkanoyl-aryloxyalkanoylamino;
  aroylaryloxyalkanamido, which may be substituted by at least one substituent of nitro, amino and halogen;
  (alkylthioalkanamidoaroyl)aryloxyalkanamido, which may be substituted by at least one substituent of halogen, amino and carboxy;
  (alkylthioalkylaminoaroyl)aryloxyalkanamido, which may be substituted by at least one substituent of amino and halogen;
  (alkanamidoaroyl)aryloxyalkanamido, which may be substituted by halogen;
  [(N-halo-N,N,N-trialkylammonio)alkanamidoaroyl]aryloxyalkanamido, which may be substituted by halogen;
  heterocycliccarbonylaryloxyalkanamido, which may be substituted by halogen;
  aralkylaminoalkylaryloxyalkanamido, which may be substituted by at least one substituent of alkoxy, carboxy-alkoxy or carboxy;
  (heterocyclicthioalkanamidoaroyl)aryloxyalkanamido; heterocyclicaryloxyalkanamido, in which heterocyclic ring may be substituted by at least one substituent of alkyl, aryl, haloaryl, halogen and amino;

(diaryloxy)alkanamido, which may be substituted by at least one substituent of halogen, amino and nitro;

arylthioalkanamido, which may be substituted by carboxy;

heterocyclicalkanamido;

bi-heterocyclicalkanamido;

heterocyclicthioalkanamido, which may be substituted by at least one substituent of hydroxy, amino, alkyl and aminoalkyl;

(aralkanamido)alkanamido, which alkane moiety and/or aryl ring may be substituted by at least one substituent of amino, halogen and carboxy;

arenesulfinylalkanamido, which may be substituted by carboxy;

arenesulfonyloxyalkanamido;

(N-aryl-N-arenesulfonamido)alkanamido;

heterocycliccarbonylamino, which may be substituted by halo-substituted aryl;

arylglyoxyoylamino;

alkoxyalkylamino;

N'-aralkyloxamoylamino;

N'-aryloxamoylamino, which may be substituted by nitro;

N'-arylureido;

guanidinocarbonylamino;

arenesulfonamido or alkane sulfonamido, which may have at least one suitable substituent of hydroxy, carboxy and halogen;

N'-aroylureido;

(N-aryloxyalkanoyl)aminooxy, (N-alkylidene)aminooxy, (N-heterocyclicalkylidene)aminooxy or (N-aralkylidene)aminooxy, which may have at least one substituent of carboxy and alkoxy;

$R_b{}^{10}$ is hydrogen or alkyl; and

A is hydrogen or a group represented by the formula;

in which $R^X$, $R^Y$ and $R^Z$ are the same as defined in the definition for the compound(I), with a proviso as stipulated above in the definition of the compound(I).

With respect to the above definition for the preferred compound(I'), the following points are to be understood.

The carboxy, amino and hydroxy group as defined in the definition of the compound (I') include the corresponding equivalents, respectively.

As the equivalents of the carboxy, there may be the derivative of carboxy, the detail of which is explained hereinabove in the explanation of the definition for the compound(I) and suitable examples of which are the same as those illustrated in the explanation of the derivative of the carboxy for "$R^Z$" of the compound(I).

As the equivalents of the amino and hydroxy, there may be the protected amino and protected hydroxy, respectively. Suitable protective group of amino and protective group of hydroxy are the same as those illustrated in the explanation of the protective group for Y of the compound(IV). It is to be noted the derivative of carboxy, the protected amino and the protected hydroxy are to be included within the scope of the compound as equivalents of the carboxy, the amino and the hydroxy in the definition of compound(I'), respectively.

With respect to various definitions for $R_b{}^2$, $R_b{}^3$, $R_b{}^4$, $R_b{}^5$, $R_b{}^6$, $R_b{}^7$, $R_b{}^8$, $R_b{}^9$ and $R_b{}^{10}$:

Suitable examples of halogen moiety may include the same examples as illustrated for $X_2$;

Suitable ones of alkyl or alkane moieties may include the same examples as illustrated in the explanation for A;

Suitable ones of dialkyl may include dimethyl, diethyl, dipropyl and the like;

Suitable ones of alkenyl or alkene moiety may include the same examples as illustrated in the explanation for $R_1$;

Suitable ones of cycloalkyl may include the same examples as illustrated in the explanation for $R_1$;

Suitable ones of aryl or arene moieties may include the same examples as illustrated for $R_{15}$;

Suitable ones of aralkyl or aralkane moieties may include the same examples as illustrated for $R_{17}$;

Suitable ones of alkanoyl may include the same examples as illustrated for $R_2$;

Suitable ones of alkoxy may include the same examples as illustrated for $R_{27}$;

Suitable ones of aralkoxy may include the same examples as illustrated for A;

Suitable ones of aralkanoyl may include the same examples as illustrated for $R_{14}$;

Suitable ones of aroyl may include the same examples as illustrated for $R_2$;

Suitable ones of t-alkyl may include t-butyl, t-pentyl, t-hexyl and the like; and Suitable ones of heterocyclic group or heterocyclic moieties may include the same examples as illustrated in the explanation for $R_1$.

The processes of this invention are explained in details hereinafter.

In this invention, as key starting compounds, there are employed FR-1923 substance, 3-amino-1-(α-carboxy-4-hydroxybenzyl)-2-azetidinone (a), 1-substituted-3-amino-2-azetidinone (b) and 3-amino-2-azetidinone (c).

Such starting compounds can be prepared, for example, by processes as shown in the following scheme.

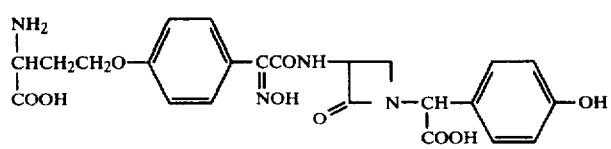

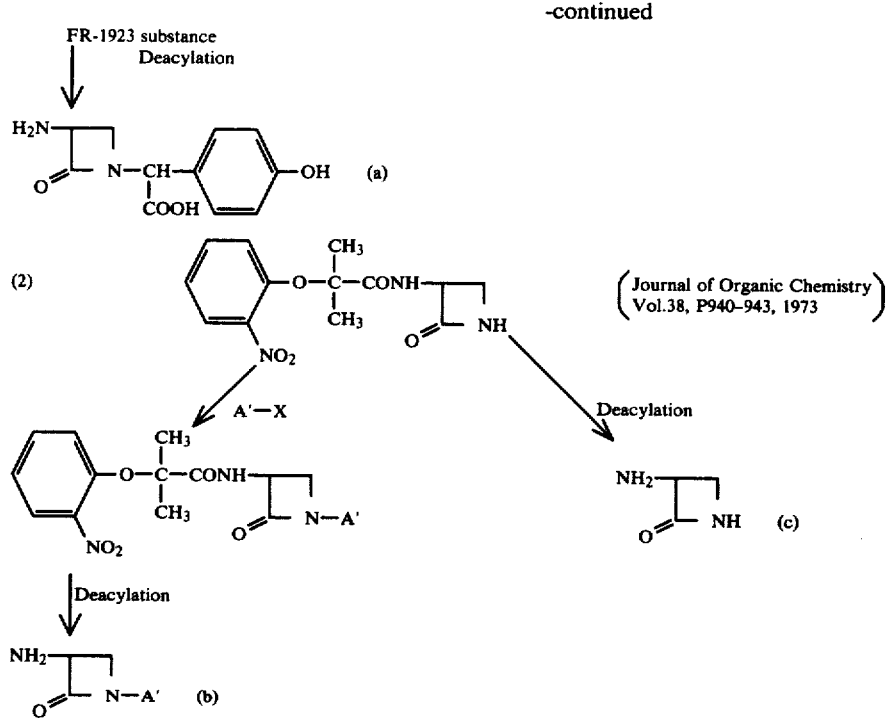

wherein X is an acid residue and A' is as defined above.

(1) Process 1: (II)→(I)

In this process, the object compound (I) can be prepared by reacting the compound (II) or its reactive derivative at the amino with an acylating agent.

As acylating agents to be used in the present reaction, there may be exemplified an organic carboxylic acid, an organic sulfonic acid and the corresponding thio-, or imido-acid, and more particularly, an aliphatic acid, an aromatic or heterocyclic carboxylic acid, and the corresponding sulfonic acid, carbamic acid, carbonic acid and thio-acid, and their reactive derivative.

As the reactive derivatives, there may be exemplified an acid anhydride, an activated amide, an activated ester, an isocyanate and an isothiocyanate, etc.

Examples of such reactive derivatives are illustrated by an acid azide;

an mixed acid anhydride with an acid such as dialkylphosphoric acid, phenylphosphoric acid; diphenylphosphoric acid, dibenzylphosphoric acid, halogenated phosphoric acid, dialkylphosphorous acid, sulfurous acid, thiosulfuric acid, hydrohalogenic acid (e.g., hydrochloric acid, hydrobromic acid, etc.), sulfuric acid, monoalkyl carbonic acid, aliphatic carboxylic acid (e.g., acetic acid, pivalic acid, pentanoic acid, isopentanoic acid, 2-ethylbutyric acid or trichloroacetic acid), aromatic carboxylic acid (e.g., benzoic acid), or symmetrical acid anhydride;

an acid amide with pyrazole, imidazole, 4-substituted imidazole, dimethylpyrazole, triazole or tetrazole; and an ester (e.g., cyanomethyl ester, methoxymethyl ester, vinyl ester, propargyl ester, p-nitrophenyl ester, 2,4-dinitrophenyl ester, trichlorophenyl ester, pentachlorophenyl ester, methanesulfonylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, or ester with N,N-dimethylhydroxylamine, 1-hydroxy-2-(1H)-pyridone, N-hydroxysuccinimide or N-hydroxyphthalimide) and the like.

The above reactive derivatives are selected according to the kind of the acid to be used. In the reaction, when free acid is used as an acylating agent, the reaction may be preferably conducted in the presence of a condensing agent such as N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, N,N'-carbonyldi-(2-methylimidazole), pentamethyleneketene-N-cyclohexylimide, diphenylketene-N-cyclohexylimine, alkoxyacetylene, 1-alkoxyl-1-chloroethylene, trialkyl phosphite, ethyl polyphosphate, isopropyl polyphosphate, phosphorus oxychloride, phosphorus trichloride, thionylchloride, oxalyl chloride, triphenylphosphine, 2-ethyl-7-hydroxybenzisoxazolium salt, 2-ethyl-5-(m-sulfophenyl)isoxazolium hydroxide(chloromethylene)-dimethylammonium chloride, 2,2,4,4,6,6-hexachloro-2,2,4,4,6,6-hexahydro-1,3,5,2,4,6-triazatriphosphorine, or a mixed condensing agent such as triphenylphosphine and a carbon tetrahalide (e.g., carbon tetrachloride, carbon tetrabromide, etc.) and the like.

The example of an acyl group to be introduced into the amino group in the compound (I) by the above acylating agent may be a dehydroxylated group of an aliphatic, aromatic and heterocyclic carboxylic acid, and the corresponding sulfonic acid, carbonic acid, carbamic acid and thio acid, etc., and more particular acyl group may be the same acyl group as illustrated in the explanation of the acyl group in the acylamino group for $R_1$.

As the reactive derivative at the amino at the 3rd position of the compound (II), there may be exemplified shiff's base, salt with acid (e.g. hydrochloric acid) and the conventional reactive derivative.

The acylation in the present process is conducted in a conventional manner known skilled in the art, for example, the acylation of 6-aminopenicillanic acid or 7-aminocephalosporanic acid to provide the corresponding 6-acylamino penicillin or 7-acylaminocephalosporin compounds.

That is, the present reaction is conducted by reacting the compound (II) or its reactive derivative at the amino with an acylating agent usually in a solvent which does not give bad influence to the reaction, for example, water, acetone, dioxane, acetonitrile, chloroform, methylene chloride, dichloroethane, tetrahydrofuran, ethyl acetate, dimethylformamide, pyridine, etc., and the hydrophilic solvent as mentioned above can be used in a mixture with water.

The present reaction can also be carried out in the presence of a base such as inorganic base (e.g., alkali metal bicarbonate, etc.) and an organic base such as trialkylamine (e.g., trimethylamine, triethylamine, tributylamine, etc.), N-methylmorpholine, N-methylpiperidine, N,N-dialkylaniline (e.g., N,N-dimethylaniline, N,N-diethylaniline, etc.), N,N-dialkylbenzylamine (e.g., N,N-diethylbenzylamine, etc.), pyridine, picoline, lutidine, 1,5-diazabicyclo[4,3,0]non-5-ene, 1,4-diazabicyclo[2,2,2]octane, 1,8-diazabicyclo[5,4,0]undecene-7, etc.

In the present reaction, a liquid base or liquid condensing agent also can be used as a solvent for the reaction.

There is no particular limitation to the present reaction temperature, and the present reaction can be preferably carried out under cooling or at ambient temperature.

(2) Process 2: (III)→(I″)

In this process, the object compound (I″) can be prepared by reacting the compound (III) with a reagent of the formula: A′-X′ wherein A′ is as defined above and X′ is an acid residue.

In the reagent of the formula: A′-X′, examples of the definitions for A′ are the same as illustrated in the explanation of the definitions for A excepting hydrogen. As examples of the acid residue for X′, there may be exemplified an acid residue of an inorganic acid (e.g. hydrochloric acid, hydrobronic acid, hydroiodic acid, sulfuric acid, etc.); an acid residue of an organic acid such as organic sulfate (e.g. methyl sulfate, ethyl sulfate, etc.), organic sulfonic acid (e.g. methane sulfonic acid, benzene sulfonic acid, toluene sulfonic acid, etc.) and organic carbamic acid (e.g. dimethylcarbamic acid, diethylcarbamic acid, etc.) and the like.

The reaction is usually conducted in a solvent. Suitable examples of the solvents are water, acetone, dioxane, acetonitrile, methylene chloride, chloroform, dichloroethane, tetrahydrofuran, ethyl acetate, dimethylformamide, pyridine, etc., among which hydrophilic solvent can be used in a mixture with water. Any other solvent which does not give bad influence to the reaction also may be used.

There is no particular limitation to the reaction temperature, and the reaction is usually conducted at ambient temperature or under cooling.

In case that the compound (I″) thus produced has the derivative of carboxy or the protected carboxy as substituent, the compound (I″) may be subjected to elimination reaction, whereby said derivative of carboxy or protective group is transformed into the corresponding carboxy group, whose reaction is also included within the scope of the present invention.

The elimination reaction is conducted by a conventional method, that is substantially the same methods as those explained in the elimination reaction for the hereinafter mentioned Process 3, e.g. solvolysis, reduction, etc.

(3) Process 3: (I′)→(II)

In this process, the object compound (II) can be prepared by eliminating the acyl group of compound (I′) in a conventional manner.

A suitable method to be used in the elimination reaction of the acyl moiety in acylamino may include solvolysis such as hydrolysis using an acid or a base; aminolysis; reduction such as chemical reduction or catalytic reduction; and combined method comprising iminohalogenation, iminoetherification and solvolysis.

In the above reaction, suitable examples of reagents to be used are as follows.

For solvolysis:

Solvolysis is preferably conducted in the presence of an acid or base.

Suitable acids are an inorganic acid (e.g. hydrochloric acid, sulfuric acid, etc.), an organic acid (e.g., formic acid, acetic acid, trifluoroacetic acid, propionic acid, benzenesulfonic acid, p-toluenesulfonic acid, etc.), an acidic ion exchange resin and the like.

Suitable bases are an inorganic base such as a hydroxide, carbonate or bicarbonate of an alkali metal (e.g., sodium, potassium, etc.), an alkaline earth metal (e.g., magnesium, calcium, etc.), and the like, an organic base such as an alkoxide of the above metal, a tertiary amine such as trialkylamine (e.g., trimethylamine, triethylamine, etc.), a disubstituted arylamine (e.g., N,N-dimethylamine, etc.) or a heterocyclic amine (e.g., N-methylmorpholine, N-methylpiperidine, N,N-dimethylpiperazine, pyridine, etc.), a basic ion exchange resin and the like.

For reduction:

Reduction is conducted with a conventional chemical reducing agent or by conventional catalytic reduction.

Suitable reducing agents are a metal (e.g., tin, zinc, iron, etc.) or a combination of metalic compound (e.g., chromium chloride, chromium acetate, etc.) and an organic or an inorganic acid (e.g., acetic acid, propionic acid, hydrochloric acid, etc.).

Suitable catalysts used in catalytic reduction are conventional ones such as platinum catalysts (e.g., platinum plate, spongy platinum, platinum black, colloidal platinum, platinum oxide or platinum wire), palladium catalysts (e.g., spongy palladium, palladium black, palladium oxide, palladium on carbon, colloidal palladium, palladium on barium sulfate or palladium on barium carbonate), nickel catalysts (e.g., reduced neckel, nickel oxide or Raney nickel), cobalt catalysts (e.g., reduced cobalt or Raney cobalt), iron catalysts (e.g., reduced iron or Raney iron) copper catalysts (e.g., reduced copper, Raney copper or Ullman copper), or other conventional catalysts.

For aminolysis:

Aminolysis is conducted with a conventional amine.

Suitable examples of amine to be used in the aminolysis include substituted or unsubstituted primary amine such as methylamine, ethylamine, propylamine, isopropylamine, butylamine, N,N-dimethyl-1,3-proanediamine and the like, and hydrozine such as hydrazine, methylhydrazine, ethylhydrazine and the like.

For combine method:

Iminohalogenation, iminoetherification, and solvolysis are conducted with a conventional iminohalogenating agent and conventional iminoetherizing agent, and then by conventional solvolysis:

Suitable iminohalogenating agents are a phosphorus compound such as phosphorus trichloride, phosphorus pentachloride, phosphorus tribromide, phosphorus pentabromide, phosphorus oxychloride, and their reaction equivalents such as thionyl chloride, phosgen, etc.

Suitable iminoetherifying agents used in the reaction with the resultant product in the foregoing iminohalogenation of the acylamino compound (I') are an alcohol such as an alkanol (e.g., methanol, ethanol, propanol, isopropanol, butanol, tert-butanol, etc.) or the corresponding alkanol having alkoxy (e.g., methoxy, ethoxy, propoxy, isopropoxy, buthoxy, etc.) as substituent(s) at the alkyl moiety thereof, and an alkoxide of such metal as mentioned above (e.g., sodium alkoxide, potassium alkoxide, calcium alkoxide, barium alkoxide, etc.), each of which is derived from said alcohol. Thus obtained reaction product is, if necessary, solvolyzed in a conventional manner.

The elimination reactions, i.e. solvolysis, aminolysis reduction and combined method comprising iminohalogenation, iminoetherification and solvolysis are conventional ones employed for the elimination of acyl group in acylamino group of penicillin and cephalosporin compounds, and said reactions may be conducted in the similar conditions to that of the elimination reaction in the penicillin and cephalosporin cases.

For example, the iminohalogenation and iminoetherification reactions are preferably conducted at ambient temperature or under cooling, and the solvolysis proceeds simply pouring the reaction mixture to water or a mixture of a hydrophilic solvent such as alcohol (e.g. methanol, ethanol, etc.) and water, and if necessary, with addition of an acid or base as exemplified above thereto.

The object compound (II) prepared in the above elimination reaction is also used as a key intermediate for the compound (I) of the present invention. That is, the introduction fo an acyl group different from that of the compound (I') to 1-substituted-3-amino-2-azetizinone (II) can produce a new 1-substituted-3-acylamino-2-azetizinone (I) having different antimicrobial activity spectrum from that of the compound (I').

(4) Process 4: (IV)→(III)

The object compound (III) can be prepared by subjecting the compound (IV) to degradative elimination reaction.

Suitable methods to be used in this elimination reaction are a conventional solvolysis such as hydrolysis (e.g., an acidic or a basic hydrolysis.) and a reduction (e.g., chemical or catalytic, reduction.), which may be optionally selected depending on a kind of a starting compound (IV).

Solvolysis such as hydrolysis is conducted preferably in the presence of an acid or a base in a conventional manner, the examples of which are the same as those illustrated in the explanation of Process 3 and to be referred to them.

Suitable examples of reducing agents for chemical reduction and catalysts for catalytic reduction are also the same as those illustrated in the explanation of Process 3, and to be referred to them.

The degradative reduction is usually conducted by reducing the compound (IV) with a reducing agent in a solvent in a conventional manner. The reaction conditions, for example, the solvent to be used and the reaction temperature are selected in accordance with the reduction method used and/or the kind of the compounds (IV) and/or (III). Generally, in the catalytic reduction method, it is preferable to employ a solvent such as methanol, ethanol, propanol, isopropanol, ethyl acetate or the like. In the method using a combination of a metalic compound and an acid, said acid is generally used as a solvent, but if necessary, there is employed a solvent such as water, acetone and the like.

The reaction temperature is not especially limited, and the reaction is usually conducted under cooling, at ambient temperature or at an elevated temperature.

The object compound (III) as prepared above is also used as a key intermediate for the compound (I') of this invention.

(5) Process 5: (V)→(VI)

In this process, the object compound (VI) is prepared by hydrolyzing the compound (V) or its derivative at carboxy. Examples of the derivative of carboxy of the starting compound is the same as illustrated in the explanation of the derivative of the carboxy for "$R^Z$" of compound (I).

The hydrolysis is conducted in a conventional manner.

That is, a suitable method to be used in this hydrolysis is conducted in the presence of an acid or base, example of which is the same one as that illustrated in the hydrolysis in the explanation for Process 3.

Though there is no particular limitation to the reaction temperature, it may be suitably selected according to the hydrolyzing condition to be used in the reaction, and the reaction is preferably conducted at ambient temperature or at somewhat elevated temperature in accordance with the kind of the solvent and other reagent used.

(6) Process 6: (VII)→(VIII)

In this process, the object compound (VIII) can be prepared by reducing the compound (VII) or its derivative at carboxy.

Example of the derivative at carboxy of the starting compound (VII) are the same as those illustrated in the explanation of the derivative of carboxy for "$R^Z$" of the compound (I).

In this reduction, the reaction is conducted by a conventional method such as a catalytic reduction; a reduction using a combination of a metal such as iron, tin or zinc and an acid such as an inorganic acid (hydrochloric acid, sulfuric acid or the like) or an organic acid (acetic acid or the like); a combination of an alloy (e.g., sodium amalgam, aluminum amalgam, etc.) a metal (e.g., zinc, tin, iron, etc.), or a salt thereof (e.g., zinc chloride, stannous chloride, ferric or ferrous chloride, etc.) and water, an alkali solution or an alcohol (e.g., methanol, ethanol, propanol or butanol); a hydrazine compound (e.g., phenyl hydrazine or hydrazine); a combination of titanium chloride and hydrochloric acid; an alkali borohydride such as sodium borohydride, and potassium borohydride; diborane; or an electrolytic reduction.

Suitable examples of catalysts for the catalytic reduction are the same one as those illustrated in the explanation of the catalyst for Process 3.

The reaction conditions for this reduction, for example, the solvent to be used and the reaction temperature may optionally be selected in accordance with the reduction method to be used. In general, it is preferable to employ a solvent such as water, an alcohol as mentioned above, dioxane, acetonitrile, tetrahydrofuran, dimethylformamide, pyridine and the like, and further the acid as mentioned above may also be used as a solvent.

The reaction temperature is not particularly limited, and the reaction is usually conducted under cooling, at ambient temperature or at an elevated temperature.

(7) Process 7: (IX)→(X)

In this process, the object compound (X) can be prepared by reacting the compound (IX) or its derivative at carboxy with an acylating agent.

Example of the derivative at carboxy of the starting compound are the same as those illustrated in the explanation of the derivative of the carboxy for "$R^Z$" of the compound (I).

As acylating agents in the present reaction, there may be exemplified the same examples as those illustrated in the explanation of the acylating agents for Process 1.

The reaction conditions, for example, the solvent to be used and the reaction temperature are also substantially the same as those explained in the acylation for Process 1.

The present acylation may include, within its scope, the case that when the starting compound (IX) has group(s) of free hydroxy and hydroxyimino, it (they) is also occasionally acylated.

(8) Process 8: (XI)→(XII)

In this process, the object compound (XII) can be prepared by reacting the compound (XI) or its reactive derivative at carboxy with a nucleophile of the formula: $R_{11}$-H wherein $R_{11}$ is residue of nucleophile, or its salt.

The nucleophile of the formula: $R_{11}$-H wherein $R_{11}$ is as defined above to be used as a reagent may include an amine such as a primary and secondary amine, a thiol compound and a hydroxy compound, respectively.

Examples of the residue of nucleophile are aliphatic hydrocarbon amino (e.g. alkylamino, alkenylamino, etc.), di-aliphatic hydrocarbon amino (e.g. di-alkylamino, etc.), aromatic amino (phenylamino, tolylamino, naphthylamino, etc.), heterocyclic amino (thienylamino, thiadiazolythio, triazolthio, etc.), and aliphatic hydrocarbon substituted by such aromatic or heterocyclic group; and aliphatic hydrocarbon thio (or oxy), aromatic thio (or oxy), heterocyclic thio (or oxy), and aliphatic hydrocarbon thio (or oxy) substituted by such aromatic or heterocyclic group; in which aliphatic hydrocarbon moiety may be saturated or unsaturated and branched or partially cyclized, and such aliphatic hydrocarbon moiety, aromatic ring and heterocyclic ring may be substituted by at least one possible substituent.

Suitable examples of aliphatic hydrocarbon residue, aromatic group, a heterocyclic group, aliphatic hydrocarbon residue substituted by aromatic or heterocyclic group may include the same ones as illustrated in the explanation of the definitions for $R_1$.

More suitable examples of the residue of nucleophile are illustrated in the explanation for the compound (XII).

In the present process, there may be employed the nucleophile for above thiol or phenolic hydroxy compound in a form of a salt such as an alkali metal (e.g., sodium, potassium, etc.) salt and an alkaline earth metal (e.g., magnesium, calcium, etc.) salt. In the case that the thiol compound has a free amino as substituent, said amino substituted thiol compound may be employed in the form of the salt of amino with an acid such as are an inorganic acid (e.g., hydrochloric acid, hydrobromic acid, etc.) and an organic acid (formic acid, p-toluenesulfonic acid, etc.).

The reaction is usually conducted in a solvent. Suitable examples of the solvents include any solvent which does not give bad influence to the reaction, and are water, acetone, methanol, ethanol, tetrahydrofuran, dioxane, dimethylformamide, methylene chloride, chloroform, carbon tetrachloride, etc., in which a hydrophilic solvent may be employed in a mixture with water.

The present reaction is preferably conducted in the presence of a base such as an alkalimetal hydroxide (e.g., sodium hydroxide, potassium hydroxide, etc.), an alkaline earth metal hydroxide (e.g., magnesium hydroxide, calcium hydroxide, etc.), and alkali metal carbonate (e.g., sodium carbonate, etc.), an alkaline earth metal carbonate (e.g., calcium carbonate, etc.), an alkali metal alkoxide (e.g., sodium alkoxide, potassium alkoxide, etc.), an alkaline earth metal alkoxide (e.g., calcium alkoxide, barium alkoxide, etc.), an organic amine (e.g., trimethylamine, etc.), a basic ionexchange resin, etc.

There is no particular limitation to the present reaction temperature, and the reaction is usually carried out under cooling, at ambient temperature or at an elevated temperature.

(9) Process 9: (XIII)→(XIV)

In this process, the object compound (XIV) can be prepared by removing the protective group at the terminal amino, hydroxy and/or carboxy group in the acylamino group at the 3rd position of the compound (XIII) or its derivative at carboxy.

Examples of protective groups at the terminal amino, hydroxy and carboxy are the same as those illustrated in the explation of a protective group for the compound (IV), including the examples of ester of the carboxy group (i.e., esterified carboxy) as illustrated in the explanation of the derivative of the carboxy for $R^Z$ of the compound (I).

Suitable methods to be used in the present reaction are conventional ones, including a conventional solvolysis, a conventional reduction, a conventional method using a heavy metal and the like, which are selected depending on a kind of a starting compound (XIII).

A solvolysis and reduction may be conducted in substantially the same manner illustrated in the explanation of the degradative elimination process for Process 4.

Suitable examples of heavy metal in the method using a heavy metal are copper, zinc, etc.

Although there is no particular limitation to the reaction temperature and a preferable temperature are employed depending on a kind of the protecting group to be removed and the method to be used, the reaction is usually carried out under cooling, at ambient temperature or at somewhat elevated temperature.

By the present reaction, the protective group at the terminal amino, hydroxy and/or carboxy group in the acylamino group at the 3rd position of the starting compound (XIII) are removed to transform the corresponding amino, hydroxy and/or carboxy, respectively, and when the derivative at carboxy in the substituent at the 1st position of the starting compound (XIII) are the ester, said ester is also transformed into the corresponding carboxy, all these cases are also included within the scope of the present process.

(10) Process 10: (XV)→(XVI)

In this process, the object compound (XVI) can be prepared by reacting the compound (XV) or its derivative at carboxy with a halogenating agent.

Examples of the derivative at carboxy of the starting compound (XV) are the same as those illustrated in the explanation of the derivative of the carboxy for $R^Z$ of the compound (II).

Suitable examples of halogenating agents may include halogen such as chlorine bromine, etc.; hypohalogenous acid or its alkyl ester such as hypochlorous acid, tert-butylhypochlorite, etc., N-halamide such as N-bromoacetamide, N-iodoacetamide, N-bromosuccinamide, N-chlorosuccinimide, N-chlorophthalimide, etc.; a cuprous halogenide such as cuprous chloride, cuprous bromide, etc.; and, pyridinium hydrobromide, perbromide, dioxane dibromide, etc., and the like.

The reaction is usually carried out in an inert solvent. A suitable solvent to be used in this reaction may include any solvent which have not adverse influence on the reaction, for example, water, methanol, ethanol, acetic acid, chloroform, methylene chloride, carbon tetrachloride, dioxane, acetonitrile, tetrahydrofuran, dimethylformamide and the like.

There is no particular limitation to the present reaction temperature, and the reaction is usually conducted under cooling, at amibient temperature or at somewhat elevated temperature.

(11) Process 11: (XVII)→(XVIII)

In this process, the object compound (XVIII) can be prepared by reacting the compound (XVII) or its derivative at carboxy with an acylating agent. The derivative at carboxy of the starting compound (XVII) are the same as those illustrated in the explanation of the derivative of carboxy for $R^Z$ of the compound (I).

Acylating agents to be used in the present reaction may include the same example as those illustrated in the explanation of the acylating agents for Process 1.

The acylation of the present process is conducted in a conventional manner, and the reaction conditions, for example, the solvent to be used and the reaction temperature are substantially the same as those explained in the acylation for Process 1.

(12) Process 12: (XIX)→(XX)

In this process, the object compound (XX) can be prepared by oxidizing the compound (XIX) or its derivative at carboxy.

The derivative at carboxy of the starting compound (XIX) are the same as those illustrated in the explanation of the derivative of the carboxy for $R_Z$ of the compound (I).

Oxidation in the present reaction is conducted in a conventional manner with a conventional oxidizing agent which can oxidize a —S— group into

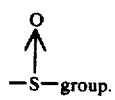
—S—group.

Suitable examples of such oxidizing agent are inorganic peracid or its salt (e.g., periodic acid, persulfuric acid, etc. or the sodium or potassium salt thereof); an organic peracid or its salt (e.g., perbenzoic acid, mchloroperbenzoic acid, performic acid, peracetic acid, chloroperacetic acid, trifluoroperacetic acid, etc. or the sodium or potassium salt thereof etc.); ozone, hydrogen peroxide, urea-hydrogen peroxide and the like.

The present reaction is preferably conducted in the presence of a compound comprising a Group Vb or VIb metal in the Periodic Table, for example, tungstic acid, molybdic acid, vanadic acid, etc. or their salt with an alkali metal (e.g., sodium, potassium, etc.), an alkaline earth metal (e.g., calcium, magnecium, etc.) or ammonium, etc., or vanadium pentoxide.

The present oxidation is usually conducted in a solvent such as water, acetic acid, chloroform, methylene chloride, alcohol (e.g., methanol, ethanol, etc.), tetrahydrofuran, dioxane, dimethylformamide or any other solvent which does not give bad influence to the present reaction.

There is no particular limitation to the reaction temperature, and the present reaction is usually conducted at ambient temperature or under cooling.

(13) Process 13: (XXI)→(XXII)

In this process, the object compound (XXII) can be prepared by reacting the compound (XXI) or its derivative at carboxy with an aryl halide of the formula; R'-X', wherein R' is aryl substituted by at least one substituent nitro and esterified carboxy and X' is halogen.

The derivative at carboxy of the starting compound (XXI) is the same as those illustrated in the explanation of the derivative of the carboxy for $R^Z$ of the compound (I).

Suitable examples of aryl in the aryl substituted by at least one substituent of nitro and esterified carboxy for R' are the same as illustrated in the explanation of the definitions of $R_{21}$ and $R_{22}$ for the compound (XXII), and suitable examples of halogen are chloride, bromine, etc. Further, examples of the ester in the esterified carboxy may include the same as those illustrated in the explanation of the ester in the reactive derivative of carboxy for $R^Z$ of the compound (I).

The present reaction is usually conducted in a solvent such as water, methanol, ethanol, propanol, tetrahydrofuran, dioxane, acetone, N,N-dimethylformamide, methylenechloride, chloroform, carbon tetrachloride or any other solvent which does not give bad influence to the present reaction.

The present reaction is preferably conducted in a base such as an inorganic or an organic base, for example, alkali metal hydroxide (e.g., sodium hydroxide, potassium hydroxide, etc.), an alkaline earth metal hydroxide (e.g., magnesium hydroxide, calcium hydroxide, etc.), an alkali metal carbonate (e.g., sodium carbonate, etc.), an alkaline earth metal carbonate (e.g., calcium carbonate, etc.), an alkali metal alkoxide (e.g., sodium alkoxide, potassium alkoxide, etc.), an alkaline metal alkoxide (e.g., calcium alkoxide, barium alkoxide, etc.), an organic amine (e.g., trimethylamine, etc.), a basic ionexchange resin, etc.

There is no particular limitation to the reaction temperature, and the present reaction is usually conducted under cooling, at ambient temperature or at an elevated temperature.

(14) Process 14: (XXIII)→(XXIV)

In this process, the object compound (XXIV) can be prepared by reacting the compound (XXIII) or its derivative at carboxy with a carbonyl compound of the formula:

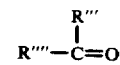

or its acetal or ketal, wherein R''' and R'''' are same or different hydrogen, alkyl, aryl or aralkyl, and then reducing the resulting product.

The derivative at carboxy of the starting compound (XXIII) are the same as those illustrated in the explanation of the derivative of the carboxy for $R^Z$ of the compound (I).

Examples of alkyl, aryl and aralkyl in the carbonyl compound, are methyl, ethyl, propyl, butyl, isobutyl, pentyl, etc. as alkyl; phenyl, tolyl, etc. as aryl; and benzyl, phenethyl, phenylpropyl, naphthylmethyl, etc. as aralkyl whose alkyl and the aryl moiety may be substituted at least one substituent of carboxy; alkoxy carbonyl, and halogen (chlorine, bromine, etc.).

Suitable examples of such carbonyl compound may include an aldehyde such as alkane aldehyde (e.g., formaldehyde, acetaldehyde, propionaldehyde, butylaldehyde, isobutylaldehyde, valeraldehyde, etc.), arene aldehyde (e.g., benzaldehyde, etc.) and aralkane aldehyde (e.g., benzaldehyde), and a ketone (e.g., acetone, methylethylketone, diethylketone, methylpropylketone, methylphenylketone, methyltolyketone, ethylbenzylketone etc.).

The resulting product which is produced by reacting the compound (XXIII) or its derivative at carboxy with the carbonyl compound can be subjected to the following reduction with isolation or without isolation thereof.

In the following reaction, the reduction is conducted in a conventional manner including the substantially same methods and reaction condition (solvent, temperature, etc.) as illustrated in the explanation for the reduction in the Process 6.

The first step of this reaction is usually conducted in solvent which does not give bad influence to the reaction such as water, dioxane, methanol, ethanol, N,N-dimethylformamide or the like. A liquid carbonyl compound may be also used as a solvent.

There is no particular limitation to the reaction temperature, which is selected depending on a kind of the carbonyl compound to be used and the reducing agent to be used, and the reaction is usually conducted under cooling or at ambient or somewhat elevated temperature.

In the course of this reaction or post-treatment, the derivative at carboxy may be transformed into the corresponding carboxy, the functional group of

may be reduced to transform a group of

and a substituent, such as halogen may be replaced by hydrogen, in some occasion.

These cases as above are included within the scope of the present invention.

(15) Process 15: (XXV)→(XXVI)

In this process, the compound (XXVI) can be prepared by reducing the compound (XXV) or its derivative at carboxy.

Examples of the derivative at carboxy of the starting compound (XXV) are the same as those illustrated in the explanation of the derivative of the carboxy for $R^Z$ of the compound (I).

In this reaction, the reduction is conducted in a conventional manner, and examples of the reducing agents and the reduction conditions are substantially the same as illustrated in the explanation of the reduction for Process 6.

(16) Process 16: (XXVII)→(XXVIII)

In this process, the compound (XXVIII) can be prepared by reacting the compound (XXVII) or its derivative at carboxy with an amine compound of the formula; $R_{27}$—$NH_2$ wherein $R_{27}$ is as defined above.

Examples of the derivative at carboxy of the starting compound (XXVII) may include same ones as illustrated in the explanation of the derivative of the carboxy for $R^Z$ of the compound (I).

Examples of alkoxy group and alkanoyl moiety of the alkanoylamino in the definitions for $R_{27}$ in the amine compound are the same as illustrated in the above explanation for the compound (XXVII).

In the reaction, the amine compound ($R_{27}$—$NH_2$) may be used in the form of its salt with an acid such as inorganic acid (e.g., hydrochloric acid, sulfuric acid, etc.) and organic acid (e.g. formic acid, acetic acid, etc.), and in this case the reaction may be preferably conducted under alkaline condition, for example, in the presence of alkali metal hydroxide (e.g., sodium hydroxide, potassium hydroxide), alkaline earth metal hydroxide (e.g., calcium hydroxide, etc.) and the like.

The reaction is usually conducted in solvent. Suitable examples of the solvent are water and a hydrophilic solvent such as methanol, ethanol, propanol, and N,N-dimethyl formamide, and any other solvent which does not give bad influence to the present reaction.

There is no particular limitation to the reaction temperature, and the present reaction is usually conducted under cooling at ambient temperature or at somewhat elevated temperature.

(17) Process 17: (XXIX)→(XXX)

In this process, the object compound (XXX) can be prepared by acylating the compound (XXIX) or its derivative at carboxy with an acylating agent.

Examples of the derivative at carboxy of the starting compound are the same as those illustrated in the explanation of the derivative of the carboxy for $R^Z$ of the compound (I).

Examples of acylating agent and acyl group in acylamino for $R_{29}$ may include the examples as those illustrated in the explanation for Process 1, respectively.

This process is conducted in a conventional manner, and may be conducted in substantially the same conditions (e.g., solvent, reaction temperature, etc.) as those mentioned in the explanation for Process 1.

(18) Process 18: (XXXI)→(XXXII)

In this process, the object compound (XXXII) can be prepared by reacting the compound (XXXI) or its derivative at carboxy with a hydroxyalkane sulfonic acid of the formula;

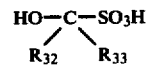

or the salt thereof, wherein $R_{32}$ and $R_{33}$ are each as defined above.

Examples of the derivative at carboxy of the starting compound (XXXI) are the same as those illustrated in the explanation of the derivative of the carboxy for $R^Z$ of the compound (I).

Examples of alkyl in the definitions of $R_{32}$ and $R_{33}$ for above hydroxyalkane sulfonic acid are the same as illustrated in the explanation for the compound (XXXII). As an example of the salts of said hydroxyalkane sulfonic acid, there may be illustrated salt with metal such as alkali metal (e.g., sodium, potassium, etc.), alkaline earth metal (e.g. calcium, magnesium, etc.) and the like.

The hydroxyalkanesulfonic acid can be prepared by reacting a carbonyl compound of the formula

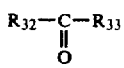

(wherein $R_{32}$ and $R_{33}$ are each as defined above) with sulfurous acid or the salt thereof (e.g. alkali or alkaline earth metal salt). Then, the object compound (XXXII) may be also prepared by reacting the compound (XXXI) with the above carbonyl compound and thereafter with the sulfurous acid or the salt thereof, the case of which is included within the scope of the present process.

The reaction is usually conducted in a solvent. As the suitable solvents, there may be illustrated water, hydrophilic solvent such as methanol, ethanol, propanol, tetrahydrofuran, dioxane, N,N-dimethylformamide, etc., and the mixture thereof, and any other solvent which does not give bad influence to the present reaction.

There is no particular limitation to the reaction temperature, and the present reaction is usually conducted under cooling, at ambient temperature or at an elevated temperature.

In the course of the reaction, amino group of the compound (XXXI) may occasionally react with the hydroxyalkanesulfonic acid or its above mentioned equivalent to be transformed into the corresponding mono- or di-substituted amino group

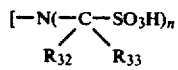

in which n is 1 or 2, or the salt thereof], these cases are also included within the scope of the present process.

When the hydroxyalkanesulfonic acid is used as a reagent, the reaction is preferably conducted in the presence of alkali or alkaline earth metal.

(19) Process 19: (XXXIII)→(XXXIV)

In this process, the compound (XXXIV) having esterified carboxy group (—$COOR_{39}$ and —$COOR_{41}$ wherein $R_{39}$ and $R_{41}$ are a group which is derived from an esterifying agent) can be prepared by reacting the compound (XXXIII) with a conventional esterifying agent.

Examples of esterified carboxy of the object compound may include the same as those illustrated in the explanation of the ester for the derivative of the carboxy for $R^Z$ of the compound (I) including silyl ester, aliphatic ester, ester containing aromatic or heterocyclic ring.

Esterifying agent may include any conventional agent which can esterify a carboxy group to provide an esterified carboxy group.

Suitable esterifying agents may include a halide compound such as alkyl halide (e.g., methyliodide, ethylbromide, ethyliodide, propylbromide, etc.), an alkenyl or alkynyl halide (e.g., allylbromide, methyllylbromide, propargylbromide, etc.); substituted alkylhalide such as alkanoyloxy alkylhalide (e.g., acetoxymethylchloride, acetoxyethylchloride, acetoxypropylbromide, etc.), aroylalkylhalide (e.g., phenacylbromide, etc.), an aralkylhalide (e.g., benzylchloride, diphenylmethylchloride, phenethylchloride etc.) and the like;

a dialkyl sulfate (e.g., dimethyl sulfate, diethyl sulfate, dipropyl sulfate, etc.); an alkyl sulfonate (e.g., methyl benzenesulfonate, methyl p-toluenesulfonate, ethyl 4-bromobenzenesulfonate, etc.); a holoformate such as alkyl haloformate (e.g., methyl chloroformate, ethyl chloroformate, propyl chloroformate, etc.), alkenyl or alkynyl haloformate (e.g., allyl chloroformate, propynyl chloroformate, etc.); a diazoalkane (e.g., diazomethane, diazoethane, etc.) and; a hydroxy compound such as alcohol, for example, an alkanol (e.g., methanol, ethanol, propanol, 2-chloroethanol, 2,2,2-trichloroethanol, butanol, 1-cyclopropylethanol, etc.), a cycloalkanol (e.g., cyclopropanol, cyclopentanol, cyclohexanol, borneol, adamantanol, etc.) and an aralkanol (e.g., benzylalcohol, diphenylmethanol, phenethylalcohol, etc.); and the like.

In case that the hydroxy compound is used as a esterifying agent in this process, the reaction may be preferably conducted in the presence of a condensing agent such as those illustrated for the condensing agent in the Process 1.

In the course of the present reaction, the hydroxy group of the starting compound (XXXIII) may occasionally reacted with the esterifying agent to form a ether group, for example, alkoxy, aralkoxy, etc. Such cases as mentioned above are included within the scope of the present process.

The reaction is usually conducted in a solvent such as water, dioxane, acetone, pyridene, N-N-dimethylformamide, ether, and the like.

There is no particular limitation to the reaction temperature, and the reaction is usually conducted under cooling at ambient temperature or an elevated temperature.

(20) Process 20: (XXXV)→(XXXVI)

In this process, the object compound (XXXVI) can be prepared by oxidizing the compound (XXXV) or its derivative at carboxy. Examples of the derivative at carboxy of the starting compound (XXXV) are the same as those illustrated in the explanation of the derivative of the carboxy for $R^Z$ of the compound (I).

The present oxidation are conducted in a conventional manner.

Examples of the oxidizing agents are the same as those illustrated in Process 12 and the reaction is also conducted under substantially the same conditions (e.g. solvent, reaction temperature, etc.) as mentioned in the explanation of Process 12.

(21) Process 21: (XXXVII)→(XXXVIII)

In this process, the object compound (XXXVIII) can be prepared by reacting the compound (XXXVII) or its derivative at carboxy with a diazotizating agent and then solvolyzing the resulting diazonium salt.

The examples of derivative at carboxy of the starting compound (XXXVII) are the same as those illustrated in the explanation of the derivative of the carboxy for $R^Z$ of the compound (I).

Suitable examples of diazotizating agent may include dinitrogen trioxide; nitrous acid or its derivative such as alkyl ester (e.g., methyl nitrite, ethyl nitrite, amyl nitrite, etc.), alkali metal salt (e.g., sodium nitrite, potassium nitrite, etc.); and mixed anhydride (e.g., nitrosyl chloride, nitrosyl bromide, notrisylsulfuric acid, nitrosylacetic acid, etc.).

The diazatization is usually conducted in a solvent such as water, methanol, ethanol, acetic acid, formic acid, N,N-dimethylformamide, dimethylsulfoxide or any other solvent which does not give bad influence to the reaction.

The resulting diazonium salt which is produced from the compound (XXXVII) or its derivative at carboxy by above reaction is then preferably solvolyzed by treating the reaction mixture per se or the isolated diazonium salt under acidic condition in the presence of an acid such as an inorganic acid (e.g., hydrochloric acid, sulfuric acid, phosphoric acid, nitric acid, etc.) and an organic acid (e.g., formic acid, acetic acid, propionic acid, butiric acid, p-toluenesulfonic acid, etc.).

There is no particular limitation to the present reaction temperature and the reaction is usually carried out under cooling, at ambient temperature, or at an elevated temperature.

In the present reaction, the amino group in the starting compound (XXXVII) is first diazotizated and then solvolyzed to the corresponding hydroxy group. Then, depending upon a kind of the diazotizating agent and or the reaction condition to be used, the object compound (XXXVIII) or its derivative at carboxy can be prepared from the compound (XXXVII) or its derivative at carboxy by one-batch process such as by diazotization of the compound (XXXVII) under acidic condition, i.e. in an acidic solvent selected from a liquid inorganic or organic acid as stated above and a mixture of the inorganic or organic acid and the solvent as mentioned above, whereby the object compound (XXXVIII) are obtained without any specific solvolysis treatment.

(22) Process 22: (XXXIX)→(XXXX)

In this process, the object compound (XXXX) can be prepared by reacting the compound (XXXIX) or its derivative at carboxy with an aryl halide of the formula; R″X′ wherein R″ is aryl which may be substituted by at least one substituent of nitro, esterified carboxy and heterocyclic group, and X′ is halogen.

Examples of the derivative at carboxy of the starting compound (XXXIX) are the same as those illustrated in the explanation of the derivative of the carboxy for $R^Z$ of the compound (I).

Suitable examples of aryl in the aryl which may be substituted by at least one substituent of nitro, esterified carboxy and heterocyclic group for $R_{43}$ which correspond to those for R″ are the same as those illustrated in the explanation for Process 13 (to be referred to the explanation of the compound (XXII)).

Further, examples of the ester in the esterified carboxy may include the same as those illustrated in the explanation of the ester in the derivative of the carboxy for $R^Z$ of the compound (I).

The reaction is conducted under substantially the same conditions (solvent, reaction temperature, etc.) as those explained in the explanation of the reaction for the Process 13.

(23) Process 23: (XXXXI)→(XXXXII)

In this reaction, the object compound (XXXXII) can be prepared by reacting the compound (XXXXI) with an alkylating agent.

Suitable alkylating agents may include, for example, alkanol (e.g., methanol, ethanol, propanol, isopropyl alcohol, butanol, etc.), diazoalkane (e.g., diazomethane, diazoethane, etc.), dialkyl sulfate (e.g., dimethyl sulfate, diethyl sulfate, dipropyl sulfate, etc.), alkyl tosylate (e.g., methyl tosylate, ethyl tosylate, etc.) and the like.

The present reaction is usually conducted in a solvent such as methanol, ethanol, acetone, ether, dimethylformamide and any other solvent which does not give bad influence to the reaction.

In the present reaction, in case that diazoalkane, dialkyl sulfate or alkyl tosylate in used as an alkylating agent, hydroxy group of the compound (XXXXI) may be occasionally alkylated together with the objective carboxy group, but in case that alkanol is used as an alkylating agent, only the carboxy group of the compound (XXXXI) is usually selectively alkylated.

When dialkyl sulfate, alkyl tosylate is employed as an alkylating agent in the present reaction, the reaction may be preferably conducted in the presence of a base such as an inorganic base (e.g., sodium hydroxide, potassium hydroxide, sodium carbonate, potassium carbonate, sodium bicarbonate, potassium bicarbonate, etc.) and an organic base (e.g., trimethylamine, triethylamine, pyridine, picoline, etc.), and when alkanol is employed as an alkylating agent in the present reaction, the reaction is preferably conducted in the presence of a conventional condensing agent such as 1-[4-chlorobenzenesulfonyloxy)-6-chloro-1H-benzotriazole, etc.

There is no particular limitation to the present reaction temperature, and it may be suitably selected in accordance with kinds of the compound (XXXXI) and, an alkylating agent to be used. For example, when diazoalkane is employed in the present reaction, the reaction may proceed under cooling or at ambient temperature.

(24) Process 24: (XXXXIII)→(XXXXIV)

In this process, the object compound (XXXXIV) can be prepared by subjecting the compound (XXXXIII) to elimination reaction of the protective group of protected amino.

The present elimination reaction is conducted in a conventional manner, that is under substantially the similar conditions as those described in the elimination reaction of the protective group of protected amino of the compound (XIII) in Process 9.

Examples of the protective group may include the same as those illustrated in the explanation with respect to the compound (IV).

In this reaction, in case that the starting compound (XXXXIII) has the other protected amino, protected hydroxy and/or protected carboxy group in its molecule, such protective groups may be occasionally eliminated to be transformed into the corresponding amino, hydroxy and/or carboxy group, whose reaction is also included within the scope of the present process.

(25) Process 25: (XXXXV)→(XXXXVI)

In this process, the object compound (XXXXVI) can be prepared by reacting the compound (XXXXV) with a reagent selected from hydrazine, hydroxyalkylamine and aralkylamine or the salt thereof.

Suitable examples of hydroxyalkylamine may include hydroxyethylamine, hydroxypropylamine and the like, and suitable examples of aralkylamine may include benzylamine, phenethylamine and the like.

Suitable examples of the salts of hydrazine, hydroxyalkylamine or aralkylamine may include an organic acid salt (e.g., acetate, maleate, tartrate, benzenesulfonate, toluenesulfonate, etc.) and an inorganic acid salt (e.g., hydrochloride, sulfate, phosphate, etc.).

This reaction can be conducted under substantially the similar conditions as those described in the acylation of the compound (II) in Process 1.

(26) Process 26: (XXXXVII)→(XXXXVIII)

In this process, the object compound (XXXXVIII) can be prepared by reacting the compound (XXXXVII) with an esterified alkene carboxylic acid.

Examples of alkene moiety in the esterified alkene carboxylic acid may include an alkenyl which may be branched, such as 1-propenyl, 1-butenyl, 1-pentenyl, isopropenyl, methylpropenyl, methylbutenyl, methylpentenyl, ethylpropenyl, ethylbutenyl, etc., and examples of ester moiety therein may include the same ones as illustrated for the ester in the derivative of the carboxy for $R^z$ of the compound (I).

This reaction is usually conducted in a solvent which does not give bad influence to the reaction such as water, methanol, ethanol, acetone, chloroform, dimethylformamide and the like, and can be preferably conducted in the presence of a base such as an inorganic base (e.g., sodium hydroxide, potassium hydroxide, sodium carbonate, potassium carbonate, sodium bicarbonate, potassium bicarbonate, etc.) and an organic base (e.g., trimethylamine, triethylamine, pyridine, picoline, etc.).

There is no particular limitation to this reaction temperature, and the reaction may proceed under cooling or warming.

(27) Process 27: (XXXXVII)→(XXXXIX)

The object compound (XXXXIX) can be prepared by reacting the compound (XXXXVII) or its salt with an esterified aliphatic $\not=$-ketocarboxylic acid.

Examples of the esterified $\beta$-ketocarboxylic acid may include esterified alkanoylacetic acid such as ethylacetoacetate, ethylpropinoylacetate, t-butylbutyrylacetate, etc.

Suitable salt of the compound (XXXXVII) may include an organic acid salt (e.g., acetate, maleate, tartrate, benzenesulfonate, toluenesulfonate, etc.) and an inorganic acid salt (e.g., hydrochloride, sulfate, phosphate, etc.).

This reaction can be conducted with or without solvent. Suitable solvents may include methanol, ethanol, propanol, ether, acetone, benzene, toluene and any other solvent which does not give bad influence to the reaction. This reaction can be preferably conducted in the presence of a base such as an inorganic base (e.g., sodium hydroxide, potassium hydroxide, sodium carbonate, potassium carbonate, sodium bicarbonate, potassium bicarbonate, etc.) and an organic base (e.g., trimethylamine, triethylamine, pyridine, picoline, etc.).

There is no particular limitation to the present reaction temperature, and the present reaction are usually conducted under warming or heating.

Thus obtained object compound (XXXIX) may include an tautomeric isomer at the alkenylamino moiety of $R_{53}$, i.e. an alkylideneamino moiety.

(28) Process 28: (XXXXXII)→(XXXXVII)

In this process, the object compound (XXXXVII) can be prepared by reducing the compound (XXXXXII).

The reduction is conducted in a conventional manner by which nitro and azido group can be reduced to amino group, including the reduction methods as those described in the Process 15.

Suitable reduction applicable to the reaction may include a chemical reduction using a metal (e.g., tin, zinc, iron, etc.) and an acid (e.g., acetic acid, hydrochloric acid, etc.) or a catalytic reduction in the presence of a metallic catalyst such as palladium carbon, Raney-nickel, platinum oxide and other conventional catalysts.

The reaction is conducted in a solvent such as methanol, ethanol, propanol and the like.

There is no particular limitation to the present reaction temperature, and it may suitably selected in accordance with kinds of the compound (XXXXXII) and reduction methods.

(29)-(a) Process 29-(a): (XXXXXIII)→(XXXXXIV)

In this process, the object compound (XXXXXIV) can be prepared by reducing the compound (XXXXXIII).

The reduction is conducted in a conventional manner. Suitable method applicable to this reduction may be, for example, reduction using an alkali metal borohydride (e.g., sodium borohydride, lithium borohydride, etc.).

The present reaction is usually conducted in a solvent which does not give bad influence to the reaction such as water, methanol, ethanol, benzene, toluene and the like.

There is no particular limitation to the present reaction temperature, and it may be suitably selected in accordance with kinds of the compound (XXXXXIII) and reduction methods.

(29)-(b) Process 29-(b): (XXXXXV)→(XXXXXVI)

In this process, the object compound (XXXXXVI) can be prepared by reacting the compound (XXXXXV) or its derivative at carboxy with an aralkylamine under reductive condition.

Suitable examples of aralkylamine are benzylamine, phenethylamine and the like, whose benzene ring may be substituted by at least one suitable substituent.

Examples of the derivative at carboxy of the starting compound (XXXXXV) are the same as illustrated in the explanation of the derivative of the carboxy for "$R^Z$" of the compound (I).

The present reaction is conducted under reductive conditions, that is by reacting the starting compound (XXXXXV) with an aralkylamine in the presence of a conventional reducing agent or by reacting the starting compound (XXXXXV) with an aralkylamine and then reducing the resulting product with a conventional reducing agent.

Suitable examples of the reducing agents are, an alkali metal borohydride (e.g., sodium borohydride, potassium borohydride, etc.), and other conventional reducing agent and methods as illustrated in Process 6 can be used.

In case that the reaction is conducted by reacting the compound (XXXXXV) with an aralkylamine and then reducing the resulting product, the reaction of the compound (XXXXXV) with an aralkylamine can be preferably conducted in the presence of base such as an inorganic base (e.g., sodium hydroxide, potassium hydroxide, sodium carbonate, potassium carbonate, sodium bicarbonate, potassium bicarbonate, etc.) and an organic base (e.g., trimethylamine, triethylamine, pyridine, picoline, etc.).

The present reaction is usually carried out in a solvent which does not give bad influence to the reaction such as methanol, ethanol, benzene, toluene and the like.

There is no particular limitation to the present reaction temperature, and it may be suitably selected in accordance with kinds of the compounds (XXXXXV), aralkylamine and reduction conditions or reduction methods.

(30) Process 30: (XXXXXVII)→(XXXXXVIII)

In this process, the object compound (XXXXXVIII) can be prepared by reacting the compound (XXXXXVII) or its derivative at carboxy with a trialkylamine.

Examples of the derivative at carboxy are the same as illustrated in the explanation of the derivative of the carboxy for "$R^Z$" of the compound (I).

Suitable trialkylamines may include trimethylamine, triethylamine, tripropylamine and the like.

The present reaction is usually conducted in a solvent which does not give bad influence to the reaction such as methanol, ethanol, acetone, ether, dimethylformamide and the like.

There is no particular limitation to the present reaction temperature, and the reaction is usually conducted at ambient temperature or under warming.

(31) Process 31: (XXXXX)→(XXXXXI)

In this process, the object compound (XXXXXI) can be prepared by reacting the compound (XXXXX) or its derivative at carboxy with an acylating agent.

The derivative at carboxy of the starting compound (XXXXX) are the same as illustrated in the explanation of the derivative of the carboxy for "$R^Z$" of the compound (I).

The acylation is conducted in a conventional manner, and the reaction is conducted under substantially the same condition (solvent, reaction temperature, etc.) as illustrated in the acylation for Process 1.

Examples of acylating agents may include the same ones as those illustrated in the Process 1.

(32) Process 32: (XXXXXII)→(XXXXXIII)

In this process, the object compound (XXXXXIII) can be prepared by reducing the compound (XXXXXII) or its derivative at the carboxy group.

Examples of the derivative at the carboxy group are the same as illustrated in the explanation of the derivative of the carboxy for "$R^Z$" of the compound (I).

The reduction is conducted by a conventional method such as chemical reduction and catalytic reduction as mentioned in the Process 3.

Suitable examples of the reduction may include a catalytic reduction using Raney nickel, Raney cobalt and the like.

The reduction is usually conducted in a solvent.

Suitable examples of the solvent include water, methanol, ethanol, propanol, dioxane and the mixture thereof, and any other solvent which has not adverse influence on the reaction.

The reduction is usually carried out at atmospheric or medium pressure.

There is no particular limitation to the reaction temperature, and the reaction is usually carried out at ambient temperature.

(33) Process 33: (XXXXXIV)→(XXXXXV)

In this process, the object compound (XXXXXV) can be prepared by reacting the compound (XXXXXIV) or its derivative at the carboxy group with an acylating agent.

Examples of the derivative at the carboxy group of the starting compound (XXXXXIV) are the same as those illustrated in the explanation of the derivative of the carboxy for "$R^Z$" of the compound (I).

Examples of the acylating agent include the same examples as illustrated in the Process 1.

The acylation is conducted in a conventional manner and in substantially the same conditions (e.g., solvent, reaction temperature, etc.) as those mentioned in the Process 1.

(34) Process 34: (XXXXXVI)→(XXXXXVII)

In this process, the object compound (XXXXXVII) can be prepared by reacting the compound (XXXXXVI) or its derivative at the carboxy group with an aralkylating agent of the formula: $R_{69}$-X'''' (wherein $R_{69}$ is as defined above and X'''' is acid residue).

Examples of the derivative at the carboxy group of the starting compound (XXXXXVI) are the same as those illustrated in the explanation of the derivative of the carboxy for "$R^Z$" of the compound (I).

Suitable examples of the acid residue for X'''' are the same as those illustrated for $X_1$ of the compound (XI).

This reaction is usually conducted in a solvent, suitable examples of which are methylene chloride, chloroform, dichloroethane, N,N-dimethylformamide and the like.

This reaction is preferably conducted in the presence of a base as mentioned in the explanation of Process 1.

There is no particular limitation to the present reaction temperature, and the reaction is usually conducted under cooling or at ambient temperature.

(35) Process 35: (XXXXXVIII)→(I)

In this process, the object compound (I) can be prepared by subjecting the compound (XXXXXVIII) to desulfuration.

The desulfuration is usually conducted by reducing the starting compound (XXXXXVIII). For this reduction, a preferred examples of the reducing agent are Raney nickel, Raney cobalt and the like.

The reaction is usually conducted in a solvent such as ether, dioxane, methanol, ethanol, propanol, tetrahydrofuran, ethyl acetate and the like.

There is no particular limitation to this reaction, and the reaction is usually carried out at ambient or somewhat elevated temperature.

(36) Process 36: (XXXXXIX)→(XXXXXX)

In this process, the object compound (XXXXXX) can be prepared by subjecting the compound (XXXXXIX) or its reactive derivative at carboxy group to intramolecular cyclization.

Suitable examples of the reactive derivative at the carboxy group of the starting compound (XXXXXIX) may include acid anhydride, an activated amide, an activated ester and acid azid as mentioned in the explanation of Process 1, and concrete examples of such reactive derivatives may include the same as those illustrated in the explanation of Process 1.

The starting compound (XXXXXIX) includes a salt of imino group (—NH—) thereof, and suitable examples of the salt may include salts with inorganic acid such as hydrochloric acid, hydrobromic acid, sulfuric acid, phosphoric acid and the like, and organic acid such as formic acid, acetic acid, trifluoroacetic acid, benzenesulfonic acid and the like.

The reaction is usually conducted in a solvent such as methylene chloride, chloroform, diethylether, ethyl acetate, N,N-dimethylformamide and the like.

The intramolecular cyclization is usually conducted by reacting the starting compound (XXXXXIX) in the presence of a base and/or a condensing agent. Examples of the base are the same as those illustrated in the explanation of Process 1, and examples of the condensing agent are acetic anhydride, and Grignard's reagent such as methylmagnesium chloride, ethylmagnesium bromide and the like.

There is no particular limitation to this reaction, and this reaction is usually conducted under cooling or at ambient temperature.

(37) Process 37: (XXXXXXI)→(XXXXXXII)

In this process, the object compound (XXXXXXII) can be prepared by subjecting the compound (XXXXXXI) to elimination reaction of a protective group at the carboxy group.

A method for this reaction to be used may include solvolysis and reduction as mentioned in the explanation of Process 3, and the other reaction conditions for this reaction are the same as those illustrated for Process 3.

(38) Process 38: (XXXXXXIV)→(XXXXXXV)

In this process, the object compound (XXXXXXV) can be prepared by reacting the compound (XXXXXXIV) with hydrazoic acid or its derivative.

Suitable examples of a derivative of hydrazoic acid may include, sodium azide, potassium azide, calcium azide, diphenylphosphoryl azide and the like.

This reaction is usually conducted in a solvent such as tetrahydrofuran, methylene chloride, ether and the like.

There is no particular limitation to this reaction and the reaction is usually conducted under cooling or at ambient temperature.

(39) Process 39: (XXXXXXV)→(XXXXXXVI)→(XXXXXXVII)

In this process, as the first step, the compound (XXXXXXV) is heated in a solvent such as benzene, toluene and the like, to provide the compound (XXXXXXVI), and as the second step said resultant compound (XXXXXXVI) is reacted with an alcohol of the formula: $R_{74}$-OH in a solvent such as tetrahydrofuran, methylene chloride, ether and the like under cooling or somewhat elevated temperature to provide the compound (XXXXXXVII). In the above reactions, the compound (XXXXXXVI) produced in the first step can be used with or without isolation thereof as a starting compound for the second step and is subjected to the reaction of the second step to provide the compound (XXXXXXVII). The object compound (XXXXXXVII) can also be prepared more preferably from the compound (XXXXXXIV) throughout the foregoing Process 38 and successively followed by this process in one batch system.

(40) Process 40: (XXXXXXIV)→(XXXXXXVIII)

In this process, the object compound (XXXXXXVIII) can be prepared by reacting the compound (XXXXXXIV) with an oxidizing agent of the formula: $P_b(OCOR_{75})_4$.

This reaction is usually conducted in a solvent such as benzene, acetic acid, ethyl acetate methylene chloride, chloroform, ether and the like.

The reaction is also preferably conducted in the presence of a radical initiator such as cupric acetate, or under ultraviolet irradiation.

The reaction is preferably conducted under heating.

(41) Process 41: (V)→(XXXXXXIX)

In this process, the object compound (XXXXXXIX) can be prepared by reacting the compound (V) or its derivative at the carboxy group with a compound of the formula: $R_{76}$-$NH_2$.

Suitable examples of the derivative at the carboxy group of the starting compound (V) are the same as those illustrated in the explanation of the derivative of the carboxy for "$R^Z$" of the compound (I).

This reaction is conducted in substantially the same manner as mentioned in Process 16.

(42) Process 42: (XV)→(XXXXXXX)

In this process, the object compound (XXXXXXX) can be prepared by reacting the compound (XV) or its derivative at the carboxy group with a compound of the formula: $R_{77}$-X''''' (wherein $R_{77}$ is as defined above and X''''' is acid residue).

Suitable examples of the derivative at the carboxy group of the starting compound (XV) are the same as those illustrated in the explanation of the derivative of the carboxy "$R^Z$" of the compound (I).

Suitable examples of the acid residue for X''''' are the same as those illustrated in the explanation for $X_1$ of the compound (XI).

This reaction is carried out in substantially the same manner as described in the Process 34.

(43) Process 43: (XXXXXXXI)→(XXXXXXXII)

In this process, the object compound (XXXXXXXII) can be prepared by reacting the compound (XXXXXXXI) or its derivative at carboxy group with an acylating agent.

Suitable examples of the derivative at the carboxy group of the starting compound (XXXXXXXI) are the same as those illustrated in the explanation of the derivative of the carboxy for "$R_Z$" of the compound (I).

Suitable examples of the acylating agent are the same as those illustrated in the Process 1.

This acylation is carried out in substantially the same manner as described in the explanation of Process 1.

(44) Process 44: (XXXXXXXIII)→(XXXXXXXIV)

This reaction is carried out in substantially the same manner as described in Process 9.

(45) Process 45: (XXXXXXXV)→(XXXXXXXVI)

This reaction is carried out in substantially the same manner as described in Process 41.

(46) Process 46: (XXXXXXXVII)→(XXXXXXXVIII)

This reaction is carried out in substantially the same manner as described in Process 43.

(47) Process 47: (XXXXXXXIX)→(XXXXXXXX)

This reaction is carried out in substantially the same manner as described in Process 9.

(48) Process 48: (XXXXXXXXI)→(XXXXXXXXII)

This reaction is carried out in substantially the same manner as described in Process 1.

(49) Process 49: (XXXXXXXXIII)→(XXXXXXXXIV)

This reaction is carried out in substantially the same manner as described in Process 9.

According to kinds of the reactions to be used in the afore-mentioned Processes, each of the alternative carboxy or corresponding derivatives at carboxy of every starting or objective compounds may occationally be transformed into each other in the course of the respective reactions or the post treatment therefor.

In the same manner, protective group(s) of the protected carboxy, protected amino and/or protected hydroxy, may be converted into the corresponding carboxy, amino and/or hydroxy group(s), respectively.

Such cases of the reactions as mentioned above also include within the scope of the Processes as concerned in this invention.

The object compounds (I) of the present invention have antimicrobial activities against various pathogenic micro-organisms and may be useful for treatment of diseases infected by such micro-organisms in human being and animals.

With regard to the representative object compounds of the present invention, their antimicrobial activities against pathogenic micro-organisms are illustrated as M.I.C. (Minimum Inhibitory Concentration) value determined in a conventional manner as followed. In the following, M.I.C. value is shown as microgram per ml.

An object compound of Example 39, *Pseudomonas aeruginosa* (3); an object compound of Example 51, *Bacillus subtilis* (12.5); an object compound of Example 112, *Escherichia coli* (60), *Proteus vulgaris* (<3), *Staphylococcus aureus* (60); an object compound of Example 157, *Bacillus subtilis* (7.5), *Staphylococcus aureus* (7.5); and object compound of Example 158, *Bacillus subtilis* (80), *Staphylococcus aureus* (80); and object compound of Example 161, *Escherichia coli* (16), *Proteus vulgaris* (8), *Staphylococcus aureus* (8); an object compound of Example 291, *Escherichia coli* (1.6), *Proteus vulgaris* (25); an object compound of Example 300, *Pseudomonas aeruginosa* (15), *Escherichia coli* (60); an object compound of Example 400, *Pseudomonas aeruginosa* (32), *Escherichia coli* (16); an object compound of Example 409, *Escherichia coli* (60), *Proteus vulgaris* (<3), *Staphylococcus aureus* (60); an object compound of Example 469, *Bacillus subtilis* (60), *Escherichia coli* (4), *Staphylococcus aureus* (4); an object compound of Example 489, *Pseudomonas aeruginosa* (15), *Escherichia coli* (3.9), *Proteus vulgaris* (60), an object compound of Example 507, *Pseudomonas aeruginosa* (6.3), *Proteus vulgaris* (25); an object compound of Example 508, *Pseudomonas aeruginosa* (6.3), *Proteus vulgaris* (25); *Staphylococcus aureus* (1.6); an object compound of Example 511, *Bacillus subtilis* (6), *Escherichia coli* (30), *Staphylococcus aureus* (60); an object compound of Example 586, *Staphylococcus aureus* (7.5); an object compound of Example 595, *Proteus vulgaris* (15); an object compound of Example 631, *Bacillus subtilis* (15); an object compound of Example 645, *Pseudomonas aeruginosa* (4); an object compound of Example 658, *Escherichia coli* (8.0) an object compound of Example 665, *Proteus vulgaris* (16), *Escherichia coli* (2.0), *Pseudomonas aeruginosa* (16); an object compound of Example 666, *Escherichia coli* (8.0); an object compound of Example 674, *Escherichia coli* (15).

The following examples are given for the purpose of illustrating the present invention.

EXAMPLE 1

3-Amino-1-(α-carboxy-4-hydroxybenzyl)-2-azetidinone (hereinafter referred to 3-aminolactacillanic acid) (0.94 g.) was suspended in water (10 ml.), whereafter to the suspension was added sodium bicarbonate (0.80 g.). To the solution was added acetone (10 ml.) and then the solution was cooled to $-7°$ C., whereafter acetone (5 ml.) containing 2-phenylacetyl chloride (0.80 g.) was added to the solution. The reaction mixture was stirred at the same temperature for 2 hrs, and then the acetone was distilled off under reduced pressure. The remaining aqueous layer was washed with ether, and then adjusted to pH 2 with 10% hydrochloric acid, whereafter twice extractions were carried out with ethyl acetate (15 ml.). The extracts obtained were combined, and washed with water and a sodium chloride-saturated-aqueous solution, respectively, whereafter it was dried over anhydrous magnesium sulfate. The solvent was distilled off from the extract and the residue obtained was treated with a small amount of a mixture of ethyl acetate and ether to give 3-(2-phenylacetamido)lactacillanic acid (0.53 g.). Mp 134° to 141° C.

The following compounds were obtained in substantially the similar manner as described above.

(I)

Structure: $R_1$—C(=O)—[azetidinone ring]—N—A

| Example | $R_1$ (note 1) | A | mp (°C.) (dec.) |
|---|---|---|---|
| 2 | CH₃CH₂CH(Br)CONH— | —CH(COOH)—C₆H₄—OH | 156–158 |
| 3 | C₆H₅—CH(NHCOOCH₂—C₆H₅)—CONH— *1 | " | 146–148 |
| 4 | C₆H₅—CH(SCH₃)—CONH— | " | 159–162 |
| 5 | C₆H₅—CH(Br)—CONH— | " | 173–175 |
| 6 | C₆H₅—CH(O—C₆H₄—Cl)—CONH— | " | (sodium salt) 195–197 |
| 7 | C₆H₅—CH(NHSO₂—C₆H₅)—CONH— *1 | " | (sodium salt) 186–189 |
| 8 | C₆H₅—CH(OCH₃)—CONH— | " | 181–185 |

-continued $$\text{(I)}$$

Structure: R₁-C(=O)-N-A (β-lactam, azetidinone)

| Example | R₁ (note 1) | A | mp (°C.) (dec.) |
|---|---|---|---|
| 9 | 4-CHO-C₆H₄-O-CH(C₆H₅)-CONH— | " | 95–96 |
| 10 | 2-naphthyl-O-CH(C₆H₅)-CONH— | " | 174–175 |
| 11 | (3-methyl-1,2,4-oxadiazol-5-yl)-CH₂CONH— | " | 167–168 |
| 12 | C₆H₅CH₂OOC-O-C₆H₄-CH₂CONH— | " | 85–89 |
| 13 | C₆H₅CH₂OOCNH-CH(C₆H₅)-CH₂CONH— | " | 169–173 |
| 14 | (1-naphthyl)-CH₂CONH— | " | 199–201 |
| 15 | C₆H₅CH₂OOCNH(CH₂)₅CONH— | " | I.R. ν cm⁻¹(Nujol): 1730, 1660 |
| 16 | (2-thienyl)-CH₂CONH— | " | 180–183 |
| 17 | C₆H₅-CH₂CONH— | —CH₂COOH | 144–145 |
| 18 | " | —CH(C₆H₅)COOH | 174–175 |
| 19 | HOOCCH₂CH₂CONH— | —CH(4-HO-C₆H₄)COOH | (disodium salt) I.R.ν cm⁻¹(KBr): 1740, 1660, 1585 |
| 20 | ClCH₂CO-O-C₆H₄-CH₂CONH— | " | 136–139 |
| 21 | (2-furyl)-CH₂CONH— | " | 171–173 |
| 22 | C₂H₅OCOCONH— | " | 210–213 |
| 23 | C₆H₅N(SO₂CH₃)CH₂CONH— | " | 116–119 |
| 24 | CH₃OCH₂CONH— | " | 125–129 |
| 25 | CH₃SO₂NHCH₂CONH— | " | (sodium salt) 160–164 |
| 26 | (4-biphenylyl)-OCH₂CONH— | " | 195–198 |
| 27 | (2-naphthyl)-OCH₂CONH— | " | 143–146 |
| 28 | C₆H₅-OCH₂CONH— | " | 180–184 |
| 29 | 2-CHO-C₆H₄-OCH₂CONH— | " | 181–183 |

-continued

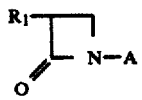
(I)

| Example | R₁ (note 1) | A | mp (°C.) (dec.) |
|---|---|---|---|
| 30 | O₂N-CH=CH-⌬-OCH₂CONH— | " | 134–135 |
| 31 | PhCH₂OOCNH-CH(CH₂-⌬-OCH₂CONH—)-COOCH₃ | " | 136–140 |
| 31 | PhCH₂OOCNH-*1-CH(CH₂-⌬-OCH₂CONH—)-COOCH₃ | " | 80–85 |
| 33 | OHC-⌬-OCH₂CONH— | " | 145–146 |
| 34 | Cl-⌬-SO₂NHCH₂CONH— | " | 168–173 |
| 35 | CH₂=CHCH₂SCH₂CONH— | " | 178–183 |
| 36 | CH₃SCH₂CONH— | " | 154–155 |
| 37 | O₂N-⌬-OCH₂CONH— | " | 137–140 |
| 38 | N₃CH₂CONH— | " | 171–173 |
| 39 | BrCH₂CONH— | " | 145–150 |
| 40 | Ph-OCH₂CONH— | —CH(COOCH₃)-⌬-OCH₃ | N.M.R. δ pm (CDCl₃): 3.14 (1H,d,d,J=3Hz,6Hz), 3.76 (3H,s), 3.81 (3H,s), 3.96 (1H, t,J=6Hz), 4.46 (2H,s), 5.08 (1H,heptet), 5.59 (1H, s), 6.80–7.40 (9H,m) |
| 41 | C₂H₅OOCCH=CH-⌬-OCH₂CONH— | —CH(COOH)-⌬-OH | 109–110 |
| 42 | ClCH₂CONH— | " | 165–167 |
| 43 | Ph-SCH₂CONH— | " | 183–185 |
| 44 | Ph-CH=CHCONH— | " | 192–193 |
| 45 | Ph-OCH₂CONH-⌬-CONH— | " | 179–180 |
| 46 | (NO₂)₂-⌬-CONH— | " | 170–175 |
| 47 | O₂N-⌬-CONH— | " | 195–197 |
| 48 | CH₃O-⌬-CONH— | " | 160–165 |
| 49 | Cl-⌬-isoxazole(CH₃)-CONH— | " | (sodium salt) I.R. ν cm⁻¹(Nujol): 1735, 1655, 1610 |
| 50 | Cl₂CHCONH— | " | 178–183 |
| 51 | (Ph)₂CHCONH— | " | 135–140 |

-continued

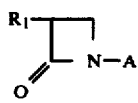

| Example | R₁ (note 1) | A | mp (°C.) (dec.) |
|---|---|---|---|
| 52 | Ph-CH₂CONH— | —CH(COOCH₃)—C₆H₄—NH₂ | I.R. ν cm⁻¹(CHCl₃) 1755, 1745, 1675 |
| 53 | Ph-SO₂NH— | —CH(COOH)—C₆H₄—OH | 172–174 |
| 54 | Ph-OCONH— | " | 198–200 |
| 55 | Ph-CH₂CONH— | —H | 178–181 |
| 56 | (2-thienyl)-CH(NHCOOCH₂CCl₃)CONH— | —CH(COOH)—C₆H₄—OH | 171–176 |

EXAMPLE 57

N-Phenylglycyl chloride hydrochloride (492 mg.) was suspended in methylene chloride (10 ml.), and the suspension was cooled to −15° C. To the suspension were added all at once a solution prepared by dissolving 3-aminolactacillanic acid (472 mg.) and, N,O-bis(trimethylsilyl)acetamide (2.03 g.) in methylene chloride (17 ml.). The mixture was stirred for 1 hour, keeping the reaction temperature of the mixture at 0° to −10° C., and then stirred for 1.5 hrs. after removing the cooling bath. The methylene chloride was distilled off from the reaction mixture, and the residue obtained was dissolved in ethyl acetate. The solution was washed with water and a sodium chloride-saturated-aqueous solution respectively, and dried. The solvent was distilled off from the solution, and to the residue was added a small amount of acetone to give crystals of 3-(N-phenylglycinamido)lactacillanic acid (116 mg.). Mp 194° to 194.5° C. The filtrate was allowed to stand under cooling to give crystals of the same object compound (60 mg.). Mp 193° to 194.5° C. Total yield was 176 mg.

The following compounds were obtained in substantially the similar manner as described above.

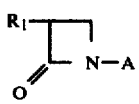

| Example | R₁ (note 1) | A | mp (°C.) (dec.) (note 2) |
|---|---|---|---|
| 58 | Ph-CH₂CONH— | *2 —CH(COOCH₃)—C₆H₄—OCH₃ | (D isomer) 145–146 (L isomer) I.R. ν cm⁻¹(CHCl₃): 1760, 1740, 1680 |
| 59 | " | *2 —CH(COOCH₂-Ph)—C₆H₄—OCH₂-Ph | (D isomer) 129–130 (L isomer) I.R. ν cm⁻¹ (liquid film): 3300, 1760–1740, 1665 |
| 60 | " | —CH(COOCH₃)—C₆H₄—NO₂ | I.R. ν cm⁻¹(CHCl₃): 1765, 1745, 1680, 1525, 1350 |

-continued (I)

| Example | R₁ (note 1) | A | mp (°C.) (dec.) (note 2) |
|---|---|---|---|
| 61 | " | 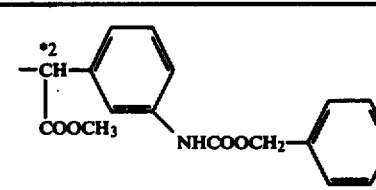 -*2 CH(COOCH₃)—C₆H₄-3-NHCOOCH₂C₆H₅ | isomer (A) I.R. ν cm⁻¹(CHCl₃): 1760(s), 1745, 1710(s), 1675 isomer (B) I.R. ν cm⁻¹(CHCl₃): 1755(s), 1745, 1710(s), 1675 |
| 62 | " | 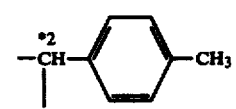 -*2 CH(COOCH₃)—C₆H₄-4-CH₃ | isomer (A) 148 isomer (B) I.R. ν cm⁻(CHCl₃): 1755, 1745, 1675 |
| 63 | " | 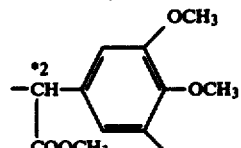 -*2 CH(COOCH₃)—C₆H₂-3,4,5-(OCH₃)₃ | isomer (A) 138–140 isomer (B) N.M.R. δ ppm(CDCl₃): 3.54(2H, m), 3.59(2H,s), 3.73(3H,s), 3.82(9H,s), 4.96(1H,m), 5.45(1H,s), 6.13(1H,d,J=9Hz), 6.43(2H,s), 7.10–7.45(5H,m) |
| 64 | " | 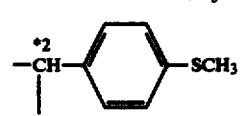 -*2 CH(COOCH₃)—C₆H₄-4-SCH₃ | isomer (A) 115–117 isomer (B) 157–159 |
| 65 | " | 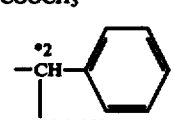 -*2 CH(COOCH₃)—C₆H₅ | isomer (A) 138–140 isomer (B) I.R. ν cm⁻¹(CHCl₃): 1770, 1745, 1678 |
| 66 | " | —CH₂COOC₂H₅ | 104–105 |
| 67 | " | —CH₂COOCH₂—C₆H₅ 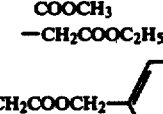 | 114–115 |
| 68 | " | 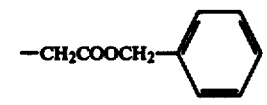 -*2 CH(COOCH₂C₆H₅)—C₆H₅ | isomer (A) 96–98 isomer (B) I.R. ν cm⁻¹(CHCl₃): 1760, 1740(s), 1678 |
| 69 | " | —CH₂CN | 175–179 |
| 70 | NC—C(=NOH)—CONH— 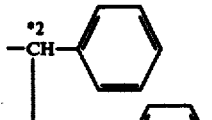 | —CH(COOH)—C₆H₄-4-OH 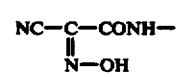 | (sodium salt) 240–245 |
| 71 | 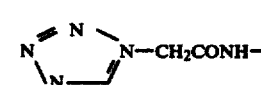 tetrazol-N—CH₂CONH— | " | 177–181 |
| 72 | H₂NCH₂CONH— | " | I.R. ν cm⁻¹(Nujol): 1730, 1665, 1610 |
| 73 | 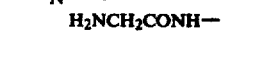 O(CH₂CH₂)₂N—CH₂CONH— | " | 201–203 |
| 74 | 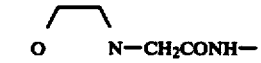 C₆H₅N(CH₃)CH₂CONH— | " | 198–199 |
| 75 | (CH₃)₃CCONH— | " | 187–188 |

-continued

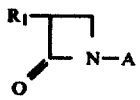
(I)

| Example | R₁ (note 1) | A | mp (°C.) (dec.) (note 2) |
|---|---|---|---|
| 76 | *1 phenyl-CHCONH— with NH₂ | " | 193-196 |
| 77 | phenyl-CHCH₂CONH— with NH₂ | " | 179-185 |
| 78 | H₂N—phenyl—CONH— | " | 190-194 |
| 79 | phenyl-CHCONH— with NH-phenyl | " | 97-101 |
| 80 | phenyl-CH₂NCH₂CONH— with CH₃ | " | 154-157 |
| 81 | naphthyl-NHCH₂CONH— | " | 182-185 |
| 82 | (oxo-pyrrolidinyl)-NHCONH— | " | 189-198 |

EXAMPLE 83

A mixture of N,N-dimethylforamide (320 mg.) and thionyl chloride (780 mg.) was heated for 30 minutes at 40° to 50° C., and the excess of the thionyl chloride was distilled off from the mixture, and the residue obtained was suspended in methylene chloride (10 ml.) To the suspension was added 4-hydroxyphenylglyoxylic acid (370 mg.) under cooling at −15° to −20° C., and the mixture was stirred for 15 minutes. After the reaction temperature of the mixture was elevated to −5° to −10° C., the mixture was stirred for 10 minutes to obtain a clear solution containing 4-hydroxyphenylglyoxyloyl chloride. Subsequently, the solution was cooled to −45° to −50° C., and to the solution was added dropwise a solution of triethylamine (440 mg.) and methylene chloride (2 ml.) during 5 minutes, and then the reaction mixture was stirred for 30 minutes. A solution, prepared by subjecting 3-aminolactacillanic acid (470 mg.) and N,O-bis(trimethylsilyl)acetamide (1.2 g.) to a dissolution in dried methylene chloride (10 ml.) at room temperature for 1 hour while stirring was added all at once to the solution, keeping the temperature at −45° to −50° C. The reaction mixture was stirred for 30 minutes, and then stirred for 1.5 hrs., elevating the reaction temperature to room temperature slowly after removing the cooling bath. The methylene chloride was distilled off from the reaction mixture, and the residue obtained was dissolved in 5% sodium bicarbonate aqueous solution (20 ml.). The solution was washed with ethyl acetate (10 ml.) twice, and ethyl acetate (50 ml.) was added to the solution, whereafter the aqueous layer was adjusted to pH 1 with 5% hydrochloric acid while shaking enough. The ethyl acetate layer was separated out, and the aqueous layer was extracted with ethyl acetate (20 ml.) twice. The ethyl acetate layers were combined, washed with a sodium chloride-saturated-aqueous solution and dried over anhydrous magnesium sulfate. The solvent was distilled off from the solution to give crude crystals of 3-(4-hydroxyphenylglyoxyloylamino)lactacillanic acid (460 mg.). This product (760 mg.) prepared by the same manner as mentioned above was dissolved in ethyl acetate (3 ml.), and the solution was subjected to column chromatography using silica.gel. The fractions containing the object compound were collected by eluting with ethyl acetate. The residue, obtained by distilling off the solvent from the eluate, was dissolved in acetone, and then an acetone solution of sodium 2-ethylhexanoate was added to the solution to give the solution of the sodium salt of the object compound, and then the acetone was distilled off from the solution. The residue was powdered by adding ether, and the powder was collected by filtration and washed with acetone to give 3-(4-hydroxyphenylglyoxyloylamino)lactacillanic acid sodium salt (170 mg.). Mp 220° to 225° C. The following compounds were obtained in substantially the similar manner described above.

methylene chloride (10 ml.). The mixed solution was reacted for 1 hour to prepare a mixed acid anhydride solution with 4-methoxyphenylglyoxylic acid and pivalic acid. On the other hand, N,O-bis(trimethylsilyl)acetamide (2.3 g.) was added to a suspension prepared by suspending 3-aminolactacillanic acid (0.680 g.) in methylene chloride (10 ml.), and the suspension was

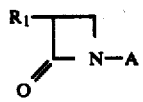
(I)

| Example | $R_1$ | A | mp (°C.) (dec.) |
|---|---|---|---|
| 84 | ⟨S⟩-CH(OH)CONH— | —CH(COOH)—C6H4—OH | 187–191 |
| 85 | ⟨S⟩-COCONH— | " | 203–204 |
| 86 | CH3COCONH— | " | 162–166 |
| 87 | CH3OOCCH2O—C6H4—COCONH— | " | (sodium salt) I.R. ν cm$^{-1}$(Nujol): 1735, 1655, 1595 |
| 88 | CH2=CHCH2O—C6H4—COCONH— | " | 151–157 |

EXAMPLE 89

Sodium bicarbonate (0.453 g.) was dissolved in water (10 ml.), and the solution was cooled to 5° C. To the solution was added 3-aminolactacillanic acid (0.427 g.), and then acetone (10 ml.) was added to the solution. To the solution was added dropwise an acetone (5 ml.) solution of butyric acid anhydride (0.38 g.) for 5 minutes. Sodium bicarbonate (0.04 g.) was added to the reaction mixture and then stirred for 1.5 hrs. at 5° C. The acetone was distilled off from the reaction mixture, and the aqueous layer was washed with ether, and then adjusted to pH 1 to 2 with 10% hydrochloric acid. The aqueous layer was extracted with ethyl acetate (30 ml.) twice respectively. The extracts were combined, washed with water (50 ml.) and then washed with a sodium chloride-saturated-aqueous solution, and dried over anhydrous magnesium sulfate. The solvent was concentrated to give crystals of 3-butyramidolactacillanic acid (112 mg.). Mp 178° to 178.5° C. (dec.).

EXAMPLE 90

Pivaloyl chloride (0.350 g.) was dissolved in methylene chloride (15 ml.) and to the solution was added a solution prepared by dissolving 4-methoxyphenylglyoxylic acid (0.520 g.) and triethylamine (0.290 g.) in stirred for 1 hour at ambient temperature. To the solution obtained was added the mixed acid anhydride solution obtained above, and the reaction mixture was reacted for 2 hrs., keeping the reaction temperature at −10° to −15° C. The methylene chloride was distilled off from the reaction mixture, and the residue obtained was dissolved in ethyl acetate. The solution was washed with 5% hydrochloric acid and a sodium chloride-saturated-aqueous solution, respectively, and then dried over anhydrous magnesium sulfate. The solvent was distilled off from the solution, and diisopropyl ether (about 30 ml.) was added to the residue, and then the mixture was stirred for 1 hour. The precipitating material obtained was collected by filtration to give the powder (1.14 g.). This powder was dissolved in ethyl acetate (30 ml.), and the solution was treated with an activated carbon (0.11 g.) and filtered. The filtrate was concentrated to the volume of about 2 ml., and crystals were obtained by scrubbing the wall of the vessel containing the solution. The crystals were collected by filtration and recrystallized from a small amount of ethyl acetate to give crystals of 3-(4-methoxyphenylglyoxyloylamino)lactacillanic acid (0.16 g.). Mp 178° to 181° C. (dec.). The following compounds were obtained in substantially the similar manner as described above.

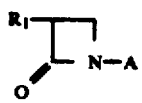

| Example | R₁ (note 1) | A | mp (°C.) (dec.) |
|---|---|---|---|
| 91 | CH₃OOCCH(CH₂)₂O—C₆H₄—CHCONH— with NHCOCH₃ on first CH and NHCOCH₃ on second CH | —CH(COOCH₃)—C₆H₄—OCH₃ | I.R. ν cm⁻¹ (CHCl₃): 1745, 1667 |
| 92 | thiophene-2-yl—CHCONH— with NHCOCH₂CH₂—C₆H₅ | —CH(COOH)—C₆H₄—OH | (sodium salt) 224–227 |
| 93 | HO—C₆H₄—CHCONH— with NHCOOCH₂—C₆H₅ | " | I.R. ν cm⁻¹ (Nujol): 1760, 1730, 1680 |
| 94 | HO—C₆H₄—CH₂CONH— | " | 171–176 |
| 95 | C₆H₅—COCH₂CH₂CONH— | " | 157–161 |
| 96 | CH₃OOCCH(CH₂)₂—O—C₆H₄—C(=NOCH₃)—CONH— with NHCOCH₃ | —CH(COOCH₃)—C₆H₄—OCH₃ | N.M.R. δ ppm(CDCl₃): 1.95(3H,s), 2.25(2H,m), 3.15(1H,d,d,J=3Hz, 6Hz), 3.70(3H,s), 3.74(3H,s), 3.78(3H,s), 3.89(3H,s), 3.96 (2H,t,J=6Hz), 4.70(1H,q,O=8Hz), 4.92(1H,m), 5.52(1H,s), 6.75 (2H,d,J=9Hz), 6.86(2H,d,J=9Hz), 7.20(2H,d,J=9Hz), 7.45(2H,d, J=9Hz) |
| 97 | CH₃OOCCH(CH₂)₂—O—C₆H₄—C(=NOCH₃)—CONH— with phthalimido N | " | N.M.R. δ ppm(CDCl₃):2.70(2H,m), 8.15(1H,d,d,J=3HHz,6Hz), 3.7(1H, m), 3.75(6H,s), 3.78(3M,s), 3.88(3H,s), 3.94(2H,m), 5.05 (1H,m), 5.16(1H,t,J=6Hz), 5.56(1H,s), 6.62(2H,d,J=9Hz), 6.84(2H,d,J=9Hz), 7.20(2H, d,J=9Hz), 7.38(2H,d,J=9Hz), 7.74(4H,m) |
| 98 | HOCH₂—C₆H₄—OCH₂CONH— | —CH(COOH)—C₆H₄—OH | 182–185 |
| 99 | Cl—C₆H₃(NO₂)—OCH₂CONHCH₂CONH— | " | 149–153 |
| 100 | HO—N=CH—C₆H₄—OCH₂CONH— | " | 150–155 |
| 101 | C₆H₅—N(COCH₂N₃)—CH₂CONH— | " | 176–180 |

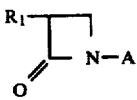

| Example | R₁ (note 1) | A | mp (°C.) (dec.) |
|---|---|---|---|
| 102 | (2-pyridyl-N-oxide)-SCH₂CONH— | " | 221–225 |
| 103 | (1,3,4-thiadiazol-2-yl)-SCH₂CONH— | " | 163–167 |
| 104 | C₂H₅O-C₆H₄-CH=N-OCH₂CONH— | " | 130–135 |
| 105 | (benzotriazol-1-yl)-O-CH₂CONH— | " | 179–181 |
| 106 | C₆H₅-CH₂OOCNHCH₂CONH— | " | (sodium salt) I.R. ν cm⁻¹ (Nujol): 1740, 1675, 1610 |
| 107 | (thieno-triazolyl)-CH₂CONH— | " | 197.5–198 |
| 108 | CH₃SCH=CHCON— | " | 174–177 |

EXAMPLE 109

3-Aminolactacillanic acid (0.944 g.) was suspended in dried methylene chloride (60 ml.), and to the suspension were added N,O-bis(trimethylsilyl)acetamide (7.0 g.) and N,N-dimethylformamide (0.7 ml.), whereafter the mixture was stirred for 2 hrs. at ambient temperature. On the other hand, to a dried methylene chloride (30 ml.) solution of ethyl chloroformate (0.523 g.) was added dropwise a dried methylene chloride (30 ml.) solution of N-benzyloxycarbonyl-2-(2-thienyl)glycine (1.40 g.) and triethylamine (0.485 g.) during 7 minutes under cooling at −5° to −10° C., and then the mixture was stirred at the same temperature for 20 minutes to prepare a mixed acid anhydride solution. To this solution was added dropwise the solution obtained above during 20 minutes, and then the reaction mixture was stirred for 3 hrs. at the same temperature, and the reaction temperature was slowly elevated to room temperature during 2 hrs. while stirring. The reaction mixture was washed with diluted hydrochloric acid and water, respectively, and then dried. The solution was concentrated to give crystals of 3-[2-(2-thienyl)-N-benzyloxycarbonylglycinamido]lactacillanic acid (1.40 g.).

I.R. absorption spectrum, $\nu_{cm-1}$ (liquid film): 1730, 1710, 1650.

The following compound was obtained in substantially the similar manner as described above.

| Example | R₁ | A | I.R. |
|---|---|---|---|
| 110 | C₆H₅-CH₂OOC-N(CH₃)-CH₂CONH- | -CH(COOH)-C₆H₄-OH | I.R. ν cm⁻¹ (liquid film): 1740, 1710, 1690, 1650 |

EXAMPLE 111

2-(4-Methoxyphenyl)-2-methoxyiminoacetic acid (500 mg.) and N,N'-dicyclohexylcarbodiimide (495 mg.) were dissolved in a mixture of chloroform (9 ml.) and dioxane (3 ml.), and the solution was stirred for 1.5 hrs. under ice-cooling. To the solution was added all at once a solution, prepared by dissolving 3-aminolactacillanic acid (472 mg.) and N,O-bis(trimethylsilyl)acetamide (1.22 g.) in chloroform (10 ml.), and then the reaction mixture was stirred for 4 hrs. at ambient temperature. The solvent was distilled off from the reaction mixture, and to the residue were added a sodium bicarbonate aqueous solution and ethyl acetate. After stirring the mixture, the aqueous layer was separated out, adjusted to pH 1 to 2 with 10% hydrochloric acid and then extracted with ethyl acetate. The extract was washed with water and then dried. The solvent was distilled off from the extract, and ether was added to the residue to give crude crystals. The crystals were collected by filtration and washed with ether to give crystals of 3-[2-(4-methoxyphenyl)2-methoxyiminoacetamido]lactacillanic acid (150 mg.). Mp 157° to 161° C. (dec.).

The following compound was obtained in substantially the similar manner as described above.

The following compounds were obtained in substantially the similar manner as described above.

| Example | R₁ | A | mp(°C.) (dec.) |
|---|---|---|---|
| 114 | phenyl-CH(OH)-CHCONH- | -CH(COOH)-C₆H₄-OH | 180–183 |
| 115 | phthalimido (benzene-1,2-dicarboximido) | " | 196–199 |

| Example | R₁ | A | I.R. |
|---|---|---|---|
| 112 | *1 thienyl-CH(NHCOCH₂O-C₆H₃(Cl)(NO₂))-CHCONH- | -CH(COOH)-C₆H₄-OH | (sodium salt) νcm⁻¹(Nujol): 1730, 1660, 1610 |

EXAMPLE 113

3-Aminolactacillanic acid (0.472 g.) was suspended in methylene chloride (10 ml.), and to the suspension was added N,O-bis(trimethylsilyl)acetamide (1.22 g.) at ambient temperature, and then the solution was cooled to −15° C. To the solution was added dropwise during 25 minutes a methylene chloride (10 ml.) solution of triethylammonium salt of acid anhydride (935 mg.) prepared from 2-phenyl-2-sulfoacetic acid and ethyl chloroformate, and the reaction mixture was stirred for 1 hour at the same temperature and further for 1.5 hrs. at ambient temperature. Water (50 ml.) was added to the reaction mixture and then the aqueous layer was separated out. The aqueous layer was washed with ethyl acetate and adjusted to pH 5 to 6 with an aqueous solution of sodium bicarbonate, and then the solution was filtered. The filtrate was concentrated, and the residue obtained was adsorbed on a column packed with nonionic adsorption resin, Amberlite XAD-4 (trade mark, maker: Rohm and Haas Co., Ltd.) (20 ml.), which had been treated in advance with methanol, and the object compound was eluted with water. The eluate was concentrated under reduced pressure, and ethanol was added to the eluate, whereafter the solvent was distilled off from the eluate under reduced pressure. Ethanol was added to the residue to give crystals. The crystals were collected by filtration to give crystals of 3-(2-phenyl-2-sulfoacetamido)lactacillanic acid (120 mg.). Further, the filtrate was concentrated, and the oily material obtained was treated with acetone to give powdery crystals of 3-(2-phenyl-2-sulfoacetamido)]lactacillanic acid disodium salt (0.45 g.). Mp 144° to 152° C.

EXAMPLE 116

2-(Benzo[d]isoxazol-3-yl)-N-benzyloxycarbonylglycine (652 mg.) and triethylamine (202 mg.) were dissolved in dried tetrahydrofuran (8 ml.). To the solution was added 1H-6-chloro-1-(4-chlorobenzenesulfonyloxy)benzotriazole (690 mg.) while stirring under ice-cooling, and then the solution was stirred at the same temperature for 3 hrs. Keeping the solution under ice-cooling, a solution, prepared by dissolving 3-aminolactacillanic acid (472 mg.) and triethylamine (202 mg.) in a mixed solution of acetone and water (1:1) (10 ml.), was added to the solution. The reaction mixture was stirred for 1 hour, and then the solvent was distilled off from the reaction mixture. To the residue obtained was added water (20 ml.), whereafter ethyl acetate was added to the solution and then the solution was acidified by adding dropwise 1 N-hydrochloric acid while shaking. Ethyl acetate layer was separated out, whereafter the aqueous layer was subjected to extraction with ethyl acetate, and the ethyl acetate extracts were combined. The extract was washed with water and then dried over anhydrous magnesium sulfate. The solvent was distilled off from the solution to obtain the residue (1.2 g.). The residue was subjected to column chromatography using silica gel and elution was conducted with ethyl acetate containing 10% methanol (500 ml.) to obtain the fractions containing the object compound. The residue obtained by concentrating the eluate was treated with ether to give crystals of 3-[2-(benzo[d]isoxazol-3-yl)-N-benzyloxycarbonylglycinamido]lactacillanic acid (180 mg.). Mp 159° to 168° C.

The following compound was obtained in substantially the similar manner as described above.

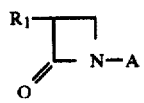

| Example | R₁ (note 1) | A | mp (° C.) (dec.) |
|---|---|---|---|
| 117 | indol-3-yl-CH₂CH(*1)CONH—, NHCOOCH₂-phenyl | —CH(COOH)—C₆H₄—OH | 235–240 |

EXAMPLE 118

3-Aminolactacillanic acid (0.472 g.) was suspended in water (20 ml.), and to the suspension was added sodium bicarbonate (0.420 g.). Acetone (20 ml.) was added to the solution, and the solution was cooled at 0° to 5° C. To the solution was added dropwise an acetone (2 ml.) solution containing phenyl isocyanate (0.286 g.), and then the solution was stirred for 2.5 hrs. at the same temperature. The acetone was distilled off from the reaction mixture, and then the residue obtained was filtered to remove insoluble materials.

The aqueous solution obtained was washed with ethyl acetate, and then adjusted to pH 1 with 10% hydrochloric acid, whereafter, extraction was conducted with ethyl acetate. The ethyl acetate layer obtained was washed with water and then dried over anhydrous magnesium sulfate. The solvent was distilled off from the solution to give the crystalline residue. The residue was washed with diisopropyl ether and collected by filtration to give crystals of 3-(N'-phenylureido)lactacillanic acid (0.470 g.). Mp 167° to 172° C.

EXAMPLE 119

Guanidinocarbohydrazide dihydrochloride (0.38 g.) was dissolved in water (2 ml.), and to the solution was added sodium nitrite (0.14 g.) under cooling at 0° to 5° C., and then the solution was stirred for 15 minutes to prepare a solution of guanidinocarbonylazide. On the other hand, 3-aminoactacillanic acid (0.240 g.) was suspended in water (7 ml.), and to the suspension was added sodium bicarbonate (0.170 g.). The aqueous solution was cooled to 0° to 5° C., and to the solution was added dropwise the solution of guanidinocarbonylazide prepared above during 10 minutes, and then the reaction mixture was stirred for 2 hrs. The reaction mixture was washed with ethyl acetate (10 ml.) and concentrated until the remaining solution became transparent, and then the ethyl acetate saturated in the aqueous layer was distilled off completely to precipitate crystals. The solution containing the crystals was allowed to stand for a while and the crystals were collected by filtration to give crystals of 3-(guanidinocarbonamido)lactacillanic acid (0.15 g.). Mp 206° to 210° C.

EXAMPLE 120

A solution containing 2-phenyl-N-(2,2,2-trichloroethoxycarbonyl)glycine (1.42 g.) and thionyl chloride (15 ml.) was heated for 1 hour under reflux. The excess of the thionyl chloride was distilled off from the solution under reduced pressure, and the residue obtained was dissolved in acetone. To the solution was added dropwise a solution containing 3-aminolactacillanic acid (1.0 g.), sodium bicarbonate (0.9 g.), water (40 ml.) and acetone (40 ml.) under cooling at 0° to 5° C. The acetone was distilled off from the reaction mixture under reduced pressure, and the remaining solution was washed with ethyl acetate. The solution was adjusted to pH 1 to 2 with 10% hydrochloric acid, and then extracted with ethyl acetate. The ethyl acetate layer was separated out and dried over anhydrous magnesium sulfate. The solvent was distilled off from the ethyl acetate solution, and the residue (2.1 g.) obtained was dissolved in ether. The ether solution was concentrated to give a residue. The residue was washed with diisopropyl ether to give crystals of 3-[2-phenyl-N-(2,2,2-trichloroethoxycarbonyl)glycinamido]lactacillanic acid (1.69 g.). Mp 130° to 132° C. (dec.).

The following compounds were obtained in substantially the similar manner as described above.

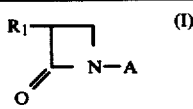

| Example | R₁ | A | mp(°C.) (dec.) |
|---|---|---|---|
| 121 | O₂N—C₆H₄—CH₂CONH— | —CH(COOH)—C₆H₄—OH | 234–236 |
| 122 | (CH₃)₃C-C₆H₂—OCH₂CONH— | " | 106–109 |

-continued

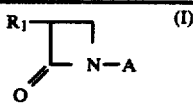

| Example | R₁ | A | mp(°C.) (dec.) |
|---|---|---|---|
| 123 | [thiophene-CH(phenyl)-CHCONH–] | " | 139–143 |
| 124 | [phenyl-CH(COOH)-CHCONH–] | " | (disodium salt) 209–214 |
| 125 | [2-NO₂-phenyl-OCH₂CONH–] | " | (sodium salt) 116 |
| 126 | [phenyl-CH₂CONH–] | –CH(CH(CH₃)CH₃)COOH | 106–109 |
| 127 | " | –CH(COOCH₃)-(3-Br-4-OH-phenyl) | 151–153 |
| 128 | " | –CH(COOH)-(3,5-diBr-4-OH-phenyl) | 161–162 |
| 129 | [phenyl-OCH₂CONH–] | –C(COOCH₃)=C(CH₃)CH₃ | 155.5–156.5 |
| 130 | [thiophene-CH₂CONH–] | –CH(COOCH₃)-(2,5-diCl-4-OH-phenyl) | I.R. νcm⁻¹(liquid film) 3270, 1760 1735, 1665 |

EXAMPLE 131

3-Aminolactacillanic acid (700 mg.) was suspended in dried methylene chloride (15 ml.), and to the suspension was added N,O-bis(trimethylsilyl)acetamide (3.6 g.), and then the mixture was stirred for 3 hrs. The solution was cooled to −50° to −40° C., and to the solution was added all at once 2-(2-pyridyloxy)acetyl chloride hydrochloride (630 mg.), and the reaction mixture was stirred for 20 minutes at the same temperature. Elevating slowly the reaction temperature to −10° C. during 40 minutes, the reaction mixture was stirred for 1 hour at the same temperature and further for 1 hour under ice-cooling. The methylene chloride was distilled off from the reaction mixture, and to the residue was added a solution containing 5% sodium bicarbonate aqueous solution (25 ml.) and ethyl acetate (30 ml.). The aqueous layer was separated out, and then washed with ethyl acetate. The aqueous layer was adjusted to pH 3 with 10% hydrochloric acid under ice-cooling, and then the aqueous solution was extracted with ethyl acetate. The ethyl acetate layer was separated out, and the remaining aqueous layer was adjusted to pH 1 to 2 with 10% hydrochloric acid, and then the aqueous solution was extracted with ethyl acetate several times. These ethyl acetate layers and the ethyl acetate layer obtained above were combined, and the solution was washed with a sodium chloride-saturated-aqueous solution, and then dried over anhydrous magnesium sulfate. The solvent was distilled off from the ethyl acetate solution, and the residue (330 mg.) obtained was powdered with ether. The powder was washed with acetone to give crystals of 3-[2-(2-pyridyloxy)acetamido]lactacillanic acid (130 mg.). Mp 192.5° to 193° C. (dec.).

EXAMPLE 132

A mixture of N,N-dimethylformamide (292 mg.) and thionyl chloride (710 mg.) was heated for 30 minutes at 50° C. The excess of the thionyl chloride was distilled off from the mixture to give a residue. The residue was washed with ether. Methylene chloride (7 ml.) was added to the residue and then the solution was cooled to 0° to 5° C., whereafter a solution prepared by dissolving 2-(5,6-dihydro-2H-pyran-3-yl)glycolic acid (455 mg.) in methylene chloride (5 ml.), was added dropwise to the solution. To the reaction mixture was added dropwise a methylene chloride (5 ml.) solution of triethylamine (600 mg.) during 10 minutes under cooling at −50° C., and the solution was stirred for 30 minutes at the same temperature. The solution was added all at once to a mixture of 3-aminolactacillanic acid (472 mg.), N,O-bis-(trimethylsilyl)acetamide (1.22 g.) and methylene chloride, which had been stirred for 2 hrs. at room temperature previously. The reaction mixture was stirred for 2 hrs. at −50° C., and further stirred for 2 hrs., elevating slowly the reaction temperature to 0° C. The solvent was distilled off from the reaction mixture, and to the remaining solution were added a sodium bicarbonate aqueous solution and ethyl acetate. The aqueous layer obtained was adjusted to pH 1 to 2 with 10% hydrochloric acid, and then the solution was extracted with ethyl acetate. The extract was washed with water, and dried over anhydrous magnesium sulfate, and then the solvent was distilled off from the extract to give crystals of 3-[2-(5,6-dihydro-2H-pyran-3-yl)glycolamido]lactacillanic acid (80 mg.).

I.R. absorption spectrum, $\nu_{cm^{-1}}$ (Nujol): 1740, 1685, 1660.

EXAMPLE 133

To the solution of methylene chloride (10 ml.) containing ethyl chloroformate (216 mg.) was added dropwise a mixture of 2-(2-bromoacetamido)-2-phenylacetic acid (576 mg.), triethylamine (200 mg.), N,N-dimethylbenzylamine (one drop) and methylene chloride (8 ml.) under cooling at −30° C., and then the reaction mixture was stirred for 30 minutes at the same temperature. A mixture of 3-aminolactacillanic acid (472 mg.), N,O-bis(trimethylsilyl)acetamide (1.2 g.), methylene chloride (10 ml.) and N,N-dimethylformamide (1 ml.), which had been stirred for a while at room temperature and cooled to 0° C. was added all at once to the reaction mixture, keeping the temperature of the reaction mixture at −30° C. The reaction mixture was stirred for 2 hrs. at −25° C. and then stirred for 1 hour, elevating slowly the reaction temperature to 0° C. The reaction mixture was concentrated, and to the residue obtained were added ethyl acetate and water. And then the mixture was adjusted to pH 1 to 2 with 10% hydrochloric acid. The ethyl acetate layer was separated out, washed with water, dried over anhydrous magnesium sulfate and then concentrated. The residue obtained was washed with diisopropyl ether, and then powdered with ethyl acetate to give 3-[2-(2-bromoacetamido)-2-phenylacetamido]lactacillanic acid (400 mg.). Further, the same compound (188 mg.) was recovered from the mother liquor. Total yield was 588 mg. Mp 156° to 161° C. (dec.).

The following compounds were obtained in substantially the similar manner as described above.

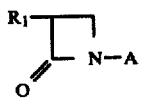

(I)

| Example | $R_1$ | A | mp (°C.) (dec.) |
|---|---|---|---|
| 134 | ![phenyl]-C(=N-OCH₂CONH-)-COOC₂H₅ | -CH(COOH)-C₆H₄-OH | (sodium salt) 157-160 |
| 135 | ![phenyl]-CH(CONH-C₆H₅)-CONH- | " | (sodium salt) 183-187 |
| 136 | ![phenyl]-CH(COOC₂H₅)-CONH- | " | 103-107 |
| 137 | (5,6-dihydro-2H-pyran-3-yl)-CH(NHCOCH₂Cl)-CONH- | " | 211-217 |
| 138 | ![phenyl]-CH(S(=O)-CH₃)-CONH- | " | I.R. $\nu$ cm$^{-1}$ (Nujol) 1740, 1720, 1665 |

| Example | R₁ | A | mp (°C.) (dec.) |
|---|---|---|---|
| 139 | ![phenyl-CHCONH- with NHCOCH2O-C6H3(Cl)(NO2)] | " | 77-81 |
| 140 | ![thienyl-CHCONH- with NHCOCH2Br] | " | 147-150 |

EXAMPLE 141

A mixture of N-phenylimidinodiacetic acid (537 mg.), N,N'-dicyclohexylcarbodiimide (495 mg.), chloroform (9 ml.) and dioxane (3 ml.) was stirred for 1.5 hrs. under ice-cooling. The insoluble materials were filtered off from the solution, and to the filtrate was added all at once a mixture of 3-aminolactacillanic acid (472 mg.), methylene chloride (10 ml.) and N,O-bis(trimethylsilyl)acetamide (1.2 g.), and then the reaction mixture was stirred for 4 hrs. at room temperature. The solvent was distilled off from the reaction mixture, and the residue was dissolved in ethyl acetate, and to the solution was added a sodium bicarbonate aqueous solution. The mixture was adjusted to pH 4.0 with 10% hydrochloric acid, and the ethyl acetate layer was separated out. The remainded aqueous layer was adjusted to pH 1 to 3 with 10% hydrochloric acid, and the aqueous solution was extracted with ethyl acetate. The ethyl acetate layers were combined, washed with water and dried, and then the solvent was distilled off from the solution to give crystals of 3-(N-carboxymethyl-N-phenylglycinamido)-lactacillanic acid (260 mg.). Mp 142.5° to 145° C. (dec.).

EXAMPLE 142

A solution, prepared by dissolving 2-[4-(3-bromopropoxy)phenyl]acetic acid (300 mg.) and thionyl chloride (300 mg.) in chloroform (2 ml.), was heated for 2 hrs. under reflux. The solvent and the excess of the thionyl chloride were distilled off from the solution and the residue obtained was dissolved in dried acetone (1 ml.). The solution was added dropwise to a solution, prepared by dissolving 3-aminolactacillanic acid (240 mg.) and sodium bicarbonate (210 mg.) in a mixture of water (10 ml.) and acetone (10 ml.), under cooling at 0° to 5° C. while stirring. The reaction mixture was stirred for 45 minutes at the same temperature. The acetone was distilled off from the reaction mixture, and to the remaining aqueous layer was added ethyl acetate (30 ml.). The mixture was adjusted to pH 1 with 10% hydrochloric acid. The ethyl acetate layer was separated out, and then the aqueous layer was extracted with ethyl acetate (20 ml.). The ethyl acetate layers were combined and washed with a sodium chloride-saturated-aqueous solution, and then dried over anhydrous magnesium sulfate. The solvent was distilled off from the solution, and the residue (510 mg.) obtained was washed with ether to give crystals of 3-[2-{4-(3-bromopropoxy)phenyl}acetamido]lactacillanic acid (420 mg.). Mp 120° to 123° C. (dec.).

The following compounds were obtained in substantially the similar manner as described above.

| Example | R₁ | A | mp(°C.) (dec.) |
|---|---|---|---|
| 143 | ![phenyl-SO3CH2CONH-] | -CH(COOH)-C6H4-OH | 142.5-144 |
| 144 | N₃(CH₂)₃O-C6H4-CH₂CONH- | " | 113-116 |
| 145 | ![phenyl-isoxazolinone-N-CH2CONH-] | " | 128-132 |

-continued

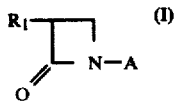

| Example | R₁ | A | mp(°C.) (dec.) |
|---|---|---|---|
| 146 | C₆H₅-CH₂OOC—NH(CH₂)₃-C₆H₄-OCH₂CONH— | " | 142–146 |
| 147 | C₆H₅-CHCONH— with NH—C(=N)—O—N=C-C₆H₅ ring | " | I.R. νcm⁻¹(Nujol): 1738, 1680, 1618 |

EXAMPLE 148

A mixture of 3-aminolactacillanic acid (472 mg.), N,O-bis(trimethylsilyl)acetamide (1.2 g.), methylene chloride (10 ml.) and N,N-dimethylformamide (1 ml.) was stirred for 1 hour at room temperature. The solution was cooled to 0° to 5° C., and to the solution was added dropwise a methylene chloride (3 ml.) solution containing hexadecanoyl chloride (548 mg.), whereafter the reaction mixture was reacted for 1.5 hrs. at the same temperature and further for 30 minutes at ambient temperature. The reaction mixture was concentrated, and to the remaining solution were added ethyl acetate and water, and then the mixture was adjusted to pH 1 to 2 with 10% hydrochloric acid. The ethyl acetate separated out was washed with water and then dried over anhydrous magnesium sulfate. The solution was concentrated to give crude 3-hexadecanoylaminolactacillanic acid (0.95 g.). Futhermore, the product (600 mg.) was subjected to column chromatography using silica-gel and elution was conducted with ethyl acetate. The solvent was distilled off from the eluate to give the purified object compound (110 mg.). Mp 157° to 161° C. (dec.).

EXAMPLE 149

To a solution of 2-[N-(2-thenylidene)aminooxy]-2-phenylacetic acid (400 mg.), triethyl amine (155 mg.) and tetrahydrofuran (10 ml.) was added dropwise a solution, prepared by dissolving pivaloyl chloride (184 mg.) in tetrahydrofuran (3 ml.), during 5 minutes under cooling at −2° to 0° C., and the mixture was stirred for 30 minutes. The solution was added all at once to a solution of 3-aminolactacillanic acid (320 mg.), N,O-bis(trimethylsilyl)acetamide (825 mg.) and methylene chloride (10 ml.) under cooling at −30° C., and the reaction mixture was reacted for 2.5 hrs., elevating slowly the reaction temperature to 10° C. The solvent was distilled off from the reaction mixture, and to the remaining solution were added a sodium bicarbonate aqueous solution and ethyl acetate. The aqueous layer separated out was adjusted to pH 1 to 2 with 10% hydrochloric acid and then extracted with ethyl acetate. The extract was washed with water and dried, and then the solvent was distilled off from the solution to give residues (300 mg.). The residues were dissolved in acetone and then sodium 2-ethylhexanoate was added to the solution to give crystals of 3-[2-{N-(2-thenylidene)aminooxy}-2-phenylacetamido]lactacillanic acid sodium salt (160 mg.).

I.R. absorption spectrum, ν$_{cm-1}$ (Nujol): 1730, 1650, 1600.

EXAMPLE 150

3-Aminolactacillanic acid (355 mg.), N,O-bis(trimethylsilyl)acetamide (0.92 g.) and N,N-dimethylformamide (0.23 ml.) were added to methylene chloride (7 ml.), and the solution was stirred for 2 hrs. at room temperature. On the other hand, 2-(2-nitrophenoxy)-2-phenoxyacetic acid (380 mg.), triethylamine (132 mg.) and N,N-dimethylbenzylamine (2 drops) were dissolved in methylene chloride (10 ml.), and the solution was cooled to −30° C. To the solution was added dropwise ethyl chloroformate (141 mg.), and the mixture was stirred for 40 minutes at the same temperature. To this solution was added the solution prepared above quickly, and the reaction mixture was stirred for 5.5 hrs. at −40° to −20° C. The solvent was distilled off from the reaction mixture under reduced pressure, and into the residue were poured ethyl acetate and a sodium bicarbonate aqueous solution. The aqueous layer separated out was adjusted to pH 1 to 2 with 10% hydrochloric acid, and then the mixture was extracted with ethyl acetate. The extract was washed with a sodium bicarbonate-saturated-aqueous solution and dried over anhydrous magnesium sulfate, and then the solvent was distilled off from the solution. The residue (540 mg.) obtained was dissolved in a small amount of acetone and sodium 2-ethylhexanoate was added to the solution. To the solution was added ether, and the precipitating crystals were collected by filtration and washed with a mixed solvent of ether and acetone to give crystals of 3-[2-(2-nitrophenoxy)-2-phenoxyacetamido]lactacillanic acid sodium salt (380 mg.). Mp 169° to 172° C. (dec.).

The following compounds were obtained in substantially the similar manner as described above.

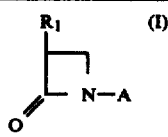
| Example | R₁ | A | mp(°C.) (dec.) |
|---|---|---|---|
| 151 | C₆H₅-CH(NHCOC₆H₅)-CONH- | -CH(COOH)-C₆H₄-OH (p) | 143–146 |
| 152 | C₆H₅-CH[CONH(CH₂)₂NHCOCH₂C₆H₅]-CONH- | " | 115–118 |
| 153 | C₆H₅-COCH₂SCH₂CONH- | " | 130–135 |
| 154 | C₆H₅-CH[NHCO(CH₂)₅NHCOOCH₂C₆H₅]-CONH- | " | 111–116 |
| 155 | C₆H₅-CH(NHCOCH₂-2-thienyl)-CONH- | " | (sodium salt) 221–224 |
| 156 | C₆H₅-CH(NHCOCH₂S-2-pyridyl N-oxide)-CONH- | " | 160–164 |
| 157 | C₆H₅-CH[NHCOCH(C₆H₅)O-2-Cl-C₆H₄]-CONH- | " | 112–116 |
| 158 | 3-(2-Cl-C₆H₄)-5-CH₃-isoxazol-4-yl-CONHCH(C₆H₅)CONH- | " | 122–124 |
| 159 | C₆H₅-CH[S(CH₂)₂NHCOCH₂O-(4-Cl-2-NO₂-C₆H₃)]-CONH- | " | 77–81 |

-continued $$\underset{O}{\overset{R_1}{\underset{\|}{\bigsqcup}}}_{N-A} \quad (I)$$

| Example | R₁ | A | mp(°C.) (dec.) |
|---|---|---|---|
| 160 | phenyl-CH(NHCOCH₂O-bornyl)CONH- | " | 130-134 |
| 161 | phenyl-CH(NHCOCH₂O-(4-chloro-2-benzoylphenyl))CONH- | " | 135-137 |
| 162 | phenyl-CH(NHCOCH₂O-(2-COOC₂H₅-phenyl))CONH- | " | 127-130 |
| 163 | phenyl-NHCOCH(NHCOCH₂-phenyl)CONH- | " | (sodium salt) 183-188 |
| 164 | phenyl-O-CH(CONH-)-O-(3-NHCOCH₃-phenyl) | " | (sodium salt) 192-197 |
| 165 | 2-thienyl-CH(NHCOCH(phenyl)NHCOOCH₂CCl₃)CONH- | " | 165-169 |
| 166 | phenyl-CH(NHCOCOOC₂H₅)CONH- | " | 118-123 |
| 167 | phenyl-CH(NHCOCONHCH₂-phenyl)CONH- | " | 149-154 |
| 168 | phenyl-CH(NHCOCH₂O-phenyl)CONH- | " | 107-111 |

-continued

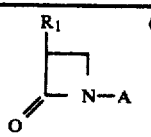

| Example | R₁ | A | mp(°C.) (dec.) |
|---|---|---|---|
| 169 | phenyl-CHCONH- with NHCOH₂OSO₂-phenyl | " | 151–155 |
| 170 | phenyl-CHCONH- with NHCOCH₂O-phenyl(CHO) | " | 191–195 |
| 171 | phenyl-CHCONH- with NHCOCH₂O-phenyl(COC₂H₅) | " | 125–130 |
| 172 | phenyl-CHCONH- with NHCOCH₂O-phenyl-CO-phenyl | " | 154–159 |
| 173 | phenyl-CHCONH- with NHCOCH₂O-phenyl-phenyl | " | 125–130 |
| 174 | phenyl-CHCONH- with NHCOCH₂O-phenyl(COO-phenyl) | " | 143–148 |

EXAMPLE 175

2-[4-{3-(4-Nitrophenylthio)propoxy}phenyl]acetic acid (260 mg.) and thionyl chloride (300 mg.) were dissolved in chloroform (10 ml.), and the solution was heated for 2 hrs. under reflux. The chloroform and the excess of the thionyl chloride were distilled off from the reaction mixture under reduced pressure, and the residue obtained was dissolved in acetone (1 ml.). The acetone solution was added dropwise to a solution of 3-aminolactacillanic acid (180 mg.), sodium bicarbonate (160 mg.), water (5 ml.) and acetone (5 ml.) under cooling at 0° to 5° C., and then the reaction mixture was stirred for 45 minutes at the same temperature. The acetone was distilled off from the reaction mixture under reduced pressure, and into the residue obtained was poured ethyl acetate (40 ml.), and then the solution was adjusted to pH 1 with 10% hydrochloric acid. The ethyl acetate layer was separated out, and the remaining aqueous layer was extracted with ethyl acetate (20 ml.). The ethyl acetate layers were combined, washed with a sodium chloride aqueous solution and dried over anhydrous magnesium sulfate. The solvent was distilled off from the solution to give crystals of 3-[2-[4-{3-(4-nitrophenylthio)propoxy}phenyl]acetamido]lactacillanic acid (400 mg.). Mp 142° to 146° C. (dec.).

EXAMPLE 176

A dried tetrahydrofuran solution (10 ml.) containing 2-[2-(2-naphthoxy)acetamidooxy]-2-phenylacetic acid (351 mg.) and triethylamine (101 mg.) was cooled to −10° C., and to the solution was added dropwise a dried tetrahydrofuran solution (5 ml.) containing pivaloyl chloride (120 mg.), and the mixture was stirred for 1 hour at the same temperature. The solution was cooled to −30° C., and to the solution was added all at once a dried methylene chloride (5 ml.) containing 3-aminolactacillanic acid (236 mg.) and N,O-bis(trimethylsilyl)acetamide (600 mg.), and the reaction mixture was stirred for 1 hour at −10° C. and for 1 hour at 0° C. The solvent was distilled off from the reaction mixture under reduced pressure, and into the residue was poured a sodium bicarbonate-saturated-aqueous solution. The aqueous solution was washed with ethyl acetate, adjusted to pH 1 to 2 with 10% hydrochloric acid and then extracted with ethyl acetate. The extract was washed with water and a sodium chloride-saturated-aqueous solution, respectively, and then dried over anhydrous magnesium sulfate. The solvent was distilled off from the solution, and the residue obtained was powdered with ether to give crystals of 3-[2-{2-(2-naphthoxy)acetamidooxy}-2-phenylacetamido]lactacillanic acid (340 mg.). Mp 109° to 112° C. (dec.).

EXAMPLE 177

2-[2-Oxo-3-(2-phenylacetamido)-1-azetidinyl]-3-methylbutyric acid (455 mg.), triethylamine (151 mg.) and N,N-dimethylbenzylamine (2 drops) were added to methylene chloride (10 ml.), and the solution was cooled to −30° C. The solution was added dropwise a methylene chloride (5 ml.) solution containing ethyl chloroformate (163 mg.). The solution was cooled to −40° C., and to the solution was added all at once a solution, prepared by dissolving 3-aminolactacillanic acid (389 mg.), N,O-bis(trimethylsilyl)acetamide (1.0 g.) and N,N-dimethylformamide (0.25 ml.) in methylene chloride (10 ml.) and then by stirring the solution for 3 hrs. at room temperature. The reaction mixture was reacted for 1.5 hrs. under stirring. The solvent was distilled off from the reaction mixture, and to the residue were added ethyl acetate and a sodium bicarbonate aqueous solution, and then the aqueous layer was separated out. The aqueous layer obtained was adjusted to pH 1 to 2 with 1 N-hydrochloric acid, and extraction was carried out by adding ethyl acetate to the solution. The ethyl acetate layer was separated out, and the remaining aqueous layer was also extracted with ethyl acetate. These ethyl acetate layers were combined, washed with a sodium chloride-saturated-aqueous solution and dried over anhydrous magnesium sulfate. The solvent was distilled off from the solution, and the powder (480 mg.) obtained was washed with ether to give crystals of 3-[2-{2-oxo-3-(2-phenylacetamido)-1-azetidinyl}-3-methylbutyramido]lactacillanic acid (359 mg.). Mp 160° to 164° C. (dec.).

The following compounds were obtained in substantially the similar manner as described above.

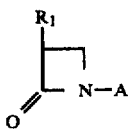

(I)

| Example | R₁ | A | mp (°C.) (dec.) |
|---|---|---|---|
| 178 | ![Ph-CHCONH-, NHCOCH₂S-phenyl-COO-phenyl] | -CH(COOH)-C₆H₄-OH | 141–146 |
| 179 | ![Ph-CHCONH-, NHCOCH₂-N-phenyl-SO₂-phenyl] | " | 137–142 |
| 180 | ![Ph-CHCONH-, NHCOCH₂O-phenyl-Cl, CO-phenyl-NO₂] | " | 148–153 |

-continued
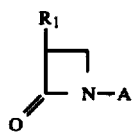
(I)
| Example | R₁ | A | mp (°C.) (dec.) |
|---|---|---|---|
| 181 | (structure) | " | 102–105 |
| 182 | (structure) | " | 158–161 |
| 183 | (structure) | " | 135–139 |
| 184 | (structure) | " | 170–174 |
| 185 | (structure) | " | 158–162 |
| 186 | (structure) | " | 118–121 |

-continued $$R_1-\underset{O}{C}-N-A \quad (I)$$

| Example | R₁ | A | mp (°C.) (dec.) |
|---|---|---|---|
| 187 | phenyl-CH(NHCOCH₂O-[2-Cl,6-(furan-CO)-phenyl])-CONH— | " | 141–144 |

EXAMPLE 188

2-Methyl-5,6-dihydro-1,4-oxathiin-3-carboxylic acid (0.320 g.) was dissolved in chloroform (10 ml.). To the solution was added a dried methylene chloride solution (5 ml.) containing thionyl chloride (7 ml.), and the mixture was heated for 4 hrs. under reflux, and then concentrated to give a solution of an acid chloride of a 2-methyl-5,6-dihydro-1,4-oxathiin-3-carboxylic acid. On the other hand, 3-aminolactacillanic acid (0.236 g.) was suspended in dried methylene chloride (20 ml.), and N,O-bis(trimethylsilyl)acetamide (1.50 g.) was added to the suspension, and then the mixture was stirred for 4 hrs. at ambient temperature. To the solution obtained was added dropwise the acid chloride solution prepared above under cooling to −5° to 0° C., and the mixture was stirred for 2 hrs. at the same temperature, and further stirred for 50 hrs. at ambient temperature. The reaction mixture was concentrated under reduced pressure to give a residue. Ethyl acetate and a sodium bicarbonate aqueous solution were poured into the residue and the mixture was stirred enough, whereafter the aqueous layer was separated out. The aqueous layer was washed with ether, and adjusted to pH 1 to 2 with diluted hydrochloric acid, and then the solution was extracted with ethyl acetate. The extract was washed with water, and dried over anhydrous magnesium sulfate. The solvent was distilled off from the solution to give a powder. Hot ethyl acetate (5 ml.) was added to the powder, and an insoluble material in the mixture was collected by filtration to give crude 3-(2-methyl-5,6-dihydro-1,4-oxathiin-3-carbonylamino)lactacillanic acid (240 mg.). This product was recrystallized from acetone to give the purified object compound (172 mg.). Mp 172.5° to 175.0° C. (dec.).

EXAMPLE 189

3-Aminolactacillanic acid (0.708 g.) was suspended in dried methylene chloride (20 ml.). To the suspension was added N,O-bis(trimethylsilyl)acetamide (2.0 g.), and the mixture was stirred for a while to dissolve it. On the other hand, N-[4-(3-benzyloxycarbonyl-5-oxo-1,3-oxazolidin-4-yl)butyryl]succinimide (1.212 g.) was dissolved in dioxane (15 ml.), and the solution was cooled to 0° to 5° C. To the solution was added dropwise the solution obtained above, and the mixture was stirred for 6 hrs. at the same temperature. The reaction mixture was concentrated under reduced pressure to give a residue, and 5% sodium bicarbonate aqueous solution and ethyl acetate were added to the residue. The aqueous layer was separated out and washed with ethyl acetate twice. The aqueous solution was adjusted to pH 1 to 2 with diluted hydrochloric acid and then extracted with ethyl acetate. The extract was washed with water and dried over anhydrous magnesium sulfate. The solvent was distilled off from the solution, and the oily material (0.470 g.) obtained was subjected to column chromatography using silica.gel (10 g.). An elution was conducted with a mixture of ethyl acetate and methanol (volume ratio, 50:1), and the fractions containing the object compound were collected. These fractions were combined, and the solvent was distilled off from the solution to give 3-[4-(3-benzyloxycarbonyl-5-oxo-1,3-oxazolidin-4-yl)butyramido]lactacillanic acid (0.100 g.).

I.R. absorption spectrum, $\nu_{cm^{-1}}$ (Nujol): 1730, 1720, 1700–1680, 1650.

EXAMPLE 190

3-Aminolactacillanic acid (472 mg.), 2-(2-propionylphenoxy)acetic acid (458 mg.), and ethyl chloroformate (238 mg.) was treated in substantially the similar manner as described in Example 109 to give 3-[2-(2-propionylphenoxy)acetamido]lactacillanic acid (40 mg.). Mp 114° to 118° C. (dec.).

EXAMPLE 191

3-Aminolactacillanic acid (0.236 g.), 2-[4-{4-chloro-N-(2,2,2-trichloroethoxycarbonyl)anilinomethyl}-phenoxy]-2-methylpropionic acid (0.610 g.) and thionyl chloride (7 ml.) were treated in substantially the similar manner as described in Example 120 to give 3-[2-[4-{4-chloro-N-(2,2,2-trichloroethoxycarbonyl)anilinomethyl}phenoxy]-2-methylpropionamido]lactacillanic acid (450 mg.). Mp 76° to 82° C. (dec.).

EXAMPLE 192

1-(1-Methoxycarbonyl-2-methyl-1-propenyl)-3-phenoxyacetamido-2-azetidinone (1.0 g.) was dissolved in methylene chloride (40 ml.). To the solution was added N,N-dimethylaniline (0.55 g.), and the solution was cooled to −35° to −30° C. Phosphorous pentachloride (0.94 g.) was added to the solution all at once under stirring, and then the reaction mixture was stirred for 1.5 hrs. at the same temperature. Methanol (0.9 g.) was added to the reaction mixture, and then the solution was stirred for an hour at the same temperature. Elevating the reaction temperature to 0° to 5° C., water (0.6 ml.) was added to the solution, and the solution was stirred for an hour. The reaction mixture was extracted with water three times (total volume: 10 ml.), and these aqueous extracts were combined and adjusted to about pH 7 with sodium bicarbonate. The aqueous solution was washed with ethyl acetate (10 ml.) and ethyl acetate (5 ml.) respectively.

The aqueous layer was salted out with sodium chloride and then extracted with chloroform (8 ml.) seven times. These chloroform extracts were combined and dried over anhydrous magnesium sulfate, and the solvent was distilled off from the solution to give crystals of 3-amino-1-(1-methoxycarbonyl-2-methyl-1-propenyl)-2-azetidinone (0.34 g.). A part of this product was treated with p-toluenesulfonic acid in a conventional manner to give p-toluensulfonic acid salt of an object compound. Mp 169° to 171° C. (dec.).

EXAMPLE 193

1-(1-Carboxy-2-methylpropyl)-3-phenylacetamido-2-azetidinone (1.52 g.) and N,N-dimethylaniline (2.15 g.) were suspended in methylene chloride (12 ml.), and to the suspension was added trimethylsilyl chloride (0.88 g.). The solution was stirred for 30 minutes at ambient temperature and cooled to −50° C. Phosphorus pentachloride (1.1 g.) was added to the solution and the solution was stirred for 2 hrs. (the reaction temperature was elevated to about −30° C. during the stirring.). The solution was cooled to −50° C., and n-butyl alcohol (1.85 g.) was added to the solution, and then the solution was stirred for 2 hrs. (in this time, the reaction temperature was elevated to about −30° C.). The solution was cooled again to −50° C., and a solution preparing by dissolving sodium bicarbonate (1.3 g) in water (15 ml.), was added to the solution (in this time, the reaction temperature was elevated to about −25° C., and the solution indicated about pH 3). The solution was adjusted to pH 4 with sodium bicarbonate, and then the aqueous layer was separated out and washed with ether. The solution was evaporated to dryness under reduced pressure, keeping the temperature of the solution under 25° C. To the residue obtained was added isopropyl alcohol (15 ml.), and the mixture was filtered to obtain an insoluble material and a filtrate. The filtrate was evaporated to dryness under reduced pressure. This operation was repeated twice to give colorless powdery 3-amino-1-(1-carboxy-2-methylpropyl)-2-azetidinone (0.3 g.). These insoluble materials in isopropyl alcohol obtained above were combined and dissolved in a small amount of water, and the solution was adjusted to pH 2.5 with 1 N-hydrochloric acid. The aqueous solution was evaporated to dryness under reduced pressure at 25° C., and the residue obtained was treated with isopropyl alcohol in the similar manner as described above to recover an object compound (0.13 g.). Total yield was 0.43 g. This product was treated in a conventional manner to give its salt of D-camphor-10-sulfonic acid, and the salt was recrystallized from a mixture of acetone and ether to give D-camphor-10-sulfonic acid salt of the object compound. Mp 178° to 183° C.

EXAMPLE 194

3-[2-{4-(3-Benzamido-3-carboxypropoxy)phenyl}-2-(3-phenylthioureido)acetamido]lactacillanic acid (7.2 g.) was dissolved in acetic acid (20 ml.), and to the solution was added dropwise concentrated hydrochloric acid (2 ml.) under cooling while stirring. The reaction mixture was stirred for 1.5 hrs, and poured into a mixture of ice-water (50 ml.) and ethyl acetate (50 ml.).

The mixture was separated into a ethyl acetate layer and an aqueous layer. The ethyl acetate layer was extracted with ice-water (20 ml.). This aqueous layer and the aqueous layer obtained above were combined, and washed with ethyl acetate (20 ml.). To the aqueous layer was added a weak basic anion-exchange resin, Amberlite IR-45 (OH type) (trade mark, maker: Rohm and Haas Co. Ltd.,) (60 ml.), and the mixture was stirred under ice-cooling, and then filtered. The resin was washed with ice-water (10 ml.), and then the washings and the filtrate were combined, and concentrated under reduced pressure to obtain a residue. Methanol was added to the residue, and then the residue was collected by filtration. The residue was washed with acetone to give 3-aminolactacillanic acid (0.59 g.). Mp 203° to 206° C. (dec.).

I.R. absorption spectrum,
$\nu_{cm^{-1}}$ (Nujol): 1763, 1742
N.M.R. absorption spectrum,
δ ppm (D$_2$O+NaOD):
   2.89 (1H, d,d, J=3 Hz, 6 Hz)
   3.79 (1H, t, J=6 Hz)
   4.22 (1H, d,d, J=3 Hz, 6 Hz)
   5.26 (1H, s)
   6.91 (2H, d, J=9 Hz)
   7.23 (2H, d, J=9 Hz)

EXAMPLE 195

3-(Phenylacetamido)lactacillanic acid was treated in substantially the similar manner as described in Example 193 to give 3-amino-lactacillanic acid, which was identified by comparing an I.R. absorption spectrum, a N.M.R. absorption spectrum and a melting point with an authentic sample.

EXAMPLE 196

3-[2-[4-{3-(3-Phenylthioureido)-3-carboxypropoxy}-phenyl]-2-(3-phenylthioureido)acetamido]lactacillanic acid (1.44 g.) was suspended in water (10 ml.), and to the suspension was added anhydrous potassium carbonate (0.56 g.). The solution (pH 9) was stirred for 27 hrs. at 30° C., and then was filtered. The filtrate was diluted by adding ethanol (50 ml.) and the solution was allowed to stand under ice-cooling to give a precipitate. The precipitate was filtered off, and the filtrate was concentrated under reduced pressure to give a residue. The residue was adjusted to pH 2 with 5% hydrochloric acid, and then washed with ethyl acetate. The solution was adjusted to pH 7.5 with sodium carbonate, and then evaporated to dryness under reduced pressure to obtain the powder (0.75 g.). Water (7 ml) was added to the powder, and an insoluble material in the water was collected by filtration and washed with water to give 3-aminolactacillanic acid (40 mg.). The filtrate and the washings were combined, and the combined solution was treated with an activated carbon to give crude crystals of 3-aminolactacillanic acid (123 mg.). These object compounds were combined and suspended in 30% aqueous methanol solution. The suspension was stirred for an hour, and, then filtered to give the purified crystals of 3-aminolactacillanic acid (133 mg.), which was identified by comparing an I.R. absorption spectrum, a N.M.R. absorption spectrum and a melting point with an authentic sample.

EXAMPLE 197

3-[2-[4-{3-(3-Phenylthioureido)-3-carboxypropoxy}-phenyl]-2-(3-phenylthioureido)acetamido]lactacillanic acid (0.36 g.) was dissolved in methanol (3 ml.), and concentrated hydrochloric acid (0.1 ml.) was added to the solution under ice-cooling, and then the reaction mixture was stirred for 30 minutes. Sodium bicarbonate (0.08 g.) was added to the reaction mixture, and the solution was stirred for 10 minutes. Ice-water (10 ml.) was poured into the solution, and the solution was filtered to remove precipitating crystals. The filtrate was washed with ethyl acetate (10 ml.) and evaporated to dryness under reduced pressure. Methanol was added to the residue to give crystals and the crystals were collected by filtration to give 3-aminolactacillanic acid (10 mg.). The mother liquor was concentrated to recover an object compound (80 mg.), which was identified by comparing an I.R. absorption spectrum, a N.M.R. absorption spectrum, and a melting point with an authentic sample.

EXAMPLE 198

3-[2-[4-{3-(3-Phenylthioureido)-3-carboxypropoxy}-phenyl]-2-(3-phenylthioureido)acetamido]lactacillanic acid (0.50 g.) was dissolved in 2,2,2-trifluoroacetic acid (4 ml.), and the solution was stirred for an hour under ice-cooling. The reaction mixture was poured into ice-water (about 10 ml.), and the solution was washed with ethyl acetate (10 ml.) twice. The aqueous solution was adjusted to pH 4 with a weak basic anion-exchange resin, Amberlite IR-45 (OH type) (trade mark, maker; Rohm and Haas Co. Ltd.,) (9.5 ml.), and the resin was filtered off from the mixture, and then the filtrate was concentrated to give residues. Methanol was added to the residues to give crystals, which were collected by filtration to give 3-amino-lactacillanic acid (30 mg.). This product was identified by comparing an I.R. absorption spectrum, a N.M.R. absorption spectrum, and a melting point with an authentic sample.

EXAMPLE 199

3-[2-{4-(3-Acetamido-3-carboxypropoxy)phenyl}-2-(3-phenylthioureido)acetamido]lactacillanic acid (0.67 g.) was dissolved in acetic acid (6.7 ml.), and to the solution was added all at once concentrated hydrochloric acid (0.15 ml.) under water-cooling while stirring, and then the reaction mixture was stirred for an hour. The reaction mixture was treated in substantially the similar manner as described in Example 198 to give 3-aminolactacillanic acid (90 mg.), which was identified by comparing an I.R. absorption spectrum and a N.M.R. absorption spectrum with an authentic sample.

EXAMPLE 200

3-[2-[4-[3-Carboxy-3-{N-ethoxy(thiocarbonyl)amino}propoxy]phenyl]-2-{ethoxy(thiocarbonyl)amino}acetamido]lactacillanic acid was treated in substantially the similar manner as described in Example 199 to give 3-aminolactacillanic acid.

EXAMPLE 201

3-[2-[4-{3-(3-Phenylthioureido)-3-carboxypropoxy}-phenyl]-2-(3-phenylthioureido)acetamido]lactacillanic acid (2.28 g.) was dissolved in acetic acid (6 ml.), and to the solution was added dropwise a mixture of concentrated hydrochloric acid (0.45 ml.) and acetic acid (6 ml.) during 15 minutes under water-cooling while stirring. Furthermore, the reaction mixture was stirred for 15 minutes, and ethyl acetate (25 ml.) and water (25 ml.) were added to the reaction mixture, whereafter the mixture was stirred. The ethyl acetate layer separated out was extracted with water (10 ml.). This extract and the aqueous layer obtained above were combined, and the combined aqueous solution was washed with ethyl acetate and adjusted to pH 3.4 with a weak basic anion-exchange resin, Amberlite IR-45 (OH type), (trade mark, maker: Rohm and Haas Co., Ltd.) (15 ml.). The resin was filtered off from the mixture, and the filtrate was concentrated under reduced pressure to give residues. Methanol was added to the residues to give crystals, which were collected by filtration to give 3-aminolactacillanic acid (0.25 g.). This product was identified by comparing an I.R. absorption spectrum, a N.M.R. absorption spectrum, and a melting point with an authentic sample.

EXAMPLE 202

3-[2-{4-(3-Benzamido-3-carboxypropoxy)phenyl}-2-(2-nitro-4-methoxycarbonylanilino)acetamido]lactacillanic acid (1.54 g.) was dissolved in a mixture of water (10 ml.) and methanol (20 ml.), and to the solution was added 10% palladium.carbon (500 mg.) as a catalyst. The solution was stirred for 2 hrs. in hydrogen atmosphere under increased pressure using a middle-pressure reduction apparatus at ambient temperature. After the reaction was completed, the catalyst was filtered off, and the methanol was distilled off from the filtrate under reduced pressure. The remaining solution was washed with ethyl acetate and cooled. Acetone was added to the solution to give precipitating crystals, which were collected by filtration to give 3-aminolactacillanic acid (83 mg.). Furthermore, the mother liquor was evaporated to dryness under reduced pressure, and the residue obtained was washed with methanol to give crystals. The crystals were collected by filtration to give an object compound (50 mg.). Total yield was 123 mg. This product was identified by comparing an I.R. absorption spectrum and a N.M.R. absorption spectrum with an authentic sample.

EXAMPLE 203

3-[2-[4-{3-(2-Nitro-4-methoxycarbonylanilino)-3-carboxypropoxy}phenyl]-2-(2-nitro-4-methoxycarbonylanilino)acetamido]lactacillanic acid was treated in substantially the similar manner as described in Example 202 to give 3-aminolactacillanic acid.

EXAMPLE 204

3-[2-{4-(3-Acetamido-3-carboxypropoxy)phenyl}-2-{3-(1-naphthyl)thioureido}acetamido]lactacillanic acid (2.5 g.) was dissolved in acetic acid (10 ml.), and to the solution was added concentrated hydrochloric acid (0.56 ml.) under water-cooling while stirring. The reaction mixture was stirred for 30 minutes, and then poured into a mixture of ice-water (10 ml.) and ethyl acetate (20 ml.), and the aqueous layer was separated out. The remaining ethyl acetate layer was extracted with ice-water (10 ml.). The aqueous layers were combined and washed with ethyl acetate (10 ml.). A weak basic anion-exchange resin, Amberlite IR-45 (OH type) (trade mark, maker; Rohm and Haas Co., Ltd.) (15 ml.) was added to the solution, and then the mixture (pH 3.4) was stirred for 5 minutes. The resin was filtered off from the mixture and washed with ice-water (5 ml.). The filtrate and the washings were combined and concentrated to give residues. The residues were washed with methanol to give crystals. The crystals were collected by filtration to give 3-aminolactacillanic acid (149 mg.). Furthermore, the mother liquor was concentrated, and the residue obtained was washed with methanol to recover an object compound (80 mg.). Total yield was 229 mg. This product was identified by comparing an I.R. absorption spectrum and a N.M.R. absorption spectrum with an authentic sample.

EXAMPLE 205

3-[2-[4-[3-Carboxy-3-{3-(1-naphthyl)thioureido}-propoxy]phenyl]-2-{3-(1-naphtyl)thi-oureido}acetamido]lactacillanic acid (2.6 g.) was reacted in substantially the similar manner as described in Example 204 to give 3-aminolactacillanic acid (190 mg.), which was identified by comparing an I.R. absorption spectrum and a melting point with an authentic sample.

EXAMPLE 206

3-(2-Phenylacetamido)-2-azetidinone (816 mg.) and benzyl 2-bromo-2-phenylacetate (1.22 g.) were dissolved in N,N-dimethylformamide (20 ml.), and to the solution was added sodium hydride (50% oily) (210 mg.) in nitrogen atmosphere under ice-cooling while stirring, and then the reaction mixture was stirred for an hour at the same temperature. Ethyl acetate (150 ml.) was added to the reaction mixture, and the solution was washed with water, a sodium bicarbonate-saturated-aqueous solution and water respectively, and then dried over anhydrous magnesium sulfate. The solution was evaporated to dryness under reduced pressure to give the yellow oily material (1.7 g.). The material was subjected to column chromatography using silica.gel (developer: chloroform) to give two isomers of 1-(α-benzyloxycarbonylbenzyl)-3-(2-phenyl)acetamido-2-azetidinone. Yield of the isomer A is 26 mg. and it of the isomer B is 65 mg.

Physical constant of isomer A:
  Oil
  Mass spectrum,
    m/e=428 (M+)
  I.R. absorption spectrum,
    $\nu_{cm^{-1}}$ (CHCl$_3$): 1760, 1740 (shoulder), 1678.
  N.M.R. absorption spectrum,
    δ ppm (CDCl$_3$):
      3.46 (2H, m), 3.55 (2H, s), 4.96
      (1H, m), 5.15 (2H, s), 5.61 (1H, s),
      6.37 (1H, d, J=8 Hz), 6.90-7.60
      (15H, m).

Physical constant of isomer B:
  Mp: 96° to 98° C.
  Mass spectrum,
    m/e=428 (M+)
  I.R. absorption spectrum,
    $\nu_{cm^{-1}}$ (Nujol): 1750, 1732, 1680.
  N.M.R. absorption spectrum:
    δ ppm (CDCl$_3$):
      3.03 (1H, d,d, J=3 Hz, 5 Hz), 3.53 (2H, s),
      3.85 (1H, d,d, J=5 Hz, 5 Hz), 4.88 (1H, m),
      5.17 (2H,s), 5.62 (1H,s), 6.05 (1H,d,
      J=8 Hz), 7.00-7.60 (15H, m).

The following compounds were obtained in substantially the similar manner as described above.

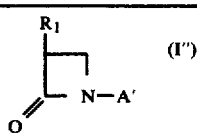

(I″)

| Ex. | R$_1$ | A′ | mp (°C.) (dec.) (Note 2) |
|---|---|---|---|
| 207 | ⟨phenyl⟩—CH$_2$CONH— | *2 —CH(COOCH$_3$)—⟨phenyl⟩—OCH$_3$ | (D isomer) 145–146<br>(L isomer) I.R. $\nu$cm$^{-1}$(CHCl$_3$): 1760, 1740, 1680 |
| 208 | " | *2 —CH(COOCH$_2$⟨phenyl⟩)—⟨phenyl⟩—OCH$_2$—⟨phenyl⟩ | (D isomer) 129–130<br>(L isomer) I.R. $\nu$cm$^{-1}$ (liquid film): 1760–1740, 1665 |
| 209 | " | *2 —CH(COOCH$_3$)—⟨phenyl⟩—NHCOOCH$_2$—⟨phenyl⟩ | isomer A) N.M.R. δppm(CDCl$_3$): 3.5(2H,m), 3.6(2H,s), 3.7(3H, s), 5.0(1H,m), 5.2(2H,s), 5.5(1H,s), 6.3(1H,d,J=8Hz), 6.9–7.6(15H,m)<br><br>isomer B) N.M.R.δppm(CDCl$_3$): 3.0(1H,d,d,J=3Hz,6Hz), 3.4 (2H,s), 3.7(3H,s), 3.8(1H, d,d,J=3Hz,6Hz), 4.9(1H,m), 5.2(2H,s), 5.6(1H,s), 6.5 (1H,d,J=8Hz), 6.9–7.6(15H,m) |
| 210 | " | *2 —CH(COOCH$_3$)—⟨phenyl⟩—CH$_3$ | isomer A) 148<br>isomer B) I.R. $\nu$cm$^{-1}$(Nujol): 1755, 1745,1675 |
| 211 | " | *2 —CH(COOCH$_3$)—⟨phenyl with 3 OCH$_3$⟩ | isomer A) 138–140<br><br>isomer B) N.M.R. δppm(CDCl$_3$): 3.54(2H,m) 3.59(2H,s), 3.73 (3H,s), 3.82(9H,s), 4.96(1H, m), 5.45(1H,s), 6.13(1H,d, J=8Hz),6.43(2H,s), 7.10–7.45 (5H,m) |
| 212 | " | —CH$_2$COOC$_2$H$_5$ | 104–105 |
| 213 | " | —CH$_2$COOCH$_2$—⟨phenyl⟩ | 114–115 |

| Ex. | R₁ | A' | mp (°C.) (dec.) (Note 2) |
|---|---|---|---|
| 214 | " | *2 —CH—(phenyl) / COOCH₃ | isomer A) 138–140<br>isomer B) I.R. $\nu cm^{-1}(CHCl_3)$: 1770, 1745, 1678<br>I.R. $\nu cm^{-1}$ (liquid film): 1745, 1720, 1675 |
| 215 | CH₃OOCCH(CH₂)₂O—(phenyl)—C(=N—OCH₃)—CONH— (with phthalimido N on CH) | —CH(COOCH₃)—(phenyl)—OCH₃ | |
| 216 | (phenyl)—OCH₂CONH— | " | I.R. $\nu cm^{-1}(NaCl)$: 1770, 1740, 1680 |

Note
1 The compound marked by *1 is D isomer at the asymmetric carbon marked by *1.
2 (a) D or L Isomer is one at the asymmetric carbon marked by *2.
(b) Isomer A or B is one at the asymmetric carbon marked by *2.

EXAMPLE 217

3-(2-Phenylacetamido)-2-azetidinone (610 mg.), methyl 2-bromo-2-(3-nitrophenyl)acetate (900 mg.) and anhydrous potassium carbonate (460 mg.) were added to ethyl methyl ketone (60 ml.), and the solution was heated for 8 hrs. under reflux while stirring. The reaction mixture was cooled and then poured into ice-water, whereafter the mixture was extracted with ethyl acetate. The extract was washed with a sodium chloride-saturated-aqueous solution, and then dried over anhydrous magnesium sulfate. The solution was evaporated to dryness, and the oily residue obtained was subjected to column chromatography. The fractions, eluted with a mixture of chloroform and methanol (100:1), was subjected to thin layer chromatography using silica.gel [developer: a mixed solvent of chloroform and methanol (40:1)] to give a mixture of two isomers of 1-(α-methoxycarbonyl-3-nitrobenzyl)-3-(2-phenylacetamido)-2-azetidinone (7.5 mg.).

I.R. absorption spectrum:
$\nu_{cm-1}$ (CHCl₃): 1765, 1745, 1680.

EXAMPLE 218

3-(Phenylacetamido)-2-azetidinone (612 mg.) and methyl 2-bromo-2-(4-methylthiophenyl)acetate (825 mg.) were dissolved in N,N-dimethylformamide (20 ml.). Keeping a temperature of the solution at 20° to 30° C., a benzene (20 ml.) solution of sodium N,N-bis(trimethylsilyl)amine (546 mg.) was added to the solution during an hour in nitrogen atmosphere, and the reaction mixture was stirred for 15 minutes at the same temperature. Ethyl acetate (150 ml.) was added to the reaction mixture, and the ethyl acetate layer was washed with water, a sodium bicarbonate-saturated-aqueous solution and water respectively, and then dried over anhydrous magnesium sulfate. The solvent was distilled off from the solution to give the oily residue (1.2 g). The residue was subjected to column chromatography using silica.gel (developer: chloroform) to give two isomers of 1-(α-methoxycarbonyl-4-methylthiobenzyl)-3-phenylacetamido-2-azetidinone. Yield of the isomer A: 10 mg, mp 115° to 117° C. (dec.): Yield of the isomer B: 43.5 mg, mp 157° to 159° C. (dec.).

EXAMPLE 219

3-(2-Phenylacetamido)-2-azetidinone (408 mg.) and 2-chloroacetonitrile (152 mg.) was dissolved in N,N-dimethylformamide (15 ml.), and to the solution was added sodium hydride (50% oily) (105 mg.) under stirring at ambient temperature, whereafter the reaction mixture was stirred for an hour at room temperature, and ethyl acetate (100 ml.) was added to the reaction mixture. The ethyl acetate layer was washed with water and dried over anhydrous magnesium sulfate, and then the solvent was distilled off from the solution under reduced pressure. The oily residue (0.25 g.) obtained was subjected to column chromatography using silica.-gel. 1-Cyanomethyl-3-(2-phenylacetamido)-2-azetidinone (56.3 mg.) was obtained from fractions eluted with chloroform. Mp 108° to 109° C. (dec.).

EXAMPLE 220

2-(2-Phenoxyacetamido)-2-azetidinone (154 mg.) was dissolved in N,N-dimethylformamide (1.75 ml.), and to the solution was added all at once thallium ethoxide (174.6 mg.), and then the mixture was stirred for 10 minutes at ambient temperature. To the reaction mixture was added dropwise a solution, prepared by dissolving ethyl 2-bromo-2-(4-ethoxycarbonyloxyphenyl)acetate (232 mg.) in N,N-dimethylformamide (0.6 ml.), was added to the reaction mixture and then the reaction mixture was stirred for 2 hrs. at ambient temperature. The reaction mixture was filtered to give insoluble materials and a filtrate. The insoluble materials were washed with ethyl acetate. The filtrate and the washing were combined and diluted with ethyl acetate. The solution was washed with water and dried over anhydrous magnesium sulfate. The solution was concentrated under reduced pressure to give the yellow oily residue, which was subjected to column chromatography using silica.gel. Oil of 1-(α-ethoxycarbonyl-4-ethoxycarbonyloxybenzyl)-3-(2-phenoxyacetamido)-2-azetidinone was obtained from fractions eluted with benzene.

I.R. absorption spectrum; $\nu_{cm-1}$ (liquid film): 1760, 1740 (shoulder), 1675.

EXAMPLE 221

An isomer B of 1-(α-benzyloxycarbonylbenzyl)-3-(2-phenylacetamido)-2-azetidinone (63 mg.) obtained in Example 206 was dissolved in isopropyl alcohol (12 ml.), and to the solution was added 10% palladium.carbon (10 mg.). The mixture was reacted in hydrogen atmosphere at ordinary temperature and ordinary atm. until the absorption of hydrogen gas was completed. The catalyst was filtered off, and the solvent was distilled off from the filtrate, and then ether was added to the residue obtained to give crystals of 1-(α-carboxybenzyl)-3-(2-phenyl-acetamido)-2-azetidinone (27 mg.), which was recrystallized from a mixture of methanol and ether to give the purified object compound. Mp 174° to 175° C. (dec.).

EXAMPLE 222

1-Carboxymethyl-3-(2-phenylacetamido)-2-azetidinone was obtained by treating 1-Benzyloxycarbonylmethyl-3-(2-phenylacetamido)-2-azetidinone in substantially the similar manner as described in Example 221. Mp 144° to 145° C.

EXAMPLE 223

3-(2-Phenylacetamido)-2-azetidinone (750 mg.) and benzyl 2-bromo-2-(4-benzyloxyphenyl)acetate (1.51 g.) was added to anhydrous N,N-dimethylformamide (10 ml.), and disdolved in it by warming for a while. The solution was cooled in an ice-water bath, and to the solution was added all at once sodium hydride (50% oily) (178 mg.) under stirring. After removing the cooling bath, the reaction mixture was stirred for 30 minutes to which ethyl acetate was added. The reaction mixture was filtered and the filtrate was washed with water, 2% hydrochloric acid and water respectively, and then dried over anhydrous magnesium sulfate. The solution was concentrated under reduced pressure to give an oily material (1.98 g.), which was subjected to column chromatography using silica.gel (40 g.). The fractions, eluted with a mixture of benzene and chloroform were subjected to thin layer chromatography using silica.gel, and the thin layer was developed with a mixture of chloroform and acetone to give two isomers of 1-(α-benzyloxycarbonyl-4-benzyloxybenzyl)-3-(2-phenylacetamido)-2-azetidinone. The isomer A recrystallized from a mixture of chloroform and ether. Yield: 90 mg. Mp: 129° to 130° C. (dec.). The isomer B is oily material. Yield: 120 mg. The isomer A (90 mg.) obtained above was dissolved in methanol (7 ml.), and to the solution was added 10% palladium carbon (30 mg.). The mixture was reacted in hydrogen atmosphere at ordinary temperature and ordinary atm. until the absorption of hydrogen gas was completed. The catalyst was filtered off from the fraction mixture, and the filtrate was concentrated under reduced pressure. The residue obtained was crystallized from a mixture of ethyl acetate and ether to give crystals of 3-(2-phenylacetamido)lactacillanic acid. The product was identified by comparing an I.R. absorption spectrum and a N.M.R. absorption spectrum and a melting point with an authentic sample synthesized by another method from 3-aminolactacillanic acid.

EXAMPLE 224

3-(2-Phenylacetamido)-2-azetidinone (300 mg.) and benzyl 2-bromo-2-(4-benzyloxyphenyl)acetate (604 mg.) were dissolved in anhydrous N,N-dimethylformamide (4 ml.) under warming. The solution was cooled in a cooling bath, to which was added all at once sodium hydride (50% oily) (71 mg.), and then the reaction mixture was stirred for a while. After removing the cooling bath, the reaction mixture was stirred for 30 minutes, whereafter ethyl acetate was added thereto. The reaction mixture was filtered and then the filtrate was washed with water, 2% hydrochloric acid and water respectively, and then dried over anhydrous magnesium sulfate. The solution was concentrated to give a oily residue (727 mg.), which was subjected to column chromatography using silica.gel (15 g.). Elution was carried out with a mixture of benzene and chloroform to obtain an oily material (255 mg.). A part of this material (200 mg.) was dissolved in methanol (14 ml.), and to the solution was added 10% palladium.carbon (60 mg.). The mixture was reacted in hydrogen atmosphere at ordinary temperature and ordinary atm. until the absorption of hydrogen gas was completed. The catalyst was filtered off from the reaction mixture, and the filtrate was concentrated under reduced pressure. The residue obtained was crystallized from a mixture of ethyl acetate and ether to give 3-(2-phenylacetamido)-lactacillanic acid.

I.R. absorption spectrum, $\nu_{cm-1}$ (Nujol): 1745, 1690, 1650. The following compounds were obtained in substantially the similar manner as described above.

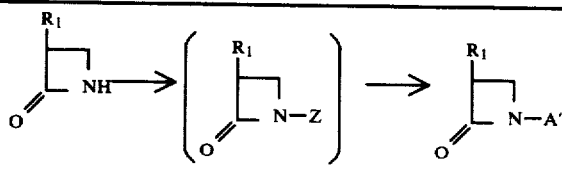

| Ex. | Compound (III) R₁ | Reagent | Compound (I") R₁ | A' | mp(°C.) (dec.) |
|---|---|---|---|---|---|
| 225 | naphthyl-CH₂CONH— | ⌬—CH₂O—⌬—CHBr / ⌬—CH₂OOC | the same as R₁ Compound (III) | —CH(—⌬—OH)COOH | I.R.υcm⁻¹ (Nujol): 1740, 1690, 1660 |
| 226 | HO—⌬—CH₂CONH— | " | the same as R₁ of Compound (III) | " | I.R.υcm⁻¹(Nujol): 1740, 1650 |
| 227 | CH₃CH₂CH₂CONH— | " | the same as R₁ Compound (III) | " | 172–177 |

-continued

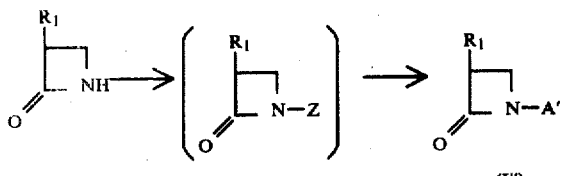

| Ex. | Compound (III) R₁ | Reagent | Compound (I″) R₁ | A′ | mp(°C.) (dec.) |
|---|---|---|---|---|---|
| 228 | CH₃OCH₂CONH— | ″ | the same as R₁ Compound (III) | ″ | 121–127 |
| 229 | ⟨phenyl⟩-⟨phenyl⟩-OCH₂CONH— | ″ | the same as R₁ of Compound (III) | ″ | 189–194 |
| 230 | CH₃O-⟨phenyl⟩-CONH— | ″ | the same as R₁ of Compound (III) | ″ | 158–162 |
| 231 | (CH₃)₃CCONH— | ″ | the same as R₁ of Compound (III) | ″ | I.R.νcm⁻¹ (Nujol): 1745, 1680, 1640 |
| 232 | phthalimido-N— | ″ | the same as R₁ of Compound (III) | ″ | 191–196 |
| 233 | (piperazinyl)N—CH₂CONH— | ″ | the same as R₁ of Compound (III) | ″ | 192–198 |
| 234 | ⟨phenyl⟩-CH(OCH₃)CONH— | ″ | the same as R₁ of Compound (III) | ″ | I.R.νcm⁻¹ (Nujol): 1740, 1695, 1660 |
| 235 | HOOCCH₂CH₂CONH— | ″ | the same as R₁ Compound (III) R₁ Compound (III) | ″ | (disodium salt) I.R.νcm⁻¹ (KBr): 1740, 1660, 1585 |
| 236 | ⟨phenyl⟩-N(CH₃)CH₂CONH— | ″ | the same as R₁ of Compound (III) | ″ | 185–192 |
| 237 | (furyl)-CH₂CONH— | ″ | the same as R₁ of Compound (III) | ″ | 164–170 |
| 238 | (naphthyl)-OCH₂CONH— | ″ | the same as R₁ of Compound (III) | ″ | 138–142 |

EXAMPLE 239

A crude product (157 mg.) without separation and purification thereof, obtained by the reacting 3-(2-phenoxyacetamido)-2-azetidinone and ethyl 2-bromo-2-(4-ethoxycarbonyloxyphenyl)acetate in the same manner as described in Example 220 similarly, was dissolved in ethanol (3 ml.). 1 N Sodium hydroxide aqueous solution (1.0 ml.) was added to the solution under cooling in ice-water bath and then the solution was stirred for 30 minutes after removing the cooling bath. The reaction mixture was concentrated under reduced pressure, and water was added to the residue obtained. The aqueous solution was washed with ethyl acetate and then the aqueous layer was adjusted to pH 1 to 2 with 1 N hydrochloric acid, whereafter was extracted with ethyl acetate. The extract was washed with a sodium chloride-saturated-aqueous solution, and dried over anhydrous magnesium sulfate. The solvent was distilled off from the solution under reduced pressure to give residues, which were washed with ether to give 3-(2-phenoxyacetamido)lactacillanic acid.

I.R. absorption spectrum;

$\nu_{cm-1}$ (Nujol): 1745, 1690, 1660

The corresponding 3-acylamino-2-azetidinone was treated in substantially the similar manner as described above, and the following compounds were obtained.

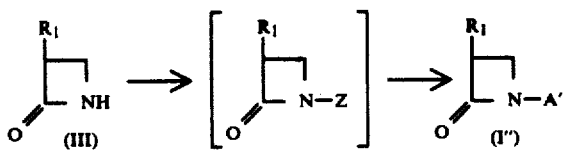

| | Compound (III) | | Compound (I'') | | |
|---|---|---|---|---|---|
| Ex. | $R_1$ | Reagent | $R_1$ | A' | mp (°C.) (dec.) |
| 240 | phenyl-O-(2-Cl-phenyl)-CHCONH— | $C_2H_5OOCO$-phenyl-CHBr-$C_2H_5OOC$ | the same as $R_1$ of Compound (III) | —CH(COOH)-phenyl-OH | (sodium salt) I.R. $vcm^{-1}$ (Nujol): 1730, 1660, 1635, 1600 |
| 241 | $CH_3$-(oxadiazole)-$CH_2CONH$— | " | the same as $R_1$ of Compound (III) | " | I.R. $vcm^{-1}$ (Nujol): 1740, 1680, 1665 |
| 242 | (thienyl-S)-$CH_2CONH$— | " | the same as $R_1$ of Compound (III) | " | I.R. $vcm^{-1}$ (Nujol): 1750, 1680, 1670 |
| 243 | phenyl-$COCH_2CH_2CONH$— | " | the same as $R_1$ of Compound (III) | " | 151–157 |
| 244 | (thienyl-S)-$COCONH$— | " | the same as $R_1$ of Compound (III) | " | I.R. $vcm^{-1}$ (Nujol): 1745, 1690, 1640 |
| 245 | $CH_3COCONH$— | " | the same as $R_1$ of Compound (III) | " | 155–161 |
| 246 | $CH_3O$-phenyl-$COCONH$— | " | the same as $R_1$ of Compound (III) | " | I.R. $vcm^{-1}$ (Nujol): 1745, 1695, 1660 |
| 247 | phenyl-N($SO_2CH_3$)$CH_2CONH$— | " | the same as $R_1$ of Compound (III) | " | 112–117 |
| 248 | (tetrazolyl)N-$CH_2CONH$— | " | the same as $R_1$ of Compound (III) | " | 170–175 |
| 249 | $CH_2=CHCH_2SCH_2CONH$— | " | the same as $R_1$ of Compound (III) | " | I.R. $vcm^{-1}$ (Nujol): 1745, 1680, 1660 |
| 250 | $CH_3SCH_2CONH$— | " | the same as $R_1$ of Compound (III) | " | 146–151 |
| 251 | $O_2N$-phenyl-$OCH_2CONH$— | " | the same as $R_1$ of Compound (III) | " | I.R. $vcm^{-1}$ (Nujol): 1745, 1660 |
| 252 | (thiadiazolyl)-$SCH_2CONH$— | " | the same as $R_1$ of Compound (III) | " | I.R. $vcm$(Nujol): 1745, 1685, 1660 |
| 253 | $C_2H_5O$-phenyl-CH=N—$OCH_2CONH$— | " | the same as $R_1$ of Compound (III) | " | 127–133 |
| 254 | (benzotriazolyl)-$O$-$CH_2CONH$— | " | the same as $R_1$ of Compound (III) | " | 172–177 |
| 255 | phenyl-CH=CHCONH— | " | the same as $R_1$ of Compound (III) | " | I.R. $vcm^{-1}$ (Nujol): 1740, 1680, 1655 |

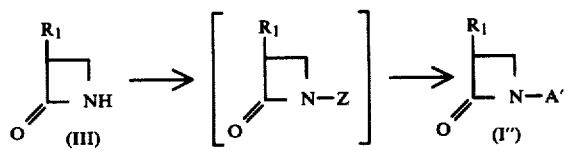

| | Compound (III) | | Compound (I″) | | |
|---|---|---|---|---|---|
| Ex. | $R_1$ | Reagent | $R_1$ | A′ | mp (°C.) (dec.) |
| 256 | ![NO2, NO2-C6H3-CONH-] | ″ | the same as $R_1$ of Compound (III) | ″ | I.R. $\nu cm^{-1}$ (Nujol): 1740, 1725 (s) 1690, 1665 |
| 257 | $O_2N$-C6H4-CONH- | ″ | the same as $R_1$ of Compound (III) | ″ | 190–195 |
| 258 | [2-Cl-C6H4-C(=N-O-)-C(CH3)=CONH-] | ″ | the same as $R_1$ of Compound (III) | ″ | (sodium salt) I.R. $\nu cm^{-1}$ (Nujol): 1735, 1655, 1610 |
| 259 | $CH_2=CHCH_2O$-C6H4-COCONH- | ″ | the same as $R_1$ of Compound (III) | ″ | I.R. $\nu cm^{-1}$ (Nujol): 1735, 1710, 1660 |
| 260 | (C6H5)2CHCONH- | ″ | the same as $R_1$ of Compound (III) | ″ | 128–135 |
| 261 | C6H5-CH(O-naphthyl)-CONH- | ″ | the same as $R_1$ of Compound (III) | ″ | I.R. $\nu cm^{-1}$ (Nujol): 1740, 1690, 1670 |
| 262 | [thienyl-tetrazolyl-CH2CONH-] | ″ | the same as $R_1$ of Compound (III) | ″ | 191–195 |
| 263 | C6H5-CH(SCH3)-CONH- | ″ | the same as $R_1$ of Compound (III) | ″ | I.R. $\nu cm^{-1}$ (Nujol): 1740, 1690, 1670, 1640 |

The 3-acylamino-2-azetidinone (III) shown in the following table was treated in substantially the similar manner as described in Example 224 to give the compound (I″) shown in the following table.

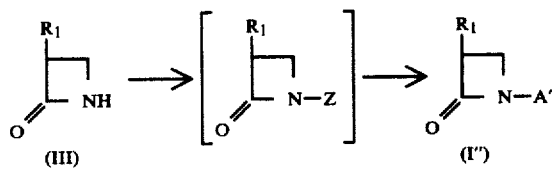

| | Compound (III) | | Compound (I″) | | |
|---|---|---|---|---|---|
| Example | $R_1$ | Reagent | $R_1$ | A′ | mp(°C.)(dec.) |
| 264 | $CH_3(CH_2)_{14}CONH-$ | [C6H5-CH2O-C6H4-CHBr-COO-CH2-C6H5] | the same as $R_1$ of Compound (III) | -CH(COOH)-C6H4-OH | 157–161 |

-continued

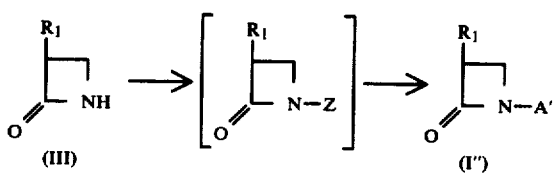

| Example | Compound (III) R₁ | Reagent | Compound (I″) R₁ | A' | mp(°C.)(dec.) |
|---|---|---|---|---|---|
| 265 | (2,4,6-trimethylphenyl with CH₂CONH—) | ″ | the same as R₁ of Compound (III) | ″ | 106–109 |
| 266 | Ph–CHCONH– with NHCOCH₂O–(2,4,6-trimethylphenyl) | ″ | the same as R₁ of Compound (III) | ″ | 130–134 |
| 267 | Ph–CHCONH– with NHCOCH₂O–(phenyl-COOC₂H₅) | ″ | the same as R₁ of Compound (III) | ″ | 127–130 |
| 268 | Ph–CHCONH– with CONH–Ph | ″ | the same as R₁ of Compound (III) | ″ | (sodium salt) 183–187 |
| 269 | Ph–CHCONH– with COOC₂H₅ | ″ | the same as R₁ of Compound (III) | ″ | 103–107 |
| 270 | Ph–CHCONH– with CONH(CH₂)₂NH–COCH₂–Ph | ″ | the same as R₁ of Compound (III) | ″ | 115–118 |

The 3-acylamino-2-azetidinone (III) shown in the following table was treated in substantially the similar manner as described in Example 239 to give the compound (I″) shown in the following table.

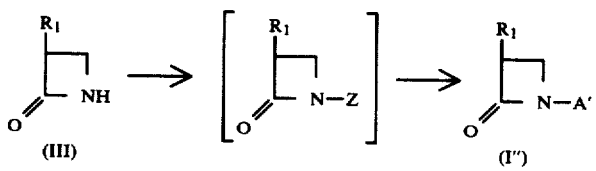

| Ex. | Compound (III) R₁ | Reagent | Compound (I″) R₁ | A' | mp (°C.) (dec.) |
|---|---|---|---|---|---|
| 271 | Ph–CH₂CONH– | $(CH_3)_2CH-CHBr-COOC_2H_5$ | the same as R₁ of Compound (III) | $-CHCH(CH_3)_2$ with COOH | 106–109 |
| 272 | (pyridyl)–OCH₂CONH– | $C_2H_5OOC$–(phenyl)–CHBr with $C_2H_5OOC$ | the same as R₁ of Compound (III) | $-CH$–(phenyl)–OH with COOH | 192.5–193 |

-continued

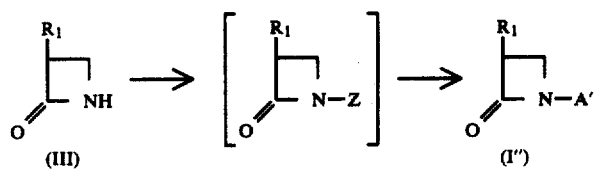

| Ex. | Compound (III) R₁ | Reagent | Compound (I'') R₁ | A' | mp (°C.) (dec.) |
|---|---|---|---|---|---|
| 273 | ⌬—CHCONH— <br>        NHCOCH₂—⌬S | " | the same as R₁ of Compounds (III) | " | (sodium salt) 221–224 |
| 274 | ⌬—CHCONH— <br>        NHCOCH₂O—⌬(Cl, NO₂) | " | the same as R₁ of Compound (III) | " | 77–81 |
| 275 | ⌬—CHCONH— <br>        NHCOCH—⌬ <br>            O—⌬(Cl) | " | the same as R₁ of Compound (III) | " | 112–116 |
| 276 | (Cl)⌬—isoxazole(CH₃)—CONHCHCONH— (⌬) | " | the same as R₁ of Compound (III) | " | 122–124 |
| 277 | ⌬—COCH₂SCH₂CONH— | " | the same as R₁ of Compound (III) | " | 130–135 |
| 278 | O₂N—⌬—CH₂CONH— | " | the same as R₁ of Compound (III) | " | 234–236 |
| 279 | ⌬—CHCONH— <br>        NHCOCH₂O—⌬(Cl, CO—⌬) | " | the same as R₁ of Compound (III) | " | 135–137 |
| 280 | ⌬—CHCONH— <br>        NHCOCO—⌬ | " | the same as R₁ of Compound (III) | " | 143–146 |
| 281 | ⌬S—CHCONH—(⌬) | " | the same as R₁ of Compound (III) | " | 139–143 |
| 282 | ⌬S—CHCONH— <br>        NHCOCH₂O—⌬(Cl, NO₂) | " | the same as R₁ of Compound (III) | " | (sodium salt) 187–190 |
| 283 | ⌬(NO₂)—OCH₂CONH— | " | the same as R₁ of Compound (III) | " | (sodium salt) 116 |

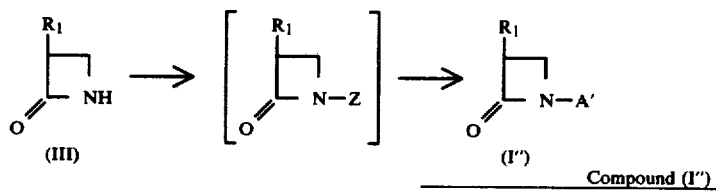

The 3-acylamino-2-azetidinone (III) was treated in substantially the similar manner as described in Example 239 to give the compound (I″) shown in the following table.

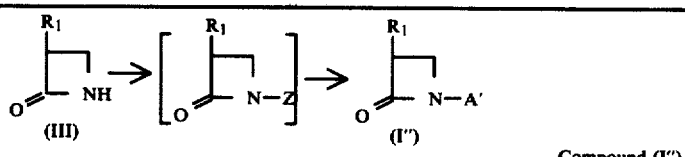

EXAMPLE 291

3-[2-{4-(3-Amino-3-carboxypropoxy)phenyl}-2-hydroxyiminoacetamido]lactacillanic acid (1.0 g.) was dissolved in 1.5% sodium bicarbonate aqueous solution (20 ml.), and to the solution was added sodium hydrogen sulfite (1.0 g.), and then the mixture was heated for 3 hrs. at 80° C. The reaction mixture was adjusted to pH 3 with 10% hydrochloric acid, and the mixture was concentrated to a volume of about 10 ml. and the concentrate was adjusted to pH 3 with 10% hydrochloric acid again to give crystals of 3-[4-(3-amino-3-carboxypropoxy)phenylglyoxyloylamino]lactacillanic acid (0.57 g.). Mp 216° C. (dec.).

EXAMPLE 292

3-[2-{4-(3-Acetamido-3-carboxypropoxy)phenyl}-2-hydroxyiminoacetamido]lactacillanic acid was treated in substantially the similar manner as described in Example 291 to give crystals of 3-[4-(3-acetamido-3-carboxypropoxy)phenylglyoxyloylamino]lactacillanic acid. Mp 96° to 102° C. (dec.).

EXAMPLE 293

3-[2-{4-(3-carboxy-3-phthalimidopropoxy)phenyl}-2-hydroxyiminoacetamido]lactacillanic acid (4.2 g.) was dissolved in methanol (40 ml.). A solution, prepared by dissolving sodium hydrogen sulfite (4.2 g.) in water (80 ml.), was added to the solution, and the mixed solution was heated for 3.5 hrs. under reflux. Subsequently, the reaction mixture was concentrated to a volume of about 30 ml., and the concentrate was adjusted to pH 2.0 with 10% hydrochloric acid under ice-cooling, and then the solution was extracted with ethyl acetate. The extract was washed with water and dried, and then the solvent was distilled off from the extract to give 3-[4-(3-carboxy-3-phthalimidopropoxy)phenylglyoxyloylamino]-lactacillanic acid (2.1 g.). Mp 115° to 120° C. (dec.).

EXAMPLE 294

3-[2-[4-{3-Carboxy-3-(3-phenylureido)propoxy}-phenyl]-2-hydroxyiminoacetamido]lactacillanic acid was treated in substanially the similar manner as described in Example 293 to give 3-[4-{3-carboxy-3-(3-phenylureido)propoxy}phenylglyoxyloylamino]lactacillanic acid. Mp 100° to 106° C. (dec.).

EXAMPLE 295

3-[2-{4-(3-Amino-3-carboxypropoxy)phenyl}-2-hydroxyiminoacetamido]lactacillanic acid (0.5 g.) was suspended in an aqueous solution (10 ml.) of ammonium acetate (1.93 g.), and 28% ammonia water (0.3 ml.) and zinc powder (0.435 g.) were added to the solution, whereafter the mixture was stirred for 24 hrs. at ambient temperature. The reaction mixture was adjusted to pH 4 with 1N-hydrochloric acid, and hydrogen sulfide gas was introduced into the solution, and then the insoluble material was filtered off. The filtrate was concentrated under reduced pressure to give a residue, and the residue was dissolved in water (10 ml.), and then to the solution was added ethanol (200 ml.). The forming precipitate was collected by filtration, and dried to give 3-[2-{4-(3-amino-3-carboxypropoxy)phenyl}-glycinamido]lactacillanic acid (420 mg.). Mp 206° to 208° C. (dec.).

EXAMPLE 296

N,N-Dimethylformamide (0.5 ml.), formic acid (0.5 ml.) and zinc powder (1.0 g) were added to a solution containing 3-[2-{4-(3-phthalimido-3-carboxypropoxy)-phenyl}-2-hydroxyiminoactamido]lactacillanic acid (1.00 g.), methanol (8 ml.) and water (2 ml.), and the mixture was stirred for 4 hrs. The zinc powder was filtered off from the reaction mixture, and hydrogen sulfide was introduced into the filtrate, and then the insoluble material was filtered off. The filtrate was concentrated under reduced pressure, to give a residue which was powdered with acetone to give 3-[2-{4-(3-phthalimido-3-carboxypropoxy)phenyl}glycinamido]-lactacillanic acid (0.68 g.). Mp 215° to 219° C. (dec.).

EXAMPLE 297

10% Palladium:carbon (0.6 g.) was added to a solution containing 3-[2-{4-(3-acetamido-3-carboxypropoxy)phenyl}-2-hydroxyiminoacetamido]lactacillanic acid (1.85 g.), sodium bicarbonate (0.6 g.) and water (20 ml.). The mixture was subjected to absorption of a calculated volume of hydrogen gas at ordinary temperature and ordinary atm. The catalyst was filtered off from the reaction mixture, and the filtrate was adjusted to pH 3 with 10% hydrochloric acid under ice-cooling, and then treated with an activated carbon. The aqueous solution obtained was crystallized from acetone (150 ml.) under ice-cooling. The crystals were collected by filtration, and washed with water (10 ml.) and acetone, respectively to give 3-[2-{4 -(3-acetamido-3-carboxypropoxy)phenyl}glycinamido]lactacillanic acid (0.38 g.). Futhermore, the washings obtained above was crystallized from acetone (10 ml.) under ice-cooling, and the crystals were washed with acetone, and then collected by filtration to recover a object compound (0.32 g.). Total yield was 0.70 g. Mp 198° to 204° C. (dec.).

EXAMPLE 298

10% palladium.carbon (3 g.) was added to a solution of 3-[2-{4-(3-benzamido-3-carboxypropoxy)phenyl}-2-hydroxyiminoacetamido]lactacillanic acid (10.0 g.), sodium bicarbonate (2.79 g.) and water (70 ml.), and the mixture was subjected to a catalytic reduction for 5 hrs. under shaking enough under 3 atm at ordinary temperature. After the reaction, the catalyst was filtered off from the reaction mixture, and the filtrate was adjusted to pH 3.0 with 10% hydrochloric acid under ice-cooling to give crystals of 3-[2-{4-(3-benzamido-3- carboxypropoxy)phenyl}glycinamido]lactacillanic acid (7.8 g.). Furthermore, a object compound (0.4 g.) was recovered from the mother liquor. Total yield was 8.2 g. Mp 171° to 176° C. (dec.).

EXAMPLE 299

3-[4-(3-Carboxy-3-phthalimidopropoxy)phenylglyoxyloylamino]lactacillanic acid (1.10 g.) was suspended in water (11 ml.), and to the suspension was added sodium bicarbonate (0.40 g.) to dissolve it. To the solution was added sodium borohydride (0.08 g.) under ice-cooling, and the mixture was stirred for 4 hrs. at the same temperature. The reaction mixture was adjusted to pH 2 with 10% hydrochloric acid to give crystals of 3-[2-{4-(3-carboxy-3-phthalimidopropoxy)-phenyl}-2-hydroxyiminoacetamido]lactacillanic acid (0.91 g.). Mp 160° to 163° C. (dec.).

EXAMPLE 300

Acetic anhydride (20 ml.) was added to a suspension, prepared by suspending 3-[2-{4-(3-amino-3-carboxypropoxy)phenyl}-2-hydroxyiminoacetamido]lactacillanic acid (10 g.) in methanol (150 ml.), and the mixture was stirred for 4.5 hrs. The reaction mixture was concentrated under reduced pressure to give a residue, to which was added toluene. The solution was concentrated under reduced pressure again to give a residue which was powdered by adding ethyl acetate to give 3-[2-{4-(3-acetamido-3-carboxypropoxy)phenyl}-2-hydroxyiminoacetamido]lactacillanic acid (10.3 g.). Mp 90° to 93° C. (dec.).

EXAMPLE 301

Acetic anhydride (6 ml.) was added to a methanol suspension (60 ml.) of 3-[4-(3-amino-3-carboxypropoxy)phenylglyoxyloylamino]lactacillanic acid (3.0 g.) under ice-cooling, and the mixture was stirred for 1 hour at the same temperature, and further stirred for 4 hrs. at ambient temperature. The reaction mixture was concentrated under reduced pressure, and the concentrate was powdered with ether to give 3-[4-(3-acetamido-3-carboxypropoxy)phenylglyoxyloylamino]lactacillanic acid (2.26 g.). Mp 96° to 102° C. (dec.).

EXAMPLE 302

3-[2-{4-(3-Amino-3-carboxypropoxy)phenyl}-glycinamido]lactacillanic acid was treated in substantially the similar manner as descriebed in Example 301 to give 3-[2-{4-(3-acetamido-3-carboxypropoxy)phenyl}-N-acetylglycinamido]lactacillanic acid.

I.R. absorption spectrum,
$v_{cm-1}$ (Nujol):1735, 1650.

EXAMPLE 303

3-[2-{4-(3-Amino-3-carboxypropoxy)phenyl}-2-hydroxyiminoacetamido]lactacillanic acid (0.50 g.) was suspended in dried methylene chloride (20 ml.). To the suspension was added N,O-bis(trimethylsilyl)acetamide (1.50 g.), and the mixture was stirred for 2 hrs. at ambient temperature, and then heated for 10 minutes under reflux. The reaction solution was cooled to 0° to 5° C., and triethylamine (0.12 g.) and 2,2,2-trifluoroacetic anhydride (0.27 g.) were added to the solution, and then the reaction solution was stirred for 1 hour. The methylene chloride was distilled off from the reaction mixture to give a residue which was dissolved in ethyl acetate (20 ml.). The solution was washed with 2% hydrochloric acid five times, with water twice and with a sodium chloride-saturated-aqueous solution once, respectively, and then dried over anhydrous magnesium sulfate. The solvent was distilled off from the solution, and benzene was added to the residue to give powdery crystals of 3-[2-[4-{3-carboxy-3-(2,2,2-trifluoroacetamido)propoxy}phenyl]-2-hydroxyiminoacetamido]lactacillanic acid (0.41 g.). Mp 143° to 147° C. (dec.).

EXAMPLE 304

N,O-Bis(trimethylsilyl)acetamide (15 ml.) was added to a suspension, prepared by suspending 3-[4-(3-amino-3-carboxypropoxy)phenylglyoxyloylamino]lactacillanic acid (4.0 g.) in dried methylene chloride (80 ml.), and the mixture was stirred for 2 hrs. to dissolve the starting material completely. To the solution was added triethylamine (0.88 g.) under ice-cooling, and then a solution, prepared by dissolving 2,2,2-trifluoroacetic anhydride (1.9 g.) in methylene chloride (5 ml.), was added dropwise to the solution during 30 minutes. The reaction mixture was stirred for 1.5 hrs. at the same temperature, and then the methylene chloride was distilled off from the reaction mixture under reduced pressure, whereafter the residue was poured into a mixture of ice-water (50 ml.) and ethyl acetate (100 ml.). The ethyl acetate layer separated out was dried over anhydrous magnesium sulfate, and then the solvent was distilled off to give a residue to which was added benzene to give powdery crystals of 3-[4-{3-carboxy-3-(2,2,2-trifluoroacetamido)propoxy}phenylglyoxyloylamino]lactacillanic acid (3.0 g.).

I.R. absorption spectrum,
$v_{cm-1}$ (Nujol):1730, 1680.

EXAMPLE 305

3-[2-{4-(3-Amino-3-carboxypropoxy)phenyl}-2-hydroxyiminoacetamido]lactacillanic acid (20.0 g.) was suspended in a mixture of water (200 ml.) and acetone (200 ml.), followed by adding sodium bicarbonate (6.8 g.) to dissolve it. Benzoyl chloride (6.7 g.) was added dropwise to the solution under ice cooling, keeping the solution in pH 8.0. The reaction mixture was stirred for 4 hrs. and the acetone was distilled off from the reaction mixture. The remaining aqueous solution was washed with ethyl acetate, and ethyl acetate (400 ml) was added to the solution. The mixture was adjusted to pH 2.0 with 10% hydrochloric acid under cooling and then the ethyl acetate layer was separated out, and washed with water and with a sodium chloride-saturated-aqueous solution, respectively, and dried. The ethyl acetate was distilled off from the solution to give a residue, followed by suspending in water (200 ml.). 1 N-Sodium hydroxide aqueous solution (160 ml.) was added to the suspension, and the solution was stirred for 2 hrs. Ethyl acetate (400 ml.) was added to the solution, and the mixture was adjusted to pH 2.0 with 10% hydrochloric acid under ice-cooling. The ethyl acetate layer separated out was washed with water and dried. The solvent was distilled off from the solution to give the powder (21.6 g.) which was crystallized from a mixture of acetone and benzene to give crystals of 3-[2-{4-(3-benzamido-3-carboxypropoxy)phenyl}-2-hydroxyiminoacetamido]lactacillanic acid (10.4 g.). Mp 170° to 172° C. (dec.).

EXAMPLE 306

3-[4-(3-Amino-3-carboxypropoxy)phenylglyoxylaylamino]lactacillanic acid (970 mg.) was suspended in water (10 ml.), and the suspension was adjusted to pH 8 to 9 with 1 N-sodium hydroxide aqueous solution under ice-cooling. An acetone solution (10 ml.) of phenyl isocyanate (360 mg.) was added dropwise to the solution, keeping the solution at pH 8 to 9 during adding dropwise. The solution was stirred for an hour, and the diphenylurea produced as a by-product was filtered off from the solution. The filtrate was adjusted to pH 1 to 2 with 10% hydrochloric acid and then extracted with ethyl acetate. The extract was washed with a sodium chloride-saturated-aqueous solution, and dried over anhydrous magnesium sulfate, whereafter the solvent was distilled off from the solution to give crystals of 3-[4-{3-carboxy-3-(3-phenylureido)propoxy}phenylglyoxyloylamino]lactacillanic acid (1.33 g.). Mp 100° to 106° C. (dec.).

EXAMPLE 307

3-[2-{4-(3-Amino-3-carboxypropoxy)phenyl}-glycinamido]lactacillanic acid (250 mg.) was suspended in water (5 ml.), and the suspension was adjusted to pH 8 with 1 N-sodium hydroxide aqueous solution to dissolve it under ice-cooling. A dried acetone solution (2 ml.) of phenyl isocyanate (150 mg.) was added to the solution under cooling, keeping the solution in pH 8 to 9 during the addition. The solution was stirred for an hour under ice-cooling, and then adjusted to pH 2 with 10% hydrochloric acid to give a precipitate. The precipitate was collected by filtration and washed with water, and then dissolved in a sodium bicarbonate aqueous solution. An insoluble materials were filtered off, and the filtrate was adjusted to pH 1 to 2 with 10% hydrochloric acid to give crystals which were collected by filtration, washed with water and then dried on phosphorus pentachloride to give crystals of 3-[2-[4-{3-carboxy-3-(3-phenylureido)propoxy}phenyl]-2-(3-phenylureido)acetamido]lactacillanic acid (0.35 g.). Mp 170° to 172° C. (dec.).

EXAMPLE 308

A suspension of 3-[2-{4-(3-amino-3-carboxypropoxy)phenyl}-2-hydroxyiminoacetamido]lactacillanic acid (10 g.), water (100 ml.) and acetone (30 ml.) was adjusted to pH 8 to 9 with 1 N-sodium hydroxide aqueous solution under ice-cooling. To the solution was added dropwise an acetone solution (5 ml.) of phenyl isocyanate (2.9 g.) at the same temperature, and the mixture was stirred for an hour. The acetone was distilled off from the reaction mixture under reduced pressure, and the remaining solution was adjusted to pH 2 with 10% hydrochloric acid, and extracted with ethyl acetate. The extract was washed with diluted hydrochloric acid and water, respectively, and dried. The ethyl acetate was distilled off from the solution to give a residue which was crystallized from ether (100 ml.) to give crystals of 3-[2-[4-{3-carboxy-3-(3-phenylureido)propoxy}phenyl]-2-hydroxyiminoacetamido]lactacillanic acid (10.3 g.). Mp 135° to 139° C. (dec.).

EXAMPLE 309

An acetone solution (5 ml.) containing ethyl phthalimidoformate (0.60 g.) was added dropwise to a solution containing 3-[2-{4-(3-amino-3-carboxypropoxy)phenyl}-2-hydroxyiminoacetamido]lactacillanic acid (0.94 g.), 10% a dipotassium hydrogenphosphate aqueous solution (20 ml.) and acetone (10 ml.), and the mixture was stirred for 2 hrs., keeping the mixture in pH 8. The acetone was distilled off from the reaction mixture under reduced pressure, and the remaining solution was adjusted to pH 2 with diluted hydrochloric acid, and then extracted with ethyl acetate. The extract was washed with water and dried over anhydrous magnesiumsulfate. The ethyl acetate was distilled off from the solution to give residue, which was crystallized from an ethanol aqueous solution to give crystals of 3-[2-{4-(3-carboxy-3-phthalimidopropoxy)phenyl}-2-hydroxyiminoacetamido]lactacillanic acid (0.69 g.). Mp 160° to 165° C. (dec.).

EXAMPLE 310

3-[2-{4-(3-Amino-3-carboxypropoxy)phenyl}-glycolamido]lactacillanic acid was treated in substantially the similar manner as described in Example 309 to give crystals of 3-[2-{4-(3-carboxy-3-phthalimidopropoxy)phenyl}glycolamido]lactacillanic acid. Mp 160° to 163° C. (dec.).

EXAMPLE 311

3-[4-(3-Amino-3-carboxypropoxy)phenylglyoxyloylamino]lactacillanic acid was treated in substantially the similar manner as described in Example 309 to give crystals of 3-[4-(3-carboxy-3-phthalimidopropoxy)phenylglyoxyloylamino]lactacillanic acid. Mp 216° C. (dec.).

EXAMPLE 312

Phenyl isothiocyanate (320 mg.) was added to a 50% pyridine aqueous solution (6 ml.) of 3-[2-{4-(3-amino-3-carboxypropoxy)phenyl}glycinamido]lactacillanic acid (250 mg.) at 40° C. under stirring. The mixture was stirred for an hour, keeping the mixture in pH 8 to 9 with a sodium bicarbonate-saturated-aqueous solution. The reaction mixture was washed with ether, and the aqueous layer was separated out, and then adjusted to pH 1 to 2 with 10% hydrochloric acid under cooling to give crystals of 3-[2-[4-{3-carboxy-3-(3-phenylthioureido)propoxy}phenyl]-2-(3-phenylthioureido)acetamido]lactacillanic acid (250 mg.). Mp 190° to 195° C. (dec.).

EXAMPLE 313

3-[2-{4-(3-Amino-3-carboxypropoxy)phenyl}-glycinamido]lactacillanic acid (2.0 g.) was suspended in a 50% pyridine aqueous solution (20 ml.), and the suspension was adjusted to pH 8.6 with 1 N-sodium hydroxide aqueous solution to dissolve it. To the solution was added 1-naphthyl isothiocyanate (1.94 g.), and the mixture was stirred for 4 hrs. The reaction mixture was washed with ether and adjusted to pH 2.0 with 10% hydrochloric acid under cooling to give a precipitate. The precipitate was collected by filtration and washed with water. The Precipitate was dissolved in a sodium bicarbonate-saturated-aqueous solution, and 10% hydrochloric acid was added to the solution to give crystals of 3-[2-[4-[3-carboxy-3-{3-(1-naphthyl)thioureido}-propoxy]phenyl]-2-{3-(1-naphthyl)thioureido}acetamido]lactacillanic acid (2.7 g.). Mp 169° to 173° C. (dec.).

EXAMPLE 314

3-[2-{4-(3-Amino-3-carboxypropoxy)phenyl}-glycinamido]lactacillanic acid (480 mg.) was suspended in water (10 ml.), and to the suspension was added 1 N-potassium hydroxide aqueous solution (5 ml.) under ice-cooling, while stirring. An acetone (5 ml.) solution of O-ethyl-S-methyl dithiocarbonate (0.72 g.) was added to the solution, and then the mixture was stirred for 5 hrs. at ambient temperature. The reaction mixture was washed with ether, and the remaining aqueous layer was separated out. The aqueous solution was adjusted to pH 1 to 2 with 10% hydrochloric acid and extracted with ethyl acetate, and then the extract was washed with water and dried. The solvent was distilled off from the solution to give 3-[2-[4-{3-carboxy-3-ethoxy(thiocarbonyl)aminopropoxy}phenyl]-2-ethoxy(thiocarbonyl)aminoacetamido]lactacillanic acid (230 mg.). Mp 112° to 119° C. (dec.).

EXAMPLE 315

3-[2-{4-(3-Amino-3-carboxypropoxy)phenyl}-2-hydroxyiminoacetamido]lactacillanic acid (1.0 g.) was dissolved in a mixture of 0.1 N-sodium hydroxide aqueous solution (40 ml.) and acetone (15 ml.). To the solution were added dropwise an acetone (5 ml.) solution containing 2-(4-chloro-2-nitrophenoxy)acetyl chloride (550 mg.) and 0.1 N-sodium hydroxide aqueous solution (40 ml.) at the same time under ice-cooling, while stirring. The mixture (pH 9.2 to 9.4) was stirred for 40 minutes at the same temperature, and further stirred for 40 minutes at ambient temperature. The reaction mixture was washed with ethyl acetate, and then ethyl acetate was added to the aqueous layer, whereafter the mixture was adjusted to pH 2 with 10% hydrochloric acid. The ethyl acetate layer was separated out, washed with water and dried over anhydrous magnesium sulfate. The solvent was distilled off from the solution to give a residue which was washed with ether several times. The residue was dissolved in ethyl acetate under warming, and an insoluble material was filtered off and then to the solution was added chloroform to give a powder which was collected by filtration to give 3-[2-[4-[3-{2-(4-chloro-2-nitrophenoxy)acetamido}-3-carboxypropoxy]phenyl]-2-hydroxyiminoacetamido]lactacillanic acid (150 mg.). Furthermore, an object compound (30 mg.) was obtained from the mother liquor. Total yield was 180 mg. Mp 145° to 150° C. (dec.).

EXAMPLE 316

An acetone (4 ml.) solution containing 2-(2-thienyl)acetyl chloride (352 mg.) was added dropwise to a solution containing 3-[2-{4-(3-amino-3-carboxypropoxy)-phenyl}-2-hydroxyiminoacetamido]lactacillanic acid (1.0 g.), sodium bicarbonate (504 mg.), water (30 ml.) and acetone (10 ml.) under ice-cooling, while stirring, keeping the solution in pH 8. The mixture was stirred for 40 minutes at the same temperature, and further stirred for 30 minutes at ambient temperature. The reaction mixture was washed with ethyl acetate, and then ethyl acetate was added to the solution, whereafter the mixture was adjusted to pH 2 with 10% hydrochloric acid. The ethyl acetate layer was separated out, and the remaining aqueous layer was extracted with ethyl acetate. These ethyl acetate layers were combined and washed with a sodium chloride-saturated-aqueous solution, and then dried over anhydrous magnesium sulfate. The solvent was distilled off from the solution, and the residue (740 mg.) obtained was added to 0.1 N-sodium hydroxide aqueous solution (30 ml.). The solution (pH 9.4) was stirred for an hour at ambient temperature, and washed with ethyl acetate, and to the solution was added ethyl acetate. The mixture was adjusted to pH 2 by adding 10% hydrochloric acid and then treated in the similar manner as described above to give a residue (450 mg.). The residue was dissolved in a mixture of acetone and n-hexane, and the solution was treated with activated carbon, followed by filtration. The filtrate was concentrated to give a residue which was washed with ether several times and with n-hexane once to give 3-[2-[4-[3-carboxy-3-{2-(2-thienyl)acetamido}propoxy]-phenyl]-2-hydroxyiminoacetamido]lactacillanic acid (400 mg.), mp 145° to 150° C. (dec.).

EXAMPLE 317

An acetone (25 ml.) solution containing α-ethoxycarbonyloxycarbonyl-α-toluenesulfonic acid triethylamine salt (3.1 g.) and an aqueous solution (10 ml.) of sodium bicarbonate (756 mg.) were added dropwise to a solution containing 3-[2-{4-(3-amino-3-carboxypropoxy)-phenyl}-2-hydroxyiminoacetamido]lactacillanic acid (2.0 g.), sodium bicarbonate (756 mg.), water (35 ml.) and acetone (15 ml.) during 15 minutes under ice-cooling. The reaction mixture (pH 7.6) was stirred for 30 minutes at the same temperature, and further stirred for 30 minutes at ambient temperature. The acetone was distilled off from the reaction mixture, and the remaining solution was adjusted to pH 3 with 10% hydrochloric acid, whereafter the solution was washed with ethyl acetate. The ethyl acetate layer was separated out, and the remaining aqueous solution was adjusted to pH 1 with 10% hydrochloric acid, and extracted with n-butyl alcohol. The extract obtained was washed with 5% hydrochloric acid once and with a sodium chloride-saturated-aqueous solution once, respectively, and dried over anhydrous magnesium sulfate. The extract was adjusted to pH 6 with an acetone (21 ml.) solution containing sodium 2-ethylhexanoate (11 mg.) to give a powder which was collected by filtration. The powder was washed with acetone to give the colorless powder (2.3 g.). A part of the powder (1.0 g.) was dissolved in water (3 ml.), and the solution was adjusted to pH 3 with 10% hydrochloric acid, and then washed with ethyl acetate, whereafter the solution was subjected to column chromatography using a nonionic adsorption resin, Amberlite XAD-2 (trade mark, maker; Rohm and Haas Co. Ltd.,), and the compound eluted with water was lyophillized to give 3-[2-[4-{3-carboxy-3-(2-phenyl-2-sulfoacetamido)propoxy}phenyl]-2-hydroxyiminoacetamido]lactacillanic acid sodium salt (350 mg.). Furthermore, an object compound (480 mg.) was recovered from the fractions, eluted with water containing methanol (20%) and methanol. Total yield was 830 mg. Mp 244° to 250° C. (dec.).

EXAMPLE 318

Potassium carbonate (0.127 g.) and water (3 ml.) were added to an acetone solution (3 ml.) containing N-methylaniline (0.200 g.), and the solution was stirred at 25° to 28° C. To the solution was added dropwise a mixture (4 ml.) of acetone and water (1:1) containing 3-(2-bromoacetamido)lactacillanic acid (0.321 g.) and sodium bicarbonate (0.067 g.), and the reaction mixture was reacted for 17 hrs. at the same temperature. The acetone was distilled off from the reaction mixture under reduced pressure, and the remaining aqueous layer was washed with ethyl acetate. The aqueous layer was adjusted to pH 3 with diluted hydrochloric acid, and then extracted with ethyl acetate. The extract was washed with water, dried and then concentrated. The residue obtained was crystallized from methanol to give crystals of 3-(N-methyl-N-phenylglycinamido)lactacillanic acid (0.208 g.). Mp 198° to 199° C. (dec.).

The following compounds were obtained in substantially the similar manner as described above.

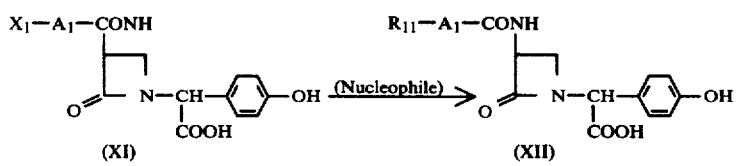

| Example | Compound (XI) | | Nucleophile | Compound (XII) | | mp(°C.) (dec.) |
|---|---|---|---|---|---|---|
| | $X_1$— | —$A_1$— | | $R_{11}$ | —$A_1$— | |
| 319 | Br— | —$CH_2$— | ⟨⟩—$NH_2$ | ⟨⟩—NH— | the same as $A_1$ of the Compound (XI) | 193–194.5 |

-continued $X_1-A_1-CONH$ ... $\xrightarrow{\text{(Nucleophile)}}$ ... $R_{11}-A_1-CONH$ ...

(XI)  (XII)

| | Compound (XI) | | | Compound (XII) | | |
|---|---|---|---|---|---|---|
| Example | $X_1-$ | $-A_1-$ | Nucleophile | $R_{11}$ | $-A_1-$ | mp(°C.) (dec.) |
| 320 | " | $-CH-$ (phenyl) | " | " | the same as $A_1$ of the Compound (XI) | 97–101 |
| 321 | " | $-CHCONHCH-$ (diphenyl) | " | " | the same as $A_1$ of the Compound (XI) | 158–161 |
| 322 | " | $-CH_2-$ | $\text{Ph-}CH_2-NH-CH_3$ | $\text{Ph-}CH_2N(CH_3)-$ | the same as $A_1$ of the Compound (XI) | 154–157 |

EXAMPLE 323

Morpholine (0.262 g.) was dissolved in a mixture (5 ml.) of acetone and water (1:1), and to the solution was added potassium carbonate (0.180 g.). The solution was cooled to 10° C., and to the solution was added dropwise a mixture (5 ml.) of acetone and water (1:1) containing 3-(2-bromoacetamido)lactacillanic acid (0.464 g.) and sodium bicarbonate (0.110 g.). The reaction mixture was reacted for 5 hrs., keeping the reaction temperature at 10° to 20° C. The acetone was distilled off from the reaction mixture under reduced pressure, and the remaining aqueous solution was washed with ethyl acetate. The aqueous solution was adjusted to pH 1 to 2 with diluted hydrochloric acid and washed with ethyl acetate. The aqueous solution was adjusted to pH 4.5 to 4.8 with sodium bicarbonate, and the solution was concentrated under reduced pressure, and then the residue was extracted with methanol. The extract was concentrated to give an oily material which was dissolved in a small amount of methanol. Acetone was added to the solution, which was filtered. The filtrate was concentrated to give an oily material (0.38 g.) which was subjected to column chromatography using a nonionic adsorption resin, Amberlite XAD-2 (trade mark, maker; Rohm and Haas Co., Ltd.) (35 ml.). Isolation and purification were carried out. Fractions eluted with water were collected and the water was distilled off from the eluate to give crystals of 3-(2-morpholinoacetamido)-lactacillanic acid (0.38 g.). Mp 201° to 203° C. (dec.).

EXAMPLE 324

A mixture containing 3-[2-(2-bromoacetamido)-2-phenylacetamido]lactacillanic acid (196 mg.) 2-mercaptobenzoic acid (62 mg.) and 0.1 N-sodium hydroxide aqueous solution (12 ml.) was stirred for an hour at ambient temperature. The reaction mixture (pH 6.8 to 7.8) was adjusted to pH 3 with 1 N-hydrochloric acid (0.4 ml.) and washed with ether and then further adjusted to pH 1 to 2 with 1 N-hydrochloric acid. The solution was extracted with ethyl acetate and the extract was washed with water and dried over anhydrous magnesium sulfate. The solution was concentrated to a volume of about 4 ml. under reduced pressure to give crystals which were washed with ether to give crystals of 3-[2-{2-(2-carboxyphenylthio)acetamido}-2-phenylacetamido]-lactacillanic acid (125 mg.). Furthermore, an object compound (50 mg.) was recovered from the filtrate. Total yield was 175 mg. Mp 143° to 146° C. (dec.).

The following compounds were obtained in substantially the similar manner as described above.

$$X_1-A_1-CONH \xrightarrow{\text{Nucleophile}} R_{11}-A_1-CONH$$

Compound (XI): $X_1-A_1-CONH-CH(COOH)-$ attached to 4-hydroxyphenyl via N
Compound (XII): $R_{11}-A_1-CONH-CH(COOH)-$ attached to 4-hydroxyphenyl via N

| Example | Compound (XI) $X_1-$ | Compound (XI) $-A_1-$ | Nucleophile | Compound (XII) $R_{11}-$ | Compound (XII) $-A_1-$ | mp(°C.) (dec.) |
|---|---|---|---|---|---|---|
| 325 | Br— | —CH$_2$— | CH$_3$SH | CH$_3$S— | the same as A$_1$ of the Compound (XI) | 154–155 |
| 326 | " | " | CH$_2$=CHCH$_2$SH | CH$_2$=CHCH$_2$S— | the same as A$_1$ of the Compound (XI) | 178–183 |
| 327 | " | " | C$_6$H$_5$SH | C$_6$H$_5$S— | the same as A$_1$ of the Compound (XI) | 183–185 |
| 328 | " | " | (1,3,4-thiadiazol-2-yl)SH | (1,3,4-thiadiazol-2-yl)S— | the same as A$_1$ of the Compound (XI) | 163–167 |
| 329 | " | " | CH$_3$SH | CH$_3$S— | the same as A$_1$ of the Compound (XI) | 159–162 |
| 330 | " | —CH(C$_6$H$_4$)— | 2-HOOC-C$_6$H$_4$-SH | 2-HOOC-C$_6$H$_4$-S— | the same as A$_1$ of the Compound (XI) | 90–95 |
| 331 | " | " | 4-Cl-2-NO$_2$-C$_6$H$_3$-OCH$_2$CONH-CH$_2$CH$_2$SH | 4-Cl-2-NO$_2$-C$_6$H$_3$-OCH$_2$CONH-CH$_2$CH$_2$S— | the same as A$_1$ of the Compound (XI) | 77–81 |
| 332 | " | " | 2-naphthyl-NHCOCH$_2$SH | 2-naphthyl-NHCOCH$_2$S— | the same as A$_1$ of the Compound (XI) | 124–128 |

-continued

| | Compound (XI) | | | | Compound (XII) | |
|---|---|---|---|---|---|---|
| | $X_1-A_1-CONH-\overset{\underset{\displaystyle|}{}}{\underset{O}{C}}\underset{N-CH}{\overset{}{}}\begin{array}{c}OH\\ \\ COOH\end{array}$ (XI) | | $\xrightarrow{\text{Nucleophile}}$ | $R_{11}-A_1-CONH-\overset{\underset{\displaystyle|}{}}{\underset{O}{C}}\underset{N-CH}{\overset{}{}}\begin{array}{c}OH\\ \\ COOH\end{array}$ (XII) | | |
| Example | $X_1-$ | $-A_1-$ | Nucleophile | $R_{11}-$ | $-A_1-$ | mp(°C.) (dec.) |
| 333 | " | | HO–⟨pyrimidine⟩–SH with H₂N | HO–⟨pyrimidine⟩–S– with H₂N | the same as A₁ of the Compound (XI) | 217–221 |
| 334 | " | $-CH_2CONHCH-\phenyl$ | ⟨phenyl⟩-S-⟨phenyl⟩-SH | ⟨phenyl⟩-S-⟨phenyl⟩-S– | the same as A₁ of the Compound (XI) | |
| 335 | " | $-(CH_2)_3\phantom{-}$ with CH₂–⟨phenyl⟩ | ⟨pyrimidine N,NH⟩–SH | ⟨pyrimidine N,NH⟩–S– | the same as A₁ of the Compound (XI) | 192–197 |
| 336 | " | $-CH_2CO\text{-}NH-\phenyl$ | $O_2N$–⟨phenyl⟩–SH | $O_2N$–⟨phenyl⟩–S– | the same as A₁ of the Compound (XI) | 142–146 |
| 337 | " | complex substituted structure with OCH₂CONH–CH–⟨phenyl⟩, CO, Cl | HOOC–CH₂SH | HOOC–CH₂S– | the same as A₁ of the Compound (XI) | 141–144 |

-continued
$X_1-A_1-CONH$ 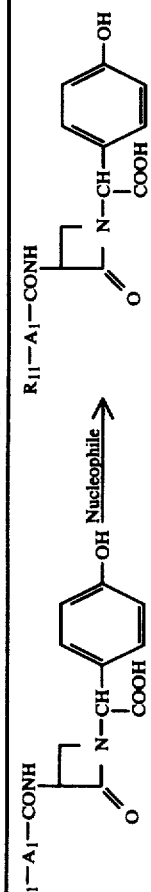 $\xrightarrow{Nucleophile}$ $R_{11}-A_1-CONH$ ...
(XI) (XII)
| Example | Compound (XI) | | Nucleophile | Compound (XII) | | mp(°C.) (dec.) |
|---|---|---|---|---|---|---|
| | $X_1-$ | $-A_1-$ | | $R_{11}-$ | $-A_1-$ | |
| 338 | " | " | HOOC—CHCH$_2$SH<br>\|<br>NH$_2$ . HCl | HOOC—CHCH$_2$S—<br>\|<br>NH$_2$ | the same as A$_1$ of the Compound (XI) | 202–206 |
| 339 | " | " | H$_2$N—CH$_2$CH$_2$SH | H$_2$NCH$_2$CH$_2$S— | the same as A$_1$ of the Compound (XI) | 191–196 |

EXAMPLE 340

3-(2-Bromo-2-phenylacetamido)lactacillanic acid (86 mg.) and cysteine hydrochloride (one hydrate) (35 mg.) were suspended in water (3 ml.), and to the suspension was added 1N-sodium hydroxide aqueous solution (0.4 ml.) under ice-cooling, while stirring. The solution was reacted for about 3 hrs. and then the mixture was adjusted to pH 8, followed by being reacted for 2 hrs. The reaction mixture was adjusted to about pH 2 with 1N-hydrochloric acid and then filtered. The filtrate was adjusted to pH 8 to 9 with a sodium bicarbonate aqueous solution, and the concentrated to give a residue which was subjected to column chromatography using a nonionic adsorption resin, Amberlite XAD-2 (trade mark, maker; Rohm and Haas Co., Ltd.) (20 ml.) which had been washed previously with methanol and water. The fractions, obtained by being eluted with water, were collected, and the eluate was evaporated to give crystals of 3-[2-(2-amino-2-carboxyethylthio)-2-phenylacetamido]lactacillanic acid disodium salt of carboxy group (20 mg.). Mp 211° to 216° C. (dec.).

EXAMPLE 341

3-(2-Bromo-2-phenylacetamido)lactacillanic acid (150 mg.) and 2-aminoethanethiol (35 mg.) were treated in substantially the similar manner as described in Example 340 to give crystals of 3-[2-(2-aminoethylthio)-2-phenylacetamido]lactacillanic acid sodium salt (54 mg.). Mp 171° to 173° C. (dec.).

EXAMPLE 342

A mixture of 3-(2-bromoacetamido)lactacillanic acid (107 mg.), water (3 ml.) and 1N-potassium hydroxide aqueous solution (0.6 ml.) was added dropwise to a solution containing cysteine hydrochloride (38 mg.), water (3 ml.) and 1N-potassium hydroxide aqueous solution (0.9 ml.) under ice-cooling while stirring, and then the solution was reacted for an hour at the same temperature. The reaction mixture was adjusted to about pH 4 with 1N-hydrochloric acid (0.9 ml.), and concentrated under reduced pressure to give a residue which was dissolved in methanol. The solution was subjected to column chromatography using a nonionic adsorption resin, Amberlite XAD-2 (trade mark, maker; Rohm and Haas Co., Ltd.). Fractions eluted with water were collected, and evaporated to give crystals of 3-[2-(2-amino-2-carboxyethylthio)acetamido]lactacillanic acid (95 mg.). Mp 105° to 110° C. (dec.).

The following compounds were obtained in substantially the similar manner as described above.

| | Compound (XI) | | | Compound (XII) | | |
|---|---|---|---|---|---|---|
| Example | $X_1$— | —$A_1$— | Nucleophile | $R_{11}$— | —$A_1$— | mp(°C.) (dec.) |
| 343 | Br— | —CH$_2$— | H$_2$NCH$_2$CH$_2$SH · HCl | H$_2$NCH$_2$CH$_2$S— | the same as $A_1$ of the compound (XI) | 171–175 |
| 344 | " | " | H$_2$NCH$_2$-(N—N/S)-SH · HCl | H$_2$NCH$_2$-(N—N/S)-S— | the same as $A_1$ of the compound (XI) | 176–180 |
| 345 | " | (S)-CH-CH$_2$CONH | HOOC—CHCH$_2$SH / NH$_2$ · HCl | HOOC—CHCH$_2$S— / NH$_2$ | the same as $A_1$ of the compound (XI) | 187–192 |
| 346 | " | —CH$_2$CONHCH— (phenyl) | HO-(pyrimidine with H$_2$N, N, N)-SH | HO-(pyrimidine with H$_2$N, N, N)-S— | the same as $A_1$ of the compound (XI) | 230–205 |
| 347 | " | " | H$_2$NCH$_2$-(N—N/S)-SH | H$_2$NCH$_2$-(N—N/S)-S— | the same as $A_1$ of the compound (XI) | 196–199 |

EXAMPLE 348

Sodium pyridine-1-oxide-2-thiolate (60 mg.) was added to a mixture of 3-[2-(2-bromoacetamido)-2-phenylacetamido]lactacillanic acid (200 mg.) and 0.1N-sodium hydroxide aqueous solution (4 ml.) under ice-cooling, and the mixture was stirred for 30 minutes. Ethyl acetate was added to the reaction mixture, and the solution was adjusted to pH 1 to 2 with 10% hydrochloric acid to give a precipitate which was collected by decantation. The precipitate was dried and washed with acetone to give 3-[2-{2-(pyridyl-1-oxide-2-thio)acetamido}2-phenylacetamido]lactacillanic acid (82 mg.). Furthermore, the acetone washings was concentrated to give a residue which was washed with diisopropyl ether to recover an object compound (33 mg.). Total yield was 115 mg. Mp 160° to 164° C. (dec.).

EXAMPLE 349

3-(2-Bromoacetamido)lactacillanic acid (285 mg.) and sodium pyridine-1-oxide-2-thiolate (120 mg.) were treated in substantially the similar manner as described in Example 348 to give 3-[2-(pyridyl-1-oxide-2-thio)acetamido]lactacillanic acid (250 mg.). Mp 221° to 225° C. (dec.).

EXAMPLE 350

8-Mercapto-9H-purine (76 mg.) was added to a mixture of 3-[2-phenyl-2-(2-phenylsulfoacetamido)acetamido]lactacillanic acid (285 mg.) and 0.1N-sodium hydroxide aqueous solution (10 ml.) under ice-cooling. After the reaction temperature was elevated to ambient temperature, the reaction mixture was stirred for 3 hrs. To the reaction mixture was added 1N-hydrochloric acid (0.5 ml.) to give a precipitate which was collected by filtration. The precipitate was washed with water and dried to give 3-[2-phenyl-2-{2-(9H-purin-8-yl-thio)acetamido}acetamido]lactacillanic acid (120 mg.) Mp 192° to 197° C. (dec.).

EXAMPLE 351

Sodium hydride (50% oily) (9.6 mg.) and phenol (19 mg.) were added to anhydrous N,N-dimethylformamide (2 ml.), and the mixture was stirred for 30 minutes, and then ice-cooled. To the solution was added all at once 3-[2-phenyl-2-(2-bromoacetamido)acetamido]lactacillanic acid (50 mg.), and the reaction mixture was stirred for an hour at the same temperature and further stirred for an hour at ambient temperature. Ether (10 ml.) was added to the reaction mixture to give a precipitate which was collected by filtration. The precipitate was dissolved in a small amount of water, and the solution was adjusted to pH 1 with 10% hydrochloric acid, and then extracted with ethyl acetate. The extract was washed with water and dried over anhydrous magnesium sulfate, and then the solvent was distilled off from the solution. The residue was powdered with ether, and collected by filtration and washed with ether sufficiently to give 3-[2-phenyl-2-(2-phenoxyacetamido)acetamido]lactacillanic acid (10 mg.).

I.R. absorption spectrum, $\nu_{cm^{-1}}$ (Nujol): 1740, 1720, 1650.

The following compounds were obtained in substantially the similar manner as described above.

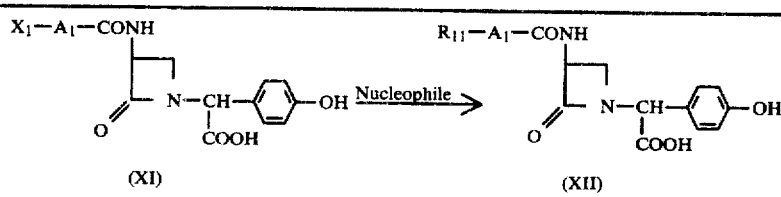

(XI) → (XII)

| | Compound (XI) | | | Compound (XII) | | |
|---|---|---|---|---|---|---|
| Ex. | X₁— | —A₁— | Nucleophile | R₁₁— | —A₁— | mp(°C.) (dec.) |
| 352 | Br— | —CH₂— | ⌬—OH | ⌬—O— | the same as A₁ of the Compound (XI). | 180–184 |
| 353 | " | " | OHC—⌬—OH | OHC—⌬—O— | the same as A₁ of the Compound (XI). | 145–146 |
| 354 | " | " | O₂N—⌬—OH | O₂N—⌬—O— | the same as A₁ of the Compound (XI). | 137–140 |
| 355 | " | " | CH₃OOCCH—⌬—OH, NHCOOCH₂—⌬ | CH₃OOCCH—⌬—O—, NHCOOCH₂—⌬ | the same as A₁ of the Compound (XI). | 80–85 |
| 356 | " | " | CH₃OOCCHCH₂—⌬—OH, NHCOOCH₂—⌬ | CH₃OOCCHCH₂—⌬—O—, NHCOOCH₂—⌬ | the same as A₁ of the Compound (XI). | 136–140 |
| 357 | " | " | C₂H₅OOCCH=CH—⌬—OH | C₂H₅OOCCH=CH—⌬—O— | the same as A₁ of the Compound (XI). | 109–110 |
| 358 | " | " | ⌬—⌬—OH | ⌬—⌬—O— | the same as A₁ of the Compound (XI). | 195–198 |
| 359 | " | " | ⌬⌬—OH | ⌬⌬—O— | the same as A₁ of the Compound (XI). | 143–146 |
| 360 | " | | ⌬—CO—⌬—OH | ⌬—CO—⌬—O— | the same as A₁ of the Compound (XI). | 154–159 |
| 361 | " | —CH— \| ⌬ —CH₂CONH— | OHC—⌬—OH | OHC—⌬—O— | the same as A₁ of the Compound (XI). | 95–96 |

EXAMPLE 362

3-[2-[2-[2-{4-(2-Chloroacetamido)benzoyl}-4-chlorophenoxy]acetamido]-2-phenylacetamido]lactacillanic acid (150 mg.) and pyridine-2-thiol (25 mg.) was treated in substantialy the similar manner as described in Example 324 to give 3-[2-[2-[2-[4-{2-(pyridin-2-yl-thio)acetamido}benzoyl]-4-chlorophenoxy]acetamido]-2-phenylacetamido]lactacillanic acid (120 mg.). Mp 109°–114° C. (dec.).

The following compounds were obtained in substantially the similar manner as described in Example 342.

| Example | Compound (XI) | | Nucleophile | Compound (XII) | | mp (°C.) (dec.) |
|---|---|---|---|---|---|---|
| | $X_1-$ | $-A_1-$ | | $R_{11}-$ | $-A_1-$ | |
| 363 | Br— | ![structure with OCH₃ and -CH₂CONHCH- / -CH₂-] | $H_2N-CHCH_2-SH$ / COOH | $H_2N-CHCH_2-S-$ / COOH | the same as $A_1$ of Compound (XI) | 161-165 |
| 364 | Cl— | | $HOCH_2(CHOH)_4CONH-\underset{S}{\underset{\|}{N=\!\!=\!\!N}}-SNa$ | $HOCH_2(CHOH)_4CONH-\underset{S}{\underset{\|}{N=\!\!=\!\!N}}-S-$ | the same as $A_1$ of Compound (XI) | 89-92 |

EXAMPLE 365

10% Palladium.carbon (25 mg) was added to a methanol solution (10 ml.) of 3-(6-benzyloxycarbonylaminohexanamido)lactacillanic acid (220 mg.), and a theoretical volume of hydrogen gas was introduced to the mixture in 2 hrs. at ordinary temperature and ordinary atmosphere. The reaction mixture was subjected to filtration, and the filtrate was concentrated under reduced pressure. The residue was pulverized with acetone, washed with acetone and subjected to filtration to give 3-(6-aminohexanamido)lactacillanic acid (100 mg.). Mp 118° to 122° C. (dec.).

The following compounds were prepared in substantially the similar manner as described above.

Compound (XIII)

$$R_{12}-NH \begin{array}{c} \\ \\ \end{array} N-CH \begin{array}{c} OR_{13} \\ \\ COOH \end{array}$$

(XIII)

$\longrightarrow$ $$R_{12}'-NH \begin{array}{c} \\ \\ \end{array} N-CH \begin{array}{c} OR_{13} \\ \\ COOH \end{array}$$

(XIV)

| Example | Compound (XIII) | | Compound (XIV) | | mp(°C.) (dec.) |
|---|---|---|---|---|---|
| | R₁₂ | R₁₃ | R₁₂' | R₁₃ | |
| 366 | C₆H₅CH₂OOCNHCH₂CO— | —H | H₂NCH₂CO— | the same as R₁₃ of Compound (XIII) | I.R. ν cm⁻¹ (Nujol): 1730, 1665, 1610 |
| 367 | C₆H₅CH₂OOCNHCH(C₆H₅)CO— | " | H₂NCH(C₆H₅)CO— | the same as R₁₃ of Compound (XIII) | 193–196 |
| 368 | C₆H₅CH₂OOCNHCH(C₆H₄OH)CO— | " | H₂NCH(C₆H₄OH)CO— | the same as R₁₃ of Compound (XIII) | 205–209 |
| 369 | C₆H₅CH₂OOCNHCH(C₆H₅)CO— | " | H₂NCH(C₆H₅)CO— | the same as R₁₃ of Compound (XIII) | 179–185 |
| 370 | (indolyl-CH₂)CH(NHCOOCH₂C₆H₅)CO— | " | (indolyl-CH₂)CH(NH₂)CO— | the same as R₁₃ of Compound (XIII) | I.R. ν cm⁻¹ (Nujol): 1730, 1660, 1600 |

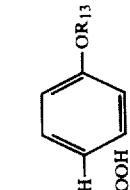

-continued

| Example | Compound (XIII) $R_{12}$ | $R_{13}$ | Compound (XIV) $R_{12}'$ | $R_{13}$ | mp(°C.) (dec.) |
|---|---|---|---|---|---|
| 377 | (structure with CH₂OOCNHCH-phenyl and SCH₂CONH-CHCO-phenyl thiazole) | " | (structure with H₂NCH₂ and SCH₂CONH-CHCO-phenyl thiazole) | the same as $R_{13}$ of Compound (XIII) | 196–199 |
| 378 | (benzophenone-chloro structure with NHCOCH₂O-CHCO-phenyl) | " | H₂NCH₂CH₂SCH₂CONH- (benzophenone-Cl with NHCOCH₂O-CHCO-phenyl) | the same as $R_{13}$ of Compound (XIII) | 191–196 |
| 379 | CH₂OOCNHCH₂-phenyl-CO- | " | H₂N-phenyl-CO- | the same as $R_{13}$ of Compound (XIII) | 190–194 |
| 380 | CH₂OOCNHCH₂ (thiazole SCH₂CO-) | " | H₂NCH₂ (thiazole SCH₂CO-) | the same as $R_{13}$ of Compound (XIII) | 176–180 |
| 381 | CH₂OOCNHCH₂CH₂SCH₂CO- | " | H₂NCH₂CH₂SCH₂CO- | the same as $R_{13}$ of Compound (XIII) | 171–175 |
| 382 | CH₂OOCNH(CH₂)₃O-phenyl-CH₂CO- | " | H₂N(CH₂)₃O-phenyl-CH₂CO- | the same as $R_{13}$ of Compound (XIII) | I.R. ν cm⁻¹(Nujol): 1730, 1660, 1610 |

EXAMPLE 383

3-[2-(2-Thienyl)-N-(2,2,2-trichloroethoxycarbonyl)-glycinamido]lactacillanic acid (0.250 g.) was dissolved in a 90% acetic acid aqueous solution (13 ml.), and the solution was cooled to 10° C. To the solution, was added gradually zinc powder (1.20 g) in 50 minutes, and the mixture was subjected to reaction for an hour at the same temperature. To the reaction mixture, was added zinc powder (0.50 g.) in 30 minutes, and then the mixture was subjected to further reaction for 2 hrs. The zinc powder was removed by filtration, and hydrogen sulfide gas was introduced to the filtrate, and then the precipitate was removed by filtration. The filtrate was washed with ethyl acetate, and the remaining aqueous layer was concentrated. The residue was crystallized from a mixture of methanol and ether to give 3-[2-(2-thienyl)glycinamido]lactacillanic acid (35 mg.). Furthermore, the ethyl acetate layer was extracted with water, and the aqueous layer was concentrated to recover the same compound (15 mg.). Total yield was 50 mg. Mp 184° to 189° C. (dec.).

The following compounds were prepared in substantially the similar manner as described above.

azetidinone (40 mg.). Furthermore, the same compound (60 mg.) was recovered from the mother liquor. Total yield was 100 mg. Mp 190° to 194° C. (dec.).

EXAMPLE 387

10% Palladium.carbon (25 mg.) was added to a methanol solution (15 ml.) of 3-[2-(4-benzyloxycarbonyloxyphenyl)acetamido]lactacillanic acid (230 mg.), and a theoretical volume of hydrogen gas was added to said mixture in 2 hrs. at ordinary temperature and ordinary atmosphere. The reaction mixture was subjected to filtration and the filtrate was concentrated under reduced pressure, and then the residue was crystallized from a mixture of acetone and ethyl acetate. The crystals were collected by filtration and washed with ethyl acetate to give 3-[2-(4-hydroxyphenyl)acetamido]lactacillanic acid (90 mg). Mp 171° to 176° C. (dec.).

EXAMPLE 388

A solution consisting of 3-(2-ethoxycarbonyl-2-phenylacetamido)lactacillanic acid (213 mg.), ethanol (5 ml.) and 1 N-sodium hydroxide aqueous solution (1.4 ml.) was subjected to reaction at ambient temperature for 1.25 hrs. After the reaction, the reaction mixture

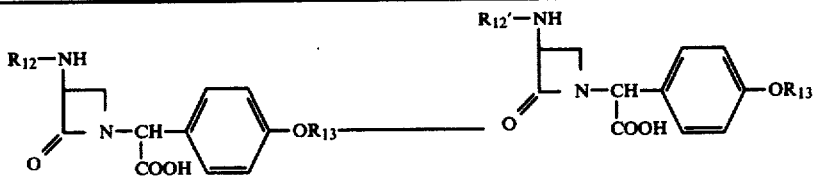

| Example | Compound (XIII) $R_{12}$ | $R_{13}$ | Compound (XIV) $R_{12}'$ | $R_{13}$ | mp(°C.) (dec.) |
|---|---|---|---|---|---|
| 384 | ![structure: thienyl-CHCO-NHCO-phenyl with Cl₃CCH₂OOCNH CH-] S⟩-CHCO-NHCO-⟨phenyl⟩, Cl₃CCH₂OOCNH CH- | —H | S⟩-CHCO-NHCO-⟨phenyl⟩, H₂NCH- | the same as $R_{13}$ of Compound (XIII) | 198–202 |
| 385 | Cl₃CCH₂OOCNHCHCO—⟨phenyl⟩ | " | H₂NCHCO—⟨phenyl⟩ | the same as $R_{13}$ of Compound (XIII) | 193–196 |

EXAMPLE 386

1-(α-Carboxy-3,5-dibromo-4-hydroxybenzyl)-3-[2-[4-{3-carboxy-3-(2,2,2-trifluoroacetamido)propoxy}-phenyl]-2-hydroxyiminoacetamido]-2-azetidinone (0.50 g.) was suspended in water (3 ml.), and 1N-sodium hydroxide aqueous solution (3 ml) was added to said suspension, and then the solution was stirred for 30 minutes. The reaction mixture was adjusted to pH 3 with 10% hydrochloric acid under ice-cooling. The precipitated crystals were collected by filtration, and the crystals were dissolved in a small amount of a sodium bicarbonate aqueous solution, and then the solution was treated with activated carbon. After the treatment, the solution was adjusted to pH 4 with 10% hydrochloric acid under ice-cooling, and the precipitate was collected by filtration to give 1-(α-carboxy-3,5-dibromo-4-hydroxybenzyl)-3-[2-{4-(3-amino-3-carboxypropoxy)phenyl}-2-hydroxyiminoacetamido]-2- was cooled and adjusted to pH 1 by adding 1 N-hydrochloric acid (1.4 ml.). Then, the mixture was adjusted to pH 6 to 7 by adding 1 N-sodium hydroxide aqueous solution, and concentrated. The residue was dissolved in water, and the solution was adjusted to pH 1 to 2 with 1 N-hydrochloric acid, and then washed with ethyl acetate. The remaining aqueous layer was adjusted to pH 6 with 1 N-sodium hydroxide aqueous solution, and concentrated. For the purpose of isolation and purification, the residue was subjected to column chromatography using a nonionic adsorption resin, Amberlite XAD-2 (trade mark, maker; Rohm and Haas Co. Ltd.,) (30 ml.) which was washed in advance with methanol and water. The fractions eluted with water were collected, and the water was distilled off from the eluate to give 3-(2-carboxy-2-phenylacetamido)lactacillanic acid, disodium salt of the carboxy group (159 mg.). Mp 209° to 214° C. (dec.).

The following compounds were prepared in substantially the similar manner as described above.

reaction mixture. The mixture was adjusted to pH 1 with 10% hydrochloric acid and extracted with ethyl acetate. The extract was washed twice with a sodium chloride aqueous solution and dried over anhydrous

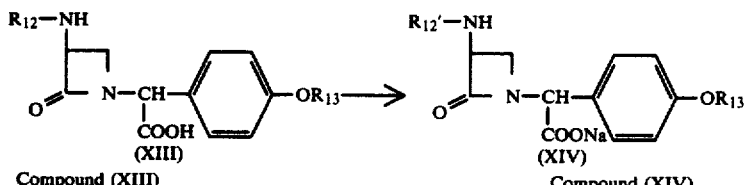

| Example | Compound (XIII) | | Compound (XIV) | | mp (°C.) (dec.) |
|---|---|---|---|---|---|
| | $R_{12}$ | $R_{13}$ | $R_{12}'$ | $R_{13}$ | |
| 389 | CH₃—OOC—CH₂CH₂CO— | —H | NaOOC—CH₂CH₂CO— | the same as $R_{13}$ of Compound (XIII) | I.R. ν cm⁻¹ (KBr): 1740, 1660, 1585 |
| 390 | CH₃COO—⟨⟩—COCO— | " | HO—⟨⟩—COCO— | the same as $R_{13}$ of Compound (XIII) | 220–225 |

EXAMPLE 391

3-[2-{2-(2-Ethoxycarbonylphenoxy)acetamido}-2-phenylacetamido]lactacillanic acid (170 mg.) was dissolved in 1 N-sodium hydroxide aqueous solution (0.9 ml.), and the solution was stirred at ambient temperature for 3.5 hrs. Water (about 10 ml.) was added to the reaction mixture.

magnesium sulfate. The solvent was distilled off from the ethyl acetate solution, and the residue was crystallized from diisopropyl ether to give 3-[2-{2-(2-carboxyphenoxy)acetamido}-2-phenylacetamido]lactacillanic acid (120 mg.). Mp 130° to 135° C. (dec.).

The following compounds were prepared in substantially the similar manner as described above.

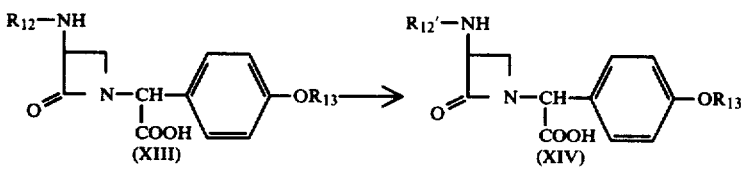

| Example | Compound (XIII) | | Compound (XIV) | | mp (°C.) (dec.) |
|---|---|---|---|---|---|
| | $R_{12}$ | $R_{13}$ | $R_{12}'$ | $R_{13}$ | |
| 392 | CH₃OOCCH₂O—⟨⟩—COCO— | —H | HOOCCH₂O—⟨⟩—COCO— | the same as $R_{13}$ of Compound (XIII) | 90–95 |
| 393 | CH₃OOCCH₂ON=CH—⟨⟩—OCH₂CO— | " | HOOCCH₂ON=CH—⟨⟩—OCH₂CO— | the same as $R_{13}$ of Compound (XIII) | 144–147 |
| 394 | CH₃OOCCH₂ON=CH—⟨⟩—OCHCO—(C₆H₅) | " | HOOCCH₂ON=CH—⟨⟩—OCHCO—(C₆H₅) | the same as $R_{13}$ of Compound (XIII) | 117–121 |
| 395 | CH₃OOC—⟨⟩—SCH₂CONHCHCO—(C₆H₅) | " | HOOC—⟨⟩—SCH₂CONHCHCO—(C₆H₅) | the same as $R_{13}$ of Compound (XIII) | 143–146 |

-continued

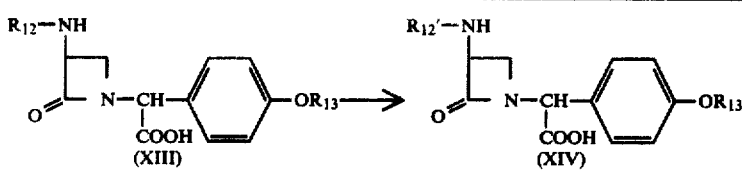

| Example | Compound (XIII) R12 | R13 | Compound (XIV) R12' | R13 | mp (°C.) (dec.) |
|---|---|---|---|---|---|
| 396 | HO—⌬(SO₂NH—⌬—CH₂CO—)(COOCH₃) | " | HO—⌬(SO₂NH—⌬—CH₂CO—)(COOH) | the same as R13 of Compound (XIII) | 150–154 |
| 397 | CH₃OOC—⌬—S(→O)CH₂CONHCHCO—(phenyl) | " | HOOC—⌬—S(→O)CH₂CONHCHCO—(phenyl) | the same as R13 of Compound (XIII) | 175–181 |
| 398 | HO—⌬(SO₂NHCHCO—(phenyl))(COOCH₃) | " | HO—⌬(SO₂NHCHCO—(phenyl))(COOH) | the same as R13 of Compound (XIII) | 162–166 |
| 399 | CH₃OOCCH₂SCH₂CONH—⌬—C=O, NHCOCH₂O—⌬(Cl), CHCO—(phenyl) | " | HOOCCH₂SCH₂CONH—⌬—C=O, NHCOCH₂O—⌬(Cl), CHCO—(phenyl) | the same as R13 of Compound (XIII) | 202–206 |
| 400 | CH₃OOCCH₂CH₂NH—CH(COOH)—(CH₂)₂O—⌬—C(=NOH)CO— | " | HOOCCH₂CH₂NH—CH(COOH)—(CH₂)₂O—⌬—C(=NOH)CO— | the same as R13 of Compound (XIII) | 193–196 |
| 401 | C₂H₅OOCCH=CH—⌬—OCH₂CO— | " | HOOCCH=CH—⌬—OCH₂CO— | the same as R13 of Compound (XIII) | 139–140 |
| 402 | C₂H₅OOCC(=N—OCH₂CO—)(phenyl) | " | HOOCC(=N—OCH₂CO—)(phenyl) | the same as R13 of Compound (XIII) | 95–101 |
| 403 | C₂H₅OOC—⌬—S—CHCO—(phenyl) | " | HOOC—⌬—S—CHCO—(phenyl) | the same as R13 of Compound (XIII) | 90–95 |
| 404 | CH₃COOCHCO—(phenyl) | " | HO—CHCO—(phenyl) | the same as R13 of Compound (XIII) | 180–183 |

-continued

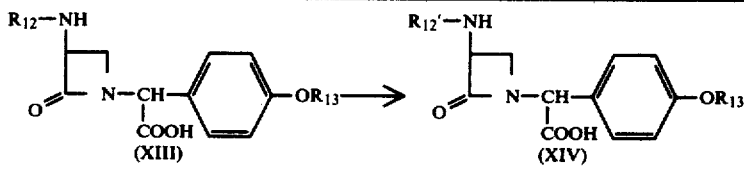

| Example | Compound (XIII) R12 | R13 | Compound (XIV) R12' | R13 | mp (°C.) (dec.) |
|---|---|---|---|---|---|
| 405 | ![thiophene]-CHCO-, OCOCH3 | " | ![thiophene]-CHCO-, OH | the same as R13 of Compound (XIII) | 187–191 |
| 406 | CH3COOCHCO- (dihydropyran) | " | HOCHCO- (dihydropyran) | the same as R13 of Compound (XIII) | I.R. νcm$^{-1}$ (Nujol): 1740, 1685, 1660 |
| 407 | HOOC-[phenyl(OCOCH3)]-SO2NH-[phenyl]-CH2CO- | " | HOOC-[phenyl(OH)]-SO2NH-[phenyl]-CH2CO- | the same as R13 of Compound (XIII) | 150–154 |
| 408 | HOOC-[phenyl(OCOCH3)]-SO2NHCHCO-(phenyl) | " | HOOC-[phenyl(OH)]-SO2NHCHCO-(phenyl) | the same as R13 of Compound (XIII) | 162–166 |
| 409 | CH3COOCHCONHCHCO- (diphenyl) | " | HO-CHCONHCHCO- (diphenyl) | the same as R13 of Compound (XIII) | 90–93 |

EXAMPLE 410

1-(α-Methoxycarbonyl-4-methoxybenzyl)-3-[2-[4-{3-methoxycarbonyl-3-(2,2,2-trifluoroacetamido)propoxy}phenyl]-2-methoxyiminoacetamido]-2-azetidinone (0.19 g.) was dissolved in acetone (2 ml.). 1 N-Sodium hydroxide aqueous solution (0.9 ml.) was added to the solution at ambient temperature, and the mixture was stirred for 5 minutes. The acetone was distilled off from the reaction mixture, and the remaining solution was adjusted to pH 3 with 10% hydrochloric acid. The separated oil material was isolated by decantation, washed with acetone and water, and then pulverized with acetonitrile to give 1-(α-carboxy-4-methoxybenzyl)-3-[2-{4-(3-amino-3-carboxypropoxy)phenyl}-2-methoxyiminoacetamido]-2-azetidinone (0.02 g.). Mp 170° to 176° C. (dec.).

EXAMPLE 411

3-[2-[4-{4-Chloro-N-(2,2,2-trichloroethoxycarbonyl)-anilinomethyl}phenoxyl]-2-methyl-propionamido]lactacillanic acid (320 mg.) was treated in substantially the similar manner as described in Example 365 to give 3-[2-{4-(4-chloroanilinomethyl)phenoxy}-2-methylpropionamido]lactacillanic acid (110 mg.). Mp 130° to 136° C. (dec.).

EXAMPLE 412

Sodium methylate (15 mg.) and absolute methanol (20 ml.) were added to 1-methoxalyl-3-(2-phenoxyacetamido)-2-azetidinone (1.1 g.), and the mixture was heated under reflux for 30 minutes. The solvent was distilled off from the reaction mixture under reduced pressure, and the residue was dissolved in acetone, and then the insoluble material was filtered off. The filtrate was concentrated and allowed to stand cool, and then the precipitated crystals were collected by filtration. The crystals were washed with acetone and dried to give 3-(2-phenoxyacetamido)-2-azetidinone (456 mg.). Furthermore, the same compound (109 mg.) was recovered from the mother liquor. Total yields was 565 mg. Mp 153° to 155° C.

EXAMPLE 413

1-Methoxalyl-3-benzyloxycarbonylamino-2-azetidinone (240 mg.) was dissolved in methanol (10 ml.), and sodium methylate (6 mg.) was added to said solution, and then the mixture was heated under reflux for 45 minutes. The methanol was distilled off from the reaction mixture, and the residue was washed with ether to give crude 3-benzyloxycarbonylamino-2-azetidinone (126 mg.). Furthermore, this product was recrystallized from acetone to give the purified compound (50 mg.). And, the purified same compound (54 mg.) was recovered from the mother liquor. Total yield was 104 mg. Mp 164° to 165° C.

EXAMPLE 414

1-(1-Acetoxy-2-methylpropyl)-3-(2-phenylacetamido)-2-azetidinone (13.8 g.) was dissolved in a solution of methanol (100 ml.) and water (100 ml.). Potassium carbonate (6 g.) and sodium borohydride (1.65 g.) were added to said solution under ice-cooling, and the mixture was subjected to reaction at 20° C. for an hour. The precipitated crystals were collected by filtration, washed with water and dried to give 3-(2-phenylacetamido)-2-azetidinone (5.15 g.). Furthermore, the same compound (1.35 g.) was recovered from the filtrate. Total yield was 6.5 g. Mp 191° to 193° C.

EXAMPLE 415

1-[1-(2,2,2-Trichloroethoxycarbonylamino)-2-methylpropyl]-3-(2-phenylacetamido)-2-azetidinone (1.13 g.) was dissolved in a 90% acetic acid aqueous solution (20 ml.), and the solution was cooled to 5° C. (Zinc powder (1.62 g.) was added dropwise to said solution in 5 minutes, and the mixture was stirred for 30 minutes. Furthermore, zinc powder (1.62 g.) was added to said mixture, and the mixture was stirred for 2 days. The reaction mixture was neutralized with a sodium bicarbonate aqueous solution, and extracted with methylene chloride. The extract was washed with water and dried over anhydrous magnesium sulfate, and then the solvent was distilled off from the solution. The residue (0.65 g.) was subjected to preparative thin layer chromatography using silica.gel [developing solvent; a mixed solvent of ethyl acetate, ethyl methyl ketone, water and formic acid (volume ratio 5:3:1:1)], isolated and purified to give 3-(2-phenylacetamido)-2-azetidinone (0.3 g.). Mp 190° to 192° C.

EXAMPLE 416

1-(α-Methoxycarbonyl-4-hydroxybenzyl)-3-[2-(2-thienyl)acetamido]-2-azetidinone (0.18 g.) was dissolved in a solution consisting of sodium borate buffer (pH 7.8) (3 ml.), methanol (5 ml.) and acetone (3 ml.), and the solution was cooled to −5° C. A methanol (0.5 ml.) solution containing tert-butyl hypochlorite (0.10 g.) was added to said solution three times every 15 minutes, and the mixture was stirred for 30 minutes. The solvent was distilled off from the reaction mixture, and the remaining solution was adjusted to pH 2 with 10% hydrochloric acid, and then extracted with ethyl acetate. The extract was separated out, washed with water and a sodium chloride-saturated-aqueous solution, and dried over anhydrous magnesium sulfate. The solvent was distilled off from the ethyl acetate solution, and the residue (0.22 g.) was subjected to column chromatography using silica.gel (10 g.). The fractions eluted with chloroform were collected, and the chloroform was distilled off from the eluate to give 1-(α-methoxycarbonyl-3,5-dichloro-4-hydroxybenzyl)-3-[2-(2-thienyl)acetamido]-2-azetidinone (50 mg.).

I.R. absorption spectrum, $\nu_{cm-1}$ (liquid film): 3270, 1760, 1755, 1665.

EXAMPLE 417

Chloroform (1.5 ml.) was added to a solution of 1-(α-methoxycarbonyl-4-hydroxybenzyl)-3-(2-phenylacetamido)-2-azetidinone (184 mg.) dissolved in dioxane (2 ml.), and a chloroform (0.5 ml.) solution containing bromine (184 mg.) was added dropwise to said mixture in 5 minutes under ice-cooling. After addition of ethyl acetate (80 ml.) to said reaction mixture, the ethyl acetate layer was separated out, washed with water and dried over anhydrous magnesium sulfate. This solution was concentrated, and the residue was dissolved in a small amount of acetone. The solution was subjected to preparative thin layer chromatography using silica.gel [developing solvent; a mixture of chloroform and methanol (5:0.3)] for isolation and purification. The product thus obtained was recrystallized from a mixture of ethyl acetate and acetone to give 1-(α-methoxycarbonyl-3-bromo-4-hydroxybenzyl)-3-(2-phenylacetamido)-2-azetidinone (18 mg.). Mp 151° to 153° C. (dec.).

EXAMPLE 418

A methanol solution (1 ml.) of bromine (352 mg.) was rapidly added dropwise to a solution (5 ml.) of 3-(2-phenylacetamido)lactacillanic acid (354 mg.) and sodium acetate (246 mg.) dissolved in absolute methanol with stirring under ice-cooling. The methanol was distilled off from the reaction mixture under reduced pressure. After addition of a mixture of ethyl acetate and water to the residue, the ethyl acetate layer was separated out and washed with water and dried over anhydrous magnesium sulfate. The solvent was distilled off from the solution, and the residue (590 mg.) as the yellow orange oily material was dissolved in a small amount of ethyl acetate, and the solution was subjected to column chromatography using silica.gel (7 g.). The fractions, eluted with a mixed solvent of ethyl acetate and acetone, were collected, and the solvent was distilled off from the eluate. The residue thus obtained was further subjected to preparative thin layer chromatography using silica.gel for isolation and purification. The fractions, eluted with a mixture of ethyl acetate and acetic acid (5:1), were collected, and the solvent was distilled off from the eluate, and then the residue was pulverized with chloroform. This powder was recrystallized from a mixture of chloroform and acetone to give 1-(α-carboxy-3,5-dibromo-4-hydroxybenzyl)-3-(2-phenylacetamido)-2-azetidinone (157 mg.). Furthermore, the same compound (26 mg.) was recovered from the mother liquor. Total yield was 183 mg. Mp 161° to 162° (dec.).

EXAMPLE 419

3-[2-[4-{3-Carboxy-3-(2,2,2-trifluoroacetamido)-propoxy}phenyl]-2-hydroxyiminoacetamido]lactacillanic acid (1.77 g.) was dissolved in methanol (20 ml.). After addition of sodium acetate (1.03 g.) to said solution, the mixture was cooled to −5° C. and a methanol solution (5 ml.) of bromine (1.06 g.) was added dropwise thereto in 15 minutes. The reaction mixture was subjected to reaction for 15 minutes, and the methanol was distilled off from the reaction mixture, and then the residue was added to a mixture of ethyl acetate (20 ml.) and water (20 ml.). After adjusting the mixture to pH 2 with 2% hydrochloric acid, the ethyl acetate layer was separated out and washed with a sodium thiosulfate aqueous solution, water and a sodium chloride-saturated-aqueous solution respectively, and then dried over anhydrous magnesium sulfate. The ethyl acetate solution was concentrated, and the residue (2.56 g.) thus obtained was subjected to precipitation repeatedly twice with a mixture of benzene and acetone to give 1-(α-carboxy-3,5-dibromo-4-hydroxybenzyl)-3-[2-[4-{3-carboxy-3-(2,2,2-trifluoroacetamido)-propoxy}phenyl]-2-hydroxyiminoacetamido]-2-azetidinone (1.16 g.)

I.R. absorption spectrum: $\nu_{cm-1}$ (liquid film): 1720 (broad), 1650.

EXAMPLE 420

3-Glycinamidolactacillanic acid (100 mg.) suspended in water (5 ml.) was dissolved by adding sodium bicarbonate (70 mg.). The solution was cooled to 0° to 5° C., and a solution of 2-(4-chloro-2-nitrophenoxy)acetyl chloride (100 mg.) dissolved in acetone (5 ml.) was added dropwise thereto. The mixture was allowed to react at the same temperature for 2 hrs. The acetone was distilled off from the reaction mixture under reduced pressure, and the remaining solution was adjusted to pH 1 to 2 by adding diluted hydrochloric acid and then extracted with ethyl acetate. The extract was washed with water and dried, and the solvent was distilled off. The oily residue was washed with ether, dissolved in a small amount of methanol, and then ether was added to the solution. The precipitated powder was collected by filtration and dried to give 3-[2-{2-(4-chloro-2-nitrophenoxy)acetamido}acetamido]lactacillanic acid (82 mg.). Mp 149° to 153° C. (dec.).

The following compounds were prepared in substantially the similar manner as described above.

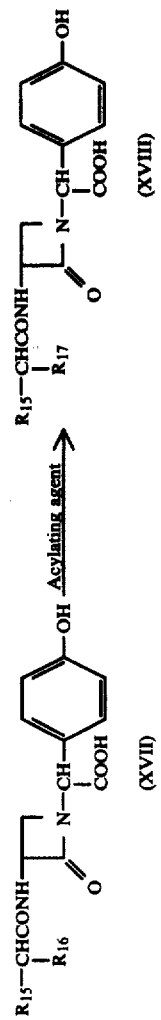

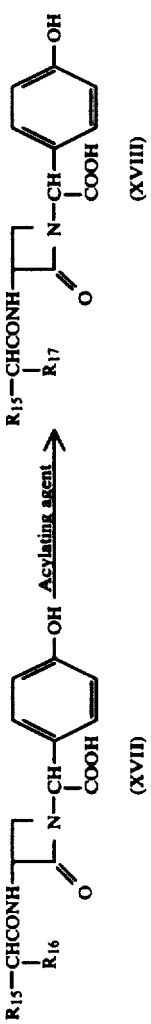

-continued $$R_{15}-CHCONH \atop R_{16} \quad \xrightarrow{\text{Acylating agent}} \quad R_{15}-CHCONH \atop R_{17}$$

(XVII) → (XVIII)

| | Compound (XVII) | | Acylating agent | Compound (XVIII) | | mp(°C.) (dec.) |
|---|---|---|---|---|---|---|
| Example | $R_{15}$ | $R_{16}$ | | $R_{15}$ | $R_{17}$ | |
| 437 | " | " | (none shown) | the same as $R_{15}$ of the Compound (XVII) | (none shown) | 118–121 |
| 438 | " | " | CH$_3$O—⌬—C(—COCl)=N—OCH$_2$—⌬ | the same as $R_{15}$ of the Compound (XVII) | CH$_3$O—⌬—C(—CONH—)=N—OCH$_2$—⌬ | 137–142 |
| 439 | " | " | ⌬—N(—CH$_2$COCl)—SO$_2$—⌬ | the same as $R_{15}$ of the Compound (XVII) | ⌬—N(—CH$_2$CONH—)—SO$_2$—⌬ | 151–155 |
| 440 | " | " | ⌬—SO$_3$CH$_2$COCl | the same as $R_{15}$ of the Compound (XVII) | ⌬—SO$_3$CH$_2$CONH— | 122–124 |
| 441 | " | " | Cl-⌬—isoxazole(CH$_3$)—COCl | the same as $R_{15}$ of the Compound (XVII) | Cl-⌬—isoxazole(CH$_3$)—CONH— | 143–146 |
| 442 | " | " | ⌬—COCOCl ; C$_2$H$_5$O—COCOCl | the same as $R_{15}$ of the Compound (XVII) | ⌬—COCONH— ; C$_2$H$_5$O—COCONH— | 113–123 |
| 443 | " | " | ClCOOCH$_2$—⌬ | the same as $R_{15}$ of the Compound (XVII) | ⌬—CH$_2$OCONH— | 146–148 |
| 444 | " | " | ClCOOCH$_2$CCl$_3$ | the same as $R_{15}$ of the Compound (XVII) | Cl$_3$CCH$_2$OCONH— | 130–132 |
| 445 | " | " | ⌬(o-COC$_2$H$_5$)—OCH$_2$COCl | the same as $R_{15}$ of the Compound (XVII) | ⌬(o-COC$_2$H$_5$)—OCH$_2$CONH— | 125–130 |

-continued $$\underset{(XVII)}{\underset{R_{16}}{\overset{R_{15}-CHCONH}{\mid}}\underset{COOH}{\overset{OH}{\longrightarrow}}} \xrightarrow{\text{Acylating agent}} \underset{(XVIII)}{\underset{R_{17}}{\overset{R_{15}-CHCONH}{\mid}}\underset{O}{\overset{OH}{\longrightarrow}}}$$

| | Compound (XVII) | | | Compound (XVIII) | |
|---|---|---|---|---|---|
| Example | R₁₅ | R₁₆ | Acylating agent | R₁₅ | R₁₇ | mp(°C.) (dec.) |
| 455 | benzisoxazolyl-CH₂– / indolyl-CH₂– | " | ClCOOCH₂–Ph | the same as R₁₅ of the Compound (XVII) | PhCH₂OCONH– | 165–168 |
| 456 | " | " | " | the same as R₁₅ of the Compound (XVII) | " | 235–240 |
| 457 | H– | CH₃NH– | " | the same as R₁₅ of the Compound (XVII) | PhCH₂OCO–N(CH₃)– | I.R. ν cm⁻¹ (liquid film): 1740, 1710 1690, 1650 |
| 458 | " | Ph-NH– | N₃CH₂COCl | the same as R₁₅ of the Compound (XVII) | N₃CH₂CO–N(Ph)– | 176–180 |
| 459 | " | H₂N–(CH₂)₄– | ClCOOCH₂–Ph | the same as R₁₅ of the Compound (XVII) | PhCH₂OCONH(CH₂)₄– | I.R. ν cm⁻¹ (Nujol): 1730, 1660 |
| 460 | " | H₂N–CH(Ph)– | " | the same as R₁₅ of the Compound (XVII) | PhCH₂OCONHCH(Ph)– | 169–173 |
| 461 | " | H₂N–CH(CH₂-C₆H₄-OCH₃)COOH | " | the same as R₁₅ of the Compound (XVII) | PhCH₂OCONHCH(CH₂-C₆H₄-OCH₃)COOH | 125–130 |
| 462 | " | H₂N–(CH₂)₃-C₆H₄-OCH₃ | " | the same as R₁₅ of the Compound (XVII) | PhCH₂OCONH(CH₂)₃-C₆H₄-OCH₃ | 142–146 |
| 463 | CH₃-C₆H₄– | H₂N–CH₂CH₂S-C₆H₄-OCH₃ | Cl-C₆H₃(NO₂)-OCH₂COCl | the same as R₁₅ of the Compound (XVII) | Cl-C₆H₃(NO₂)-OCH₂CONHCH₂CH₂S– | 77–81 |

EXAMPLE 469

3-(2-Phenylglycinamido)lactacillanic acid as a starting material and 2-[4-chloro-2-(α-acetoxyiminobenzyl)-phenoxy]acetyl chloride as an acylating agent were treated in substantially the similar manner as described in Example 420 to give 3-[2-[2-{4-chloro-2-(α-hydroxyiminobenzyl)phenoxy}acetamido]-2-phenylacetamido]lactacillanic acid, in which the protective group (i.e. acetyl) on the hydroxyimino group of the starting material was eliminated. Mp 171° to 176° C. (dec.).

EXAMPLE 470

A suspension of 3-(2-Phenylglycinamido)lactacillanic acid (200 mg.) in a solution consisting of methylene chloride (10 ml.), N,N-dimethylformamide (1 ml.) and N,O-bis(trimethylsilyl)acetamide (1 ml.), was stirred at ambient temperature for an hour. 2-Anilino-2-phenylacetyl chloride hydrochloride (140 mg.) was added to the reaction mixture under ice-cooling, and the mixture was stirred at the same temperature for an hour for dissolution. Furthermore, the reaction mixture was stirred at ambient temperature for an hour and then concentrated under reduced pressure. After addition of ethyl acetate and water to the residue, the ethyl acetate layer was separated out and extracted with a sodium bicarbonate aqueous solution. After adjusting the aqueous layer to pH 1 to 2 with 1 N-hydrochloric acid, it was extracted with ethyl acetate and the extract thus obtained was washed with water and dried over anhydrous magnesium sulfate. After solvent was distilled off, ether was added to the residue thus obtained and then the mixture was stirred for an hour. The separated powder was collected by filtration to give 3-[2-phenyl-2-(2-anilino-2-phenylacetamido)acetamido]lactacillanic acid (89 mg.). Mp 158° to 161° C. (dec.).

EXAMPLE 471

A mixture of N,N-dimethylformamide (50 mg.) and thionyl chloride (200 mg.) was stirred at 40° to 50° C. for 30 minutes. After the excess of the thionyl chloride was distilled off, the residue was dissolved in methylene chloride (5 ml.), and then the solution was cooled to −10° to −5° C. 2-[5-(2-Thienyl)tetrazol-1-yl]acetic acid (114 mg.) was added to this solution at once and dissolved by adding N,N-dimethylformamide (2 drops), and then the mixture was stirred for 15 minutes. This solution was cooled to −60° to −50° C., and a methylene chloride (2 ml.) solution of triethylamine (65 mg.) was added thereto, and then the mixture was stirred at the same temperature for 30 minutes. To the solution cooled to −60° to −50° C., there was added at once a solution which had been prepared in advance by stirring a suspension consisting of 3-(2-phenyglycicinamido)lactacillanic acid (200 mg.), N,O-bis(trimethylsilyl)acetamide (430 mg.), methylene chloride (10 ml.) and N,N-dimethylformamide (1 ml.) at the same temperature for an hour. The reaction mixture was stirred for 30 minutes at the same temperature and for an hour at −20° to −10° C. and further for an hour at −10° to −0° C. The solvent was distilled off from the reaction mixture to leave the residue, to which ethyl acetate and a sodium bicarbonate aqueous solution were added. The aqueous layer was separated out, adjusted to pH 4 with 10% hydrochloric acid and then extracted with ethyl acetate. The ethyl acetate layer was separated out, washed with water, dried over anhydrous magnesium sulfate and then the solvent was distilled off. The residue (70 mg.) thus obtained was washed with ether to give crude 3-[2-phenyl-2-[2-{5-(2-thienyl)tetrazol-1-yl}acetamido]acetamido]lactacillanic acid (60 mg.). Furthermore, the product was dissolved in ethyl acetate, and ether was added to the solution to precipitate crystals. The crystals were collected by filtration to give the purified product (30 mg.). Mp 170° to 174° C. (dec.).

EXAMPLE 472

2-Phenylglycolic acid, instead of the 2-[5-(2-thienyl)-tetrazol-1-yl]acetic acid, was treated in substantially the similar manner as described in Example 471 to give 3-[2-(2-hydroxy-2-phenylacetamido)-2-phenylacetamido]lactacillanic acid. Mp 90° to 93° C. (dec.).

EXAMPLE 473

Acetone (5 ml.) was added to an aqueous solution (5 ml.) of 3-[2-(2-thienyl)glycinamido]lactacillanic acid (0.358 g.) and sodium bicarbonate (0.185 g.), and the solution was cooled to 0° to 5° C. To the solution, there was added dropwise a dried acetone (5 ml.) solution of 2-(4-chloro-2-nitrophenoxy)acetyl chloride (0.230 g.), and the mixture was allowed to react at the same temperature for 2 hrs. After the acetone was distilled off from the reaction mixture under reduced pressure, the remaining aqueous layer was washed with ethyl acetate, adjusted to pH 1 to 2 with diluted hydrochloric acid and then extracted with ethyl acetate. The extract was washed with water and dried, and the solvent was distilled off to give the residue (0.34 g.). The residue was dissolved in methanol (2 ml.), and to the solution, there was added an acetone (1 ml.) solution of sodium 2-ethylhexanoate (0.88 g.) and then ether (15 ml.). The precipitated powder was collected and washed three times with ether to give sodium salt of 3-[2-{2-(4-chloro-2-nitrophenoxy)acetamido}-2-(2-thienyl)acetamido]lactacillanic acid (0.140 g.). Mp 187° to 190° C. (dec.).

The following compounds were prepared in substantially the similar manner as described above.

$R_{15}-CHCONH$, $R_{16}$ on one ring system with N-CH-phenol-OH and COOH → (Acylating agent) → $R_{15}-CHCONH$, $R_{17}$ with N-CH-phenol-OH and COONa (XVII) → (XVIII)

| Example | Compound (XVII) $R_{15}$ | $R_{16}$ | Acylating agent | Compound (XVIII) $R_{15}$ | $R_{17}$ | mp (°C.) (dec.) |
|---|---|---|---|---|---|---|
| 474 | H— | $H_2N$— | ClCOOCH$_2$—phenyl | the same as $R_{15}$ of the Compound (XVII) | phenyl-CH$_2$OCONH— | I.R.νcm$^{-1}$ (Nujol): 1740, 1675, 1610 |
| 475 | " | " | CH$_3$SO$_2$Cl | the same as $R_{15}$ of the Compound (XVII) | CH$_3$SO$_2$NH— | 160–164 |
| 476 | phenyl- | " | thienyl-CH$_2$COCl | the same as $R_{15}$ of the Compound (XVII) | thienyl-CH$_2$CONH— | 221–224 |
| 477 | " | " | phenyl-SO$_2$Cl | the same as $R_{15}$ of the Compound (XVII) | phenyl-SO$_2$NH— | 186–189 |
| 478 | thienyl- | " | phenyl-CH$_2$CH$_2$COCl | the same as $R_{15}$ of the Compound (XVII) | phenyl-CH$_2$CH$_2$CONH— | 224–227 |
| 479 | phenyl-O— | phenyl(NH$_2$)-O— | CH$_3$COCl | the same as $R_{15}$ of the Compound (XVII) | phenyl(NHCOCH$_3$)-O— | 192–197 |
| 480 | phenyl- | $H_2N$— | phenyl(OCH$_2$COCl)-CH$_2$-N(COOCH$_2$CCl$_3$)-CH$_2$-phenyl-OCH$_2$COCl | the same as $R_{15}$ of the Compound (XVII) | phenyl(OCH$_2$CONH—)-CH$_2$-N(COOCH$_2$CCl$_3$)-CH$_2$-phenyl-OCH$_2$COONa | 181–187 |

EXAMPLE 481

Sodium nitrite (140 mg.) was little by little added to a solution of guanidinocarbohydrazide dihydrochloride (380 mg.) dissolved in water (3 ml.) under cooling at 0° to 5° C., and the mixture was stirred for 10 minutes to provide a solution of guanidinocarbonylazide. On the other hand, 3-(2-phenylglycinamido)lactacillanic acid (220 mg.) and sodium bicarbonate (150 mg.) were dissolved in a mixture of water (8 ml.) and acetone (4 ml.), and the solution was stirred at 0° to 5° C. for 15 minutes. After removal of the insoluble material by filtration from said solution, the solution as prepared above was added dropwise to the filtrate in 5 minutes and then the mixture was stirred at 0° to 5° C. for 2 hrs, while the reaction mixture was kept at pH 7.5 to 8.0 by adding 5% sodium bicarbonate aqueous solution. The precipitated crystals in the reaction mixture were collected by filtration to give 3-(2-guanidinocarbonylamino-2-phenylacetamido)-lactacillanic acid (20 mg.). Furthermore, the filtrate was concentrated to a volume of about 5 ml. to precipitate crystals, which were collected by filtration to recover the same compound (60 mg.). Total yield was 80 mg. Mp 198° to 202° C. (dec.).

EXAMPLE 482

3-[2-(2-Thienyl)glycinamido]lactacillanic acid (375 mg.) suspended in water (5 ml.) was dissolved by adding potassium carbonate (104 mg.) (the nature of the solution indicated about pH 9). To said solution, there was added a solution (10 ml.) of acetone and water (1:1) and then was added dropwise a dried acetone (5 ml.) solution of benzoyl isothiocyanate (163 mg.) with stirring at ambient temperature. The mixture was stirred for 3 hrs. (during that time, the reaction mixture was kept at pH 8.5 by adding a solution of potassium carbonate (104 mg.) in water (7 ml.)). The acetone was distilled off from the reaction mixture. The aqueous residue was washed with ethyl acetate, adjusted to pH 1 to 2 with diluted hydrochloric acid and extracted with ethyl acetate. The extract was washed with water and dried, and the solvent was distilled off. The oily residue (469 mg.) was chromatographed on silica gel (7 g.) and eluted with a mixture of ethyl acetate and methanol to give 3-[2-(3-benzoylthioureido)-2-(2-thienyl)acetamido]lactacillanic acid (97 mg.) Mp 124° to 129° C. (dec.)

EXAMPLE 483

85% 3-Chloroperbenzoic acid (50 mg.) was added to a solution of 3-(2-methylthio-2-phenylacetamido)-lactacillanic acid (100 mg.) dissolved in methanol (5 ml.) under ice-cooling, and the mixture was allowed to react with stirring at the same temperature for an hour. The reaction mixture was concentrated under reduced pressure, and the residue was washed with chloroform to give 3-(2-methylsulfinyl-2-phenylacetamido)lactacillanic acid (86 mg.).

I.R. absorption spectrum,
$v_{cm^{-1}}$ (Nujol): 1740, 1720, 1665, 1020.

EXAMPLE 484

85% Chloroperbenzoic acid (61 mg.) was added to a solution of 3-[2-{N-(2-naphthyl)carbamoylmethylthio}-2-phenylacetamido)lactacillanic acid (171 mg.) dissolved in acetone (7 ml.) under ice-cooling, and the mixture was allowed to react with stirring at the same temperature for an hour. The reaction mixture was concentrated, and the residue was crystallized from chloroform to give 3-[2-{N-(2-naphthyl)carbamoylmethylsulfinyl}-2-phenylacetamido]lactacillanic acid (134 mg.). Mp 151° to 155° C. (dec.).

EXAMPLE 485

3-[2-{4-(3-Amino-3-carboxypropoxy)phenyl}-glycinamido]lactacillanic acid. (1.00 g.) was dissolved in an aqueous solution (20 ml.) of sodium bicarbonate (0.66 g.), and acetone (10 ml.) was added thereto. After the solution was ice-cooled, an acetone solution (5 ml.) of 2,4-dinitro-1-fluorobenzene (0.75 g.) was added dropwise thereto with stirring, and then the mixture was stirred at the same temperature for 30 minutes and further at ambient temperature for 5 hours. The reaction mixture was washed with ethyl acetate and was adjusted to pH 2 with 10% hydrochloric acid, and then extracted with ethyl acetate. The ethyl acetate layer was separated, and the solvent was distilled off under reduced pressure. The residue was pulverized with ether to give 3-[2-[4-{3-carboxy-3-(2,4-dinitroanilino)-propoxy}phenyl]-2-(2,4-dinitroanilino)acetamido]lactacillanic acid (1.50 g.).

I.R. absorption spectrum,
$v_{cm^{-1}}$ (Nujol): 1735, 1700 (shoulder), 1520, 1340.

EXAMPLE 486

3-[2-{4-(3-Amino-3-carboxypropoxy)phenyl}-glycinamido]lactacillanic acid (0.49 g.) and sodium bicarbonate (0.49 g.) were dissolved in water (10 ml.), and methanol (5 ml.) was added the to the solution. To the solution, there was added dropwise a methanol solution (7 ml.) of methyl 4-fluoro-3-nitrobenzoate (0.80 g.), and the mixture was allowed to react at ambient temperature for 17 hrs. and further at 50° C. for 4 hours. After cooling the reaction mixture for a while, the precipitate was removed by filtration. The methanol was distilled off from the filtrate under reduced pressure, and the aqueous residue was washed with ether, adjusted to pH 3 with 1 N-hydrochloric acid and extracted with ethyl acetate. The ethyl acetate layer was separated and dried over anhydrous magnesium sulfate, and then the solvent was distilled off under reduced pressure. The residue was pulverized with benzene to give 3-[2-[4-{3-carboxy-3 -(4-methoxycarbonyl-2-nitroanilino)propoxy}-phenyl]-2-(4-methoxycarbonyl-2-nitroanilino)acetamido]lactacillanic acid (0.86 g.) Mp 150° to 155° C. (dec.)

EXAMPLE 487

3-[2-{4-(3-Benzamido-3-carboxypropoxy)phenyl}-glycinamido]lactacillanic acid (8.9 g.) and sodium bicarbonate (5.4 g.) was dissolved in water (100 ml.), and methanol (100 ml.) and methyl 4-fluoro-3-nitrobenzoate (4.5 g.) was added thereto. The mixture was allowed to react with stirring at 40° to 50° C. for 4 hours. The methanol was distilled off from the reaction mixture under reduced pressure, and the residue was washed with ethyl acetate, adjusted to pH 2 with 10% hydrochloric acid and extracted with ethyl acetate. The extract was washed with diluted hydrochloric acid and water, and dried. The solvent was distilled off from the ethyl acetate layer under reduced pressure, and the residue was pulverized with ether and collected by filtration to give 3-[2-{4-(3-benzamido-3-carboxypropoxy)phenyl}-2-(4-methoxycarbonyl-2-nitroanilino)acetamido]lactacillanic acid (9.23 g.).

I.R. absorption spectrum,
$v_{cm^{-1}}$ (Nujol): 1730, 1620, 1528, 1352.

EXAMPLE 488

3-[2-{4-(3-Carboxy-3-phthalimidopropoxy)phenyl}-glycinamido]lactacillanic acid (0.68 g.) was dissolved in an aqueous solution (10 ml.) of sodium bicarbonate (0.40 g.). To the solution, there was added methanol (10 ml.) and then methyl 4-fluoro-3-nitrobenzoate (0.30 g.), and the mixture was allowed to react at 50° C. under stirring for 3 hrs. The methanol was distilled off from the reaction mixture, and the aqueous residue was washed with ethyl acetate, adjusted to pH 2 with 10% hydrochloric acid and then extracted with ethyl acetate. The ethyl acetate layer was separated and dried over anhydrous magnesium sulfate. The solvent was distilled off from the ethyl acetate layer under reduced pressure, and the residue was pulverized with ether to give 3-[2-{4-(3-carboxy-3-phthalimidopropoxy)phenyl}-2-(4-methoxycarbonyl-2-nitroanilino)acetamido]lactacillanic acid (0.53 g.). Mp 155° to 160° C. (dec.).

EXAMPLE 489

Sodium salt of 3-[2-{4-(3-amino-3-carboxypropoxy)-phenyl}-2-hydroxyiminoacetamido]lactacillanic acid (0.50 g.) was dissolved in water (10 ml.). Acetone (2 ml.) was added to the solution, and after stirring the solution for a while sodium borohydride (0.30 g.) was added little by little thereto, and then the mixture was stirred for 3 hrs. Acetone (2 ml.) was added to the reaction mixture, and the solution was adjusted to pH 3 with 10% hydrochloric acid. The precipitated crystals were collected by filtration to give 3-[2-[4-{3-carboxy-3-(N-isopropylamino)propoxy}phenyl]-2-hydroxyiminoacetamido]lactacillanic acid (0.05 g.). Furthermore, the mother liquor was concentrated to nearly half of its original volume, and the precipitated crystals were collected by filtration to recover the same product (0.17 g.). Total yield was 0.22 g. Mp 193° to 194° C. (dec.).

EXAMPLE 490

3-[2-{4-(3-Amino-3-carboxypropoxy)phenyl}-2-hydroxyiminoacetamido]lactacillanic acid as a starting material and methyl 2-formylacetate as a carbonyl compound were treated in substantially the similar manner as described in Example 489 to give 3-[2-[4-[3-carboxy-3-{N-(2-methoxycarbonylethyl)amino}propoxy]-phenyl]-2-hydroxyiminoacetamido]lactacillanic acid. Mp 175° to 179° C. (dec.).

EXAMPLE 491

Sodium salt of 3-[2-{4-(3-amino-3-carboxypropoxy)-phenyl}-2-hydroxyiminoacetamido]lactacillanic acid (0.50 g.) was dissolved in water (10 ml.), 30% formaldehyde aqueous solution (1 ml.) was added thereto under ice-cooling. The mixture was stirred for a while, and sodium borohydride (0.15 g.) was added gradually thereto. After stirring the mixture for 30 minutes, it was adjusted to pH 3 with 10% hydrochloric acid under ice-cooling. The precipitated crystals were collected by filtration, washed with water and acetone, and dried at 40° C. under reduced pressure to give 3-[2-[4-{3-carboxy-3-(N,N-dimethylamino)propoxy}phenyl]-2-hydroxyiminoacetamido]lactacillanic acid (0.28 g.). Mp 193° to 194° C. (dec.).

EXAMPLE 492

3-(4-Nitrobenzamido)lactacillanic acid (235 mg.) was dissolved in methanol (20 ml.), and palladium. carbon (40 mg.) as a catalyst was added thereto. The mixture was shaken in a stream of hydrogen at ambient temperature under ordinary atmosphere, while a calculated volume (44 ml.) of hydrogen was absorbed in about an hour. The catalyst was removed by filtration from the reaction mixture, and the filtrate was evaporated to dryness under reduced pressure. The residue was treated with ether and collected by filtration to give 3-(4-aminobenzamido)lactacillanic acid (200 mg.). Mp 190° to 194° C. (dec.).

EXAMPLE 493

3-(3,5-Dinitrobenzamido)lactacillanic acid (210 mg.) was dissolved in methanol (20 ml.), and palladium carbon (40 mg.) as a catalyst was added thereto. The mixture was shaken in a stream of hydrogen at ambient temperature under ordinary atmosphere, while a calculated volume (70 ml.) of hydrogen was absorbed in 2 hrs. The catalyst was removed by filtration from the reaction mixture, and the filtrate was evaporated to dryness under reduced pressure. The residue was washed with ether and dissolved in acetone. After the acetone solution was filtered, ethyl acetate was added to the filtrate, and then the solution was concentrated. The concentrate was filtered, and the filtrate was evaporated to dryness under reduced pressure. The residue was treated with ether and collected by filtration to give 3-(3,5-diaminobenzamido)lactacillanic acid (60 mg.). Mp 116° to 121° C. (dec.).

EXAMPLE 494

3-[2-(4-Formylphenoxy)acetamido]lactacillanic acid (200 mg.) was added to a solution of hydroxylamine hydrochloride (70 mg.) dissolved in water (1 ml.) and 1 N-sodium hydroxide aqueous solution (1.5 ml.), and the mixture was stirred at ambient temperature for 30 minutes. Ethyl acetate was added to the reaction mixture and 1 N-hydrochloric acid (1.5 ml.) was added thereto. The mixture was shaken and the ethyl acetate layer was separated. The layer was washed with water and dried over anhydrous magnesium sulfate, and then the solvent was distilled off. The residue (190 mg.) was allowed to crystallize. A mixed solvent of ethyl acetate and chloroform (1:1) was added to the residue to precipitate crystals, and the solution was stirred at ambient temperature for an hour. The crystals were collected by filtration to give 3-[2-(4-hydroxyiminomethylphenoxy)acetamido]-lactacillanic acid (130 mg.). Mp 150° to 155° C. (dec.).

EXAMPLE 495

3-[2-(4-Formylphenoxy)acetamido]lactacillanic acid (200 mg.) was added to a solution consisting of 2-aminooxyacetic acid.½ hydrochloride (66 mg.) and 1 N-sodium hydroxide aqueous solution (1.5 ml.), and the mixture was stirred at ambient temperature for 2 hrs. The reaction mixture was adjusted to pH 2 with 1 N-hydrochloric acid, and then extracted with ethyl acetate. The ethyl acetate layer was separated, washed with water and dried over anhydrous magnesium sulfate. After the solvent was distilled off from the extract, ether was added to the residue and then the mixture was stirred at ambient temperature for 2 hrs. The precipitated crystals were collected by filtration, and the crystals (150 mg.) was washed with ethyl acetate to give 3-[2-(4-carboxymethoxyiminomethylphenoxy)acetamido]lactacillanic acid (110 mg.). Mp 144° to 147° C. (dec.).

EXAMPLE 496

3-]2-(4-Formylphenoxy)-2-phenylacetamido]lactacillanic acid (237 mg.) was added to a solution consisting of 2-aminooxyacetic acid.½ hydrochoride (106 mg.) and 1 N-sodium hydroxide aqueous solution (1.8 ml.), and the mixture was stirred at ambient temperature for 2 hrs. The reaction mixture was adjusted to pH 1 to 2 with 10% hydrochloric acid and extracted with ethyl acetate. The ethyl acetate layer was separated, washed with water and dried over anhydrous magnesium sulfate. After the solvent was distilled off from the extract, the residue was washed with diisopropyl ether and collected by filtration to give 3-[2-(4-carboxymethoxyiminomethylphenoxy)-2-phenylacetamido]lactacillanic acid (190 mg.). Mp 117° to 121° C. (dec.).

EXAMPLE 497

3-[2-(4-Formylphenoxy)acetamido]lactacillanic acid (200 mg.) was added to a solution of 1 N-sodium hydroxide aqueous solution (5 ml.) and N-(carbazoylmethyl)-N,N,N-trimethylammonium chloride (90 mg.), and the mixture was stirred at ambient temperature for 2 hrs. Further, N-(carbazoylmethyl)-N,N,N-trimethylammonium chloride (90 mg.) was added to this solution, and the mixture was allowed to stand overnight. To the reaction mixture, there were added 1 N-hydrochloric acid (0.5 ml.) and acetic acid (100 mg.), and then the solution was washed with ethyl acetate and ether. The aqueous layer was separated, and the organic solvent saturated in the layer was completely distilled off under reduced pressure. The residue was chromatographed on a nonionic adsorption resin, Amberlite XAD-2 (50 ml.) (trade mark, maker; Rohm and Haas Co., Ltd.). Elution was conducted with water and then methanol, and the fractions containing an objective compound, which can be eluted with methanol, were collected. The fractions combined together was concentrated. The residue was washed with ethanol and collected by filtration to give N-[3-[4-[N-{1-(α-carboxy-4-hydroxybenzyl)-2-oxo-3-azetidinyl}carbamoylmethoxy]benzylidene]carbazoylmethyl]-N,N,N-trimethylammonium chloride (188 mg.). Mp 199° to 205° C. (dec.).

EXAMPLE 498

A solution of hydroxylamine hydrochloride (35 mg.) in water was added to 0.1 N-sodium hydroxide aqueous solution (5 ml.) of 3-[2-{2-(2-benzoyl-4-chlorophenoxy)acetamido}-2-phenylacetamido]lactacillanic acid (160 mg.). The solution was adjusted to pH 6.0 to 6.2 by adding a small amount of hydroxylamine hydrochloride and stirred for 10 minutes. Methanol (5 ml.) was added to the mixture, and the reaction solution, after stirred at ambient temperature for 3 hrs. was allowed to stand overnight in a refrigerator. The precipitated crystals were collected by filtration to give 3-[2-[2-{4-chloro-2-(α-hydroxyiminobenzyl)phenoxy}acetamido]-2-phenylacetamido]lactacillanic acid (100 mg.). Mp 171° to 176° C. (dec.).

EXAMPLE 499

3-[2-{4-(3-Acetamido-3-carboxypropoxy)phenyl}-glycinamido]lactacillanic acid (1.3 g.) was dissolved in 50% pyridine aqueous solution (26 ml.), and the solution was adjusted to pH 8.4 with 1 N-sodium hydroxide aqueous solution. Phenyl isothiocyanate (0.40 g.) was added to the solution under ice-cooling, and the mixture was stirred for 4.5 hrs. The reaction mixture was washed with ether, and the separated aqueous layer was adjusted to pH 2 with 10% hydrochloric acid to give precipitates, which were collected by filtration. The precipitates were dissolved in a sodium bicarbonate aqueous solution, and the solution was adjusted to pH 2 with 10% hydrochloric acid. The precipitated crystals were collected by filtration to give 3-[2-{4-(3-acetamido-3-carboxypropoxy)phenyl}-2-(3-phenylthioureido)acetamido]lactacillanic acid (0.92 g.). Mp 150° to 156° C. (dec.).

EXAMPLE 500

3-[2-{4-(3-Acetamido-3-carboxypropoxy)phenyl}-glycinamido]lactacillanic acid (2.0 g.) was dissolved in 50% pyridine aqueous solution (20 ml.), and the solution was adjusted to pH 8.6 with 1 N-sodium hydroxide aqueous solution under ice-cooling. 1-Naphthyl isothiocyanate (0.74 g.) was added to said solution at the same temperature, and the mixture was stirred at ambient temperature for 4 hrs. The reaction mixture was washed with ether, and the separated aqueous layer was adjusted to pH 2 with 10% phosphoric acid under ice-cooling. The precipitated solid material was collected by filtration, washed with water and then dissolved in a sodium bicarbonate-saturated-aqueous solution. The solution was adjusted to pH 2 with 10% phosphoric acid, and then the precipitated crystals were collected by filtration to give 3-[2-{4-(3-acetamido-3-carboxypropoxy)phenyl}-2-{3-(1-naphthyl)thioureido}acetamido]lactacillanic acid (2.5 g.). Mp 142° to 147° C. (dec.).

EXAMPLE 501

3-[2-{4-(3-Acetamido-3-carboxypropoxy)phenyl}-glycinamido]lactacillanic acid as a starting material and acetyl chloride as an acylating agent were treated in substantially the similar manner as described in Example 500 to give 3-[2-{4-(3-acetamido-3-carboxypropoxy)phenyl}-2-acetamidoacetamido]lactacillanic acid.

I.R. absorption spectrum,
$\nu_{cm-1}$ (Nujol): 1735, 1650.

EXAMPLE 502

3-[2-{4-(3-Benzamido-3-carboxypropoxy)phenyl}-glycinamido]lactacillanic acid (7.8 g.) was dissolved in 50% pyridine aqueous solution (160 ml.), and the solution was adjusted to pH 8.6 by adding 1 N-sodium hydroxide aqueous solution. Phenyl isothiocyanate (2.64 g.) was added to said solution at the same temperature, and the mixture was stirred for 3 hrs. The reaction mixture was washed with ether, and the separated aqueous layer was adjusted to pH 2 with 10% phosphoric acid under cooling. The separated oily material was collected and dissolved in sodium bicarbonate-saturated-aqueous solution. The solution was adjusted to pH 2 with 10% phosphoric acid, and the precipitated crystals were collected by filtration to give 3-[2-{4-(3-benzamido-3-carboxypropoxy)phenyl}-2-(3-phenylthioureido)acetamido]lactacillanic acid (9.6 g.). Mp 133° to 138° C. (dec.).

The following compounds were prepared in substantially the similar manner as described in Example 502.

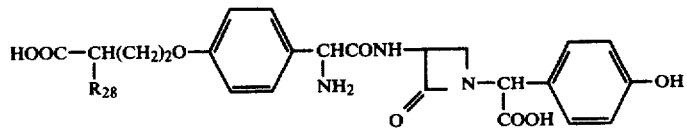

(XXIX)

Acylating agent

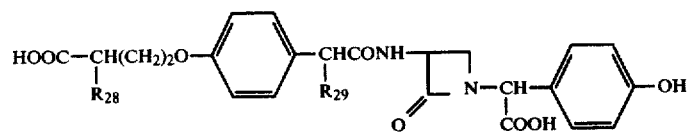

(XXX)

| | | Compound (XXIX) | | Compound (XXX) | | |
|---|---|---|---|---|---|---|
| Example | R28 | Acylating agent | R28 | R29 | | mp(°C.) (dec.) |
| 503 | ⟨phenyl⟩—NH—C(=O)—NH— | ⟨phenyl⟩—N=C=O | the same as R28 of Compound (XXIX) | ⟨phenyl⟩—NH—C(=O)—NH— | | 170–172 |
| 504 | ⟨phenyl⟩—NH—C(=S)—NH— | ⟨phenyl⟩—N=C=S | the same as R28 of Compound (XXIX) | ⟨phenyl⟩—NH—C(=S)—NH— | | 190–195 |

(XXIX)

↓ Acylating agent

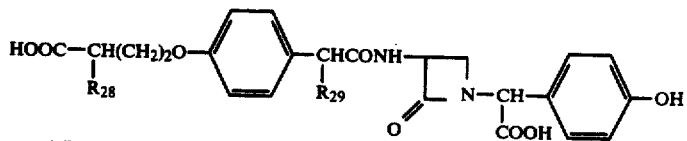

(XXX)

| | Compound (XXIX) | | Compound (XXX) | | |
|---|---|---|---|---|---|
| Example | $R_{28}$ | Acylating agent | $R_{28}$ | $R_{29}$ | mp(°C.) (dec.) |
| 505 | ![naphthyl]-NH-C(=S)-NH- | ![naphthyl]-N=C=S | the same as $R_{28}$ of Compound (XXIX) | ![naphthyl]-NH-C(=S)-NH- | 169–173 |
| 506 | $C_2H_5O$-C(=S)-NH- | $C_2H_5O$-C(=S)-SCH$_3$ | the same as $R_{28}$ of Compound (XXIX) | $C_2H_5O$-C(=S)-NH- | 112–119 |

EXAMPLE 507

3-[2-{4-(3-Amino-3-carboxypropoxy)phenyl}-2-hydroxyiminoacetamido]lactacillanic acid (2.0 g.) suspended in water (20 ml.) was dissolved by adding 1 N-sodium hydroxide aqueous solution (4.5 ml.) thereto, and then sodium hydroxymethanesulfonate (1 hydrate) (0.66 g.) was added to said solution.

The mixture was stirred at ambient temperature for 2.5 hrs. The reaction mixture was filtered, and the filtrate was concentrated to about two third of its original volume under reduced pressure. Acetone (40 ml.) was added to the residue, and the precipitated powder was collected by filtration to give disodium salt of 3-[2-[4-{3-carboxy-3-(N-sulfomethylamino)propoxy}phenyl]-2-hydroxyiminoacetamido]lactacillanic acid (1.85 g.)

I.R. absorption spectrum,
$\nu_{cm-1}$ (Nujol): 1730, 1600, 1240.

EXAMPLE 508

3-[4-(3-Amino-3-carboxypropoxy)phenylglyoxyloylamino]lactacillanic acid (0.50 g.) suspended in water (10 ml.) was dissolved by adding 1 N-sodium hydroxide aqueous solution (1.1 ml.) thereto. Sodium hydroxymethanesulfonate (1 hydrate) (0.152 g.) was added to said solution, and the mixture was stirred at ambient temperature for 4 hrs. The water was distilled off from the reaction mixture under reduced pressure, and the residue was pulverized with acetone. The powder (0.49 g.) was dissolved in a small amount of water, and acetone was added gradually to said solution. The precipitated crystals were collected by filtration to give disodium salt of 3-[4-{3-carboxy-3-(N-sulfomethylamino)propoxy}phenylglyoxyloylamino]lactacillanic acid (63 mg.).

I.R. absorption spectrum,
$\nu_{cm-1}$ (Nujol): 1720, 1650, 1260.

EXAMPLE 509

A mixture of 3-[2-{4-(3-amino-3-carboxypropoxy)phenyl}-2-hydroxyiminoacetamido]lactacillanic acid (500 mg.) in water (6 ml.) was dissolved by adding 1 N-sodium bicarbonate aqueous solution (1.2 ml.) under cooling. To the solution, there was added a solution of acetaldehyde (220 mg.) and sodium hydrogensulfite (520 mg.) dissolved in water (5 ml.), and the mixture was stirred at room temperature for 3 hrs. and further at 45° C. for an hour. The reaction mixture was concentrated to about one third of its original volume under reduced pressure. Ethanol (10 ml.) was added to the residue, and the precipitated crystals were collected by filtration to give 3-[2-[4-[3-carboxy-3-{N-(1-sulfoethyl)amino}propoxy]phenyl]-2-hydroxyiminoacetamido]lactacillanic acid disodium salt (0.3 g.). Mp 224.5° to 229° C. (dec.).

EXAMPLE 510

3-[2-{2-(2-Carboxyphenylthio)acetamido}-2-phenylacetamido]lactacillanic acid (169 mg.) was dissolved in acetone (6 ml.), and 85% 3-chloroperbenzoic acid (61 mg.) was added to the solution under ice-cooling, and then the mixture was stirred at the same temperature for an hour. After the reaction mixture was concentrated under reduced pressure, ethyl acetate (about 3 ml.) was added to the residue and then the solution was stirred for 2 hrs. The precipitated crystals were collected by filtration, washed with ethyl acetate and dried to give 3-[2-{2-(2-carboxyphenylsulfinyl)acetamido}-2-phenylacetamido]lactacillanic acid (120 mg.). Mp 175° to 181° C. (dec.).

EXAMPLE 511

3-[2-[4-{3-Carboxy-3-(2,2,2-trifluoroacetamido)propoxy}phenyl]-2-hydroxyiminoacetamido]lactacillanic acid (0.59 g.) was dissolved in a solution of acetone (10 ml.) and water (10 ml.), and sodium bicarbonate (0.34 g.) and sodium iodide (0.15 g.) were added to the solution and then the mixture was allowed to stand for a while. Chloromethyl pivalate (0.60 g.) was added to said solution, and the mixture was heated under reflux for 4 hrs. The acetone was distilled off from the reaction mixture under reduced pressure, and the residue was added to a mixture of ethyl acetate (20 ml.) and water (20 ml.). The separated ethyl acetate layer was washed with a sodium bicarbonate aqueous solution, water and then a sodium chloride—saturated—aqueous solution respectively, and dried over anhydrous magnesium sulfate. The solvent was distilled off from the ethyl acetate solution under reduced pressure, and the residue was pulverized with benzene. The powder (0.19 g.) thus obtained was chromatographed on silica.gel (10 g.). Elution was conducted with a mixture of chloroform and methanol (99:1), the fractions containing the object compound were collected, and then the solvent was distilled off from the fractions. The residue was recrystallized from a mixture of ether and diisopropyl ether to give 1-(α-pivaloyloxymethoxycarbonyl-4-hydroxybenzyl)-3-[2-[4-{3-pivaloyloxymethoxycarbonyl-3-(2,2,2-trifluoroacetamido)propoxy}phenyl]-2-hydroxyiminoacetamido]-2-azetidinone (0.12 g.). Mp 135° to 140° C. (dec.).

EXAMPLE 512

Triethylamine (1.0 g.) and pyridine (6.4 g.) was added to a solution of 3-[2-[4-{3-carboxy-3-(3-phenylthioureido)propoxy}phenyl]-2-(3-phenylthioureido)acetamido]lactacillanic acid (3.04 g.) dissolved in dried acetone (30 ml.). The mixture, after stirred for a while, was cooled to −20° to −15° C., and a solution of 2,2,2-trichloroethyl chloroformate (2.1 g.) dissolved in dried acetone (20 ml.) was added dropwise thereto in 15 minutes, and then the mixture was stirred at the same temperature for 2 hrs. The acetone was distilled off from the reaction mixture under reduced pressure, and the residue was added to a mixture of water (200 ml.) and ethyl acetate (200 ml.). The ethyl acetate layer was separated, washed with a sodium bicarbonate aqueous solution and a sodium chloride-saturated-aqueous solution, and then dried over anhydrous magnesium sulfate. The solvent was distilled off from the ethyl acetate layer, and the residue was pulverized with ether. The powder (1.2 g.) thus obtained was chromatographed on silica.gel (50 g.). Elution was conducted with a mixture of chloroform and methanol (99:1). The fractions containing the object compound were collected, and the solvent was distilled off to give 1-[α-(2,2,2-trichloroethoxycarbonyl)-4-hydroxybenzyl]-3-[2-[4-{3-(3-phenylthioureido)-3-(2,2,2-trichloroethoxycarbonyl)propoxy}phenyl]-2-(3-phenylthioureido)acetamido]-2-azetidinone (0.16 g.).

I.R. absorption spectrum,
$\nu_{cm-1}$ (Nujol): 1750, 1680, 1220.

EXAMPLE 513

An ether solution of diazomethane was added dropwise to a solution of 3-[2-{4-(3-acetamido-3-carboxypropoxy)phenyl}-2-hydroxyiminoacetamido]lactacillanic acid (5.5 g.) dissolved in methanol (150 ml.) until the color of the diazomethane came to not disappear in the latter solution. The reaction mixture was allowed to stand overnight in a refrigerator, and the solvent was distilled off. The residue was chromatographed on silica.gel. Elution was conducted with a mixture of chloroform and methanol (98:2), and the fractions containing the object compound were collected. The solvent was distilled off to give 1-(α-methoxycarbonyl-4-methoxybenzyl)-3-[2-{4-(3-acetamido-3-methoxycarbonylpropoxy)phenyl}-2-methoxyiminoacetamido]-2-azetidinone (3.50 g.).

N.M.R. absorption spectrum,
δ ppm (CDCl$_3$):
1.95 (3H, s), 2.25 (2H, m), 3.15 (1H, d,d,
J=3 Hz, 6 Hz), 3.70 (3H, s), 3.74 (3H, s), 3.78 (3H, s), 3.89 (3H, s), 3.96 (2H,
t, J=6 Hz), 4.70 (1H, q, J=8 Hz), 4.92
(1H, m), 5.52(1H, s), 6.75 (2H, d,
(9 Hz), 6.86 (2H, d, J=9 Hz), 7.20 (2H,
d,J=9 Hz), 7.45 (2H, d, J=9 Hz)

EXAMPLE 514

3-[2-[4-{3-Carboxy-3-(2,2,2-trifluoroacetamido)propoxy}phenyl]-2-hydroxyiminoacetamido]lactacillanic acid (2.0 g) was dissolved in a mixture of ether (20 ml.) and methanol (15 ml.), and the solution was ice-cooled. An ether solution of diazomethane was added dropwise to said solution until the color of the diazomethane came to not disappear in the latter solution. The reaction mixture was stirred at the same temperature for 4 hrs. and further at ambient temperature for 2 hrs. The solvent was distilled off from the reaction mixture, and the residue (2.10 g.) was chromatographed on silica.gel (50 g.), and then the elution was conducted with chloroform. The fractions containing the object compound were collected, and the chloroform was distilled off to give 1-(α-methoxycarbonyl-4-methoxybenzyl)-3-[2-[4-{3-methoxycarbonyl-3-(2,2,2-trifluoroacetamido)propoxy{phenyl]-2-methoxyiminoacetamido]-2-azetidinone (1.29 g.).

I.R. absorption spectrum,
$\nu_{cm-1}$ (liquid film): 1730, 1700, 1650.

EXAMPLE 515

3-[2-{4-(3-Carboxy-3-phthalimidopropoxy)phenyl}-2-hydroxyiminoacetamido]-2-azetidinone (3.50 g.) was dissolved in methanol (30 ml.), and the solution was ice-cooled. An ether solution of diazomethane was added dropwise to said solution, until the color of the diazomethane came to not disappear in the latter solution. The mixture was stirred for 5 hrs., and then allowed to stand one day and night in a refrigerator. The solvent was distilled off from the reaction mixture, and the residue was chromatographed on silica.gel (80 g.). Elution was conducted with chloroform, and then with a mixture of chloroform and methanol (98:2). The fractions, which were eluted with a mixture of chloroform and methanol, were collected, and the solvent was distilled off to give 1-(α-methoxycarbonyl-4-methoxybenzyl)-3-[2-{4-(3-phthalimido-3-methoxycarbonylpropoxy)phenyl}-2-methoxyiminoacetamido]-2-azetidinone (1.20 g.).

N.M.R. absorption spectrum,
δ ppm (CDCl$_3$):
2.70 (2H, s), 3.15 (1H, d, d, J=3 Hz,
6 Hz), 3.70 (1H, m), 3.75 (6H, s),
3.78 (3H, s), 3.88 (3H, s), 3.94 (2H, m),
5.05 (1H, m), 5.16 (1H, t, J=6 Hz),
5.56 (1H, s), 6.62 (2H, d, J=9 Hz),
6.84 (2H, d, J=9 Hz), 7.20 (2H, d, J=9 Hz),
7.38 (2H, d, J=9 Hz), 7.74 (4H, m).

EXAMPLE 516

An ether solution of diazomethane was added dropwise to a solution of 3-[2-{4-(3-acetamido-3-carboxypropoxy)phenyl}2-acetamidoacetamido]lactacillanic acid (0.70 g.) dissolved in methanol (20 ml.) until the color of the diazomethane came to not disappear in the latter solution. Then, the mixture was allowed to stand over night in a refrigerator. The solvent was distilled off from the reaction mixture and the residue was chromatographed on silica gel (25 g.). Elution was conducted with chloroform, and then with three kind of a mixture of chloroform and methanol (99:1), (98:2) and (97:3). The fractions containing the object compound were collected and the solvent was distilled off to give 1-(α-methoxycarbonyl-4-methoxybenzyl)-3-[2-{4-(3-acetamido-3-methoxycarbonylpropoxy)phenyl}-2-acetamidoacetamido]-2-azetidinone (0.30 g.).

I.R. absorption spectrum,
$\nu_{cm-1}$ (CHCl$_3$): 1745, 1667, 1195.

EXAMPLE 517

3-[4-(3-Amino-3-carboxypropoxy)phenylgloxyloylamino]lactacillanic acid (2.50 g.) was dissolved in dimethylsulfoxide (17.5 ml.), and acetic acid (12.5 ml.) and water (12.5 ml.) was added to said solution under ice-cooling, and then the mixture was stirred for a while. To the solution, there was added an aqueous solution of sodium nitrite (0.50 g.) in water (2 ml.), and the mixture was stirred at ambient temperature for 2 hrs. The reaction mixture was added to ice-water (50 ml.) and the solution was extracted with ethyl acetate (50 ml.) three times. The ethyl acetate layer was separated, washed twice with water (20 ml.) and once with a sodium chloride-saturated-aqueous solution, and dried over anhydrous magnesium sulfate. The solvent was distilled off, and the residue was crystallized from a mixture of ethyl acetate and ether to give 3-[4-(3-carboxy-3-hydroxypropoxy)phenylglyoxyloylamino]lactacillanic acid (0.49 g.). Furthermore, the same object product (0.21 g.) was recovered from the mother liquor. Total yield was 0.70 g. Mp 196° to 201° C. (dec.).

EXAMPLE 518

3-[2-{4-(3-Carboxy-3-phthalimidopropoxy)phenyl}-glycinamido]lactacillanic acid as a starting material was treated in the similar manner as described in Example 517 to give 3-[2-{4-(3-carboxy-3-phthalimidopropoxy)phenyl}-2-hydroxyacetamido]lactacillanic acid. Mp 160° to 163° C. (dec.).

EXAMPLE 519

3-[2-Glycinamido-2-(2-thienyl)acetamido]lactacillanic acid (200 mg.) was dissolved in an aqueous solution (5 ml.) of sodium bicarbonate (168 mg.). To the solution, there was added methanol (5 ml.) and then methyl 4-fluoro-3-nitrobenzoate (80 mg.), and the mixture was stirred at 50° C., for 3 hrs. The methanol was distilled off from the reaction mixture under reduced pressure, and the aqueous residue was washed with ethyl acetate. The aqueous solution was adjusted to pH 2 to 3 with 10% hydrochloric acid under cooling and extracted with ethyl acetate twice. The extracts were combined together, washed with water, dried over anhydrous magnesium.sulfate and then evaporated to dryness under reduced pressure. The residue (90 mg.) was crystallized from ether to give crude 3-[2-{N-(4-methoxycarbonyl-2-nitrophenyl)glycinamido}-2-(2-thienyl)acetamido]lactacillanic acid (70 mg.). Furthermore, this product was chromatographed on silica.gel (2 g.), and the fractions eluted with ethyl acetate were collected, and the solvent was distilled off from the eluate to give the purified same product (11 mg.). Mp 160° to 164° C. (dec.).

EXAMPLE 520

3-(2-Phenylglycinamido)lactacillanic acid (369 mg.) was dissolved in a solution of sodium carbonate (10 hydrate) (572 mg.) in water (8 ml.). To the solution, was added a solution of 5-chloro-3-phenyl-1,2,4-oxadiazole (180 mg.) dissolved in acetone (7 ml.), and the mixture was allowed to react at ambient temperature for 5 hrs. The reaction mixture was adjusted to pH 7.0 with sodium bicarbonate and washed with ethyl acetate. The aqueous solution thus obtained was adjusted to about pH 3 with diluted hydrochloric acid and then extracted with ethyl acetate. The ethyl acetate layer was separated, washed with water and dried over anhydrous magnesium sulfate, and the solvent was distilled off. The oily residue (270 mg.) was chromatographed on silica.gel (7 g.). The fractions, eluted with a mixture of ethyl acetate and methanol (97:3), were collected, and the solvent was distilled off to give 3-[2-phenyl-N-(3-phenyl-1,2,4-oxadiazol-5-yl)glycinamido]lactacillanic acid (95 mg.) as powder.

I.R. absorption spectrum,
$\nu_{cm-1}$ (Nujol): 1738, 1680, 1618

EXAMPLE 521

3-(2-Phenylacetamido)lactacillanic acid (0.19 g.) was suspended in methanol (5 ml.), and to the suspension was added an ether solution containing diazomethane under ice-cooling, continuing to be added until a color of the diazomethane in the reaction mixture was not disappeared. The reaction mixture was stirred for 2 hrs. at the same temperature, and then the reaction mixture was concentrated under reduced pressure. The residue, obtained was dissolved in chloroform, and the solution was washed with a sodium bicarbonate aqueous solution, water and a sodium chloride-saturated-aqueous solution respectively, and then dried over anhydrous magnesium sulfate. The chloroform was distilled off from the solution under reduced pressure to give a residue which was powdered with ether. The powder was collected by filtration to give 1-(α-methoxycarbonyl-4-methoxybenzyl)-3-(2-phenylacetamido)lactacillanic acid (0.12 g.), which was recrystallized from ether to give the purified object compound (0.06 g.). Mp 145° to 146° C. (dec.)

EXAMPLE 522

3-[2-{4-(3-Amino-3-carboxypropoxy)phenyl}-2-hydroxyiminoacetamido]lactacillanic acid (3.0 g.) was dissolved in a methanol solution (60 ml.) containing sodium hydroxide (480 mg.). To the solution was added a methanol solution (20 ml.) containing methyl acetoacetate (835 mg.), and the mixture was heated for 6 hrs. at 74° C. under stirring. The methanol was distilled off from the reaction mixture, and to the residue obtained was suspended in ethanol (300 ml.). The suspension was stirred for an hour at ambient temperature. The insoluble material was collected by filtration and washed with ether to give 3-[2-[4-{3-carboxy-3-(2-methoxycarbonyl-1-methylvinylamino)propoxy}phenyl]-2-hydroxyiminoacetamido]lactacillanic acid disadium salt (1.2 g.). Furthermore, the mother liquor was concentrated to give a residue, and to the residue was added ether, and then the powder was collected by filtration to recover an object compound (2.4 g.). Total yield was 3.6 g.

N.M.R. absorption spectrum,
δ ppm (D$_2$O):
1.8 (3H, s), 2.2 (2H, m), 3.1 (1H, m),
3.8 (2H, m), 3.56 (3H, s), 4.1 (2H, broad s), 5.0 (1H, m), 5.3 (1H, s),
6.7–7.5 (8H, m).

EXAMPLE 523

3-[4-(3-Benzyloxycarbonyl-5-oxo-1,3-oxazol-4-yl)butyramido]lactacillanic acid (200 mg.) was dissolved in methanol (15 ml.), and to the solution was added 10% palladium carbon (50 mg.) as a catalyst. The mixture was reacted in hydrogen atmosphere at ordinary atm. A theoretical volume of hydrogen gas was introduced into the mixture in 4 hrs. The reaction mixture was subjected to filtration, and the filtrate was concentrated under reduced pressure. The residue obtained was pulverized with acetone and the powder was collected by filtration to give 3-(5-amino-5-carboxyvalerylamino)lactacillanic acid (97 mg.).

N.M.R. absorption spectrum,
δ ppm (D$_2$O+NaHCO$_3$):
1.64–1.90 (4H, m), 2.24 (2H, t, J=4 Hz), 2.90, 2.94 (1H, d, d, J=2Hz, 6 Hz), 3.67 (1H, t, J=6 Hz), 5.19 (1H, s), 6.79 (2H, d, J=8 Hz), 7.12 (2H, d, J=8 Hz).

EXAMPLE 524

3-[2-[2-{4-Chloro-2-(4-nitrobenzoyl)phenoxy}acetamido]-2-phenylacetamido]lactacillanic acid (103 mg.) was dissolved in methanol (15 ml.). To the solution was added 10% palladium carbon (45 mg.) as a catalyst, and the mixture was stirred in hydrogen atmosphere. A calculated volume of hydrogen was absorbed into the mixture in 2.5 hrs. The methanol was distilled off from the reaction mixture, and the residue (80 mg.) obtained was washed with ether to give 3-[2-[2-{2-(4-aminobenzoyl)-4-chlorophenoxy}acetamido]-2-phenylacetamido]lactacillanic acid (70 mg.). Mp 150° to 153° C. (dec.).

EXAMPLE 525

3-[2-{2-(2-Phenoxycarbonylphenoxy)acetamido}-2-phenylacetamido]lactacillanic acid (190 mg.) and 80% hydrazine hydrate aqueous solution (60 mg.) were dissolved in methanol (6 ml.), and the solution was stirred for 3 hrs. at ambient temperature. The methanol was distilled off from the reaction mixture to give a residue which was powdered with ether. A small amount of ethanol was added to the powder (180 mg.) and the mixture was stirred for an hour, whereafter an insoluble material was collected by filtration to give 3-[2-{2-(2-hydrazinocarbonylphenoxy)acetamido}-2-phenylacetamido]lactacillanic acid hydrazine salt (100 mg.). Mp 178° to 182° C. (dec.).

EXAMPLE 526

3-[2-{4-(3-Azidopropoxy)phenyl}acetamido]lactacillanic acid (52 mg.) was dissolved in methanol (10 ml.). To the solution was added 10% palladium carbon as a catalyst, and the mixture was stirred in hydrogen atmosphere. A calculated volume of hydrogen was absorbed into the mixture in 1.5 hrs. The catalyst was filtered off from the reaction mixture, and the methanol was distilled off from the filtrate. The residue obtained was treated with acetone to give 3-[2-{4-(3-aminopropoxy)phenyl}acetamido]lactacillanic acid (38 mg.).
I.R. absorption spectrum,
ν$_{cm-1}$ (Nujol): 1730, 1660, 1610.

EXAMPLE 527

3-(2-Ethoxalylamino-2-phenylacetamido)lactacillanic acid (200 mg.) was dissolved in ethanol (4 ml.), and to the solution was added an ethanol solution (3.5 ml.) containing benzylamine (136 mg.), and then the mixture was stirred for 6.5 hrs. at ambient temperature. The reaction mixture was concentrated to give a residue which was poured into a mixture of water and ethyl acetate. 1 N-Hydrochloric acid (1 ml.) was added to the mixture, and then the ethyl acetate layer was separated out and washed with 1% hydrochloric acid and water respecitively. The ethyl acetate layer was dried over anhydrous magnesium sulfate whereafter the solvent was distilled off from the solution to give a residue which was washed with diisopropyl ether to give crystals (160 mg.). The crystals were recrystallized from a mixture of acetone and ethyl acetate to give crystals of 3-[2-(N-benzyloxamoyl)amino-2-phenylacetamido]lactacillanic acid (70 mg.). Mp 149° to 154° C. (dec.).

EXAMPLE 528

An acetone solution (2 ml.) containing 2-phenylacetyl chloride (240 mg.) was added dropwise to a mixture of 3-guanidinocarbonylaminolactacillanic acid (160 mg.), 0.1 N-potassium hydroxide aqueous solution (10 ml.), sodium bicarbonate (130 mg.), water (5 ml.) and acetone (10 ml.) at 0° to 5° C., and the mixture was stirred for 3.5 hrs. at the same temperature to give crystals of 3-[3-(2-phenylacetyl)guanidinocarbonylamino]lactacillanic acid (120 mg.). Mp 159° to 161° C. (dec.).

EXAMPLE 529

3-[2-(4-Formylphenoxy)acetamido]lactacillanic acid (200 mg.) was dissolved in 0.1 N-sodium hydroxide aqueous solution under ice-cooling. To the solution was added sodium borohydride (20 mg.), and the mixture was stirred for 50 minutes. Acetone (0.5 ml.) and ethyl acetate (10 ml.) were added to the reaction mixture, and then the mixture was adjusted to pH 1 to 2 with 1 N-hydrochloric acid. The ethyl acetate layer was separated out, and washed with water and a sodium chloride aqueous solution, respectively, and then dried over anhydrous magnesium sulfate. The solvent was distilled off from the solution, and the residue obtained was crystallized from ethyl acetate to give 3-[2-(4-hydroxymethylphenoxy)acetamido]lactacillanic acid (110 mg.). Mp 182° to 185° C. (dec.).

EXAMPLE 530

3-[2-{2-(2-Formylphenoxy)acetamido}-2-phenylacetamido]lactacillanic acid (200 mg.) was treated in substantially the similar manner as described in Example 529 to give 3-[2-{2-(2-hydroxymethylphenoxy)acetamido}-2-phenylacetamido]lactacillanic acid (130 mg.). Mp 95° to 101° C. (dec.).

EXAMPLE 531

3-(2-Phenyl-2-phenylglyoxyloylaminoacetamido)lactacillanic acid (170 mg.) was dissolved in 0.1 N-sodium hydroxide aqueous solution (3.5 ml.), and to the solution was added dropwise an aqueous solution (1 ml.) containing sodium borohydride (13 mg.), and then the mixture was stirred for 40 minutes. To the reaction mixture was added ethyl acetate (30 ml.), and the mixture was adjusted to pH 1 with 10% hydrochloric acid. The ethyl acetate layer was separated, and the remaining aqueous solution was extracted with ethyl acetate (20 ml.). These extracts were combined washed with a sodium chloride aqueous solution and dried over anhydrous magnesium sulfate. The solvent was distilled off from the solution, and the residue obtained was powdered with ether to give 3-[2-(2-phenylglycolamido)-2-phenylacetamido]lactacillanic acid (140 mg.). Mp 90° to 93° C. (dec.).

EXAMPLE 532

Sodium borohydride (40 mg.) was added to a mixture of 3-[2-(4-formylphenoxy)acetamido]lactacillanic acid (200 mg.), 0.1 N-sodium hydroxide aqueous solution (5 ml.), benzylamine (106 mg.) and ethanol (2 ml.) under ice-cooling, and the reaction mixture was stirred for 30 minutes at the same temperature. The reaction mixture was washed with ether twice, and adjusted to about pH 4 with 10% hydrochloric acid to give an isolating oily material which was separated by decantation. The oily material was powdered with acetone, and the powder was collected by filtration and washed with acetone to give 3-[2-(4-benzylaminomethylphenoxy)acetamido]-lactacillanic acid (105 mg.). Mp 172° to 177° C. (dec.).

EXAMPLE 533

3-[2-{4-(1-Benzyloxycarbonylamino-1-methoxycarbonylmethyl)phenoxy}acetamido]lactacillanic acid (200 mg.) was dissolved in methanol (15 ml.). To the solution was added 10% palladium carbon (35 mg.) as a catalyst, and the mixture was reacted for 2 hrs. in hydrogen atmosphere at ordinary temperature and ordinary atm. After a calculated volume of hydrogen was absorbed into the mixture, the catalyst was filtered off from the reaction mixture, and then the filtrate was concentrated under reduced pressure. The residue obtained was powdered with acetone and treated with acetone to give 3-[2-{4-(1-amino-1-methoxycarbonylmethyl)phenoxy}acetamido]lactacillanic acid (90 mg.). Mp 190° to 194° C. (dec.).

EXAMPLE 534

3-[2-{4-(2-Benzyloxycarbonylamino-2-methoxycarbonylethyl)phenoxy}acetamido]lactacillanic acid (1.35 g.) was dissolved in 1 N-sodium hydroxide aqueous solution (6.7 ml.), and the solution was stirred for an hour at ambient temperature. A small amount of water was added to the reaction mixture, and then the solution was washed with ethyl acetate, whereafter the aqueous solution was adjusted to pH 1 with 1N-hydrochloric acid. The solution was extracted with ethyl acetate and the ethyl acetate layer was separated out, and washed with water and then dried over anhydrous magnesium sulfate. The solvent was distilled off from the solution, and the residue was crystallized from chloroform to give crystals of 3-[2-{4-(2-benzyloxycarbonylamino-2-carboxyethyl)phenoxy}acetamido]lactacillanic acid (1.07 g.). Mp 125° to 130° C. (dec.).

EXAMPLE 535

3-[2-{4-(1-Benzyloxycarbonylamino-1-methoxycarbonylmethyl)phenoxy}acetamido]lactacillanic acid (118 mg.) was dissolved in 0.1 N-sodium hydroxide aqueous solution (4 ml.), and the solution was stirred for 2 hrs. at ambient temperature. Subsequently, 0.1 N-hydrochloric acid (4 ml.) was added to the reaction mixture, and then the solution was extracted with ethyl acetate. The extract was washed with water and dried over anhydrous magnesium sulfate. The solvent was distilled off from the solution, and the residue was crystallized from a small amount of acetone. The crystals were treated with ethyl acetate to give crystals of 3-[2-{4-(1-benzyloxycarbonylamino-1-carboxymethyl)phenoxy}acetamido]lactacillanic acid (30 mg.). Mp 134° to 138° C. (dec.).

EXAMPLE 536

2-(4-Benzyloxyplenyl)-2-(2,2-dichloroacetoxyimino)acetic acid (0.382 g.) was suspended in benzene (7 ml.) and the suspension was cooled to 0° to 5° C. To the suspension was added all at once phosphorus pentachloride (0.250 g.), and the mixture was stirred for an hour at the same temperature. The benzene was distilled off from the mixture under reduced pressure under water-cooling. Benzene (7 ml.) was added to the residue, and the benzene was distilled off from the solution under reduced pressure, and this operation was repeated three times. The residue obtained was dissolved in dried methylene chloride (10 ml.). On the other hand, 3-aminolactacillanic acid (0.236 g.) was suspended in dried methylene chloride (20 ml.), and to the suspension was added N,O-bis(trimethylsilyl)acetamide (0.87 g.), and the mixture was stirred for a while at ambient temperature. This solution was added the methylene chloride solution obtained above under cooling at 0° to 5° C. in 30 minutes, and the reaction mixture was stirred for an hour at the same temperature. The reaction mixture was washed with water, and concentrated under reduced pressure to give a residue. Ethyl acetate and 5% sodium bicarbonate aqueous solution were added to the residue, and the mixture was stirred enough. The aqueous layer was separated out, and adjusted to pH 1 to 2, and then extracted with ethyl acetate. The ethyl acetate layer was separated out and dried over anhydrous magnesium sulfate. The solvent was distilled off from the layer obtained under reduced pressure to give an oily residue which was washed with ether and powdered with chloroform. The powder (108 mg.) obtained was dissolved in acetone (2 ml.), and to the solution was added an aqueous solution (1.2 ml.) containing sodium 2-ethylhexanoate (612 mg.). To the mixture was added ether (3 ml.) to give a powder which was collected by filtration. The powder was washed with ether and dissolved in water. The aqueous solution was adjusted to pH 1 to 2 with diluted hydrochloric acid, and then the solution was extracted with ethyl acetate. The extract was washed with water and dried over anhydrous magnesium sulfate. The solvent was distilled off from the solution, and the residue was crystallized from chloroform to give crystals of 3-[2-(4-benzyloxyphenyl)-2-hydroxyimino]lactacillanic acid (95 mg.). Mp 137° to 140° C. (dec.).

The following compounds were obtained in substantially the similar manner as described above.

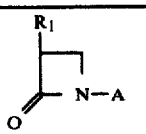

| Example | Acylating agent | Compound (I) R₁ | A | mp (°C.) (dec.) |
|---|---|---|---|---|
| 537 | Ph-C(=N-OCOCHCl₂)-COCl | Ph-C(=N-OH)-CONH- | -CH(COOH)-C₆H₄-OH | 197–199 |
| 538 | (thienyl)-C(=N-OCOCH₃)-COCl | (thienyl)-C(=N-OH)-CONH- | " | N.M.R. δ ppm (CD₃OD): 3.25 (1H,m) 3.90 (1H,m) 5.10 (1H,m) 5.50 (1H,s) 6.85 (2H,d,J = 9Hz) 7.2 (1H,m) 7.25 (2H,d,J = 9Hz) 7.65 (1H,d,J = 5Hz) 7.95 (1H,d,J = 4Hz) |
| 539 | NC-C(=N-OCOCH₃)-COCl | NC-C(=N-OH)-CONH- | " | 240–245 |

EXAMPLE 540

3-(2-Phenylacetamido)-1-(α-methoxycarbonyl-3-benzyloxycarbonylaminobenzyl)-2-azetizinone (14 mg.) was dissolved in isopropyl alcohol (4 ml.), and 10% palladium carbon (10 mg.) was added as a catalyst to the solution. The reaction mixture was subjected to reaction in hydrogen stream at 50° C. under ordinary atmosphere. A calculated volume of hydrogen gas was absorbed into the reaction mixture in an hour. The catalyst was removed by filtration, and the filtrate was concentrated to give oily 3-(2-phenylacetamido)-1-(α-methoxycarbonyl-3-aminobenzyl)-2-azetidinone (7 mg.).

I.R. absorption spectrum,
$v_{cm-1}$ (CHCl₃): 3425, 1755, 1745, 1675, 1620

EXAMPLE 541

3-[2-[4-Chloro-2-{4-(2-chloroacetamido)benzoyl}-phenoxy]acetamido-2-phenylacetamido]lactacillanic acid (150 mg.) and 30% trimethylamine aqueous solution (160 mg.) was dissolved in methanol (4 ml.), and the solution was stirred at 50° C. for 1.5 hrs. 30% Trimethylamine aqueous solution (160 mg.) was added to said solution four times, respectively every an hour. The solvent was distilled off from the reaction mixture, and the residue was washed with acetone, whereafter water (5 ml.) was added to the residue (150 mg.), and the mixture was stirred for 30 minutes. The insoluble material was collected by filtraction, and acetone (10 ml.) was added to the material. The mixture was stirred for 30 minutes and the insoluble material was collected by filtration to give crystals of N-[N-[4-[3-chloro-2-[N-[1-[N-{1-(α-carboxy-4-hydroxybenzyl)-2-oxo-3-azetidinyl}carbamoyl]-1-phenylmethyl]carbamoylmethoxy]benzoyl]phenyl]carbamoylmethyl]-N,N,N-trimethylammonium chloride (120 mg.). Mp 214° to 220° C. (dec.).

EXAMPLE 542

3-[2-{4-(3-Amino-3-carboxypropoxy)phenyl}-2-hydroxyiminoacetamido]lactacillanic acid (1.0 g.) was dissolved in a mixture of 1 N-sodium hydroxide aqueous solution (4 ml.) and water (20 ml.). A methanol solution (4 ml.) containing methyl acrylate (0.34 g.) was added to said soluton little by little, and the mixture was stirred for 5.5 hrs. under ice-cooling. The reaction mixture was adjusted to pH 3 with 10% hydrochloric acid, and then precipitated crystals were collected by filtration. The crystals were dissolved in a small amount of a sodium bicarbonate aqueous solution, whereafter the solution was adjusted to pH 3 with 10% hydrochloric acid. The precipitated crystals in the aqueous solution were collected by filtration to give crystals of 3-[2-[4-{3-carboxy-3-(2-methoxycarbonylethylamino)propoxy}-phenyl]-2-hydroxyiminoacetamido]lactacillanic acid (0.57 g.). Mp 175° to 179° C. (dec.).

EXAMPLE 543

3-[2-{2-Oxo-3-(2-phenylacetamido)-1-azetidinyl}-3-methylbutyramido]-2-azetidinone and benzyl 2-bromo-2-(p-benzyloxyphenyl)acetate were treated in substantially the similar manner as described in Example 224 to give 3-[2-{2-Oxo-3-(2-phenylacetamido)-1-azetidinyl}-3-methylbutyramido]lactacillanic acid. Mp 160° to 164° C. (dec.).

EXAMPLE 544

Benzyl chloroformate (7.9 g.) was dissolved in methylene chloride (50 ml.). A methylene chloride (20 ml.) solution containing 3-amino-1-(1-methoxycarbonyl-2-methyl-1-propenyl)-2-azetidinone (2.42 g.) and triethylamine (3.7 g.) was added dropwise to the solution at −15° to −10° C. in the course of 1.33 hours with stirring, whereafter the mixture was stirred at the same temperature for 1.25 hours. The reaction mixture was evaporated to dryness under reduced pressure to give a residue, which was dissolved in ethyl acetate (150 ml.). The solution was washed three times with 5% hydrochloric acid and once with an aqueous sodium chloride, and then dried over magnesium sulfate. The solvent was removed by distillation and a residue (7.3 g.) was treated with n-hexane to give crude object compound, 3-benzyloxycarbonylamino-1-(1-methoxycarbonyl-2-methyl-1-propenyl)-2-azetidinone (3.27 g.). The compound (3.71 g.) thus obtained was subjected to column chromatography on silica gel (60 g.), and elution was carried out with chloroform and a mixture of chloroform and methanol (volume ratio; 10:1). The fractions containing the desired compound were collected and the solvent was distilled off from the eluate under reduced pressure to give the purified object compound (3.05 g.).

M.p. 135° to 137° C.

EXAMPLE 545

3-Aminolactacillanic acid (944 mg.) was suspended in dried methylene chloride (30 ml.), and to the suspension, there were added bis(trimethylsilyl)acetamide (3.50 g.) and N,N-dimethylformamide (0.2 ml.). The mixture was stirred at embient temperature for 4 hours and then triethylamine (404 mg.) was added thereto at −10° C.

A dried methylene chloride (10 ml.) solution containing phenylglyoxyloyl chloride (672 mg.) was added dropwise to the mixture obtained above at −10° C. in the source of 20 minutes, whereafter the mixture was stirred at the same temperature for 2 hours. The reaction mixture was washed with dilute hydrochloric acid and water, and then dried over magnesium sulfate. The solvent was distilled off from the solution under reduced pressure to give an oily residue (1.57 g.), which was subjected to column chromatography on silica gel (25 g.). Elution was carried out with ethyl acetate and the fractions containing a desired compound were collected. The solvent was distilled off from the eluate under reduced pressure and the residue obtained was powdered with ethyl acetate to give a crystalline 3-phenylglyoxyloylaminolactacillanic acid (404 mg.).

M.p. 190.5° to 192° C. (dec.).

EXAMPLE 546

N,N-Dimethylformamide (292 mg.) and thionyl chloride (710 mg.) were treated in a conventional manner to prepare Vilsmeier reagent, and methylene chloride (10 ml.) was added thereto. A methylene chloride (10 ml.) solution containing 2-(2-furyl)glycolic acid (341 mg.) and triethylamine (500 mg.) was added dropwise to the solution at −50° C. in a stream of nitrogen gas in the course of 10 minutes, whereafter the mixture was stirred at the same temperature for 15 minutes. To the solution, there was all at once added methylene chloride (10 ml.) solution containing 3-aminolactacillanic acid (472 mg.) and bis(trimethylsilyl)acetamide (1.2 g.) at −50° C., whereafter the mixture was stirred at −50° to −30° C. for 2 hours and additionally at −30° to 0° C. for 1.5 hours. The reaction mixture was evaporated to dryness under reduced pressure to give a residue and aqueous sodium bicarbonate was added thereto, and then the mixture was stirred at ambient temperature for half an hour. The insoluble materials were filtered off from the mixture and the aqueous layer was separated from the filtrate. The aqueous solution was adjusted to pH 1 to 2 with 10% hydrochloric acid, and ethyl acetate (30 ml.) and a small amount of sodium chloride were added thereto. The ethyl acetate layer was separated, washed with water and dried over magnesium sulfate. The solvent was distilled off from the solution under reduced pressure to give 3-[2-(2-furyl)glycolamido]lactacillanic acid (35 mg.). A part of this compound was dissolved in a small amount of acetone and the object compound was transformed into its sodium salt by adding sodium hexanoate thereto.

I.R. absorption spectrum
$\nu_{cm^{-1}}$ (KBr):
3350, 1735, 1615,
1380, 1240, 743.

EXAMPLE 547

2-(2-Azidoacetamido)-2-(2-thienyl)acetic acid (0.53 g.), triethylamine (0.221 g.) and N,N-dimethylbenzylamine (one drop) were dissolved in methylene chloride (10 ml.). A methylene chloride (5 ml.) solution containing ethyl chloroformate (0.238 g.) was added dropwise to the solution at −30° C. and the mixture was stirred at the same temperature for 45 minutes. To the solution, there was all at once added methylene chloride (10 ml.) solution containing 3-aminolactacillanic acid (0.472 g.) and bis(trimethylsilyl)acetamide (1.22 g.) at −40° C., whereafter the mixture was stirred at the same temperature for 3 hours. The reaction mixture was evaporated to dryness under reduced pressure to give a residue and saturated aqueous sodium bicarbonate was added thereto. The aqueous solution was washed with diethyl ether, adjusted to pH 1 with 10% hydrochloric acid under ice-water cooling, and then extracted with ethyl acetate. The extract was washed with water and then dried over magnesium sulfate. The solvent was distilled off from the solution under reduced pressure to give a residue, which was powdered with diisopropyl ether. The powder was collected by filtration to give 3-[2-(2-azidoacetamido)-2-(2-thienyl)acetamido]lactacillanic acid (550 mg.). Further, the object compound (100 mg.) was recovered from the mother liquor. Total yield was 650 mg., m.p. 120° to 125° C. (dec.).

EXAMPLE 548

2-Benzyloxyimino-2-(4-methoxyphenyl)acetic acid (695 mg.) and N,N'-dicyclohexylcarbodiimide (495 mg.) were added to a mixture of chloroform (6 ml.) and dioxane (4 ml.), whereafter the mixture was stirred under ice-cooling for 1.5 hours. The insoluble materials were filtered off from the mixture. To the filtrate, there was dropwise added chloroform (10 ml.) solution containing 3-aminolactacillanic acid (472 mg.) and bis(-trimethylsilyl)acetamide (1.22 g.) under ice-cooling, whereafter the mixture was stirred at the same temperature for 2.5 hours. The reaction mixture was evaporated to dryness under reduced pressure, and saturated aqueous sodium bicarbonate and ethyl acetate were added thereto, whereafter the mixture was stirred for a while. The aqueous layer was separated from the mixture, adjusted to pH 2 with 10% hydrochloric acid and extracted with ethyl acetate. The extract was washed with water and then dried over magnesium sulfate. The solvent was distilled off from the solution under reduced pressure to give a residue, which was subjected to column chromatography on silica gel. Elution was carried out with a mixture of chloroform and methanol (volume ratio, 99:1) and the fractions containing a desired compound were collected. The solvent was distilled off from the eluate under reduced pressure to give 3-[2-benzyloxyimino-2-(4-methoxyphenyl)acetamido]lactacillanic acid (20 mg.).

M.p. 138° to 148° C. (dec.)

EXAMPLE 549

A mixture of thionyl chloride (472 mg.) and N,N-dimethylformamide (292 mg.) were warmed at 50° to 60° C. for half an hour, whereafter the unreacted thionyl chloride was distilled off from the mixture under reduced pressure. The residue obtained was suspended in dried methylene chloride (10 ml.) at −25° to −20° C.

and to the suspension, there was added 2-(2,2-dichloroacetoxyimino)-2-(4-hydroxyphenyl)acetic acid (584 mg.), whereafter the mixture was stirred at the same temperature for half an hour. A methylene chloride (2 ml.) solution containing triethylamine (400 mg.) was added dropwise to the reaction mixture, whereafter the mixture obtained was stirred at the same temperature for 10 minutes. To the solution, there was added all at once methylene chloride (10 ml.) solution containing 3-aminolactacillanic acid (472 mg.), bis(trimethylsilyl)acetamide (1.2 g.) and N,N-dimethylformamide (1 ml.) at −40° C., whereafter the mixture was allowed to cool to ambient temperature. The reaction mixture was evaporated to dryness under reduced pressure to give a residue. Ethyl acetate (100 ml.) and water (30 ml.) were added thereto, and then the mixture was stirred at ambient temperature for half an hour. The ethyl acetate layer was separated, washed with 2% hydrochloric acid and water, and then dried over magnesium sulfate. The solvent was distilled off from the solution under reduced pressure to give a residue, which was powdered with diisopropyl ether. The powder (240 mg.) obtained was subjected to column chromatography on silica gel (10 g.) and elution was carried out with ethyl acetate. The fractions containing a desired compound were collected. The solvent was distilled off from the eluate under reduced pressure and the residue obtained was powdered with diisopropyl ether to give 3-[2-hydroxyimino-2-(4-hydroxyphenyl)acetamido]lactacillanic acid (47 mg.).

I.R. absorption spectrum
$v_{cm-1}$ (Nujol): 1740, 1695

EXAMPLE 550

2-[2-(2,2,2-Trichloroethoxycarbonylaminomethyl)-phenoxy]acetyl chloride (0.393 g.) was suspended in dried benzene (7 ml.), and to the suspension, there were added N,N-dimethylformamide (one drop) and thionyl chloride (3 ml.), whereafter the mixture was refluxed under heating for 3 hours. The unreacted thionyl chloride was distilled off from the mixture under reduced pressure to give a residue, which was dissolved in acetone (5 ml.) to give a acetone solution. On the other hand, 3-aminolactacillanic acid (0.236 g.) was suspended in water (10 ml.) and to the suspension, there was added sodium bicarbonate (0.184 g.). To this solution obtained was dropwise added the above acetone solution at 0° to 5° C. in the course of half an hour, whereafter the mixture was stirred at the same temperature for 2 hours. The reaction mixture was evaporated to dryness under reduced pressure to give a residue, which was washed with ethyl acetate. The residue obtained was adjusted to pH 1 to 2 with dilute hydrochloric acid and then extracted with ethyl acetate. The solvent was distilled off from the extract under reduced pressure to give a residue, which was powdered with diethyl ether. The powder was collected by filtration to give 3-[2-{2-(2,2,2-trichloroethoxycarbonylaminomethyl)phenoxy}acetamido]lactacillanic acid (0.49 g.).

I.R. absorption spectrum
$v_{cm-1}$ (KBr):
3275, 1740,
1715, 1660.

EXAMPLE 551

3-Amino-1-(2-methoxycarbonyl-1-phenylethyl)-2-azetidinone (1.3 g.) was added to methylene chloride (30 ml.), and then bis(trimethylsilyl)acetamide (3.05 g.) was added thereto. To the solution, there was dropwise added methylene chloride (30 ml.) solution containing 2-(2,2-dichloroacetoxyimino)-2-phenylacetic acid (1.9 g.) and phosphorus pentachloride (1.7 g.) at −40° to −35° C. in the course of 5 minutes. The mixture was stirred at the same temperature for 15 minutes and additionally stirred at 5° C. for 15 minutes. An aqueous sodium bicarbonate was added to the reaction mixture and the mixture was stirred at ambient temperature for 5 minutes. The methylene chloride layer was separated from the mixture, washed with dilute hydrochloric acid, an aqueous sodium bicarbonate and water in turn, and then dried over magnesium sulfate. The solvent was removed by distillation under reduced pressure to give a residue, which was subjected to column chromatography on silica gel (100 g.). Elution was carried out with chloroform and the fractions containing a desired compound were collected. The solvent was distilled off from the eluate under reduced pressure to give crystals of 3-(2-hydroxyimino-2-phenylacetamido)-1-(2-methoxycarbonyl-1-phenylethyl)-2-azetidinone (0.74 g.).
M.p. 161° to 163° C.
I.R. absorption spectrum
$v_{cm-1}$ (Nujol): 3220, 1730, 1720, 1620

EXAMPLE 552

3-Aminolactacillanic acid (0.472 g.) was suspended in methylene chloride and to the suspension, there was added bis(trimethylsilyl)acetamide (0.812 g.), whereafter the mixture was stirred at ambient temperature for 5 hours. Orotoyl chloride (0.420 g.) was added to the solution obtained above at 0° to 5° C. and then the mixture was stirred at the same temperature for 4 hours. The reaction mixture was filtered and the filtrate was extracted with 5% aqueous sodium bicarbonate. The aqueous extract was adjusted to pH 3 with dilute hydrochloric acid and then extracted with ethyl acetate. The extract was washed with water and then dried over magnesium sulfate. The solvent was removed by distillation under reduced pressure to give an oily residue, which was dissolved in acetone. An acetone (3.3 ml.) solution containing sodium 2-ethylhexanoate (about 173 mg.) was added to the solution and additionally diethyl ether (15 ml.) was added thereto. The precipitating materials were collected by filtration to give sodium 3-orotoylaminolactacillanate (0.240 g.).

M.p. 164° to 171.5° C.

EXAMPLE 553

2-(2-Thienyl)-N-(2,2,2-trichloroethoxycarbonyl)glycine (1.66 g.) and thionyl chloride (150 ml.) were dissolved in a dried acetone (10 ml.), and the solution was refluxed under heating for 2 hours. The unreacted thionyl chloride was removed under reduced pressure to give a residue, which was dissolved in a dried acetone (10 ml.) to give an acetone solution. On the other hand, 3-amino-1-(1-carboxy-2-methylpropyl)-2-azetidinone (0.75 g.) was suspended in a mixture of water (15 ml.) and acetone (15 ml.), and sodium bicarbonate (0.76 g.) was added thereto. To this solution, there was dropwise added the above acetone solution at 3° to 5° C. in the course of half an hour, whereafter the mixture was stirred at the same temperature for 2 hours. The acetone was removed from the reaction mixture under reduced pressure and the remaining aqueous solution was washed with ethyl acetate. The aqueous solution was adjusted to pH 2 with dilute hydrochloric acid and then extracted with ethyl acetate. The extract was washed with water and then dried over magnesium sulfate. The solvent was removed by distillation from the solution under reduced pressure and the residue obtained was powdered with diethyl ether to give 3-[2-(2-thienyl)-N-(2,2,2-trichloroethoxycarbonyl)glycinamido]-1-(1-carboxy-2-methylpropyl)-2-azetidinone (1.70 g.).

I.R. absorption spectrum
$\nu_{cm^{-1}}$ (KBr):
3300 to 3200, 1735,
1715, 1700, 1660.

EXAMPLE 554

2-[2-{N-(2,2,2-Trichloroethoxycarbonyl)-2-(carboxymethoxy)benzylaminomethyl}phenoxy]acetic acid (1.20 g.) and thionyl chloride (10 ml.) were refluxed under heating for an hour. The unreacted thionyl chloride was removed from the mixture under reduced pressure to give a residue, which was dissolved in dried methylene chloride (10 ml.) to give a methylene chloride solution. On the other hand, 3-aminolactacillanic acid (0.472 g.) was suspended in dried methylene chloride (10 ml.) and to the suspension, there was added bis(trimethylsilyl)acetamide (0.812 g.), whereafter the mixture was stirred at ambient temperature for 5 hours. To this solution, there was dropwise added the above methylene chloride solution at 0° to 5° C., whereafter the mixture was stirred at the same temperature for 1.5 hours. The reaction mixture was washed with dilute hydrochloric acid and water, and then dried over magnesium sulfate. The solvent was removed by distillation under reduced pressure and the oily residue obtained was powdered with diethyl ether to give 3-[2-[2-{N-(2,2,2-trichloroethoxycarbonyl)-2-(carboxymethoxy)benzylaminomethyl}phenoxy]acetamido]-lactacillanic acid (1.15 g.).

M.p. 141.5° to 144° C. (dec.)

EXAMPLE 555

3-Aminolactacillanic acid (0.706 g.) was suspended in methylene chloride (25 ml.) and to the suspension, there was added bis(trimethylsilyl)acetamide (3.50 g.), whereafter the mixture was stirred at ambient temperature for a while to give a methylene chloride solution. On the other hand, 2-benzyloxyimino-2-phenylacetic acid (0.950 g.) was suspended in dried benzene and to the suspension, there were added N,N-dimethylformamide (0.3 ml.) and oxalyl chloride (0.910 g.), whereafter the mixture was stirred at ambient temperature for an hour. The reaction mixture was evaporated to dryness under reduced pressure to give a residue, which was dissolved in methylene chloride. This solution was added dropwise to the above methylene chloride solution at 0° to 5° C., whereafter the mixture was stirred at the same temperature for an hour, and additionally at ambient temperature for 17 hours. Water was poured into the reaction mixture and the methylene chloride layer was separated. The methylene chloride solution was evaporated to dryness under reduced pressure to give a residue, which was dissolved in ethyl acetate. The solution was washed with dilute hydrochloric acid and water, and then dried over magnesium sulfate. The solvent was removed by distillation from the solution under reduced pressure to give a residue (1.36 g.), which was subjected to column chromatography on silica gel (20 g.). Elution was carried out with ethyl acetate and the fractions containing a desired compound were collected. The solvent was distilled off from the solution under reduced pressure to give an oily residue, which was dissolved in diethyl ether. An acetone (4 ml.) solution containing sodium hexanoate (about 166 mg.) was added to the ethereal solution, and the precipitating materials were collected by filtration and washed with diethyl ether to give sodium 3-(2-benzyloxyimino-2-phenylacetamido)lactacillanate (0.420 g.).

M.p. 210° to 213° C. (dec.)

EXAMPLE 556

4-(3-tert-Butoxycarbonylamino-3-methoxycarbonylpropoxy)phenylglyoxylic acid (1.15 g.) was suspended in methylene chloride (10 ml.), and to the suspension, there were added triethylamine (0.31 g.) and N,N-dimethylbenzylamine (two drops). A methylene chloride (5 ml.) solution containing ethyl chloroformate (0.33 g.) was added dropwise to the solution at −60° C. in the course of a few minutes. The reaction temperature was elevated stepwise to −40° C. in the course of about an hour with stirring. On the other hand, 3-aminolactacillanic acid (0.71 g.) was suspended in a mixture of methylene chloride (15 ml.) and N,N-dimethylformamide (0.5 ml.). Bis(trimethylsilyl)acetamide (1.83 g.) was added to the suspension with stirring, and then the mixture was stirred at ambient temperature for 3 hours. To this solution, there was added all at once the solution prepared before at −70° C., whereafter the mixture was stirred at the same temperature for half an hour. While elevating stepwise the reaction temperature, the mixture was reacted at about −50° C. for an hour. Further, the reaction mixture was elevated to −20° C. while stirring for half an hour. The reaction mixture was poured into ice-water, and then sodium bicarbonate was added thereto to adjust to pH 8. The aqueous layer was separated from the mixture, adjusted to pH 2 with hydrochloric acid, and then extracted with ethyl acetate (200 ml.). The extract was washed with water and then dried over magnesium sulfate. The solvent was removed by distillation from the solution under reduced pressure to give a residue, which was powdered with diisopropyl ether. The powder was collected by filtration to give 3-[4-(3-tert-butoxycarbonylamino-3-methoxycarbonylpropoxy)phenylglyoxyloylamino]lactacillanic acid (1.54 g.).

I.R. absorption spectrum
$\nu_{cm^{-1}}$ (Nujol): 1740, 1680, 1660.
N.M.R. absorption spectrum
[internal standard: sodium 2,2,3,3-tetradeutero-3-(trimethylsilyl)propionate]
δ ppm (D$_2$O+N$_a$HCO$_3$):
1.26 (9H, s)
2.14 (2H, m)
3.06 (1H, q, J=5 Hz, 2 Hz)
3.60 (3H, s)
3.4 to 4.4 (4H, m.)
5.04 (1H, q, J=5 Hz, 2 Hz)
5.34 (1H, s)
6.84, 7.24 (4H, AB-q, J=8 Hz)
6.82, 7.86 (4H, AB-q, J=8 Hz)

EXAMPLE 557

3-Phthalimido-1-(α-methoxycarbonylbenzyl)-2-azetidinone (0.36 g.) and N,N-dimethyl-1,3-propanediamine (0.22 g.) were added to a mixture of methanol (5 ml.) and chloroform (5 ml.), whereafter the mixture was stirred at ambient temperature for 18 hours. The reaction mixture was evaporated to dryness under reduced pressure, and ethyl acetate (20 ml.) and water were poured into the residue obtained. The ethyl acetate layer was separated out from the mixture and the remaining aqueous layer was further extracted with ethyl acetate (10 ml.). The combined ethyl acetate solution was extracted with 1 N hydrochloric acid (3 ml.) and water (10 ml.) respectively. The combined aqueous extracts were adjusted to pH 8.6 with an aqueous sodium bicarbonate. The aqueous solution was extracted with two 10 ml. portions of ethyl acetate. The combined extracts were washed with saturated aqueous sodium chloride and then dried over magnesium sulfate. The solvent was removed by distillation from the solution under reduced pressure to give oily 3-amino-1-(α-methoxycarbonylbenzyl)-2-azetidinone (0.13 g.).

I.R. absorption spectrum
$\nu_{cm-1}$ (liquid film): 3400, 1750, 1710.

EXAMPLE 558

3-Phthalimido-1-(α-carboxybenzyl)-2-azetidinone (350 mg.) and N,N-dimethyl-1,3-propanediamine (310 mg.) were added to methanol (6 ml.), and the mixture was stirred at ambient temperature for 18 hours. Water (6 ml.) was poured into the reaction mixture under ice-cooling and then the mixture was adjusted to pH 5.8 to 6.0 with cation-exchange resin IRC-50 (Trade Mark, maker: Rohm & Haas Co.,) (20 ml.). The resin was removed by filtration and the filtrate was evaporated to dryness under reduced pressure. Acetonitrile was added to the residue (190 mg.) obtained and then the mixture was stirred under ice-cooling for 2.5 hours. The powder was collected by filtration to give 3-amino-1-(α-carboxybenzyl)-2-azetidinone (120 mg.).

M.p. 143° to 147° C. (dec.)
I.R. absorption spectrum
$\nu_{cm-1}$ (Nujol):
 2660 to 2250,
 1780, 1620
N.M.R. absorption spectrum
[internal standard: sodium 2,2,3,3-tetradeutero-3-(trimethylsilyl)propionate]
δ ppm (D$_2$O):
 3.04 (1H, q, J=2 Hz, 5 Hz)
 3.83 (1H, t, J=5 Hz)
 3.30 (1H, s)
 4.35 (1H, q, J=2 Hz, 5 Hz)
 7.42 (5H, s)

EXAMPLE 559

3-Phthalimido-1-(2-methoxycarbonyl-1-phenylethyl)-2-azetidinone (1.90 g.) and N,N-dimethyl-1,3-propanediamine (1.14 g.) were added to a mixture of methanol (20 ml.) and chloroform (5 ml.), whereafter the mixture was stirred at ambient temperature for 17 hours. The reaction mixture was evaporated to dryness under reduced pressure to give a residue, which was dissolved in ethyl acetate (20 ml.). The solution was extracted with three portions of an aqueous solution consisting of 1 N hydrochloric acid (5.3 ml.) and water (11.3 ml.), and then the combined extract was washed with ethyl acetate. The aqueous solution was adjusted to pH 8 with sodium bicarbonate under ice-cooling and then extracted with three 10 ml. portions of chloroform. The extracts were washed with water and then dried over magnesium sulfate. The solvent was removed by distillation from the solution under reduced pressure to give oily 3-amino-1-(2-methoxycarbonyl-1-phenylethyl)-2-azetidinone (1.030 g.).

I.R. absorption spectrum
$\nu_{cm-1}$ (liquid film): 3400, 1755, 1740, 1715.

EXAMPLE 560

3-[2-{4-(3-tert-Butoxycarbonylamino-3-carboxypropoxy)phenyl}-2-hydroxyiminoacetamido]lactacillanic acid (12.0 g.) and sodium bicarbonate (3.36 g.) were dissolved in water (75 ml.). 10% Palladium on carbon as a catalyst (3.0 g.) was added to the aqueous solution, and the mixture was stirred under conditions of ambient temperature and 3.5 atmospheric pressure for 4 hours in a stream of a hydrogen gas. After a calculated volume of the hydrogen gas was absorbed into the mixture, the catalyst was filtered off from the reaction mixture. The filtrate was concentrated to 20 ml. under reduced pressure and the concentrate was adjusted to pH 4 with 5% hydrochloric acid. Acetone was added slowly to the solution until the powder was not come out in the solution. The powder was collected by filtration to give 3-[2-{4-(3-tert-butoxycarbonylamino-3-carboxypropoxy)phenyl}glycinamido]lactacillanic acid (10.05 g.).

M.p. 255° to 258° C. (dec.)
I.R. absorption spectrum
$\nu_{cm-1}$ (Nujol):
 3300 (broad),
 1735, 1690
N.M.R. absorption spectrum
[internal standard: sodium 2,2,3,3-tetradeutero-3-(trimethylsilyl)propionate]
δ ppm (D$_2$O+N$_a$HCO$_3$):
 1.33 (9H, s)
 2.12 (2H, m)
 3.71 (1H, m)
 3.9 to 4.3 (3H, m)
 5.32 (1H, s)
 6.8 to 7.0 (4H, m)
 7.1 to 7.4 (4H, m)

EXAMPLE 561

Sodium 3-[2-{4-(3-amino-3-carboxypropoxy)phenyl}-2-hydroxyiminoacetamido]lactacillanate (20.0 g.) was dissolved in water (50 ml.) containing triethylamine (3.84 g.). A dioxane (50 ml.) solution containing 2-tert-butoxycarbonyloxyimino-2-phenylacetonitrile (8.50 g.) was added to the solution and the mixture was stirred at ambient temperature for 6 hours. Water (100 ml.) and ethyl acetate (200 ml.) were added to the reaction mixture, whereafter the mixture was stirred for a while. The aqueous layer was separated from the mixture and washed with ethyl acetate. The aqueous solution was adjusted to pH 3 with 1 N hydrochloric acid and then was saturated with sodium chloride. The solution obtained was extracted with two 200 ml. portions of ethyl acetate, and the extracts were washed with saturated aqueous sodium chloride and then dried over magnesium sulfate. The solution was evaporated to dryness under reduced pressure to give a residue, which was powdered with chloroform. The powder was collected by filtration to give 3-[2-{4-(3-carboxy-3-tert-butoxycarbonylaminopropoxy)phenyl}-2-hydroxyiminoacetamido]lactacillanic acid (18.30 g.).

M.p. 193° to 197° C. (dec.)
I.R. absorption spectrum
$\nu_{cm-1}$ (Nujol):
 3280 (broad),
 1730 (broad),
 1680 (shoulder)

N.M.R. absorption spectrum
(internal standard: tetramethylsilane)
δ ppm (d$_6$-dimethylsulfoxide):
1.35 (9H, s)
2.11 (2H, m)
3.13 (1H, m)
3.7 to 4.3 (4H, m)
5.03 (1H, m)
5.37 (1H, s)
6.7 to 7.6 (8H, m)
9.17 (1H, d, J=8 Hz)

EXAMPLE 562

3-[4-(3-Carboxy-3-tert-butoxycarbonylaminopropoxy)phenylglyoxyloylamino]lactacillanic acid (1.34 g.) was obtained by reacting 3-[4-(3-amino-3-carboxypropoxy)phenylglyoxyloylamino]lactacillanic acid (2.43 g.) with 2-tert-butoxycarbonyloxyimino-2-phenylacetonitrile (1.36 g.) in substantially the similar manner as described in Example 561.

I.R. absorption spectrum
$\nu_{cm-1}$ (Nujol):
3350 to 3200,
1750, 1730, 1710
1680, 1660.

N.M.R. absorption spectrum
(internal standard: tetramethylsilane)
δ ppm [(CD$_3$)$_2$CO]:
1.40 (3H, s)
2.34 (2H, m)
3.30, 3.38 (1H, d, d, J=2 Hz, 5 Hz)
3.96 (1H, t, J=5 Hz)
4.26 (2H, t, J=6 Hz)
4.40 (1H, m)
5.12 to 5.28 (1H, m)
5.56 (1H, s)
6.32 (1H, d, J=8 Hz)
6.84 to 7.32 (6H, m)
8.18 (2H, d, J=8 Hz)
8.72 (1H, d, J=8 Hz)
8.96 (2H, broad s)

EXAMPLE 563

3-[2-[2-{N-(2,2,2-Trichloroethoxycarbonyl)-2-(carboxymethoxy)benzylaminomethyl}phenoxy]acetamido]lactacillanic acid (300 mg.) was dissolved in acetic acid (2 ml.). Zinc powder (500 mg.) was added to the solution at 15° to 20° C., whereafter the mixture was stirred at the same temperature for 2.5 hours. The unreacted zinc powder was filtered off from the reaction mixture and the filtrate was washed with ethyl acetate. Ice-water (20 ml.) was poured into the residue obtained and the mixture was filtered. The filtrate was washed with ethyl acetate and evaporated to dryness under reduced pressure on a water-bath. The residue obtained was powdered with acetone to give 3-[2-[2-{2-(carboxymethoxy)benzylaminomethyl}phenoxy]acetamido]lactacillanic acid (205 mg.).

M.p. 159.5° to 164.5° C.

EXAMPLE 564

3-[2-{2-(2,2,2-Trichloroethoxycarbonylaminomethyl)phenoxy}acetamido]lactacillanic acid (250 mg.) was dissolved in 90% acetic acid (3 ml.). Zinc powder (450 mg.) was added to the solution with stirring and the mixture was stirred at ambient temperature for an hour. The unreacted zinc powder was filtered off from the reaction mixture and then a hydrogen sulfide gas was introduced into the filtrate. The precipitating materials were collected by filtration and washed with water. This washings and the filtrate were combined and washed with ethyl acetate. The aqueous solution was evaporated to dryness under reduced pressure to give a residue, which was powdered with acetone. The powder was collected by filtration to give 3-[2-(2-aminomethylphenoxy)acetamido]lactacillanic acid (0.09 g.).

I.R. absorption spectrum
$\nu_{cm-1}$ (Nujol): 1725, 1650, 1600.

EXAMPLE 565

3-[2-{4-(3-Carboxy-3-tert-butoxycarbonylaminopropoxy)phenyl}-2-(5-chlorosalicyloylamino)acetamido]lactacillanic acid (725 mg.) was suspended in benzene (12 ml.), and to the suspension, there was dropwise added 2,2,2-trifluoroacetic acid (3.42 g.) under ice-cooling, whereafter the mixture was stirred at the same temperature for an hour. Diethyl ether was added to the reaction mixture, and the precipitating powders were collected by filtration and washed with diethyl ether to give crude 3-[2-{4-(3-amino-3-carboxypropoxy)phenyl}-2-(5-chlorosalicyloylamino)acetamido]lactacillanic acid (590 mg.).

M.p. 222° to 226° C. (dec.)
I.R. absorption spectrum
$\nu_{cm-1}$ (Nujol):
3200 (shoulder),
1750, 1730 (shoulder),
1680, 1610

N.M.R. absorption spectrum
(internal standard: tetramethylsilane)
δ ppm (d$_6$-dimethylsulfoxide):
2.20 (2H, m)
3.24 (1H, m)
3.69 (2H, m)
4.10 (2H, m)
4.48 (1H, s)
4.67 (1H, m)
5.27 (1H, s)
6.8 to 7.4 (11H, m)

EXAMPLE 566

3-[2-{4-(3-Carboxy-3-aminopropoxy)phenyl}-2-(3-phenylureido)acetamido]lactacillanic acid (116 mg.) was obtaind by reacting 3-[2-{4-(3-carboxy-3-tert-butoxycarbonylaminopropoxy)phenyl}-2-(3-phenylureido)acetamido]lactacillanic acid (705 mg.) with 2,2,2-trifluoroacetic acid (3.42 g.) in substantially the same manner as described in Example 565.

I.R. absorption spectrum
$\nu_{cm-1}$ (Nujol):
3300, 1730, 1650 (broad),
1610, 1600.

N.M.R. absorption spectrum
(internal standard: tetramethylsilane)
δ ppm (d$_6$-dimethylsulfoxide+D$_2$O):
2.20 (2H, m)
2.96 (1H, m)
4.83 (1H, m)
5.23 (1H, s)
5.39 (1H, s)
6.8 to 7.6 (13H, m)

EXAMPLE 567

3-[2-{4-(3-Carboxy-3-tert-butoxycarbonylaminopropxy)phenyl}-2-(2-oxoimidazolidine-1-carboxamido)acetamido]lactacillanic acid (350 mg.) was suspended in benzene (6 ml.) and to the suspension, there was dropwise added 2,2,2-trifluoroacetic acid (1.72 g.) under ice-cooling with stirring, whereafter the mixture was stirred at the same temperature for 1.5 hours. Diethyl ether was added to the reaction mixture and the precipitating powder was collected by filtration. The powder was washed with diethyl ether and then dried. The powder was subjected to column chromatography on an adsorption resin Amberlite XAD-4 (Trade Mark, maker: Rohm & Haas Co.) (130 ml.). Elution was carried out with 3 to 4% aqueous sodium chloride (150 ml.), water (300 ml.) and a mixture of water and methanol (volume ratio is gradually changed from 10:1 to 10:8) respectively, and the fractions containing a desired compound were collected. The solvent was removed by distillation under reduced pressure to give 3-[2-{4-(3-amino-3-carboxypropoxy)phenyl}-2-(2-oxoimidazolidine-1-carboxamido)acetamido]lactacillanic acid (101 mg.).

M.p. 200° to 203° C. (dec.)
I.R. absorption spectrum
$\nu_{cm-1}$ (Nujol):
    3300 (broad),
    1720, 1660 (shoulder),
    1610.
N.M.R. absorption spectrum
(internal standard: tetramethylsilane)
$\delta$ ppm ($d_6$-dimethylsulfoxide):
    2.14 (2H, m)
    2.89 (1H, m)
    3.1 to 3.9 (3H, m)
    4.09 (2H, m)
    6.6 to 7.3 (8H, m)
    7.70 (1H, s)
    8.94 (1H, m)

EXAMPLE 568

3-[4-(3-tert-Butoxycarbonylamino-3-carboxypropoxy)phenylglyoxyloylamino]lactacillanic acid (1.10 g.) was suspended in a mixture of benzene (15 ml.) and anisole (0.5 ml.) and to the suspension, there was added 2,2,2-trifluoroacetic acid (5.5 g.) under ice-cooling, whereafter the mixture was stirred at the same temperature for 1.5 hours. Diethyl ether was added to the reaction mixture, and the precipitating materials were separated by decantation and then washed with diethyl ether. The materials were poured into water and the solution was adjusted to pH 3 with sodium bicarbonate. The aqueous solution was allowed to stand for a while, and the precipitating crystals were collected by filtration, and then washed with water and acetone to give crystalline 3-[4-(3-amino-3-carboxypropoxy)phenylglyoxyloylamino]lactacillanic acid (0.60 g.).

M.p. 225° to 230° C. (dec.)
I.R. absorption spectrum
$\nu_{cm-1}$ (Nujol): 1725, 1650.

EXAMPLE 569

Methyl 3-[2-{4-(3-methoxycarbonyl-3-tert-butoxycarbonylaminopropoxy)phenyl}-2-hydroxyiminoacetamido]lactacillanate (2.26 g.) was suspended in benzene (20 ml.) and to the suspension, there was added 2,2,2-trifluoroacetic acid (7 ml.) at 7° C., whereafter the mixture was stirred at the same temperature for 3.5 hours. 8% Hydrochloric acid (30 ml.) and ethyl acetate (20 ml.) were added to the reaction mixture, and then the mixture obtained was stirred for a while. The aqueous layer was separated from the mixture and allowed to stand under ice-cooling for a while. The precipitating crystals in the mixture were collected by filtration, washed with ethanol and diethyl ether to give crystalline methyl 3-[2-{4-(3-amino-3-methoxycarbonyl-carboxypropoxy)phenyl}-2-hydroxyiminoacetamido]lactacillanate hydrochloride (700 mg.).

M.p. 191° to 193° C. (dec.)
I.R. absorption spectrum
$\nu_{cm-1}$ (Nujol):
    3200, 1750, 1725,
    1655, 1620

EXAMPLE 570

3-[2-(2-Thienyl)-N-(2,2,2-trichloroethoxycarbonyl)-glycinamido]-1-(1-carboxy-2-methylpropyl)-2-azetidinone (1.0 g.) was dissolved in N,N-dimethylformamide (5 ml.), and acetic acid (3 ml.) was added thereto. To the solution, there was added zinc powder (1.2 g.) at 15° C. in the course of about half an hour, whereafter the mixture was stirred at 15° to 20° C. for 3 hours. The unreacted zinc powder was filtered off and washed with a small amount of N,N-dimethylformamide, and then this washings and the filtrate were combined. Diethyl ether (about 80 ml.) was added to the combined solution and the precipitating materials were collected by filtration, washed with diethyl ether and then dried to give 3-[2-(2-thienyl)glycinamido]-1-(1-carboxy-2-methylpropyl)-2-azetidinone (690 mg.).

I.R. absorption spectrum
$\nu_{cm-1}$ (Nujol):
    1740, 1660, 1610 to 1600.

EXAMPLE 571

3-(2-Phenylglycinamido)lactacillanic acid (200 mg.) and sodium bicarbonate (170 mg.) were dissolved in a mixture of water (10 ml.) and acetone (8 ml.). An acetone (1 ml.) solution containing 2-nitroanilinooxalyl chloride (114 mg.) was added to the solution under ice-cooling and the mixture was stirred at the same temperature for an hour. Water (30 ml.) was poured into the reaction mixture, whereafter the mixture obtained was adjusted to pH 2 with dilute hydrochloric acid, and then extracted with ethyl acetate. An aqueous sodium bicarbonate was added to the extract and the mixture was stirred for a while. The aqueous layer was separated and adjusted to pH 4 to 5 with dilute hydrochloric acid, and then extracted with ethyl acetate. The extract was washed with water and then dried over magnesium sulfate. The solvent was removed by distillation from the solution under reduced pressure to give a residue, which was powdered with diisopropyl ether. The powder was collected by filtration to give 3-[2-[N-{N-(2-nitrophenyl)oxamoyl}amino]-2-phenylacetamido]lactacillanic acid (55 mg.).

M.p. 155° to 159° C. (dec.)

EXAMPLE 572

3-[2-(2-Aminomethylphenoxy)acetamido]lactacillanic acid (250 mg.) was suspended in water (5 ml.) and to the suspension, there were added sodium bicarbonate (105 mg.) and acetone (5 ml.). An acetone (5 ml.) solution containing 2-(4-chloro-2-nitrophenoxy)acetyl chloride (0.13 g.) was added dropwise to the solution obtained above at 0° to 5° C. and the mixture was stirred at the same temperature for 2 hours. The acetone was distilled off from the reaction mixture under reduced pressure and the remaining aqueous solution was washed with ethyl acetate. The aqueous solution was adjusted to pH 1 to 2 with dilute hydrochloric acid and then extracted with ethyl acetate. The extract was washed with water and dried over magnesium sulfate. The solution was evaporated to dryness under reduced pressure to give an oily residue (220 mg.), which was dissolved in acetone (3 ml.). An acetone (0.7 ml.) solution containing sodium 2-ethylhexanoate (about 40 mg.) was added to the acetone solution and the solution was allowed to stand for an hour. The solution was filtered and then diethyl ether (about 40 ml.) was added to the filtrate. The precipitating crystals in the solution were collected by filtration and treated with diethyl ether to give sodium 3-[2-[2-{2-(4-chloro-2-nitrophenoxy)acetamidomethyl}phenoxy]acetamido]lactacillanate (108 mg.).

M.p. 117.5° to 122° C.

EXAMPLE 573

3-[2-(2-aminomethylphenoxy)acetamido]lactacillanic acid (250 mg.) was suspended in water (5 ml.) and to the suspension, there were added sodium bicarbonate (105 mg.) and acetone (5 ml.). To the solution, there was added a dried acetone (5 ml.) solution containing 2-bromoacetyl chloride (80 mg.) was added at 0° to 5° C., and the mixture was stirred at the same temperature for 2 hours. The acetone was removed by distillation from the reaction mixture under reduced pressure, whereafter the remaining aqueous solution was adjusted to pH 1 to 2 with dilute hydrochloric acid and then extracted with ethyl acetate. The extract was washed with water and dried over magnesium sulfate. The solvent was distilled off from the solution under reduced pressure to give an oily residue, which was powdered with diethyl ether. The powder was collected by filtration to give 3-[2-{2-(2-bromoacetamidomethyl)phenoxy}acetamido]lactacillanic acid (130 mg.).

M.p. 152° to 155.5° C.

EXAMPLE 574

3-[2-(2-Thienyl)glycinamido]-1-(1-carboxy-2-methylpropyl)-2-azetidinone (690 mg.) was suspended in a mixture of acetone (10 ml.) and water (10 ml.), and to the suspension, there was added sodium bicarbonate (220 mg.). A dried acetone (7 ml.) solution containing 2-(2-nitro-4-chlorophenoxy)acetyl chloride (550 mg.) was added dropwise to the solution obtained above at 0° to 5° C. in the course of 45 minutes, whereafter the mixture was stirred at the same temperature for 2 hours. The acetone was removed from the reaction mixture under reduced pressure on a water bath and the remaining aqueous solution was washed with ethyl acetate. This aqueous solution was adjusted to pH 2 with dilute hydrochloric acid and then extracted with ethyl acetate. The extract was washed with water and then dried over magnesium sulfate. The solvent was removed by distillation from the solution under reduced pressure to give a residue, which was dissolved in acetone. An acetone (2 ml.) solution containing sodium 2-ethylhexanoate (100 mg.) was added to the acetone solution, and additionally diethyl ether was added thereto until the precipitating materials were not produced. The materials were collected by filtration and then dried to give sodium salt of 3-[2-(2-thienyl)-2-{2-(2-nitro-4-chlorophenoxy)acetamido}acetamido]-1-(1-carboxy-2-methylpropyl)-2-azetidinone (700 mg.).

I.R. absorption spectrum $\nu_{cm^{-1}}$ (Nujol):
3400, 3300, 1740,
1670, 1610.

EXAMPLE 575

3-[2-{4-(3-Carboxy-3-tert-butoxycarbonylaminopropoxy)phenyl}glycinamido]lactacillanic acid (1.76 g.) was suspended in 80% aqueous tetrahydrofuran (15 ml.) and the suspension was adjusted to pH 7.5 with triethylamine. 2-Oxoimidazolidine-1-carbonyl chloride (490 mg.) was added dropwise to the solution obtained above in the course of 10 minutes and the mixture was stirred at ambient temperature for an hour, and in the same time the reaction mixture was adjusted to pH 7 to 8 with triethylamine. Water (30 ml.) was poured into the reaction mixture and then the tetrahydrofuran was removed from the mixture under reduced pressure, whereafter the remaining aqueous solution was washed with ethyl acetate. Ethyl acetate (50 ml.) was added to the aqueous solution and the mixture was adjusted to pH 2 with 1 N hydrochloric acid under ice-cooling. The separated ethyl acetate solution was washed with saturated aqueous sodium chloride and then dried over magnesium sulfate. The solvent was removed by distillation from the solution under reduced pressure to give 3-[2-{4-(3-carboxy-3-tert-butoxycarbonylaminopropoxy)phenyl}-2-(2-oxomidazolidine-1-carboxamido)acetamido]lactacillanic acid (0.15 g.). The remaining aqueous solution was allowed to stand for a while, and the precipitating materials were collected by filtration. The materials were crystallized from diethyl ether to recover the object compound (1.06 g.).

Total yield was 1.21 g.

I.R. absorption spectrum $\nu_{cm^{-1}}$ (Nujol):
3300, 1730,
1660 (shoulder), 1610.

N.M.R. absorption spectrum
(internal standard: tetramethylsilane)
δ ppm (d$_6$-dimethylsulfoxide):
1.38 (9H, s)
2.07 (2H, m)
2.97 (1H, m)
3.2 to 4.2 (7H, m)
4.85 (1H, m)
5.25 (1H, m)
5.32 (1H, s)
6.7 to 7.5 (8H, m)
7.62 (1H, s)
9.00 (1H, m)

EXAMPLE 576

3-[2-{4-(3-Carboxy-3-tert-butoxycarbonylaminopropoxy)phenyl}glycinamido]lactacillanic acid (1.76 g.) was dissolved in water (15 ml.), in which sodium bicarbonate (550 mg.) was dissolved. A dried acetone (5 ml.) solution containing phenyl isocyanate (490 mg.) was added dropwise to the solution under ice-cooling in the course of 5 minutes, and the mixture was stirred at the same temperature for an hour. The acetone was removed from the reaction mixture under reduced pressure and the remaining aqueous solution was washed with ethyl acetate. The aqueous solution was adjusted to pH 2 with 1 N hydrochloric acid and extracted with ethyl acetate. The extract was washed with saturated aqueous sodium chloride and then dried over magnesium sulfate. The solution was evaporated to dryness under reduced pressure to give a residue, which was powdered with diethyl ether. The powder was collected by filtration to give 3-[2-{4-(3-carboxy-3-tert-butoxycarbonylaminopropoxy)phenyl}-2-(3-phenylureido)acetamido]lactacillanic acid (1.60 g.).

M.p. 194° to 196° C. (dec.)
I.R. absorption spectrum
$\nu_{cm^{-1}}$ (Nujol):
3350, 1740, 1720 (shoulder),
1660 (shoulder)
N.M.R. absorption spectrum
(internal standard: tetramethylsilane)
δ ppm (d$_6$-dimethylsulfoxide):
1.38 (9H, s)
2.09 (2H, m)
3.00 (1H, m)
3.75 (1H, m)
3.90 to 4.20 (3H, m)
4.88 (1H, m)
5.25 (1H, d, J=7 Hz)
5.32 (1H, s)
6.8 to 7.6 (13H, m)
8.70 (1H, s)
9.00 (1H, m)

EXAMPLE 577

3-[2-{4-(3-Carboxy-3-tert-butoxycarbonylaminopropoxy)phenyl}glycinamido]lactacillanic acid (1.76 g.) was dissolved in water (15 ml.) containing sodium bicarbonate (810 mg.). An acetone (5 ml.) solution containing benzoyl chloride (520 mg.) was added dropwise to the solution under ice-cooling in the course of 15 minutes, whereafter the mixture was stirred at the same temperature for 2.5 hours. The acetone was removed by distillation from the reaction mixture under reduced pressure to give an aqueous solution, which was washed with ethyl acetate. The aqueous solution was adjusted to pH 2 with 1 N hydrochloric acid and extracted with ethyl acetate. The extract was washed with saturated aqueous sodium chloride and then dried over magnesium sulfate. The solvent was distilled off from the solution under reduced pressure to give an oily residue, which was powdered with diethyl ether. The powder was collected by filtration and then dried to give 3-[2-{4-(3-carboxy-3-tert-butoxycarbonylaminopropoxy)-phenyl}-N-benzoylglycinamido]lactacillanic acid (1.40 g.).

M.p. 188° to 191° C. (dec.)
I.R. absorption spectrum
$\nu_{cm^{-1}}$ (Nujol):
3300, 1740, 1720 (shoulder),
1640, 1610.
N.M.R. absorption spectrum
(internal standard: tetramethylsilane)
δ ppm (d$_6$-dimethylsulfoxide):
1.38 (9H, s)
3.03 (1H, m)
3.77 (1H, m)
3.9 to 4.3 (3H, m)
4.90 (1H, m)
5.33 (1H, s)
5.60 (1H, m)
6.7 to 7.6 (13H, m)
7.92 (1H, m)
8.80 (1H, m)

EXAMPLE 578

5-Chlorosalicylic acid (1.25 g.), aluminum trichloride (10 mg. and thionyl chloride (6 ml.) were warmed at 50° C. on an oil bath for 1.5 hours with stirring. The unreacted thionyl chloride was removed from the mixture under reduced pressure and to the residue, there was added dried benzene. The mixture was evaporated to dryness under reduced pressure to give a residue, which was dissolved in acetone (6 ml.). On the other hand, 3-[2-{4-(3-carboxy-3-tert-butoxycarbonylaminopropoxy)phenyl}glycinamido]lactacillanic acid (3.52 g.) was dissolved in water (30 ml.) containing sodium bicarbonate (1.03 g.). To this solution, there was dropwise added the above acetone solution under ice-cooling in the course of 20 minutes with stirring. The solution was adjusted to pH 7 to 8 with an aqueous sodium bicarbonate during the addition. The solution was stirred at the same temperature for 40 minutes and at ambient temperature for 2 hours. Ethyl acetate was added to the reaction mixture and the solution was stirred for a while. The aqueous layer was separated, adjusted to pH 3 with 1 N hydrochloric acid and then extracted with five portions of ethyl acetate. The combined extracts were dried over magnesium sulfate and then the solvent was removed from the solution under reduced pressure to give a residue, which was powdered with diethyl ether. The powder (0.99 g.) was collected by filtration and washed with diethyl ether to give 3-[2-{4-(3-carboxy-3-tert-butoxycarbonylaminopropoxy)phenyl}-N-5-chlorosalicyloylglycinamido]lactacillanic acid (0.94 g.).

M.p. 218° to 223° C. (dec.)
I.R. absorption spectrum
$\nu_{cm^{-1}}$ (Nujol):
3300 (broad),
1740, 1680 (shoulder),
1610.
N.M.R. absorption spectrum
(internal standard: tetramethylsilane)
δ ppm (d$_6$-dimethylsulfoxide):
1.34 (9H, s)
3.26 (1H, m)
3.66 (1H, m)
4.00 (2H, m)
4.48 (1H, s)
4.70 (1H, m)
5.29 (1H, s)
6.7 to 7.4 (11H, m)

EXAMPLE 579

3-[2-{4-(3-Amino-3-carboxypropoxy)phenyl}-2-hydroxyiminoacetamido]lactacillanic acid (5.0 g.) was dissolved in a mixture of dimethylsulfoxide (90 ml.) and methanol (10 ml.). To this solution, there was dropwise added an ethereal solution containing diazomethane under ice-cooling until the color of diazomethane did not disappear in the reaction mixture, whereafter the reaction mixture was stirred at the same temperature for 10 minutes. The reaction mixture was poured into ice-water (950 ml.) and the mixture was allowed to stand overnight in a refrigerator. The precipitated materials were collected by centrifugation and then dried to give a powder (3.3 g.). A part of this powder (1.5 g.) was subjected to column chromatography on silica gel. Elution was carried out with a mixture of chloroform and methanol (volume ratio; 30:1), and the fractions containing a desired compound were collected. The solvent was removed from the eluate under reduced pressure to give methyl 3-[2-{4-(3-amino-3-methoxycarbonylpropoxy)phenyl}-2-hydroxyiminoacetamido]lactacillanate (0.70 g.). This compound was dissolved in acetone and to the solution, there was added a methanol solution containing equimolar hydrogen chloride. The solution was evaporated to dryness under reduced pressure, and the residue was recrystallized from a mixture of ethanol and methanol to give a hydrochloric acid salt of the object compound (0.48 g.)

M.p. 200° to 201° C.

EXAMPLE 580

3-[2-{4-(3-Carboxy-3-tert-butoxycarbonylaminopropoxy)phenyl}-2-hydroxyiminoacetamido]lactacillanic acid (4.5 g.) was dissolved in ethyl acetate (30 ml.). To this solution, there was dropwise added an ethereal solution containing diazomethane under ice-cooling with stirring until a color of the diazomethane did not disappear in the reaction mixture. The reaction mixture was washed with 5% aqueous sodium bicarbonate, whereafter the remaining aqueous solution was washed with water and then dried over magnesium sulfate. The solvent was removed by distillation from the solution under reduced pressure to give an oily residue, which was subjected to column chromatography on silica gel (100 g.). Elution was carried out with chloroform, and a mixture of chloroform and methanol (volume ratio; 50:1). The fractions containing a desired compound were collected and the solvent was removed by distillation from the eluate under reduced pressure. The residue obtained was powdered with chloroform to give crystalline methyl 3-[2-{4-(3-methoxycarbonyl-3-tert-butoxycarbonylaminopropoxy)phenyl}-2-hydroxyiminoacetamido]lactacillanate (3.28 g.).

M.p. 143° to 146° C.

I.R. absorption spectrum $\nu_{cm^{-1}}$ (Nujol):
3350 to 3250,
1745, 1720,
1700, 1645,
1610.

EXAMPLE 581

3-Ethoxyalylaminolactacillanic acid (100 mg.) was suspended in ethanol (2 ml.) and to the suspension, there was added an ethanol (3.5 ml.) solution containing benzylamine (96 mg.), whereafter the mixture was stirred at ambient temperature for 6 hours. Ethanol (2 ml.) was added to the reaction mixture and the solution was stirred at ambient temperature over night. The reaction mixture was evaporated to dryness under reduced pressure, and ethyl acetate (20 ml.) and 1 N hydrochloric acid (0.7 ml.) were poured into the residue obtained. After the stirring for a while, the ethyl acetate layer was separated, washed with 1 to 2% hydrochloric acid, water and an aqueous sodium chloride in turn, and then dried over magnesium sulfate. The solvent was removed by distillation from the solution under reduced pressure to give a residue, which was powdered with ethyl acetate. The powder was treated with diisopropyl ether to give crystalline 3-[N-(N-benzyloxamoyl)amino]lactacillanic acid (90 mg.).

M.p. 125° to 129° C. (dec.)

EXAMPLE 582

3-[N-{N-(2-Hydroxyethyl)oxamoyl}amino]lactacillanic acid (87 mg.) was obtained by reacting 3-ethoxyalylaminolactacillanic acid (200 mg.) with ethanolamine (110 mg.) in substantially the same manner described in Example 581.

I.R. absorption spectrum $\nu_{cm^{-1}}$ (KBr): 3300, 1735, 1660, 1510.

EXAMPLE 583

3-[2-(2-Azidoacetamido)-2-(2-thienyl)acetamido]lactacillanic acid (200 mg.) was dissolved in methanol (10 ml.) and 10% palladium on carbon (150 mg.) as a catalyst was added thereto. The catalystic reduction was carried out in a stream of a hydrogen gas at ordinary temperature for 2 days. After a calculated volume of hydrogen gas was absorbed into the reaction mixture, the catalyst was removed by filtration. The filtrate was evaporated to dryness under reduced pressure to give a residue, which was powdered with diethyl ether. The powder was treated with diethyl ether to give 3-[2-(2-aminoacetamido)-2-(2-thienyl)acetamido]lactacillanic acid (40 mg.).

M.p. 195° to 198° C. (dec.)

EXAMPLE 584

3-Phthalimidolactacillanic acid (366 mg.) and triethylamine (202 mg.) were dissolved in methanol (6 ml.) and to the solution, there was added N,N-dimethyl-1,3-propanediamine (240 mg.) under ice-cooling, whereafter the mixture was stirred at the same temperature for an hour and then at ambient temperature for 24 hours. The reaction mixture was evaporated to dryness under reduced pressure to give an oily residue, which was dissolved in methanol (10 ml.) and water (10 ml.). The solution was adjusted to pH 5.8 to 6.0 with an cation-exchange resin Amberlite IRC-50 (Trade Mark, maker: Rohm & Haas Co.) (20 ml.). The resin was filtered off from the solution and the filtrate was evaporated to dryness under reduced pressure. The residue obtained was crystallized and treated with ethanol (10 ml.) to give 3-aminolactacillanic acid (140 mg.). This crystals were recrystallized with methanol to give the purified object compound.

M.p. 207° to 209° C. (dec.)

EXAMPLE 585

4-(3-tert-Butoxycarbonylamino-3-methoxycarbonylpropoxy)phenylglyoxylic acid (1.15 g), trimethylamine (0.31 g) and N,N-dimethylbenzylamine (two drops) were dissolved in methylene chloride (10 ml), whereafter a methylene chloride (5 ml) solution containing ethylchloroformate (0.33 g) was added dropwise to the solution at −60° C. in the course of a few minutes with stirring. The reaction temperature was elevated gradually to −40° C. in the course of an hour to prepare the mixed acid anhydride solution. On the other hand, 3-aminolactacillanic acid (0.71 g) was suspended in a mixture of methylene chloride (15 ml) and N,N-dimethylformamide (0.5 ml), and to the suspension, there was added bis(trimethylsilyl)acetamide (1.83 g), whereafter the mixture was stirred at ambient temperature for an hour to dissolve it. To this solution, there was all at once added the mixed acid anhydride solution prepared above at −70° C., whereafter the mixture was stirred at the same temperature for half an hour. The stirring was continued at −50° C. for an hour and then the reaction temperature was gradually elevated to −20° C. in the course of half an hour with stirring. The reaction mixture was poured into ice-water and the resulting mixture was adjusted to pH 8 with sodium bicarbonate. The aqueous layer was separated from the mixture, adjusted to pH 2 with dilute hydrochloric acid and then extracted with ethyl acetate (200 ml). The extract was washed with water and dried over magnesium sulfate. The solvent was removed by distillation from the solution under reduced pressure to give a residue, which was powdered with diisopropyl ether to give a powdery 3-[4-(3-tert-butoxycarbonylamino-3-methoxycarbonylpropoxy)phenylglyoxyloylamino]lactacillanic acid (1.54 g).

I.R. absorption spectrum
$\nu_{cm-1}$ (Nujol): 1740, 1680, 1660
N.M.R. absorption spectrum
δ ppm ($D_2O$+$NaHCO_3$):
1.26 (9H, s)
2.14 (2H, m)
3.06 (1H, q, J=5 Hz, 2 Hz)
3.4 to 4.4 (4H, m)
3.60 (3H, s)
5.04 (1H, q, J=5 Hz, 2 Hz)
5.34 (1H, s)
6.89, 7.24 (4H, AB-q, J=8 Hz)
6.82, 7.86 (4H, AB-q, J=8 Hz)

EXAMPLE 586

3-(2-Hydroxyimino-2-phenylacetamido)-1-(α-carboxybenzyl)-2-azetidinone (195 mg.) was obtained by reacting 3-amino-1-(α-carboxybenzyl)-2-azetidinone (500 mg) with 2-(2,2-dichloroacetoxyimino)-2-phenylacetyl chloride, which was prepared from the corresponding acetic acid (0.96 g) and phosphorus pentachloride (0.79 g), in substantially the same manner as described in Example 585, mp 145° to 149° C.

I.R. absorption spectrum
$\nu_{cm-1}$ (Nujol): 3340, 1745, 1700, 1655
N.M.R. absorption spectrum
(internal standard: tetramethylsilane)
δ ppm ($CD_3OD$):
3.28 (1H, d,d, J=2.5 Hz, 5 Hz)
3.93 (1H, t, J=5 Hz)
5.05 (1H, d,d, J=2.5 Hz, 5 Hz)
5.59 (1H, s)
7.22 to 7.72 (10H, m)

EXAMPLE 587

3-Benzyloxycarbonylamino-1-(α-carboxy-4-benzyloxycarbonyloxybenzyl)-2-azetidinone (1.55 g) was obtained by 3-aminolactacillanic acid (1.20 g) and benzyl chloroformate (2.50 g) in substantially the same manner as described in Example 585, mp 138° to 141° C. (dec.).

I.R. absorption spectrum
$\nu_{cm-1}$ (Nujol): 3300, 1760, 1740, 1720, 1703

EXAMPLE 588

3-[2-Benzoyloxyimino-2-{4-(3-tert-butoxycarbonylamino-3-methoxycarbonylpropoxy)phenyl}-acetamido]lactacillanic acid (100 mg) was obtained by reacting 3-aminolactacillanic acid (200 mg) with 2-benzoyloxyimino-2-[4-(3-tert-butoxycarbonylamino-3-methoxycarbonylpropoxy)phenyl]acetyl chloride, which was prepared from the corresponding acetic acid (470 mg) and thionyl chloride (91 mg), in substantially the same manner as described in Example 585.

I.R. absorption spectrum
$\nu_{cm-1}$ (film):
3400, 1750, 1720 to 1700, 1680
1660

The object compound (100 mg) thus obtained was dissolved in a mixture of methanol and 0.1 N aqueous sodium hydroxide (volume ratio; 1:3, total volume, 10 ml), whereafter the mixture was stirred at ambient temperature for 3 hours. The methanol was removed by distillation from the reaction mixture under reduced pressure to give an aqueous solution, which was adjusted to pH 2 with dilute hydrochloric acid. The resultant solution was extracted with ethyl acetate and the extract was washed with water and then dried over magnesium sulfate. The solvent was removed by distillation from the solution under reduced pressure to give a residue, which was powdered with chloroform to give 3-[2-{4-(3-carboxy-3-tert-butoxycarbonylaminopropoxy)phenyl}-2-hydroxyiminoacetamido]lactacillanic acid.

I.R. absorption spectrum
$\nu_{cm-1}$ (Nujol):
3280(broad), 1730(broad),
1680(shoulder)

EXAMPLE 589

3-Bromopyruvoylaminolactacillanic acid (50 mg) was obtained by reacting 3-aminolactacillanic acid (236 mg) with bromopyruvoyl chloride, which was prepared from the corresponding pyruvic acid (195 mg) and phosphorus oxychloride (337 mg), in substantially the same manner as described in Example 585, mp 188° to 192° C.

I.R. absorption spectrum
$\nu_{cm-1}$ (Nujol):
3400(shoulder), 3320, 1750
1690(shoulder), 1680
N.M.R. absorption spectrum
(internal standard: tetramethylsilane)
δ ppm [($CD_3$)$_2CO$]:
3.27 (1H, d,d, J=3 Hz, 6 Hz)
3.88 (1H, t, J=6 Hz)
4.60 (1H, s)
4.88 (1H, s)
5.11 (1H, d,d,d, J=3 Hz, 6 Hz, 10 Hz)
5.48 (1H, s)
6.88 (2H, d, J=8 Hz)
7.26 (2H, d, J=8 Hz)
8.73 (1H, d, J=10 Hz)

EXAMPLE 590

3-Benzyloxycarbonylamino-2-azetidinone (770 mg) and acetic acid (250 mg) were dissolved in ethanol (70 ml), and to the solution, there was added 10% palladium on carbon (350 mg). The mixture was subjected to catalytic reduction in a stream of hydrogen gas at ordinary temperature and ordinary atmospheric pressure. After a calculated volume of the hydrogen gas was absorbed into the mixture, the catalyst was removed by filtration. The filtrate was evaporated to dryness under reduced pressure to give a residue, which was washed with diethyl ether. The residue (380 mg) was dissolved in hot ethyl acetate (60 ml), whereafter the solution was concentrated to a volume of about 3 ml. The precipitating crystals were collected by filtration to give acetic acid salt of 3-amino-2-azetidinone (286 mg), mp 130° to 131.5° (dec.).

EXAMPLE 591

3-[4-(3-tert-Butoxycarbonylamino-3-carboxypropoxy)phenylglyoxyloylamino]-1-(α-carboxy-4-benzyloxybenzyl)-2-azetidinone (330 mg) was suspended in water (3 ml), and to the suspension, there was added sodium bicarbonate (95 mg) to dissolve it. To the resultant solution, there was added sodium borohydride (25 mg) at ambient temperature, whereafter the mixture was stirred for 2 hours. After the reaction, the reaction mixture was adjusted to pH 2.5 to 3 with dilute hydrochloric acid and the precipitating crystals were collected by filtration to give 3-[2-{4-(3-tert-butoxycarbonylamino-3-carboxypropoxy)phenyl}-glycoloylamino]-1-(α-carboxy-4-benzyloxybenzyl)-2-azetidinone (260 mg).

I.R. absorption spectrum
$\nu_{cm^{-1}}$ (Nujol):
3400, 3300 to 3200, 1740 to 1720, 1710, 1680

EXAMPLE 592

Sodium 3-[2-{4-(3-amino-3-carboxypropoxy)phenyl}-2-hydroxyiminoacetamido]lactacillanate (1.0 g) was dissolved in water (10 ml) and to the solution, there was dropwise added acetic anhydride (2 ml) under ice-cooling in the course of an hour. In the same time, the reaction mixture was adjusted to pH 8 to 10 with 10% aqueous sodium hydroxide. The reaction mixture was adjusted to pH 2 with 10% hydrochloric acid, and the precipitating materials were collected and washed with water to give powdery 3-[2-{4-(3-acetamido-3-carboxypropoxy)phenyl}-2-acetoxyiminoacetamido]1-(α-carboxy-4-acetoxybenzyl)-2-azetidinone (0.66 g).

I.R. absorption spectrum
$\nu_{cm^{-1}}$ (Nujol): 3250(broad), 1735(broad), 1650
N.M.R. absorption spectrum
(internal standard: tetramethylsilane)
δ ppm [(CD$_3$)$_2$CO]:
1.96 (3H, s)
2.08 (3H, s)
2.24 (3H, s)
3.20 (2H, m)
3.37 (1H, d,d, J=6 Hz, 2 Hz)
3.9 to 4.3 (3 H, m)
4.70 (1H, q, J=7 Hz)
5.20 (1H, m)
5.65 (1H, s)
6.8 to 7.8 (8H, m)

EXAMPLE 593

Water (3 ml) containing 3-bromopyruvoylaminolactacillanic acid (111 mg) and 1 N aqueous potassium hydroxide (0.56 ml) was added dropwise to an aqueous solution (3 ml) containing cysteine hydrochloride (44.2 mg) and 1 N aqueous potassium hydroxide (0.84 ml) under ice-cooling with stirring, whereafter the mixture was stirred at the same temperature for 1.5 hours. After the reaction mixture was adjusted to pH 4 with dilute hydrochloric acid, the resultant mixture was evaporated to dryness under reduced pressure to give a residue, which was dissolved in methanol (20 ml). Insoluble materials were removed by filtration to give a filtrate, which was evaporated to dryness under reduced pressure and the resultant residue was dissolved in a small amount of water. The aqueous solution was subjected to column chromatography on an absorption resin Amberlite XAD-2 (Trade Mark, maker; Rohm & Haas Co.,) (20 ml). Elution was carried out with water and the fractions containing a desired compound were collected. The solvent was removed by distillation from the solution under reduced pressure to give a residue, which was crystallized from ethanol to give 3-(2-amino-2-carboxyethylthiopyruvoylamino)lactacillanic acid (67 mg), mp 162° to 169° C. (dec.).

I.R. absorption spectrum
$\nu_{cm^{-1}}$ (KBr): 3400, 1740, 1610

N.M.R. absorption spectrum
(internal standard: sodium 2,2,3,3-tetradeutero-3-(trimethylsilyl)propionate)
δ ppm (D$_2$O):
3.04 to 3.20 (2H, m)
3.33 (1H, m)
3.70 (2H, m)
3.97 (1H, t, J=6 Hz)
4.05 to 4.20 (1H, m)
5.27 (1H, s)
6.95 (2H, m)
7.28 (2H, m)

EXAMPLE 594

3-[2-{4-(3-tert-Butoxycarbonylamino-3-carboxypropoxy)-phenyl}-2-hydroxyiminoacetamido]-1-(α-carboxy-4-benzyloxybenzyl)-2-azetidinone (240 mg) was suspended in benzene (2 ml), and to the suspension, there was added 2,2,2-trifluoroacetic acid (0.5 ml) at 7° C. with stirring. The mixture was stirred at the same temperature for 2 hours, and diethyl ether (about 25 ml) was added to the reaction mixture, and then the precipitating crystals were collected by filtration. The crystals were suspended in ethyl acetate and then the suspension was stirred at ambient temperature for half an hour. The crystals were collected by filtration and washed with diethyl ether to give 3-[2-{4-(3-amino-3-carboxypropoxy)phenyl}-2-hydroxyiminoacetamino]-1-(α-carboxy-4-benzyloxybenzyl)-2-azetidinone (180 mg), mp 164° to 167.5° C.

I.R. absorption spectrum
$\nu_{cm^{-1}}$ (Nujol): 3400 to 3250, 1740, 1660, 1610

EXAMPLE 595

3-[4-(3-Amino-3-carboxypropoxy)phenylglyoxyloylamino]-1-(α-carboxy-4-benzyloxybenzyl)-2-azetidinone (140 mg) was obtained by reacting 3-[4-(3-tert-butoxycarbonylamino-3-carboxypropoxy)phenylglyoxyloylamino]-1-(α-carboxy-4-benzyloxybenzyl)-2-azetidinone (220 mg) with 2,2,2-trifluoro acetic acid (0.5 ml) in substantially the same manner as described in Example 594, mp 170° to 175° C. (dec.)

I.R. absorption spectrum
$\nu_{cm^{-1}}$ (Nujol):
3400 to 3200, 1740 to 1730, 1720, 1680, 1660, 1600

EXAMPLE 596

3-[4-(3-Amino-3-carboxypropoxy)phenylglyoxyloylamino]-1-(α-carboxy-4-benzoyloxybenzyl)-2-azetidinone (110 mg) was obtained by reacting 3-[4-(3-tert-butoxycarbonylamino-3-carboxypropoxy)phenylglyoxyloylamino]-1-(α-carboxy-4-benzoyloxybenzyl)-2-azetidinone (650 mg) with 2,2,2-trifluoro acetic acid (4 ml) in substantially the same manner as described in Example 594, mp 181.5° to 184° C. (dec.).

I.R. absorption spectrum
$\nu_{cm^{-1}}$ (Nujol):
3500, 3300, 1740, 1720, 1700
1660, 1600

EXAMPLE 597

3-[4-(3-Amino-3-carboxypropoxy)phenylglyoxyloylamino]-1-(α-carboxy-4-benzyloxycarbonyloxybenzyl)-2-azetidinone (100 mg) was obtained by reacting 3-[4-(3-tert-butoxycarbonylamino-3-carboxypropoxy)phenylglyoxyloylamino]-1-(α-carboxy-4-benzyloxycarbonyloxybenzyl)-2-azetidinone (650 mg) with 2,2,2-trifluoroacetic acid (4 ml) in substantially the same manner as described in Example 594, mp 133° to 139° C.(dec.).

I.R. absorption spectrum $\nu_{cm-1}$ (Nujol): 3500, 3300 to 3200, 1760, 1720, 1680, 1660, 1600

EXAMPLE 598

3-[2-{4-(3-Amino-3-carboxypropoxy)phenyl}-glycoloylamino]-1-(α-carboxy-4-benzyloxybenzyl)-2-azetidinone (120 mg) was obtained by reacting 3-[2-{4-(3-tert-butoxycarbonylamino-3-carboxypropoxy)-phenyl}glycoloylamino]-1-(α-carboxy-4-benzyloxybenzyl)-2-azetidinone (200 mg) with 2,2,2-trifluoroacetic acid (0.5 ml) in substantially the same manner as described in Example 594, mp 149° to 154° C.(dec.).

I.R. absorption spectrum $\nu_{cm-1}$ (Nujol):
3400 to 3200, 1730 to 1720,
1660, 1610

EXAMPLE 599

3-[4-(3-tert-Butoxycarbonylamino-3-methoxycarbonylpropoxy)phenylglyoxyloylamino]lactacillanic acid (1.50 g) was dissolved in methanol (20 ml), and to the solution, there was added 1 N aqueous sodium hydroxide (about 10 ml) in the course of 5 hours with stirring. The reaction mixture was adjusted to pH 7 with 1 N hydrochloric acid and evaporated to dryness under reduced pressure to give a residue, to which water was added. The resulting mixture was adjusted to pH 2 with dilute hydrochloric acid, and then extracted with ethyl acetate. The extract was dried over magnesium sulfate and the solvent was removed by distillation from the solution under reduced pressure. The obtained residue was powdered with diisopropyl ether to give 3-[4-(3-tert-butoxycarbonylamino-3-carboxypropoxy)-phenylglyoxyloylamino]-lactacillanic acid (1.20 g).

I.R. absorption spectrum $\nu_{cm-1}$ (Nujol): 1740, 1680, 1660

N.M.R. absorption spectrum (internal standard: sodium 2,2,3,3-tetradeutero-3-(trimethylsilyl)propionate]

δ ppm (D$_2$O+NaHCO$_3$):
1.34 (9H, s)
2.20 (2H, m)
3.07 (1H, q, J=5 Hz, 2 Hz)
3.83 (1H, t, J=5 Hz)
4.0 to 4.3 (3H, m)
4.98 (1H, q, J=5 Hz, 2 Hz)
6.92, 7.26 (4H, ABq, J=9 Hz)
6.94, 7.88 (4H, ABq, J=9 Hz)

EXAMPLE 600

3-[2-{4-(3-Amino-3-carboxypropoxy)phenyl}-2-carboxymethoxyiminoacetamido]lactacillanic acid (160 mg) was obtained by reacting 3-[2-{4-(3-amino-3-carboxypropoxy)phenyl}-2-ethoxycarbonylmethoxyiminoacetamido]lactacillanic acid (280 mg) with 1 N aqueous sodium hydroxide (2 ml) in substantially the same manner as described in Example 599, mp 178° to 180° C.(dec.).

I.R. absorption spectrum $\nu_{cm-1}$ (Nujol):
3400 to 3200, 1740, 1720,
1660, 1600

EXAMPLE 601

1 N Aqueous sodium hydroxide (about 7 ml) was added dropwise to a methanol solution (10 ml) containing 3-[4-(3-tert-butoxycarbonylamino-3-methoxycarbonylpropoxy)phenylglyoxyloylamino]lactacillanic acid (1.0 g) under ice-cooling with stirring in the course of 5 hours. After the reaction, the reaction mixture was adjusted to pH 8 with 1 N hydrochloric acid and washed with ethyl acetate. The resultant aqueous solution was adjusted to pH 2 and then extracted with ethyl acetate, whereafter the extract was dried over magnesium sulfate. The solution was evaporated to dryness under reduced pressure to give a crude 3-[4-(3-tert-butoxycarbonylamino-3-carboxypropoxy)phenylglyoxyloylamino]lactacillanic acid (1.0 g). This crude compound (1.0 g) was treated with 2,2,2-trifluoroacetic acid (5 ml) in substantially the same manner as described in Example 594 to give 3-[4-(3-amino-3-carboxypropoxy)-phenylglyoxyloylamino]lactacillanic acid (0.41 g), mp 232° to 236° C.(dec.).

EXAMPLE 602

A diethyl ether solution containing diazomethane was added dropwise to a methanol solution (10 ml) containing 3-[2-{4-(3-acetamido-3-carboxypropoxy)-phenyl}-2-acetoxyiminoacetamido]-1-(α-carboxy-4-acetoxybenzyl)-2-azetidinone (0.40 g) under ice-cooling until a color of the diazomethane was appeared, whereafter the mixture was stirred at the same temperature for 2 hours. The reaction mixture was evaporated to dryness under reduced pressure to give a residue, which was subjected to column chromatography on silica gel (50 mg). Elution was carried out with a mixture of chloroform and methanol (volume ratio, 10:1) and the fractions containing a desired compound were collected. The solvent was removed by distillation from the solution under reduced pressure to give 3-[2-{4-(3-acetamido-3-methoxycarbonylpropoxy)-phenyl}-2-acetoxyiminoacetamido]-1-(α-methoxycarbonyl-4-acetoxybenzyl)-2-azetidinone (150 mg), mp 120° to 123° C.(dec.).

I.R. absorption spectrum $\nu_{cm-1}$ (Nujol): 3300, 1740(broad), 1655

EXAMPLE 603

3-(2-Phenylacetamido)-1-(α-methoxycarbonyl-4-benzyloxybenzyl)-2-azetidinone (70 mg) was dissolved in absolute ethanol (10 ml), and to the solution, there was added 10% palladium on carbon (30 mg). The mixture was subjected to catalytic reduction in a stream of hydrogen gas at ordinary temperature and ordinary atmospheric pressure. After a calculated volume of the hydrogen gas was absorbed into the mixture in the course of 3 hours, the catalyst was removed by filtration to give a filtrate, which was evaporated to dryness under reduced pressure. The resultant residue was treated with diethyl ether to give 3-(2-phenylacetamido)-1-(α-methoxycarbonyl-4-hydroxybenzyl)-2-azetidinone (40 mg), mp 171.5° to 175° C.

I.R. absorption spectrum $\nu_{cm-1}$ (Nujol): 3250, 1750, 1730, 1670

N.M.R. absorption spectrum (internal standard: tetramethylsilane)

δ ppm (CD$_3$OD):
3.05 (1H, q. J=3 Hz, 6 Hz)
3.50 (2H, s)
3.75 (3H, s)

3.83 (1H, t, J=6 Hz)
4.90 (1H, m)
5.52 (1H, s)
6.87, 7.23 (4H, ABq, J=10 Hz)
7.28 (5H, s)

EXAMPLE 604

3-Phthalimido-1-(α-methoxycarbonyl-4-hydroxybenzyl)-2-azetidinone (30 mg) was obtained by reducing 3-phthalimido-1-(α-methoxycarbonyl-4-benzyloxybenzyl)-2-azetidinone (0.27 g) by 10% palladium on carbon (100 mg) in substantially the same manner as described in Example 603, mp 203° to 204.5° C.

I.R. absorption spectrum
$v_{cm-1}$ (Nujol): 3250, 1780, 1740, 1720

EXAMPLE 605

3-Phthalimidolactacillanic acid (0.95 g) was obtained by reducing 3-phthalimido-1-(α-benzyloxycarbonyl-4-benzyloxybenzyl)-2-azetidinone (1.81 g) by 10% palladium on carbon (1.0 g) in substantially the same manner as described in Example 603, mp 195° to 199° C.(dec.).

EXAMPLE 606

3-[2-(5-Oxo-3-phenyl-4,5-dihydro-1,2,4-oxadiazol-4-yl)acetamido]lactacillanic acid (400 mg) was dissolved in water (20 ml) containing sodium bicarbonate (84 mg), and to the solution, there was added Reney nickel (0.8 ml), whereafter the mixture was subjected to catalytic reduction in a stream of hydrogen gas at ordinary temperature and under 3 atmospheric pressure. After a calculated volume of the hydrogen gas was absorbed into the mixture in the course of about 2 hours, the catalyst was removed by filtration from the reaction mixture. The filtrate was adjusted to pH 6.0 with dilute hydrochloric acid and concentrated to a volume of about 5 ml. The concentrate was subjected to column chromatography on an adsorption resin Amberlite XAD-2 (Trade Mark, maker; Rohm & Haas Co., 30 ml). Elution was carried out with 50% aqueous methanol and the fractions containing a desired compound were collected. The solvent was removed by distillation from the solution under reduced pressure to give 3-[2-(α-iminobenzylamino)acetamide]lactacillanic acid (70 mg), mp 175° to 178.5° C. (dec.).

EXAMPLE 607

3-(2-Hydroxyimino-2-phenylacetamido)lactacillanic acid (383 mg) was suspended in water (10 ml), and to the suspension, there were added 1 N aqueous sodium hydroxide (1 ml) and acetone (10 ml) at 0° to 5° C. to dissolve it. A dried acetone solution (10 ml) containing benzoyl chloride (335 mg) was added dropwise to the solution obtained above in the course of half an hour at 0° to 5° C. with stirring, while adjusting to pH 7.5 to 8.0 by gradually adding 1 N aqueous sodium hydroxide (2.2 ml) thereto. The stirring was continued at the same temperature for additional 1.5 hours. The acetone was removed by distillation from the reaction mixture under reduced pressure to give an aqueous solution, which was washed with ethyl acetate and adjusted to pH 1 to 2 with dilute hydrochloric acid. The resultant aqueous solution was extracted with ethyl acetate, and the extract was washed with water and then dried over magnesium sulfate. The solution was evaporated to dryness under reduced pressure to give an oily residue, which was dissolved in a small amount of diethyl ether. Cyclohexane was added to the etheral solution, until the precipitates were not produced, and the precipitates were collected by filtration and treated with cyclohexane to give 1-(4-benzoyloxy-α-carboxybenzyl)-3-(2-benzoyloxyimino-2-phenylacetamido)-2-azetidinone (430 mg), mp 119° to 123° C.

I.R. absorption spectrum
$v_{cm-1}$ (Nujol): 3300, 1760, 1740, 1680

EXAMPLE 608

3-[2-{4-(3-Amino-3-carboxypropoxy)phenyl}-2-hydroxyiminoacetamido]lactacillanic acid (2.0 g) was suspended in dried methylene chloride (40 ml), and to the suspention, there was added bis(trimethylsilyl)acetamide (5.6 g). The mixture was stirred at ambient temperature for 1.5 hours and the refluxed under heating for 5 minutes. Triethylamine (0.6 g) was added to the resultant solution under ice-cooling, whereafter trityl chloride (1.68 g) was added dropwise thereto under ice-cooling in the course of about 10 minutes with stirring. The stirring was continued at the same temperature for 10 minutes and then at ambient temperature for additional 4 hours. The reaction mixture was evaporated to dryness under reduced pressure to give a residue, to which ethyl acetate and water were added. After the mixture was stirred for a while, the ethyl acetate layer was separated. To the ethyl acetate solution, there was added an aqueous sodium bicarbonate, and then the resultant mixture was stirred for a while. The aqueous layer was separated, adjusted to pH 3 with 5% phosphoric acid and then extracted with ethyl acetate, whereafter the extract was dried over magnesium sulfate. The solvent was removed by distillation from the solution under reduced pressure to give a residue, which was precipitated with a mixture of acetone and benzene to give 3-[2-{4-(3-carboxy-3-tritylaminopropoxy)phenyl}-2-hydroxyiminoacetamido]lactacillanic acid (1.70 g), mp 163° to 173° C.

I.R. absorption spectrum
$v_{cm-1}$ (Nujol): 3250, 1735, 1720, 1650

EXAMPLE 609

1-(α-Methoxycarbonylbenzyl)-4-methylthio-3-(2-phenylacetamido)-2-azetidinone (mixture of two trans isomers at the third and fourth positions of the azetidine ring) (0.50 g) was dissolved in dried dioxane (10 ml), and to the solution, there was added an dioxane solution (10 ml) containing Raney nickel (5 ml). The mixture was stirred at 60° C. for 2 hours. Raney nickel was removed by filtration to give a filtrate, which was evaporated to dryness under reduced pressure. The residue obtained was subjected to column chromatography on silica gel (10 g) and elution was carried out with chloroform. The fractions containing a desired compound were collected and the solvent was distilled off from the solution under reduced pressure to give 1-(α-methoxycarbonylbenzyl)-3-(2-phenylacetamido)-2-azetidinone (mixture of two isomers at the third position of the azetidine ring, 320 mg). Additionally this mixture was subjected to column chromatography on silica gel and elution was carried out with chloroform. The eluate was treated in a conventional manner to give each isomer a: 180 mg and b: 140 mg of the above compound.

Physical constant:
Isomer a;
mp 138° to 140° C.
I.R. absorption spectrum
$v_{cm-1}$ (Nujol): 3260, 1750, 1730, 1680
N.M.R. absorption spectrum (internal standard: tetramethylsilane)
δ ppm (CDCl$_3$):
  3.06 (1H, q, J=3 Hz, 5 HZ)
  3.50 (2H, s)
  3.73 (3H, s)
  3.86 (1H, t, J=5 Hz)
  4.88 (1H, m)
  5.56 (1H, s)
  6.46 (1H, d, J=7 Hz)
  7.08 to 7.28 (10H, m)
Isomer b;
  I.R. absorption spectrum
    $\nu_{cm-1}$ (film): 3290, 1760, 1740, 1660
  N.M.R. absorption spectrum
  (internal standard: tetramethylsilane)
  δ ppm (CDCl$_3$):
    3.32 to 3.60 (2H, m)
    3.50 (2H, s)
    3.71 (3H, s)
    4.94 (1H, m)
    5.55 (1H, s)
    6.74 (1H, d, J=7 Hz)
    7.08 to 7.28 (10H, m)

EXAMPLE 610

3-(2-Phenylacetamido)-1-(α-methoxycarbonyl-4-benzyloxybenzyl)-2-azetidinone (mixture of two isomers at the third position of the azetidine ring, 130 mg) was obtained by reacting 3-(2-phenylacetamido)-1-(α-methoxycarbonyl-4-benzyloxybenzyl)-4-methylthio-2-azetidinone (0.73 g) with Raney nickel (7.3 ml) in substantially the same manner described in Example 585. This mixture of the object compound was subjected to column chromatography in a conventional manner to give each isomer a: 70 mg and b: 30 mg of the above object compound.
Physical constant:
Isomer a;
  mp 150.5° to 154.5° C.
  I.R. absorption spectrum
    $\nu_{cm-1}$ (Nujol): 3280, 1755, 1730, 1680
  N.M.R. absorption spectrum
  (internal standard: tetramethylsilane)
  δ ppm (CDCl$_3$):
    3.02 (1H, q, J=3 Hz, 6 Hz)
    3.49 (2H, s)
    3.72 (3H, s)
    3.82 (1H, t, J=6 Hz)
    4.90 (1H, m)
    5.05 (2H, s)
    5.53 (1H, s)
    6.69 (1H, d, J=7 Hz)
    6.84 to 7.65 (14H, m)
Isomer b;
  I.R. absorption spectrum
    $\nu_{cm-1}$ (CHCl$_3$): 1760, 1745, 1675
  N.M.R. absorption spectrum
  (internal standard: tetramethylsilane)
  δ ppm (CDCl$_3$):
    3.25 to 3.63 (2H, m)
    3.57 (2H, s)
    3.70 (3H, s)
    4.95 (1H, m)
    5.05 (2H, s)
    5.49 (1H, s)
    6.68 (1H, d, J=8 Hz)
    6.88 to 7.55 (14H, m)

EXAMPLE 611

3-Phthalimido-1-(2-methyl-1-methoxycarbonyl-1-propenyl)-2-azetidinone (14.6 g) was obtained by reacting 3-phthalimido-1-(2-methyl-1-methoxycarbonyl-1-propenyl)-4-(2-benzothiazolyldithio)-2-azetidinone (47 g) with Raney nickel (470 ml) in substantially the same manner as described in Example 585, mp 127° to 128° C.
I.R. absorption spectrum
  $\nu_{cm-1}$ (Nujol): 1767, 1758, 1730, 1715
N.M.R. absorption spectrum
(internal standard: tetramethylsilane)
δ ppm (CD$_3$OD):
  2.14 (3H, s)
  2.24 (3H, s)
  3.8 (3H, s)
  3.96 (2H, d, J=5 Hz)
  5.64 (1H, t, J=6 Hz)
  7.86 (4H, s)

EXAMPLE 612

3-(2-Phenoxyacetamido)-1-(2-methyl-1-methoxycarbonyl-1-propenyl)-2-azetidinone (3.09 g) was obtained by reacting 3-(2-phenoxyacetamido)-1-(2-methyl-1-methoxycarbonyl-1-propenyl)-4-(2-benzothiazolyldithio)-2-azetidinone (13 g) with Raney nickel (75 g) in substantially the same manner as described in Example 585, mp 154° to 155° C.
I.R. absorption spectrum
  $\nu_{cm-1}$ (Nujol): 3320, 1745, 1710, 1685
N.M.R. absorption spectrum
(internal standard: tetramethylsilane)
δ ppm (CDCl$_3$):
  2.02 (3H, s)
  2.23 (3H, s)
  3.57 (1H, d,d, J=3 Hz, 5 Hz)
  3.85 (1H, t, J=5 Hz, 5 Hz)
  4.54 (2H, s)
  5.07 (1H, m)
  6.86 to 7.42 (5H, m)

EXAMPLE 613

3-Phthalimido-1-(1-carboxy-2-methyl-1-propenyl)-2-azetidinone (240 mg) was obtained by reacting sodium salt of 3-phthalimido-1-(1-carboxy-2-methyl-1-propenyl)-4-(2-benzothiazolyldithio)-2-azetidinone (2.0 g) with Raney nickel (20 ml) in substantially the same manner as described in Example 585.
I.R. absorption spectrum
  $\nu_{cm-1}$ (Nujol): 1780, 1770, 1760, 1720
N.M.R. absorption spectrum
(internal standard: tetramethylsilane)
δ ppm (CD$_3$OD):
  2.40 (3H, s)
  2.80 (3H, s)
  4.00 to 4.18 (2H, m)
  5.67, 5.83 (1H, d,d, J=7 Hz)
  8.13 (4H, s)

EXAMPLE 614

Crude 3-(2-phenoxyacetamido)-1-(1-methoxycarbonyl-2-methyl-1-propenyl)-2-azetidinone (45 mg) was obtained by reacting 3-(2-phenoxyacetamido)-1-(1-methoxycarbonyl-2-methyl-1-propenyl)-4-[1-(1-methoxycarbonyl-2-methyl-1-propenyl)-2-oxo-3-(2-phenoxyacetamido)-4-azetidinyldithio]-2-azetidinone (50 mg) with Raney nickel (1 ml) in substantially the same manner as described in Example 585.

I.R. absorption spectrum
$\nu_{cm-1}$ (Nujol): 3320, 1745, 1710, 1685

EXAMPLE 615

3-(1-Methoxycarbonyl-2-methylpropylamino)-2-(2-phenylacetamido)propionic acid (0.92 g) was dissolved in ethyl acetate (100 ml), and to the solution, there were added 4-methylmorpholine (0.66 g) and 1-(4-chlorobenzenesulfonyloxy)-6-chloro-1H-benzotriazole (1.11 g) under ice-cooling. The mixture was stirred at the same temperature for 18 hours and the insoluble materials were removed by filtration from the reaction mixture and ice-water (30 ml) was poured into the filtrate, whereafter the resultant mixture was stirred enough. The ethyl acetate layer was separated from the mixture, washed three times with an aqueous sodium bicarbonate and once with water, and then dried over magnesium sulfate. The solution was evaporated to dryness under reduced pressure to give a residue, which was subjected to column chromatography on silica gel (15 g). Elution was carried out with chloroform and the fractions containing a desired compound were collected. The solvent was removed by distillation from the eluate under reduced pressure to give 1-(1-methoxycarbonyl-2-methylpropyl)-3-(2-phenylacetamido)-2-azetidinone (10 mg), mp 105° to 107° C.

EXAMPLE 616

1-(α-Methoxycarbonyl-4-hydroxybenzyl)-3-(2-phenylacetamido)-2-azetidinone (40 mg) was dissolved in acetone (5 ml), and to the solution, there was added 0.1 N aqueous sodium hydroxide (3 ml) under ice-cooling. The mixture was stirred at the same temperature for 10 minutes. The acetone was removed by distillation under reduced pressure to give an aqueous solution, which was washed with ethyl acetate. The aqueous solution was adjusted to pH 2 with 1 N hydrochloric acid and extracted with ethyl acetate. The extract was washed with water and then dried over magnesium sulfate. The solvent was removed by distillation from the solution under reduced pressure to give a residue, which was crystallized from acetone to give 3-(2-phenylacetamido)lactacillanic acid (20 mg), mp 134° to 141° C.

EXAMPLE 617

1-(2-Carboxy-1-phenylethyl)-3-(2-hydroxyimino-2-phenylacetamido)-2-azetidinone (0.31 g) was obtained by reacting 1-(2-methoxycarbonyl-1-phenylethyl)-3-(2-hydroxyimino-2-phenylacetamido)-2-azetidinone (0.49 g) with 1 N aqueous sodium hydroxide (3 ml) in substantially the same manner as described in Example 616, mp 157° to 158° C.

I.R. absorption spectrum
$\nu_{cm-1}$ (Nujol): 3180, 1720, 1710, 1635

EXAMPLE 618

1-(α-Methoxycarbonyl-4-hydroxybenzyl)-3-phthalimido-2-azetidinone (0.05 g) was dissolved in dried pyridine (1 ml), and to the solution, there was added lithium iodide (0.05 g). The mixture was refluxed under heating for 3.5 hours and the reaction mixture was poured into a mixture of ice-water and ethyl acetate (100 ml, volume ratio, 1:1) and the resultant mixture was adjusted to pH 1 to 2 with 10% hydrochloric acid. The ethyl acetate layer was separated, washed with dilute hydrochloric acid and water, and then dried over magnesium sulfate. The solution was evaporated to dryness under reduced pressure to give an oily residue (0.03 g), which was crystallized from ethyl acetate to give 3-phthalimidolactacillanic acid (0.01 g).

I.R. absorption spectrum
$\nu_{cm-1}$ (Nujol): 3360, 1780, 1740, 1720, 1700

EXAMPLE 619

1-(α-Carboxybenzyl)-3-phthalimido-2-azetidinone (260 mg) was obtained by reacting 1-(α-methoxycarbonylbenzyl)-3-phthalimido-2-azetidinone (364 mg) with lithium iodide (420 mg) in pyridine (5 ml) in substantially the same manner as described in Example 618, mp 176° to 183° C.

I.R. absorption spectrum
$\nu_{cm-1}$ (Nujol): 2750 to 2500, 1780, 1760, 1720

EXAMPLE 620

1-(α-Benzyloxycarbonylbenzyl)-3-phthalimido-2-azetidinone (1.32 g) was dissolved in ethyl acetate (30 ml), and to the solution, there was added 10% palladium on carbon (500 mg), and the mixture was subjected to catalytic reduction in a stream of hydrogen gas at ordinary temperature and ordinary atmospheric pressure. After a calculated volume of the hydrogen gas was absorbed into the reaction mixture in the course of 3 hours. The reaction mixture was adjusted to about pH 8 with 2% aqueous sodium bicarbonate. The catalyst was removed by filtration from the reaction mixture and the aqueous layer was separated from the resultant filtrate. The aqueous solution was adjusted to pH 2 with 1 N hydrochloric acid and extracted with ethyl acetate. The extract was washed with a saturated aqueous sodium chloride and then dried over magnesium sulfate. The solvent was removed by distillation from solution under reduced pressure to give an crystalline residue, which was washed with diethyl ether to give 1-(α-carboxybenzyl)-3-phthalimido-2-azetidinone (0.85 g), mp 182° to 183° C.

I.R. absorption spectrum
$\nu_{cm-1}$ (Nujol):
1780(shoulder), 1760,
(shoulder), 1710

EXAMPLE 621

A tetrahydrofuran solution (5 ml) containing triethylamine (1.02 g) was added to a tetrahydrofuran solution (40 ml) containing 1-(1-carboxy-2-methylpropyl)-3-(2-phenylacetamido)-2-azetidinone (3.04 g) at −20° C. with stirring. To this solution, there was dropwise added a tetrahydrofuran solution (5 ml) containing ethyl chloroformate (1.14 g) at −10° C. in the course of 5 minutes, whereafter the mixture was stirred at −10° to 0° C. for 2 hours. To the resultant mixture, there was all at once added water (8 ml), in which sodium azide (1.23 g) was dissolved at the same temperature, and the stirring was continued for additional half an hour. The reaction mixture was poured into ice-water (200 ml) and the resultant mixture was extracted with three portions of 100 ml methylene chloride. The extracts were washed with three portions of 100 ml water and dried over calcium chloride. The solution was evaporated to dryness under reduced pressure to give oily 1-(1-azidocarbonyl-2-methylpropyl)-3-(2-phenylacetamido)-2-azetidinone (3.0 g).

I.R. absorption spectrum
$\nu_{cm-1}$ (Nujol): 3300, 2250, 1700, 1650

EXAMPLE 622

1-(1-Azidocarbonyl-2-methylpropyl)-3-(2-phenylacetamido)-2-azetidinone (2.6 g) was dissolved in absolute toluene (50 ml) and the solution was refluxed under heating for 20 minutes. Insoluble materials were removed by filtration to give a filtrate, to which 1-methylimidazole (0.1 ml) and 2,2,2-trichloroethanol (1.45 g) were added. After the mixture was heated at 80° C. for an hour, the solvent was removed by distillation from the reaction mixture under reduced pressure to give a viscous oily residue, which was adsorbed to silica gel (8 g). This silica gel was subjected to column chromatography on additional silica gel (30 g) for isolation and purification to give 1-[1-(2,2,2-trichloroethoxycarbonylamino)-2-methylpropyl]-3-(2-phenylacetamido)-2-azetidinone (2.66 g).

I.R. absorption spectrum
$\nu_{cm-1}$ (Nujol):
3300, 1765, 1740(shoulder),
1650

EXAMPLE 623

A mixture of 1-(1-carboxy-2-methylpropyl)-3-(2-phenylacetamido)-2-azetidinone (1.50 g), triethylamine (0.51 g), diphenylphosphoryl azide (1.4 g) and tert-butyl alcohol (30 ml) was heated gradually, and refluxed under heating for 5 hours. After the reaction, the tert-butyl alcohol was removed by distillation from the reaction mixture under reduced pressure to give a residue, which was subjected to column chromatography on silica gel. Elution was carried out with a mixture of benzene and ethyl acetate, and the fractions containing a desired compound were collected. The eluate was evaporated to dryness under reduced pressure to give 1-(1-tert-butoxycarbonylamino-2-methylpropyl)-3-(2-phenylacetamido)-2-azetidinone (1.1 g), mp 64° to 66° C.

EXAMPLE 624

Copper acetate (one hydrate, 199 mg) was added to an ethyl acetate solution (200 ml) containing 1-(1-carboxy-2-methylpropyl)-3-(2-phenylacetamido)-2-azetidinone (3.04 g) with stirring. To the resultant mixture, there was added lead tetraacetate (4.9 g) at ambient temperature in the course of 5 minutes, whereafter the mixture was refluxed under heating for half an hour with stirring. The insoluble materials were removed by filtration to give a filtrate, which was washed with water, an aqueous sodium chloride and an aqueous sodium bicarbonate and then washed with an aqueous sodium chloride twice in turn, whereafter dried over magnesium sulfate. The ethyl acetate was removed by distillation from the solution under reduced pressure to give oily 1-(1-acetoxy-2-methylpropyl)-3-(2-phenylacetamido)-2-azetidinone (2.7 g).

I.R. absorption spectrum
$\nu_{cm-1}$ (film): 1760, 1735(shoulder), 1665

EXAMPLE 625

3-[4-(3-Carboxy-3-tert-butoxycarbonylaminopropoxy)phenylglyoxyloylamino]-1-(α-carboxy-4-benzyloxybenzyl)-2-azetidinone (320 mg) was suspended in water (5 ml), and to the suspension, there was added hydroxylamine hydrochloride (75 mg). The mixture was adjusted to pH 7 to 7.5 with sodium bicarbonate (170 mg), whereafter the resultant mixture was stirred at 45° to 50° C. for 4 hours. The reaction mixture was adjusted to pH 2 with dilute hydrochloric acid, whereafter the precipitating solid was collected by filtration, washed with water and then dried to give 3-[2-{4-(3-carboxy-3-tert-butoxycarbonylaminopropoxy)phenyl}-2-hydroxyiminoacetamido]-1-(α-carboxy-4-benzyloxybenzyl)-2-azetidinone (280 mg), mp 149.5° to 153° C. (dec.).

I.R. absorption spectrum
$\nu_{cm-1}$ (Nujol):
3300(broad), 1750 to 1720,
1670

EXAMPLE 626

Sodium 3-[2-{4-(3-amino-3-carboxypropoxy)phenyl}-2-methoxyiminoacetamido]lactacillanate (2.61 g) was obtained by reacting 3-[4-(3-amino-3-carboxypropoxy)phenylglyoxyloylamino]lactacillanic acid (3.00 g) with methoxyamine hydrochloride (1.05 g) in substantially the same manner as described in Example 625, mp 210° to 215° C. (dec.)

EXAMPLE 627

3-[2-{4-(3-Amino-3-carboxypropoxy)phenyl}-2-ethoxycarbonylmethoxyiminoacetamido]lactacillanic acid (310 mg) was obtained by reacting 3-[4-(3-amino-3-carboxypropoxy)phenylglyoxyloylamino]lactacillanic acid (0.500 g) with ethyl 2-aminooxyacetate tosylate (0.300 g) in substantially the same manner as described in Example 625.

I.R. absorption spectrum
$\nu_{cm-1}$ (Nujol):
3300 to 3200, 1740, 1720,
1670, 1610 to 1600

N.M.R. absorption spectrum
[internal standard: sodium 2,2,3,3-tetradeutero-3-(trimethylsilyl)propionate]
δ ppm (NaHCO$_3$+D$_2$O):
1.13 (3H, t, J=7 Hz)
2.38 (2H, m)
3.15, 3.19 (1H, d,d, J=2 Hz, 4 Hz)
3.80 to 4.04 (3H, m)
4.66 (2H, s)
4.98, 5.02 (1H, d,d, J=2 Hz, 4 Hz)
5.35 (1H, s)
6.84 to 7.73 (8H, m)

EXAMPLE 628

3-[2-{4-(3-Amino-3-carboxypropoxy)phenyl}-2-benzyloxyiminoacetamido]lactacillanic acid (0.33 g) was obtained by reacting 3-[4-(3-amino-3-carboxypropoxy)phenylglyoxyloylamino]lactacillanic acid (0.50 g) with benzyloxyamine (0.27 g) in substantially the same manner as described in Example 625, mp 180° to 184° C. (dec.).

EXAMPLE 629

3-[2-{4-(3-Amino-3-carboxypropoxy)phenyl}-2-carbamoylhydrazonoacetamido]lactacillanic acid (160 mg) was obtained by reacting 3-[4-(3-amino-3-carboxypropoxy)phenylglyoxyloylamino]lactacillanic acid (0.50 g) with semicarbazide hydrochloride (0.23 g) in substantially the same manner as described in Example 625.

I.R. absorption spectrum
$\nu_{cm-1}$ (Nujol):
3400, 3300 to 3200, 1740, 1720,
1660 to 1640, 1600

N.M.R. absorption spectrum

[internal standard: sodium 2,2,3,3-tetradeutero-3-(trimethylsilyl)propionate]
δ ppm (D$_2$O+NaHCO$_3$):
2.24 to 2.36 (2H, m)
3.14, 3.20 (1H, d,d, J=2 Hz, 5 Hz)
3.72 to 4.08 (2H, m)
4.19 (2H, t, J=6 Hz)
4.93, 4.99 (1H, d,d, J=2 Hz, 5 Hz)
5.30 (1H, s)
6.84 to 7.50 (13H, m)

EXAMPLE 630

3-[2-{4-(3-Amino-3-carboxypropoxy)phenyl}-2-thiocarbamoylhydrazonoacetamido]lactacillanic acid (100 mg) was obtained by reacting 3-[4-(3-amino-3-carboxypropoxy)phenylglyoxyloylamino]lactacillanic acid (500 mg) with thiosemicarbazide (300 mg) in substantially the same manner as described in Example 625, mp 206° to 207.5° C. (dec.).

I.R. absorption spectrum
$\nu_{cm-1}$ (Nujol):
3300 to 3100, 1730, 1710, 1660, 1610

EXAMPLE 631

3-[2-(2-Thienyl)acetamido]lactacillanic acid (480 mg) was suspended in water (10 ml), and to the suspension, there was added sodium bicarbonate (520 mg) to dissolve it. Acetone (10 mg) was added to the solution, whereafter a dried acetone solution (5 ml) containing benzoyl chloride (560 mg) was added dropwise thereto under ice-cooling with stirring. The stirring was continued at the same temperature for about 4.2 hours and then at ambient temperature for additional 5 hours. The acetone was removed by distillation from the reaction mixture under reduced pressure to give an aqueous solution, which was washed with ethyl acetate. The aqueous solution was adjusted to pH 1 to 2 with dilute hydrochloric acid and extracted with ethyl acetate. The extract was washed with water and then dried over magnesium sulfate. The solution was evaporated to dryness under reduced pressure to give a residue, which was subjected to column chromatography on silica gel (20 g). Elution was carried out with ethyl acetate and the fractions containing a desired compound were collected. The solvent was removed by distillation from the solution under reduced pressure to give a residue, which was crystallized from ethyl acetate to give 1-(4-benzoyloxy-α-carboxybenzyl)-3-[2-(2-thienyl)acetamido]-2-azetidinone (240 mg), mp 129° to 131° C.

EXAMPLE 632

Sodium salt of 1-(α-carboxy-4-benzyloxycarbonyloxybenzyl)-3-[2-(2-thienyl)acetamido]-2-azetidinone (310 mg) was obtained by reacting 3-[2-(2-thienyl)acetamido]lactacillanic acid (360 mg) with benzyl chloroformate (0.221 g) in substantially the same manner as described in Example 631, mp 128° to 130° C.

EXAMPLE 633

3-[4-(3-tert-Butoxycarbonylamino-3-carboxypropoxy)-phenylglyoxyloylamino]-1-(α-carboxy-4-benzyloxycarbonyloxybenzyl)-2-azetidinone (1.2 g) was obtained by reacting 3-[4-(3-tert-butoxycarbonylamino-3-carboxypropoxy)phenylglyoxyloylamino]lactacillanic acid (1.17 g) with benzyl chloroformate (0.450 g) in substantially the same manner as described in Example 631.

I.R. absorption spectrum
$\nu_{cm-1}$ (Nujol):
3400 to 3300, 1750, 1730 to 1710, 1690, 1670
N.M.R. absorption spectrum
(internal standard: tetramethylsilane)
δ ppm [(CD$_3$)$_2$CO]:
1.39 (3H, s)
2.20 to 2.44 (2H, m)
3.37, 3.43 (1H, d,d, J=2 Hz, 5 Hz)
3.81 (1H, t, J=5 Hz)
4.25 (2H, t, J=6 Hz)
5.12 to 5.26 (1H, m)
5.28 (2H, s)
5.64 (1H, s)
6.24 (1H, d, J=8 Hz)
7.00 to 7.60 (11H, m)
8.20 (1H, d, J=8 Hz)
8.68 (1H, d, J=8 Hz)

EXAMPLE 634

3-[4-(3-tert-Butoxycarbonylamino-3-carboxypropoxy)phenylglyoxyloylamino]-1-(α-carboxy-4-benzoyloxybenzyl)-2-azetidinone (1.10 g) was obtained by reacting 3-[4-(3-tert-butoxycarbonylamino-3-carboxypropoxy)phenylglyoxyloylamino]-lactacillanic acid (960 mg) with benzoyl chloride (281 mg) in substantially the same manner as described in Example 631.

I.R. absorption spectrum
$\nu_{cm-1}$ (Nujol):
3400 to 3200, 1740, 1720 to 1710, 1680, 1670
N.M.R. absorption spectrum
(internal standard: tetramethylsilane)
δ ppm [(CD$_3$)$_2$CO]:
1.38 (3H, s)
2.26 to 2.44 (2H, m)
3.39, 3.45 (1H, d,d, J=2 Hz, 5 Hz)
4.00 (2H, t, J=5 Hz)
4.24 (2H, t, J=6 Hz)
4.38 (1H, m)
5.06 to 5.30 (1H, m)
5.68 (1H, s)
6.24 (1H, d, J=8 Hz)
7.00 to 8.24 (13H, m)
8.72 (1H, d, J=8 Hz)

EXAMPLE 635

3-[4-(3-tert-Butoxycarbonylamino-3-carboxypropoxy)phenylglyoxyloylamino]-1-[α-carboxy-4-{N-(2,2,2-trichloroacetyl)-carbamoyloxy}benzyl]-2-azetidinone (610 mg) was obtained by reacting 3-[4-(3-tert-butoxycarbonylamino-3-carboxypropoxy)phenylglyoxyloylamino]lactacillanic acid (585 mg) with 2,2,2-trichloroacetic isocyanic anhydride (1.0 g) in substantially the same manner as described in Example 631.

I.R. absorption spectrum
$\nu_{cm-1}$ (Nujol):
3350 to 3250, 1780, 1740, 1720, 1660
N.M.R. absorption spectrum
(internal standard: tetramethylsilane)
δ ppm [(CD$_3$)$_2$CO]:
1.55 (3H, s)
2.36 to 2.62 (2H, m)
3.38, 3.44 (1H, d,d, J=2 Hz, 5 Hz)
3.99 (1H, t, J=5 Hz)
4.20 to 4.42 (3H, m)

5.10 to 5.30 (1H, m)
5.64 (1H, s)
6.96 to 7.60 (6H, m)
8.16 (2H, d, J=8 Hz)
8.68 (1H, d, J=8 Hz)

EXAMPLE 636

3-[4-(3-tert-Butoxycarbonylamino-3-carboxypropoxy)phenylglyoxyloylamino]lactacillanic acid (585 mg) was dissolved in dioxane (5 ml), and to the solution, there were added 1 N aqueous sodium hydroxide and additionally benzyl bromide (680 mg) under ice-cooling, whereafter the mixture was stirred at the same temperature for an hour, and then at 10° to 15° C. for additional 16 hours. Water (about 80 ml) was added to the reaction mixture and the resultant solution was washed with ethyl acetate. The aqueous solution was adjusted to pH 2 with dilute hydrochloric acid and extracted with ethyl acetate. The extract was washed with water and then dried over magnesium sulfate. The solvent was removed by distillation from the solution under reduced pressure to give 3-[4-(3-tert-butoxycarbonylamino-3-carboxypropoxy)phenylglyoxyloylamino]-1-(α-carboxy-4-benzyloxybenzyl)-2-azetidinone (590 mg).

I.R. absorption spectrum
$\nu_{cm-1}$ (Nujol):
  3300 to 3200, 1740 to 1710,
  1690, 1660
N.M.R. absorption spectrum
(internal standard: tetramethylsilane)
δ ppm [(CD$_3$)$_2$CO]:
  1.42 (3H, s)
  2.28 to 2.54 (2H, m)
  3.32 to 3.38 (1H, d,d, J=2 Hz, 5 Hz)
  3.93 (1H, t, J=5 Hz)
  4.26 (2H, t, J=6 Hz)
  4.32 to 4.52 (1H, m)
  5.14 (2H, s)
  5.55 (1H, s)
  6.26 (1H, d, J=8 Hz)
  7.02 to 7.46 (11H, m)
  8.24 (2H, d, J=8 Hz)
  8.70 (1H, d, J=8 Hz)

EXAMPLE 637

Cupric chloride (two hydrate, 0.47 g) was dissolved in water (20 ml), and to the aqueous solution, there was added 3-[2-{4-(3-amino-3-carboxypropoxy)phenyl}-glycinamido]lactacillanic acid (2.5 g). The mixture was adjusted to pH 7.6 with 10% ammonia water and then dioxane (8 ml) was added thereto. An dioxane solution (5 ml) containing 2-phenylacetyl chloride (0.85 g) was added dropwise to the resultant solution under ice-cooling in the course of 40 minutes with stirring. At the same time, the reaction mixture was adjusted to pH 7.2 to 7.6 with 10% ammonia water, and then the stirring was continued at the same temperature for additional an hour. After the reaction, the reaction mixture was adjusted to pH 3 with 10% hydrochloric acid and the precipitating crystals were collected by filtering. After the crystals were suspended in water (10 ml), the suspension was adjusted to pH 7.0 with 10% ammonia water to dissolve it. The aqueous solution was subjected to column chromatography on Diaion CR-10 (Trade Mark, maker: Mitsubishi Kasei Co., Ltd, 150 ml). Elution was carried out with 5% ammonia water and the fractions containing a desired compound were collected. The eluate was concentrated to half of the original volume under reduced pressure and then the concentrate was treated with activated charcoal. The resultant filtrate was adjusted to pH 3 with 10% hydrochloric acid and the precipitating crystals were collected by filtrating to give 3-[2-{4-(3-amino-3-carboxypropoxy)-phenyl}-N-(2-phenylacetyl)glycinamido]lactacillanic acid (0.12 g), mp 178° to 182° C.

I.R. absorption spectrum
$\nu_{cm-1}$ (Nujol):
  3250, 1740, 1720(shoulder),
  1650, 1610

EXAMPLE 638

3-[4-{3-tert-Butoxycarbonylamino-3-(4-methoxybenzyloxycarbonyl)propoxy}phenylglyoxyloylamino]-1-(α-methoxycarbonylbenzyl-2-azetidinone (0.98 g) was obtained by reacting 3-amino-1-(α-methoxycarbonylbenzyl)-2-azetidinone (0.420 g) with 4-[3-tert-butoxycarbonylamino-3-(4-methoxycarbonylbenzyloxycarbonyl)propoxy]phenylglyoxylic acid (0.898 g) in substantially the same manner as described in Example 556.

I.R. absorption spectrum
$\nu_{cm-1}$ (film):
  3400, 1760, 1740, 1710, 1680,
  1660
N.M.R. absorption spectrum
(internal standard: tetramethylsilane)
δ ppm (CDCl$_3$):
  1.49 (9H, s)
  2.28 to 2.46 (2H, m)
  3.02 to 4.12 (4H, m)
  3.73 (3H, s)
  4.39 to 4.70 (1H, m)
  5.11 (2H, s)
  5.22 to 5.33 (1H, m)
  5.67 and 5.70 (1H, s)
  6.76 to 8.36 (13H, m)
  7.74 and 7.93 (1H, d, J=8 Hz)

EXAMPLE 639

3-[4-(3-tert-Butoxycarbonylamino-3-methoxycarbonylpropoxy)phenylglyoxyloylamino]-1-(α-carboxybenzyl)-2-azetidinone (450 mg) was obtained by reacting 3-amino-1-(α-carboxybenzyl)-2-azetidinone (550 mg) with 4-(3-tert-butoxycarbonylamino-3-(methoxycarbonylpropoxy)phenylglyoxylic acid (955 mg) in substantially the same manner as described in Example 556.

Infrared absorption spectrum
$\nu_{cm-1}$ (film):
  3400 to 3300, 1760, 1740, 1710,
  1680 to 1660
N.M.R. absorption spectrum
(internal standard: tetramethylsilane)
δ ppm (CDCl$_3$):
  1.42 (9H, s)
  2.20 to 2.38 (2H, m)
  3.10 to 4.20 (4H, m)
  4.32 to 4.52 (1H, m)
  5.01 to 5.16 (1H, m)
  5.64 (1H, broad s)
  6.82 to 8.30 (9H, m)

EXAMPLE 640

3-[4-(3-Amino-3-carboxypropoxy)phenylglyoxyloylamino]-1-(α-carboxybenzyl)-2-azetidinone (260 mg) was obtained by reacting 3-[4-(3-tert-butoxycarbonylamino-3-carboxypropoxy)phenylglyox-
yloylamino]-1-(α-carboxybenzyl)-2-azetidinone (420 mg) with 2,2,2-trifluoroacetic acid (1 ml) in substantially the same manner as described in Example 565.

I.R. absorption spectrum
νhd cm$_{-1}$ (Nujol):
3450 to 3350, 1760, 1740,
1710, 1690, 1660
N.M.R. absorption spectrum
[internal standard: sodium 2,2,3,3-tetradeutero-3-trimethylsilyl)propionate]
δ ppm (D$_2$O+NaHCO$_3$):
2.24 to 2.48 (2H, m)
3.12 to 4.02 (3H, m)
4.20 to 4.36 (2H, m)
4.98 to 5.08 (1H, m)
5.36, 5.43 (1H, s)
7.00 to 8.06 (9H, m)

EXAMPLE 641

3-[4-(3-tert-Butoxycarbonylamino-3-carboxypropoxy)phenylglyoxyloylamino]-1-(α-carboxybenzyl)-2-azetidinone (490 mg) was obtained by reacting 3-[4-(3-tert-butoxycarbonylamino-3-methoxycarbonylpropoxy)phenylglyoxyloylamino]-1-(α-carboxybenzyl)-2-azetidinone (630 mg) with 1 N aqueous sodium hydroxide (2 ml) in substantially the same manner as described in Example 388.

I.R. absorption spectrum
ν$_{cm-1}$ (film):
3450 to 3300, 1750, 1740, 1700,
1690 to 1660
N.M.R. absorption spectrum
(internal standard: tetramethylsilane)
δ ppm [(CD$_3$)$_2$CO]:
1.40 (9H, s)
2.24 to 2.38 (2H, m)
3.33 to 4.52 (5H, m)
5.20 to 5.32 (1H, m)
5.62 to 5.66 (1H, s)
7.04 to 8.28 (9H, m)

EXAMPLE 642

To a mixture of 3-[4-{3-tert-butoxycarbonylamino-3-(4-methoxybenzyloxycarbonyl)propoxy}phenylglyoxyloylamino]-1-(α-carboxybenzyl)-2-azetidinone (870 mg), benzene (4 ml) and anisol (1 ml), there was added 2,2,2-trifluoroacetic acid (2 ml) under ice-cooling. The mixture was stirred at the same temperature for 1.5 hours and then diethyl ether (50 ml) was added thereto. The mixture was stirred for half an hour and insoluble materials were collected by filtration and suspended in ethyl acetate (30 ml). After the suspension was stirred at ambient temperature for half an hour, insoluble materials were collected by filtration and then treated with diethyl ether to give 3-[4-(3-amino-3-carboxypropoxy)-phenylglyoxyloylamino]-1-(α-carboxybenzyl)-2-azetidinone (0.52 g).

I.R. absorption spectrum
ν$_{cm-1}$ (Nujol):
3450 to 3350, 1760, 1740,
1710, 1690, 1660
N.M.R. absorption spectrum
[internal standard: sodium 2,2,3,3-tetradeutero-3-(trimethylsilyl)propionate]
δ ppm (D$_2$O+NaHCO$_3$):
2.38 to 2.48 (2H, m)
3.12 to 4.02 (3H, m)
4.20 to 4.36 (2H, m)
4.98 to 5.08 (1H, m)
5.36 and 5.43 (1H, s)
7.00 to 8.06 (9H, m)

EXAMPLE 643

Crude 3-[4-{3-tert-butoxycarboxylamino-3-(4-methoxybenzyloxycarbonyl)propoxy}phenylglyoxyloylamino]-1-(α-carboxybenzyl)-2-azetidinone (0.89 g) was obtained by reacting 3-[4-{3-tert-butoxycarbonylamino-3-(4-methoxybenzyloxycarbonyl)propoxy}phenylglyoxyloylamino]-1-(α-methoxycarbonylbenzyl)-2-azetidinone (0.94 g) with 1 N aqueous sodium hydroxide (4 ml) in substantially the same manner as described in Example 616.

I.R. absorption spectrum
ν$_{cm-1}$ (film):
3400 to 3300, 1760, 1740, 1710,
1680 to 1660

EXAMPLE 644

3-[2-{4-(3-tert-Butoxycarbonylamino-3-carboxypropoxy)phenyl}-2-hydroxyiminoacetamido]-1-(α-carboxybenzyl)-2-azetidinone (0.270 g) was obtained by reacting 3-[4-(3-tert-butoxycarbonylamino-3-carboxypropoxy)phenylglyoxyloylamino]-1-(α-carboxybenzyl)-2-azetidinone (0.340 g) with hydroxylamine hydrochloride (0.135 g) in substantially the same manner as described in Example 625.

I.R. absorption spectrum
ν$_{cm-1}$ (film):
3450 to 3300, 1760, 1740, 1700,
1660
N.M.R. absorption spectrum
(internal standard: tetramethylsilane)
δ ppm [(CD$_3$)$_2$CO]:
1.41 (9H, s)
2.20 to 2.36 (2H, m)
3.28 to 4.46 (5H, m)
5.10 to 5.24 (1H, m)
5.56 and 5.60 (1H, s)
6.22 (1H, broad d, J=8 Hz)
6.90 to 7.60 (9H, m)
8.26 (1H, broad d, J=8 Hz)

EXAMPLE 645

3-[2-{4-(3-Amino-3-carboxypropoxy)phenyl}-2-hydroxyiminoacetamido]-1-(α-carboxybenzyl)-2-azetidinone (270 mg) was obtained by reacting 3-[4-(3-amino-3-carboxypropoxy)phenylglyoxyloylamino]-1-(α-carboxybenzyl)-2-azetidinone (470 mg) with hydroxylamine hydrochloride (150 mg) in substantially the same manner as described in Example 625.

I.R. absorption spectrum
ν$_{cm-1}$ (Nujol):
3400 to 3300, 1760, 1660 to
1640, 1600
N.M.R. absorption spectrum
[internal standard: sodium 2,2,3,3-tetradeutero-3-(trimethylsilyl)propionate]
δ ppm (D$_2$O+NaHCO$_3$):
2.30 to 2.48 (2H, m)
3.12 to 3.99 (3H, m)
4.10 to 4.24 (2H, m)
4.98 to 5.08 (1H, m)
5.34 and 5.43 (1H, s)
6.92 to 7.56 (9H, m)

EXAMPLE 646

3-Aminolactacillanic acid was suspended (0.236 g.) in dried dichloromethane (15 ml.), and to the suspension there was added N,O-bis(trimethylsilyl)acetamide (1.0 g.), whereafter the mixture was stirred at ambient temperature for 5 hours. Thionyl chloride (180 mg.) was added to dimethylformamide (80 ml.) and the mixture was heated to 40°–50° C. for 30 minutes and then thionyl chloride was removed therefrom under reduced pressure to give a white crystal. Ethyl acetate (20 ml.) was added to the crystal and then 2-methoxyimino-2-[2-(2,2,2-trifluoroacetamido)-4-thiazolyl]acetic acid (265 mg.) was added to the mixture at 0°–5° C. while stirring. The stirring was continued at the same temperature for 40 minutes, thereafter the mixture was cooled at $-30°$ C. To this solution was added the above 3-aminolactacillanic acid-solution and then the mixture was stirred at $-30°$ C. for 2.5 hours. The mixture was warmed to 0°–5° C. and then reacted at the same temperature. The reaction mixture was further warmed to ambient temperature and then allowed to stand overnight. The mixture was evaporated to dryness under reduced pressure to give a residue, which was dissolved into ethyl acetate. The solution was washed with water and then concentrated under reduced pressure to give an oil (0.450 g.). The oil was subjected to column chromatography on silica gel and elution was carried out with ethyl acetate to give 3-[2-methoxyimino-2-{2-(2,2,2-trifluoroacetamido)-4-thiazolyl}acetamido]-lactacillanic acid (280 mg.)

NMR
δ ppm [(CD$_3$)$_2$CO]:
3.24, 3.32 (1H, d,d, J=2,5 Hz),
3.84 (3H, s), 3.98 (1H, t, J=5 Hz),
5.14 to 5.32 (1H, m), 5.52 (1H, s),
6.82 (2H, d, J=8 Hz), 7.22 (2H, d, J=8 Hz),
7.96 (1H, s), 8.20 (1H, broad s),
8.44 (1H, d, J=8 Hz)

The following compounds (Examples 647 to 656) were obtained in substantially the same manner as described in Example 646.

EXAMPLE 647

3-[4-(3-tert-Butoxycarbonylamino-3-methoxycarbonylpropoxy)-3-chlorophenylglyoxyloylamino]lactacillanic acid.

IR $\nu_{cm^{-1}}$ (film): 3320, 1760 to 1720, 1670

EXAMPLE 648

3-[4-(3-Methoxycarbonylpropoxy)phenylglyoxyloylamino]lactacillanic acid, mp 139° to 142° C.

EXAMPLE 649

3-[3-(3-tert-Butoxycarbonylamino-3-methoxycarbonylpropoxy)phenylglyoxyloylamino]lactacillanic acid.

IR $\nu_{cm^{-1}}$ (Nujol): 3350, 1740, 1730, 1670

EXAMPLE 650

3-[4-(3-phthalimidopropoxy)phenylglyoxyloylamino]lactacillanic acid, mp 173° to 175.5° C. (dec.).

EXAMPLE 651

2-[3-{4-(3-tert-Butoxycarbonylamino-3-methoxycarbonylpropoxy)phenylglyoxyloylamino}-2-oxo-1-azetidinyl]-2-phenyl acetic acid.

NMR
δ ppm (CDCl$_3$):
1.42 (9H, s), 2.20 to 2.38 (2H, m),
3.10 to 4.20 (4H, m), 4.32 to 4.52 (1H, m),
5.01 to 5.16 (1H, m), 5.64 (1H, broad s),
6.82 to 8.30 (9H, m)

EXAMPLE 652

Ethyl 3-phenyl-2-[3-(2-phenylacetamido)-2-oxo-1-azetidinyl]acrylate.

NMR
δ ppm (CDCl$_3$):
1.28 (3H, t, J=6 Hz), 3.53 (2H, s),
4.24 (2H, q, J=6 Hz), 3.40, 3.44 (1H, d, d, J=2,4 Hz), 3.73 (1H, t,
J=4 Hz), 4.96 to
5.12 (1H, m), 6.92 (1H, d, J=8 Hz),
7.26 to 7.52 (11H, m)

EXAMPLE 653

3-Phenyl-2-[3-(2-phenylacetamido)-2-oxo-1-azetidinyl]acrylic acid.

NMR
δ ppm (CD$_3$OD):
3.42, 3.46 (1H, d,d, J=2,4 Hz),
3.54 (2H, s), 3.68 (1H, t), 7.20 to 7.53
(11H, m)

EXAMPLE 654

Methyl 2-[3-{4-(3-tert-butoxycarbonylamino-3-methoxycarbonylpropoxy)phenylglyoxyloylamino}-2-oxo-1-acetidinyl]-3-methyl-2-butenoate.

NMR
δ ppm (CDCl$_3$):
1.42 (9H, s), 2.04 (3H, s),
2.24 (3H, s), 2.20 to 2.37 (2H, m),
3.72 (3H, s), 3.76 (3H, s), 3.63, 3.70
(1H, q, J=2,5 Hz), 3.88 (1H, t, J=5 Hz),
4.14 (2H, t, J=6 Hz), 4.40 to 4.60
(1H, m), 5.02 to 5.20 (1H, m),
5.28 (1H, d, J=8 Hz), 6.93 (2H, d, J=9 Hz),
7.82 (1H, d, J=8 Hz), 8.37 (2H, d, J=9 Hz)

EXAMPLE 655

Benzyl 2-[3-{2-(2-thienyl)acetamido}-2-oxo-1-acetidinyl]acetate.

NMR
δ ppm (CDCl$_3$):
3.26, 3.31 (2H, d,d, J=2 Hz, 5 Hz),
3.73 (1H, t, J=6 Hz), 3.78 (2H, s),
4.04 (2H, s), 5.16-4.07 (1H, m),
5.17 (2H, s), 7.26-6.81 (9H, m)

EXAMPLE 656

3-[2-(4-hydroxyphenyl)-N-t-butoxycarbonylglycinamido]lactacillanic acid.

NMR
δ (ppm) [(CD$_3$)$_2$CO]:
1.39 (9H, s), 2.89, 3.04
(1H, dd, J=2 Hz, 5 Hz), 3.78 (1H, t, J=6 Hz)
5.08–4.92 (1H, m), 5.04 (1H, d, J=8 Hz),
5.42 (1H, s), 6.72 (2H, d, J=8 Hz), 6.83 (2H, d, J=8 Hz),
7.20 (4H, d, J=8 Hz), 7.97 (1H, d, J=8 Hz)

EXAMPLE 657

3-[3-(3-t-butoxycarbonylamino-3-carboxypropoxy)-phenylglyoxyloylamino]lactacillanic acid (1.38 g) was suspended in a mixture of benzene (15 ml.) and anisole (1 ml.) and then 2,2,2-trifluoroacetic acid (5 ml.) was added to the suspension under cooling while stirring. The stirring was continued for 1.5 hours, and then acetone (20 ml.) was added thereto, followed by stirring vigorously for 20 minutes to give a powder. The powder was washed with ether to give a crude object compound, 3-[3-(3-amino-3-carboxypropoxy)phenylglyoxyloylamino]lactacillanic acid (1.10 g.). The crude object compound (300 mg.) was dissolved in water (5 ml.) and the solution was adjusted to pH 3.0 with sodium bicarbonate aqueous solution to give an oil. The oil was subjected to column chromatography on Amberlite XAD-4 (trade mark, made by Rohm & Haas Co.) and elution was carried out with methanol. Eluate was crystallized with acetone to give a purified object compound, 3-[3-(3-amino-3-carboxypropoxy)phenylglyoxyloylamino]lactacillanic acid (160 mg.), mp 182° to 183° C.

The following compounds (Examples 658 to 664) were obtained by reacting the corresponding 3-acylamino-2-azetidinone compounds having t-butoxy carbonylamino group with 2,2,2-trifluoroacetic acid in substantially the same manner as described in Example 657.

EXAMPLE 658

3-[2-{4-(3-Amino-3-carboxypropoxy)-3-chlorophenyl}-2-hydroxyiminoacetamido]lactacillanic acid, mp 175 (dec.).

EXAMPLE 659

3-[4-(3-Amino-3-carboxypropoxy)-3-chlorophenylglyoxyloylamino]lactacillanic acid, mp 190° to 192° C. (dec.).

EXAMPLE 660

2-[3-[2-{4-(3-Amino-3-carboxypropoxy)phenyl}-2-hydroxyiminoacetamido]-2-oxo-1-azetidinyl]-3-methyl-2-butenoic acid.

NMR $\delta$ ppm ($D_2O + N_aHCO_3$):
1.84 (3H, s), 1.96 (3H, s),
2.08 to 2.40 (2H, m), 3.68, 3.75 (1H, q, J=2,5 Hz), 3.88 (1H, t, J=5 Hz), 4.12 (2H, t, J=5 Hz), 5.09, 5.16 (1H, q, J=2,5 Hz), 6.98 (2H, d, J=8 Hz), 7.50 (2 H, d, J=8 Hz)

EXAMPLE 661

2-[3-{4-(3-Amino-3-carboxypropoxy)phenylglyoxyloylamino}-2-oxo-1-azetidinyl]-2-(4-carbamoyloxyphenyl)acetic acid.

IR $\nu_{cm-1}$ (Nujol):
3500 to 3200, 1730, 1720, 1660, 1600

EXAMPLE 662

3-[2-{4-(3-Amino-3-carboxypropoxy)phenyl}2-hydrazonoacetamido]lactacillanic acid.

NMR $\delta$ ppm ($D_2O + N_aHCO_3$):
2.30 to 2.48 (2H, m), 2.88 to
3.12 (1H, m), 3.64 to 3.76 (1H, m), 3.88 to 4.60 (3H, m), 4.71 and 4.72 (1H, each s),
6.84 to 7.40 (8H, m)

EXAMPLE 663

3-[2-[4-{3-(2-phenylglycinamido)-3-carboxypropoxy}phenyl]-2-hydroxyiminoacetamido]lactacillanic acid.

NMR $\delta$ ppm ($D_2O + N_aHCO_3$):
2.18 to 2.40 (2H, m), 3.12,
(1H, q, J=2,5 Hz), 3.78 to 4.00 (3H, m),
4.32 to 4.56 (1H, m), 5.02, 5.08 (1H, q,
J=2, 5 Hz), 5.16 (1H, s), 5.36 (1H, s),
6.75 to 7.40 (13H, m)

EXAMPLE 664

3-[2-{4-(3-Amino-3-carboxypropoxy)phenyl}-2-(2-aminoethoxyimino)acetamido]lactacillanic acid (190 mg.) was obtained by reacting 3-[2-{4-(3-tert-butoxycarbonylamino-3-carboxypropoxy)phenyl}-2-(2-tert-butoxycarbonylaminoethoxyimino)acetamido]lactacillanic acid (0.32 g.) with 2,2,2-trifluoroacetic acid (3 ml.) in substantially the same manner as one described in Example 657.

NMR $\delta$ ppm ($D_2O + N_aHCO_3$):
2.32 to 2.50 (2H, m),
3.28 to 3.38 (3H, m), 3.84 to 4.54 (6H, m),
4.40 (1H, s), 6.92 to 7.60 (8H, m)

EXAMPLE 665

2-[4-(2-Phenylacetoxy)phenyl]-2-[3-[2-{4-(3-carboxy-3-tritylaminopropoxy)phenyl}-2-hydroxyiminoacetamido]-2-oxo-1-azetidinyl]acetic acid (0.5 g.) was dissolved in 80% acetic acid (10 ml.) and the mixture was stirred for 45 minutes. Insoluble materials were filtered off from the reaction mixture and the filtrate was evaporated to dryness under reduced pressure. The residue obtained was triturated with ethyl acetate to give a powder (0.27 g.). This powder (0.2 g.) was dissolved in an aqueous sodium bicarbonate and the solution was adjusted to pH 3 with 10% hydrochloric acid to give crystals of
2-[3-[2-{4-(3-amino-3-carboxypropoxy)phenyl}-2-hydroxyiminoacetamido]-2-oxo-1-azetidinyl]-2-[4-(2-phenylacetoxy)phenyl]acetic acid (0.14 g.).

IR $\nu_{cm-1}$ (Nujol): 3250, 1750, 1730, 1670

EXAMPLE 666

3-[2-(2-Amino-4-thiazolyl)-2-methoxyiminoacetamido]lactacillanic acid (110 mg.) was obtained by reacting 3-[2-methoxyimino-2-{2-(2,2,2-trifluoroacetamido)-4-thiazolyl}acetamido]lactacillanic acid (240 mg.) with sodium acetate (340 mg.) in water (4 ml.) in substantially the same manner as one described in Example 665.

NMR $\delta$ ppm ($D_2O + N_aHCO_3$):
3.12, 3.20 (1H, d,d, J=2,5 Hz),
3.88 (4H, m), 5.02, 5.10 (1H, d,d, J=2,5 Hz),
5.32 (1H, s), 6.82 (1H, s), 6.90 (2H, d,
J=8 Hz), 7.28 (2H, d, J=8 Hz)

EXAMPLE 667

A methanol solution (17 ml.) containing 3-[4-(3-phthalimidopropoxy)phenylglyoxyloylamino]lactacillanic acid (1.13 g.), triethylamine (0.41 g.) and N,N-dimethyl-1,3-propanediamine (0.45 g.) was stirred at 0° C. for 72 hours. The reaction mixture was evaporated to dryness under reduced pressure to give a residue, to which water (10 ml.) was added. The aqueous solution was adjusted to pH 4.8 with 10% hydrochloric acid and the solution was subjected to column chromatography on an adsorption resin, Amberlite XAD-4 (Trade Mark, maker: Rohm & Haas Co.) (100 ml.). Elution was carried out with water and then with methanol, and the fractions containing a desired compound were collected. The eluate was evaporated to dryness under reduced pressure to give a residue, which was powdered with acetone. The powder (480 mg.) was crystallized with water to give 3-[4-(3-aminopropoxy)phenylglyoxyloylamino]lactacillanic acid, mp 221° to 223° C.

EXAMPLE 668

3-[2-{4-(3-Carboxy-3-glycinamidopropoxy)phenyl}-2-hydroxyiminoacetamido]lactacillanic acid (80 mg.) was obtained by reacting 3-[2-[4-{3-(N-phthaloylglycinamido)-3-carboxypropoxy}phenyl]-2-hydroxyiminoacetamido]lactacillanic acid (300 mg.) with N,N-dimethyl-1,3-propanediamine (200 mg.) in substantially the same manner as one described in Example 667.

NMR

δ ppm ($D_2O + N_aHCO_3$):

2.18 to 2.32 (2H, m)
3.09, 3.15 (1H, q, J=2,5 Hz), 3.76 (2H, s),
3.96 (1H, t, J=5 Hz), 4.10 (2H, t, J=6 Hz),
4.35 to 4.52 (1H, m), 5.01, 5.07 (1H, q,
J=2,5 Hz), 5.36 (1H, s,), 6.88 to 7.51 (8H, m)

EXAMPLE 669

To a methanol (20 ml.) solution containing 3-[3-(3-t-butoxycarbonylamino-3-methoxycarbonylpropoxy)-phenylglyoxyloylamino]lactacillanic acid (1.62 g.), there was added dropwise 1 N sodium hydroxide (11 ml.) under ice-cooling while stirring, keeping the solution to pH 9-10. The stirring was continued for about 7 hours. The solution was adjusted to pH 7 with 10% hydrochloric acid and then the methanol was distilled off therefrom. The residual solution was adjusted to pH 2 with 10% hydrochloric acid and elution was carried out with ethyl acetate. Eluate was washed with water and dried over magnesium sulfate to give an oil (1.70 g.). The oil was crystallized with isopropyl ether to give 3-[3-(3-tert-butoxycarbonylamino-3-carboxypropoxy)-phenylglyoxyloylamino]lactacillanic acid (1.48 g.), mp 123 to 127° C. (dec.).

The following compounds (Examples 670 and 671) were obtained by hydrolyzing the corresponding 3-acylamino-2-azetidinone compounds having methyl ester bond with 1 N sodium hydroxide in substantially the same manner as described in Example 669.

EXAMPLE 670

3-{4-(3-Carboxypropoxy)phenylglyoxyloylamino}-2-oxo-1-azetidinyl]lactacillanic acid, mp 157° to 158° C. (dec.).

EXAMPLE 671

3-[4-(3-tert-Butoxycarbonylamino-3-carboxypropoxy)-3-chlorophenylglyloxyloylamino]lactacillanic acid.

IR $\nu_{cm-1}$ (film): 3350, 1740 to 1720, 1680

EXAMPLE 672

3-[4-(3-amino-3-carboxypropoxy)phenylglyoxylamino]lactacillanic acid (0.97 g.) was suspended in water (15 ml.) and sodium bicarbonate (0.4 g.) was added thereto. To this solution was added sodium borohydride (0.08 g.) and the mixture was stirred under ice-cooling for 4.5 hours. The reaction mixture was adjusted to pH 3 with 10% hydrochloric acid and acetone (135 ml.) was added thereto, followed by allowing to stand it in cooling to give a crystal. The crystal was filtered to give 3-[2-{4-(3-amino-3-carboxypropoxy)phenyl}-2-hydroxyacetamido]lactacillanic acid (0.31 g.). The same object compound (0.16 g.) was removed from the filtrate.

IR (Nujol): 3350, 3200, 1725, 1660, 1615, 1580 cm$^{-1}$

EXAMPLE 673

3-[4-(3-t-Butoxycarbonylamino-3-carboxypropoxy)-3-chlorophenylglyoxylamino]lactacillanic acid (760 mg.) was suspended in water (10 ml.), and to the suspension was added hydroxylamine hydrochloride (330 mg.). The mixture was adjusted to pH 7 with sodium bicarbonate, whereafter the resultant mixture was stirred at 55° C. for 2 hours. The aqueous layer was washed with ethyl acetate and then adjusted to pH 2 with 10% hydrochloric acid and extraction was carried out twice with ethyl acetate. The ethyl acetate layer was washed with water and dried over magnesium sulfate and then concentrated under reduced pressure to give 3-[2-{4-(3-tert-butoxycarbonylamino-3-carboxypropoxy)-3-chlorophenyl}-2-hydroxyiminoacetamido]-lactacillanic acid (0.51 g.). IR $\nu_{cm-1}$ (Nujol): 3350, 1740, 1700, 1640

The following compounds (Examples 674 to 678) were obtained by reacting a compound having a carbonyl group with hydroxylamine hydrochloride in substantially the same manner as described in Example 673.

EXAMPLE 674

3-[2-{3-(3-Amino-3-carboxypropoxy)phenyl}-2-hydroxyiminoacetamido]lactacillanic acid, mp 179° to 180° C. (dec.).

EXAMPLE 675

3-[2-{4-(3-Carboxypropoxy)phenyl}-2-hydroxyiminoacetamido]lactacillanic acid, mp 154° to 156° C.(dec.).

EXAMPLE 676

2-[3-[2-{4-(3-tert-Butoxycarbonylamino-3-carboxypropoxy)phenyl}-2-hydroxyiminoacetamido]-2-oxo-1-azetidinyl]-3-methyl-2-butenic acid. IR $\nu_{cm-1}$ (film): 3400 to 3300, 1760, 1720 to 1700, 1670 to 1650

EXAMPLE 677

3-[2-{4-(3-tert-Butoxycarbonylamino-3-carboxypropoxy)phenyl}-2-(2-tert-butoxycarbonylaminoethoxyimino)acetamido]lactacillanic acid.

NMR

δ ppm (CD$_3$OD):

1.21 (18H, s), 3.82 to 4.40 (6H, m),
5.04, 5.10 (1H, q, J=2,5 Hz), 5.56 (1H, s),
6.84 to 7.64 (8H, m)

EXAMPLE 678

3-[2-{4-(3-tert-Butoxycarbonylamino-3-carboxypropoxy)phenyl}-2-hydrazonoacetamido]lactacillanic acid.

NMR

δ ppm [(CD$_3$)$_2$SO]:

1.36 (9H, s), 2.00 to 2.12
(2H, m), 3.04 to 3.14 (1H, m), 3.58 to
3.70 (1H, m), 3.94 to 4.12 (2H, m),
4.84 to 4.94 (2H, m), 5.31 (1H, s),
6.76 to 7.36 (8H, m), 8.66 (1H, d, J=8 Hz)

EXAMPLE 679

Raney nickel (5 ml.) in dry dioxane (15 ml.) was added to methyl 2-(4-benzyloxyphenyl)-2-(4-methylthio-2-oxo-3-phtahlimido-1-azetidinyl)acetate (a mixture of two trans isomers a and b at the third and fourth positions of the azetidine ring) (0.50 g.) in dry dioxane (5 ml.), and the mixture was stirred at 40°–50° C. for 2.75 hours. The Raney nickel was filtered off and then dioxane was distilled off under reduced pressure. The residue thus obtained was dissolved in ethyl acetate, washed with water and dried over magnesium sulfate to give an oil (0.26 g.). The oil was subjected to column chromatography on silica gel and elution was carried out with a mixture of benzene and acetone (8.5:1.5) to give methyl 2-(4-benzyloxyphenyl)-2-(2-oxo-3-phthalimido-1-azetidinyl)acetate (a mixture of two isomers a and b at the third position of the azetidine ring) (0.07 g.)

NMR
Isomer a
$\delta$ ppm (CDCl$_3$):
3.42 (1H, d,d, J=2.5,6 Hz),
3.78 (3H, s), 3.90 (1H, t, J=6 Hz),
5.04 (2H, s), 5.72 (1H, s), 7.00 (2H,
d, J=9 Hz), 7.33 (2H, d, J=9 Hz), 7.37
(5H, s), 7.70 (4H, m)
Isomer b
ppm (CDCl$_3$):
3.66 (1H, t, J=6 Hz), 4.06
(1H, d,d J=2.5,6 Hz), 4.97 (2H, s),
5.32 (1H, d,d, J=2.5,6 Hz), 5.65
(1H, s), 6.98 (2H, d, J=9 Hz), 7.35
(2H, d, J=9 Hz), 7.37 (5H, s), 7.70 (4H, m)

EXAMPLE 680

3-[2-{4-(3-carboxy-3-tritylaminopropoxy)phenyl}-2-hydroxyiminoacetamido]lactacillanic acid (0.75 g.) was dissolved in a mixture of water (20 ml.) and acetone (20 ml.), and 1 N-sodium hydroxide (2 ml.) was added thereto under cooling. The solution was stirred for a few minute at 5° C., and 2-phenylacetyl chloride (0.16 g.) and 1 N-sodium hydroxide (1 ml.) were added thereto, keeping the solution pH 9–11. The acetone was distilled off from the solution under reduced pressure to give a residue. The residue was adjusted to pH 5 with 50% acetic acid under cooling to give an oil, which was extracted twice with ethyl acetate. The ethyl acetate layer was washed with water and dried over magnesium sulfate. The ethyl acetate was distilled off to give a residue which was crystallized with ether to give 2-[3-[2-{4-(3-carboxy-3-tritylaminopropoxy)phenyl}-2-hydroxyiminoacetamido]-2-oxo-1-azetidinyl]-2-[4-(2-phenylacetoxy)phenyl]acetic acid (0.44 g.).

IR $\nu_{cm-1}$ (Nujol): 3240, 1750, 1730, 1655

EXAMPLE 681

2-Chloroacetyl chloride (3.36 g.) dissolved in acetone (20 ml.) was added dropwise to a mixture of water (150 ml.) and acetone (50 ml.) containing 3-[2-{4-(3-amino-3-carboxypropoxy)phenyl}-2-hydroxyiminoacetamido]-lactacillanic acid (10 g.) and sodium bicarbonate (5.83 g.). The mixture was stirred at ambient temperature for 4 hours and then the acetone was removed by distillation from the reaction mixture. The remaining aqueous solution was washed with diethyl ether. The aqueous solution was adjusted to pH 2 with dilute hydrochloric acid under ice-cooling and then extracted with ethyl acetate. The extract was washed with water and saturated sodium chloride aqueous solution, and then dried over magnesium sulfate. The solution was evaporated to dryness under reduced pressure to give a residue, which was powdered with benzene to obtain 3-[2-[4-{3-(2-chloroacetamido)-3-carboxypropoxy}-phenyl]-2-hydroxyiminoacetamido]lactacillanic acid (8.01 g.), mp 128° to 137° C. (dec.).

The following compounds (Examples 682 to 686) were obtained by reacting 2-[3-[2-{4-(3-amino-3-carboxypropoxy)phenyl}-2-hydroxyiminoacetamido]lactacillanic acid with the corresponding acylating agent in substantially the same manner as one described in Example 681.

EXAMPLE 682

3-[2-[4-{3-Carboxy-3-(N-phthaloylglycinamido)-propoxy}phenyl]-2-hydroxyiminoacetamido]lactacillanic acid.

NMR
$\delta$ ppm (CD$_3$OD):
2.20 to 2.40 (2H, m), 3.92 (1H,
t, J=5 Hz), 4.12 (2H, t, J=6 Hz),
4.42 (2H, s), 4.64 to 4.80 (1H, m),
5.09, 5.15 (1H, q, J=2,5 Hz), 5.56 (1H, s),
6.84 to 7.91 (12H, m)

EXAMPLE 683

3-[2-[4-{3-Carboxy-3-(3-amidinoureido)propoxy}-phenyl]-2-hydroxyiminoacetamido]lactacillanic acid, mp 210° to 214° C. (dec.).

EXAMPLE 684

3-[2-[4-{3-(N-tert-Butoxycarbonylglycinamido)-3-carboxypropoxy}phenyl]-2-hydroxyiminoacetamido]-lactacillanic acid.

NMR
$\delta$ ppm [(CD$_3$)$_2$SO]:
1.38 (9H, s), 2.04 to 2.24
(2H, m), 3.11, 3.16 (1H, q, J=2,5 Hz),
3.58 (2H, d, J=4 Hz), 3.82 (1H, t, J=5 Hz),
4.04 (1H, t, J=6 Hz), 4.30 to 4.52 (1H, m),
4.92 to 5.08 (1H, m), 5.32 (1H, s),
6.80 (2H, d, J=8 Hz), 6.97 (2H, d, J=8 Hz),
7.20 (2H, d, J=8 Hz), 7.47 (2H, d, J=8 Hz),
8.10 (1H, d, J=8 Hz), 9.15 (1H, d, J=8 Hz).

EXAMPLE 685

3-[2-[4-{3-Carboxy-3-(2-phenyl-N-tert-butoxycarbonylglycinamido)propoxy}phenyl]-2-hydroxyiminoacetamido]lactacillanic acid.

NMR
$\delta$ ppm [(CD$_3$)$_2$SO]:
1.38 (9H, s), 2.12 to 2.32
2H, m), 3.12, 3.18 (2H, q, J=2,5 Hz),
3.83 (1H, t, J=5Hz), 4.03 (2H, t, J=6Hz),
4.36 to 4.52 (1H, m), 4.96 to 5.08 (1H, m),
5.24 (1H, d, J=8Hz), 5.48 (1H, s),
6.78 to 7.48 (13H, m), 8.48 (1H, d, J=8Hz)
9.16 (1H, d, J=8Hz)

EXAMPLE 686

3-[2-{4-(3-Carboxy-3-foramidopropoxy)phenyl}-2-hydroxyiminoacetamido]lactacillanic acid, mp 119°–123° C. (dec.).

EXAMPLE 687

2-[3-{4-(3-tert-Butoxycarbonylamino-3-carboxypropoxy)phenylglyoxyloylamino}-2-oxo-1-azetidinyl]-2-[4-{N-(2,2,2-trichloroacetyl)carbamoyloxy}phenyl]acetic acid (550 mg.) was suspended in water (5 ml.), and to the suspension there were added sodium bicarbonate (250 mg.) and methanol (1 ml.). The mixture was stirred at ambient temperature for 7 hours. The reaction mixture was adjusted to pH 2 with dilute hydrochloric acid and the precipitating material was collected by filtration. The material was washed with water and then dried to give 2-[3-{4-(3-tert-butoxycarbonylamino-3-carboxypropoxy)phenylglyoxyloylamino}-2-oxo-1-azetidinyl]-2-(4-carbamoyloxyphenyl)acetic acid.

IR $\nu$ cm$^{-1}$ (Nujol): 3300 to 3150, 1750, 1730, 1660

EXAMPLE 688

2-(3phthalimido-2-oxo-1-azetidinyl)acetate was dissolved in a mixture (5 ml.) of chloroform and ethanol (1:1), and 1N ethanol solution of hydrozene monohydrate (1ml.) was added thereto at ambient temperature while stirring. The stirring was continued for 72 hours. The reaction mixture was filtered and the filtrate was concentrated under reduced pressure. The residue thus obtained was dissolved in ethanol, and then ethanol solution (1 ml.) of p-toluenesulfonyl chloride monohydrate (190 mg.) was added thereto. The mixture was concentrated under reduced pressure, and to the residue thus obtained there were added ethanol (1 ml.) and ethyl acetate (2 ml.) to give crystalline benzyl 2-(3-amino-2-oxo-1-azetidinyl)acetate p-toluenesulfonic acid salt, mp 147.5°–149° C.

What is claimed is:

1. An azetidinone compound substantially free of other azetidinones, and having the formula:

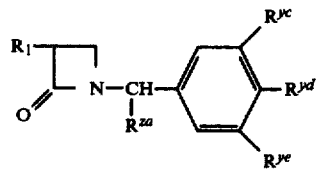

wherein:
  $R_1$ is amino or acylamino excepting 2-[4-(3-amino-3-carboxypropoxy)phenyl]-2-hydroxyiminoacetamido, the acyl moiety of the acylamino group consisting of a carboxylic acid acyl or a benzenesulfonyl;
  $R^{Yc}$ is hydrogen, amino, nitro, halogen, alkoxy containing up to 6 carbon atoms, or alkylthio containing up to 6 carbon atoms;
  $R^{Yd}$ is hydrogen, hydroxy, alkyl containing up to 6 carbon atoms, alkylthio containing up to 6 carbon atoms, or benzyloxy;
  $R^{Ye}$ is hydrogen, halogen, alkoxy containing up to 6 carbon atoms, or alkylthio containing up to 6 carbon atoms; and
  $R^{za}$ is carboxy, a pharmaceutically acceptable salt or as ester thereof,
  excepting 2-(4-hydroxyphenyl)-2-(2-oxo-3-(2-hydroxyimino-2-(4-hydroxyphenyl) acetamido-1-azetidinyl) acetic acid.

2. A. Compound according to claim 1, wherein
  $R_{d1}$ is acylamino as defined, and
  $R^Y$ is hydrogen, hydroxy, alkyl containing up to 6 carbon atoms, or alkylthio containing up to 6 carbon atoms.

3. A compound according to claim 1, wherein
  $R_1$ and $R^{Ye}$ are each hydrogen, and
  $R^{Yd}$ is hydroxy.

4. A compound according to claim 1, wherein
  $R_1$ is amino,
  $R^{Yc}$ and $R^{Ye}$ are each hydrogen, and
  $R^{Yd}$ is hydroxy.

* * * * *